US010875929B2

(12) United States Patent
Pittman et al.

(10) Patent No.: US 10,875,929 B2
(45) Date of Patent: Dec. 29, 2020

(54) TISSUE FACTOR PATHWAY INHIBITOR ANTIBODIES AND USES THEREOF

(71) Applicant: Pfizer Inc., New York, NY (US)

(72) Inventors: Debra Pittman, Windham, NH (US); James R. Apgar, Newton, MA (US); Zong Sean Juo, Cambridge, MA (US); Macy Jin, Lexington, MA (US); Mark Stahl, Lexington, MA (US); Gregory J. Carven, Maynard, MA (US); Matthew Holsti, Boston, MA (US); Susan Benard, Melrose, MA (US); Sunita R. Hett, Arlington, MA (US); Reema Jasuja, Cambridge, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/716,790

(22) Filed: Dec. 17, 2019

(65) Prior Publication Data

US 2020/0190214 A1 Jun. 18, 2020

Related U.S. Application Data

(62) Division of application No. 15/239,556, filed on Aug. 17, 2016, now Pat. No. 10,550,200.

(60) Provisional application No. 62/360,205, filed on Jul. 8, 2016, provisional application No. 62/207,229, filed on Aug. 19, 2015.

(51) Int. Cl.

| | |
|---|---|
| ***C07K 16/38*** | (2006.01) |
| ***A61K 39/00*** | (2006.01) |
| ***A61K 38/48*** | (2006.01) |
| ***A61K 39/395*** | (2006.01) |

(52) U.S. Cl.

CPC .......... *C07K 16/38* (2013.01); *A61K 38/4846* (2013.01); *A61K 39/0011* (2013.01); *A61K 39/3955* (2013.01); *C12Y 304/21021* (2013.01); *A61K 2039/505* (2013.01); *A61K 2039/5158* (2013.01); *A61K 2039/55522* (2013.01); *C07K 2317/21* (2013.01); *C07K 2317/24* (2013.01); *C07K 2317/33* (2013.01); *C07K 2317/34* (2013.01); *C07K 2317/565* (2013.01); *C07K 2317/622* (2013.01); *C07K 2317/76* (2013.01); *C07K 2317/92* (2013.01)

(58) Field of Classification Search

None

See application file for complete search history.

(56) References Cited

U.S. PATENT DOCUMENTS 8,361,469 B2 * 1/2013 Hilden .................. C07K 16/38 424/145.1

8,481,030 B2 * 7/2013 Wang .................... C07K 16/38 424/133.1

FOREIGN PATENT DOCUMENTS

| | | |
|---|---|---|
| EP | 2746294 | 6/2014 |
| WO | 2008147196 | 12/2008 |
| WO | 2010017196 | 2/2010 |
| WO | 2010072687 | 7/2010 |
| WO | 2010072691 | 7/2010 |
| WO | 2011104381 | 9/2011 |
| WO | 2011109452 | 9/2011 |
| WO | 2011147921 | 12/2011 |
| WO | 2012001087 | 1/2012 |
| WO | 20120135671 | 10/2012 |
| WO | 2013023251 | 2/2013 |
| WO | 2013148248 | 10/2013 |
| WO | 2014036071 | 3/2014 |
| WO | 2014140240 | 9/2014 |
| WO | 2014144577 | 9/2014 |
| WO | 2014144689 | 9/2014 |
| WO | 2015007880 | 1/2015 |
| WO | 2016084912 | 6/2016 |
| WO | 2016137108 | 9/2016 |
| WO | 2020075083 | 4/2020 |

OTHER PUBLICATIONS

Agerso et al; "Pharmacokinetics an anti-TFPI monoclonal antibody (concizumab) blocking the TFPI interaction with the active site of FXa in Cynomolgus monkeys after iv and sc administration" European Journal of Pharmaceutical Sciences, vol . 56, Feb. 22, 2014 pp. 65-69.

Anonymous: "Anti-Human TFPI (KUNITZ-2)", XP55313565, Retrieved from the Internet: URL:http://www.sanquin.nl/repository/reagentia/ifu/MW1845.pdf; 2008.

Hilden et al. "Hemostatic effect of a monoclonal antibody mAb 2021 blocking the interaction between FXa and TFPI in a rabbit hemophilia mode" Blood, vol. 119; No. 24; May 4, 2012; pp. 5871-5878.

Hansen et al. "Target-mediated clearance and bio-distribution of a monoclonal antibody against the Kunitz-type protease inhibitor 2 domain of Tissue Factor Pathway Inhib", Thrombosis Research, vol . 133, No. 3, Dec. 17, 2013; pp. 464-471.

Petersen Lars C; "Hemostatic properties of a TFPI antibody", Thrombosis Research, vol. 129, No. Suppl. 2, May 1, 2012, pp. S44-S45.

Sprecher et al. "Molecular cloning, expression, and partial characterization of a second human tissue-factor-pathway inhibitor" Proc. Nat. Acad. Sci.; vol. 91; 1994 ; pp. 3353-3357.

(Continued)

*Primary Examiner* — Michael Szperka

(57) ABSTRACT

The invention relates to antibodies, and antigen-binding fragments thereof, that specifically bind TFPI and inhibit an activity thereof. Such antibodies and fragments are useful for treating bleeding disorders and shortening clotting time.

18 Claims, 29 Drawing Sheets

Specification includes a Sequence Listing.

(56) References Cited

OTHER PUBLICATIONS

Janeway et al., Immunobiology, 3rd edition, 1999, Garland Publishing, Inc. 3:1-3:11.
Rudikoff et al., Proc. Natl. Acad. Sci. USA, Mar. 1982; 79(6):1979-83.
Abumiya T. et al. "An anti-tissue factor pathway inhibitor (TFPI) monoclonal antibody recognized the third Kunitz domain (K3) of free-form TFPI but not lipoprotein-associated forms in plasma." The Journal of Biochemistry, 1995, 118(1): 178-182.
Anonymous: Job result Jul. 24, 2019, XP055608630 URL: http://ibis.internal.epo.org/exam/jobResult?id=586435.
Fizika belka: Kurs lektcii s tcvetnymi i stereoskopicheskimi illiustratciiami i zadachami: uchebnoe posobie / A.V. Finkelshtein, O.B. Ptitcyn, –4-e izdanie, ispr. i dop.—M: KDU, 2012, p. 23 (English Translation).
Yarilin A.A., "Osnovy immunologii", M.: Meditsina, 1999, pp. 169-179 (English Translation).

* cited by examiner

FIG. 1F
TFPI-K2
clone 23
R107
FXa binding
clone 24
2A8
4D8
R&D
Novo 2021

SEQUENCE LISTING

```
<160> NUMBER OF SEQ ID NOS: 178

<210> SEQ ID NO 1
<211> LENGTH: 149
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp
145


<210> SEQ ID NO 2
<211> LENGTH: 254
<212> TYPE: PRT
<213> ORGANISM: Homo sapiens

<400> SEQUENCE: 2

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45
```

```
Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys
                245                 250


<210> SEQ ID NO 3
<211> LENGTH: 189
<212> TYPE: PRT
<213> ORGANISM: Homo sapiens

<400> SEQUENCE: 3

Asp Ala Ala Gln Glu Pro Thr Gly Asn Asn Ala Glu Ile Cys Leu Leu
1               5                   10                  15

Pro Leu Asp Tyr Gly Pro Cys Arg Ala Leu Leu Leu Arg Tyr Tyr Tyr
            20                  25                  30

Asp Arg Tyr Thr Gln Ser Cys Arg Gln Phe Leu Tyr Gly Gly Cys Glu
        35                  40                  45

Gly Asn Ala Asn Asn Phe Tyr Thr Trp Glu Ala Cys Asp Asp Ala Cys
    50                  55                  60

Trp Arg Ile Glu Lys Val Pro Lys Val Cys Arg Leu Gln Val Ser Val
65                  70                  75                  80

Asp Asp Gln Cys Glu Gly Ser Thr Glu Lys Tyr Phe Phe Asn Leu Ser
                85                  90                  95

Ser Met Thr Cys Glu Lys Phe Phe Ser Gly Gly Cys His Arg Asn Arg
            100                 105                 110

Ile Glu Asn Arg Phe Pro Asp Glu Ala Thr Cys Met Gly Phe Cys Ala
        115                 120                 125

Pro Lys Lys Ile Pro Ser Phe Cys Tyr Ser Pro Lys Asp Glu Gly Leu
    130                 135                 140

Cys Ser Ala Asn Val Thr Arg Tyr Tyr Phe Asn Pro Arg Tyr Arg Thr
145                 150                 155                 160

Cys Asp Ala Phe Thr Tyr Thr Gly Cys Gly Gly Asn Asp Asn Asn Phe
```

```
                165                 170                 175

Val Ser Arg Glu Asp Cys Lys Arg Ala Cys Ala Lys Ala
            180                 185


<210> SEQ ID NO 4
<211> LENGTH: 146
<212> TYPE: PRT
<213> ORGANISM: Artificial Sequence
<220> FEATURE:
<223> OTHER INFORMATION: Synthetic Construct

<400> SEQUENCE: 4

Leu Ser Glu Glu Ala Asp Asp Thr Asp Ser Glu Leu Gly Ser Met Lys
1               5                   10                  15

Pro Leu His Thr Phe Cys Ala Met Lys Ala Asp Asp Gly Pro Cys Lys
            20                  25                  30

Ala Met Ile Arg Ser Tyr Phe Phe Asn Met Tyr Thr His Gln Cys Glu
        35                  40                  45

Glu Phe Ile Tyr Gly Gly Cys Glu Gly Asn Glu Asn Arg Phe Asp Thr
    50                  55                  60

Leu Glu Glu Cys Lys Lys Thr Cys Ile Pro Gly Tyr Glu Lys Thr Ala
65                  70                  75                  80

Val Lys Ala Ala Ser Gly Ala Glu Arg Pro Asp Phe Cys Phe Leu Glu
                85                  90                  95

Glu Asp Pro Gly Leu Cys Arg Gly Tyr Met Lys Arg Tyr Leu Tyr Asn
            100                 105                 110

Asn Gln Thr Lys Gln Cys Glu Arg Phe Val Tyr Gly Gly Cys Leu Gly
        115                 120                 125

Asn Arg Asn Asn Phe Glu Thr Leu Asp Glu Cys Lys Lys Ile Cys Glu
    130                 135                 140

Asn Pro
145


<210> SEQ ID NO 5
<211> LENGTH: 149
<212> TYPE: PRT
<213> ORGANISM: Artificial Sequence
<220> FEATURE:
<223> OTHER INFORMATION: Synthetic Construct

<400> SEQUENCE: 5

Asp Ser Glu Glu Asp Glu Glu Tyr Thr Ile Ile Thr Asp Thr Glu Leu
1               5                   10                  15

Pro Pro Leu Lys Leu Met His Ser Phe Cys Ala Phe Lys Pro Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Gly Gly Asn Gln Asn
    50                  55                  60

Arg Phe Glu Ser Met Glu Glu Cys Lys Lys Val Cys Thr Arg Asp Asn
65                  70                  75                  80

Val Asn Arg Ile Ile Gln Thr Ala Leu Gln Lys Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Ser Lys Gln Cys Glu Arg Phe Lys Tyr Gly
        115                 120                 125
```

```
Gly Cys Leu Gly Asn Met Asn Asn Phe Glu Thr Leu Glu Glu Cys Lys
    130                 135                 140

Asn Thr Cys Glu Asp
145


<210> SEQ ID NO 6
<211> LENGTH: 149
<212> TYPE: PRT
<213> ORGANISM: Artificial Sequence
<220> FEATURE:
<223> OTHER INFORMATION: Synthetic Construct

<400> SEQUENCE: 6

Ala Ala Glu Glu Asp Glu Glu Phe Thr Asn Ile Thr Asp Ile Lys Pro
1               5                   10                  15

Pro Leu Gln Lys Pro Thr His Ser Phe Cys Ala Met Lys Val Asp Asp
            20                  25                  30

Gly Pro Cys Arg Ala Tyr Ile Lys Arg Phe Phe Phe Asn Ile Leu Thr
        35                  40                  45

His Gln Cys Glu Glu Phe Ile Tyr Gly Gly Cys Glu Gly Asn Glu Asn
    50                  55                  60

Arg Phe Glu Ser Leu Glu Glu Cys Lys Glu Lys Cys Ala Arg Asp Tyr
65                  70                  75                  80

Pro Lys Met Thr Thr Lys Leu Thr Phe Gln Lys Gly Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Ser Lys Gln Cys Glu Arg Phe Lys Tyr Gly
        115                 120                 125

Gly Cys Leu Gly Asn Leu Asn Asn Phe Glu Ser Leu Glu Glu Cys Lys
    130                 135                 140

Asn Thr Cys Glu Asn
145


<210> SEQ ID NO 7
<211> LENGTH: 148
<212> TYPE: PRT
<213> ORGANISM: Artificial Sequence
<220> FEATURE:
<223> OTHER INFORMATION: Synthetic Construct

<400> SEQUENCE: 7

Leu Pro Glu Glu Asp Asp Asp Thr Ile Asn Thr Asp Ser Glu Leu Arg
1               5                   10                  15

Pro Met Lys Pro Leu His Thr Phe Cys Ala Met Lys Ala Glu Asp Gly
            20                  25                  30

Pro Cys Lys Ala Met Ile Arg Ser Tyr Tyr Phe Asn Met Asn Ser His
        35                  40                  45

Gln Cys Glu Glu Phe Ile Tyr Gly Gly Cys Arg Gly Asn Lys Asn Arg
    50                  55                  60

Phe Asp Thr Leu Glu Glu Cys Arg Lys Thr Cys Ile Pro Gly Tyr Lys
65                  70                  75                  80

Lys Thr Thr Ile Lys Thr Thr Ser Gly Ala Glu Lys Pro Asp Phe Cys
                85                  90                  95

Phe Leu Glu Glu Asp Pro Gly Ile Cys Arg Gly Phe Met Thr Arg Tyr
            100                 105                 110

Phe Tyr Asn Asn Gln Ser Lys Gln Cys Glu Gln Phe Lys Tyr Gly Gly
        115                 120                 125
```

Cys Leu Gly Asn Ser Asn Asn Phe Glu Thr Leu Glu Glu Cys Arg Asn
    130                 135                 140

Thr Cys Glu Asp
145

<210> SEQ ID NO 8
<211> LENGTH: 35
<212> TYPE: PRT
<213> ORGANISM: Artificial Sequence
<220> FEATURE:
<223> OTHER INFORMATION: Synthetic Construct

<400> SEQUENCE: 8

Gly Gly Gly Ser Gly Gly Gly Leu Asn Asp Ile Phe Glu Ala Gln Lys
1               5                   10                  15

Ile Glu Trp His Glu Gly Gly Pro Pro His His His His His His His
            20                  25                  30

His His His
        35

<210> SEQ ID NO 9
<211> LENGTH: 20
<212> TYPE: PRT
<213> ORGANISM: Artificial Sequence
<220> FEATURE:
<223> OTHER INFORMATION: Synthetic Construct

<400> SEQUENCE: 9

Met Glu Thr Asp Thr Leu Leu Leu Trp Val Leu Leu Leu Trp Val Pro
1               5                   10                  15

Gly Ser Thr Gly
            20

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Arg Ala Ser Gln Gly Ile Ser Ser Ser Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Ala Ala Ser Thr Leu Gln Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Leu Asp Ser Tyr Pro Leu Ser 1 5

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asp Ser Tyr Pro Leu
                85                  90                  95

Ser Phe Gly Gln Gly Thr Lys Leu Glu Ile Lys
            100                 105
```

<210> SEQ ID NO 14
<211> LENGTH: 107
<212> TYPE: PRT
<213> ORGANISM: Homo sapiens

<400> SEQUENCE: 14

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 15
<211> LENGTH: 214
<212> TYPE: PRT
<213> ORGANISM: Artificial Sequence
<220> FEATURE:
<223> OTHER INFORMATION: Synthetic Construct

<400> SEQUENCE: 15

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
```

35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Leu Asp Ser Tyr Pro Leu
85 90 95

Ser Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Gly Tyr Thr Phe Thr Gly Tyr Tyr Met His
1 5 10

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Trp Ile Asn Pro Asn Ser Gly Gly Thr Asn Tyr Ala Gln Lys Phe Gln
1 5 10 15

Gly

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Gly Ile Ala Arg Leu Gln Trp Leu Pro Thr Glu Ala Asp Phe Asp Tyr
1 5 10 15

<210> SEQ ID NO 19
<211> LENGTH: 125

<212> TYPE: PRT
<213> ORGANISM: Artificial Sequence
<220> FEATURE:
<223> OTHER INFORMATION: Synthetic Construct

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ile Ala Arg Leu Gln Trp Leu Pro Thr Glu Ala Asp Phe
            100                 105                 110

Asp Tyr Trp Gly Gln Gly Thr Leu Val Thr Val Ser Ser
        115                 120                 125
```

<210> SEQ ID NO 20
<211> LENGTH: 329
<212> TYPE: PRT
<213> ORGANISM: Homo sapiens

<400> SEQUENCE: 20

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 21
<211> LENGTH: 454
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ile Ala Arg Leu Gln Trp Leu Pro Thr Glu Ala Asp Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Ala Pro Ser Val Phe Leu Phe Pro Pro Lys Pro Lys
```

```
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Thr Gly Ser Ser Ser Asn Ile Gly Ala Gly Tyr Asp Val His
1               5                   10


<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Gly Asn Ser Asn Arg Pro Ser
1               5


<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Gln Ser Tyr Asp Ser Ser Leu Ser Gly Ser Val Val
1               5                   10
```

<210> SEQ ID NO 25
<211> LENGTH: 113
<212> TYPE: PRT
<213> ORGANISM: Artificial Sequence
<220> FEATURE:
<223> OTHER INFORMATION: Synthetic Construct

<400> SEQUENCE: 25

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Phe Tyr Cys Gln Ser Tyr Asp Ser Ser
                85                  90                  95

Leu Ser Gly Ser Val Val Phe Gly Gly Gly Thr Lys Val Thr Val Leu
            100                 105                 110

Gly
```

<210> SEQ ID NO 26
<211> LENGTH: 105
<212> TYPE: PRT
<213> ORGANISM: Homo sapiens

<400> SEQUENCE: 26

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 27
<211> LENGTH: 218
<212> TYPE: PRT
<213> ORGANISM: Artificial Sequence
<220> FEATURE:
<223> OTHER INFORMATION: Synthetic Construct

<400> SEQUENCE: 27

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

```
Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Phe Tyr Cys Gln Ser Tyr Asp Ser Ser
                85                  90                  95

Leu Ser Gly Ser Val Val Phe Gly Gly Gly Thr Lys Val Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215


<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Gly Phe Thr Phe Ser Ser Tyr Ala Met Ser
1               5                   10


<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Ala Ile Ser Gly Ser Gly Gly Ser Thr Tyr Tyr Ala Asp Ser Val Lys
1               5                   10                  15

Gly


<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Leu Gly Ala Thr Ser Leu Ser Ala Phe Asp Ile
1               5                   10


<210> SEQ ID NO 31
```

```
<211> LENGTH: 120
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser
        115                 120


<210> SEQ ID NO 32
<211> LENGTH: 449
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Thr Gly Ser Ser Ser Asn Ile Gly Ala Gly Tyr Asp Val His
1               5                   10


<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Gly Asn Ser Asn Arg Pro Ser
1               5


<210> SEQ ID NO 35
<211> LENGTH: 12
<212> TYPE: PRT
```

<213> ORGANISM: Artificial Sequence
<220> FEATURE:
<223> OTHER INFORMATION: Synthetic Construct

<400> SEQUENCE: 35

Gln Ser Tyr Asp Ser Ser Leu Ser Gly Ser Gly Val
1 5 10

<210> SEQ ID NO 36
<211> LENGTH: 113
<212> TYPE: PRT
<213> ORGANISM: Artificial Sequence
<220> FEATURE:
<223> OTHER INFORMATION: Synthetic Construct

<400> SEQUENCE: 36

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Ser Gly Val Phe Gly Gly Gly Thr Lys Leu Thr Val Leu
100 105 110

Gly

<210> SEQ ID NO 37
<211> LENGTH: 218
<212> TYPE: PRT
<213> ORGANISM: Artificial Sequence
<220> FEATURE:
<223> OTHER INFORMATION: Synthetic Construct

<400> SEQUENCE: 37

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly Ser Gly Val Phe Gly Gly Gly Thr Lys Leu Thr Val Leu
100 105 110

Gly Gln Pro Lys Ala Ala Pro Ser Val Thr Leu Phe Pro Pro Ser Ser
115 120 125

Glu Glu Leu Gln Ala Asn Lys Ala Thr Leu Val Cys Leu Ile Ser Asp
130 135 140

Phe Tyr Pro Gly Ala Val Thr Val Ala Trp Lys Ala Asp Ser Ser Pro
145 150 155 160

Val Lys Ala Gly Val Glu Thr Thr Thr Pro Ser Lys Gln Ser Asn Asn
165 170 175

Lys Tyr Ala Ala Ser Ser Tyr Leu Ser Leu Thr Pro Glu Gln Trp Lys
180 185 190

Ser His Arg Ser Tyr Ser Cys Gln Val Thr His Glu Gly Ser Thr Val
195 200 205

Glu Lys Thr Val Ala Pro Thr Glu Cys Ser
210 215

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Gly Phe Thr Phe Ser Ser Tyr Ala Met Ser
1 5 10

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Ala Ile Ser Gly Ser Gly Gly Ser Thr Tyr Tyr Ala Asp Ser Val Lys
1 5 10 15

Gly

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Leu Gly Ala Thr Ser Leu Ser Ala Phe Asp Ile
1 5 10

<210> SEQ ID NO 41
<211> LENGTH: 120
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr

```
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser
        115                 120


<210> SEQ ID NO 42
<211> LENGTH: 449
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

Ser Gly Ser Thr Ser Asn Ile Gly Thr Met Tyr Val His
1               5                   10


<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Arg Asn Asn His Arg Pro Ser
1               5


<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

Leu Ala Trp Asp Asp Thr Leu Arg Ala Tyr Val
1               5                   10


<210> SEQ ID NO 46
<211> LENGTH: 111
<212> TYPE: PRT
<213> ORGANISM: Artificial Sequence
<220> FEATURE:
<223> OTHER INFORMATION: Synthetic Construct

<400> SEQUENCE: 46

Gln Ser Val Leu Thr Gln Pro Pro Ser Val Ser Gly Thr Pro Gly Gln
1               5                   10                  15
```

```
Arg Val Thr Ile Ser Cys Ser Gly Ser Thr Ser Asn Ile Gly Thr Met
            20                  25                  30

Tyr Val His Trp Tyr Gln His Val Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Gly Ser Leu Ala Ile Ser Gly Leu Arg
65                  70                  75                  80

Ser Glu Asp Glu Ala Asp Tyr Tyr Cys Leu Ala Trp Asp Asp Thr Leu
                85                  90                  95

Arg Ala Tyr Val Phe Gly Thr Gly Thr Lys Val Thr Val Leu Gly
            100                 105                 110
```

<210> SEQ ID NO 47
<211> LENGTH: 216
<212> TYPE: PRT
<213> ORGANISM: Artificial Sequence
<220> FEATURE:
<223> OTHER INFORMATION: Synthetic Construct

<400> SEQUENCE: 47

```
Gln Ser Val Leu Thr Gln Pro Pro Ser Val Ser Gly Thr Pro Gly Gln
1               5                   10                  15

Arg Val Thr Ile Ser Cys Ser Gly Ser Thr Ser Asn Ile Gly Thr Met
            20                  25                  30

Tyr Val His Trp Tyr Gln His Val Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Gly Ser Leu Ala Ile Ser Gly Leu Arg
65                  70                  75                  80

Ser Glu Asp Glu Ala Asp Tyr Tyr Cys Leu Ala Trp Asp Asp Thr Leu
                85                  90                  95

Arg Ala Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gly Leu Thr Ile Asp Asn Tyr Ala Met Gln
1 5 10

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Gly Ile Ser Gly Asn Ser Arg Ser Ile Gly Tyr Ala Asp Ser Val Lys
1 5 10 15

Gly

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Phe Leu His Glu Ser Asp Tyr
1 5

<210> SEQ ID NO 51
<211> LENGTH: 116
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Ser Val Gln Pro Gly Arg
1 5 10 15

Ser Leu Arg Leu Ser Cys Ala Val Ser Gly Leu Thr Ile Asp Asn Tyr
20 25 30

Ala Met Gln Trp Val Arg Gln Arg Pro Gly Lys Gly Leu Glu Trp Val
35 40 45

Ser Gly Ile Ser Gly Asn Ser Arg Ser Ile Gly Tyr Ala Asp Ser Val
50 55 60

Lys Gly Arg Leu Thr Ile Ser Arg Asp Asn Ala Lys Asn Ser Leu Tyr
65 70 75 80

Leu Gln Ile Asp Ser Leu Arg Ala Asp Asp Thr Ala Leu Tyr Tyr Cys
85 90 95

Ala Ile Phe Leu His Glu Ser Asp Tyr Trp Gly Gln Gly Thr Leu Val
100 105 110

Thr Val Ser Ser
115

<210> SEQ ID NO 52
<211> LENGTH: 445
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Ser Val Gln Pro Gly Arg
1 5 10 15

```
Ser Leu Arg Leu Ser Cys Ala Val Ser Gly Leu Thr Ile Asp Asn Tyr
            20                  25                  30

Ala Met Gln Trp Val Arg Gln Arg Pro Gly Lys Gly Leu Glu Trp Val
        35                  40                  45

Ser Gly Ile Ser Gly Asn Ser Arg Ser Ile Gly Tyr Ala Asp Ser Val
    50                  55                  60

Lys Gly Arg Leu Thr Ile Ser Arg Asp Asn Ala Lys Asn Ser Leu Tyr
65                  70                  75                  80

Leu Gln Ile Asp Ser Leu Arg Ala Asp Asp Thr Ala Leu Tyr Tyr Cys
                85                  90                  95

Ala Ile Phe Leu His Glu Ser Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

Asn His Tyr Thr Gln Lys Ser Leu Ser Leu Ser Pro Gly
435 440 445

<210> SEQ ID NO 53
<211> LENGTH: 14
<212> TYPE: PRT
<213> ORGANISM: Artificial Sequence
<220> FEATURE:
<223> OTHER INFORMATION: Synthetic Construct

<400> SEQUENCE: 53

Thr Gly Ser Ser Ser Asn Leu Gly Ala Asp Tyr Asp Val Gln
1 5 10

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Gly Asn Asn Asn Arg Pro Ser
1 5

<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Gln Ser Tyr Asp Arg Ser Leu Ser Gly Ser Met Val
1 5 10

<210> SEQ ID NO 56
<211> LENGTH: 113
<212> TYPE: PRT
<213> ORGANISM: Artificial Sequence
<220> FEATURE:
<223> OTHER INFORMATION: Synthetic Construct

<400> SEQUENCE: 56

Gln Ser Val Leu Thr Gln Pro Pro Ser Leu Ser Gly Ala Pro Gly Gln
1 5 10 15

Arg Val Thr Ile Ser Cys Thr Gly Ser Ser Ser Asn Leu Gly Ala Asp
20 25 30

Tyr Asp Val Gln Trp Tyr Gln Gln Leu Pro Gly Thr Ala Pro Lys Leu
35 40 45

Leu Ile Phe Gly Asn Asn Asn Arg Pro Ser Gly Val Pro Asp Arg Phe
50 55 60

Ser Gly Ser Arg Ser Gly Thr Ser Ala Ser Leu Ala Ile Thr Gly Leu
65 70 75 80

Gln Ala Glu Asp Glu Ala Asn Tyr Tyr Cys Gln Ser Tyr Asp Arg Ser
85 90 95

Leu Ser Gly Ser Met Val Phe Gly Gly Gly Thr Lys Leu Thr Val Leu
100 105 110

Gly

<210> SEQ ID NO 57
<211> LENGTH: 218
<212> TYPE: PRT

<213> ORGANISM: Artificial Sequence
<220> FEATURE:
<223> OTHER INFORMATION: Synthetic Construct

<400> SEQUENCE: 57

Gln Ser Val Leu Thr Gln Pro Pro Ser Leu Ser Gly Ala Pro Gly Gln
1 5 10 15

Arg Val Thr Ile Ser Cys Thr Gly Ser Ser Ser Asn Leu Gly Ala Asp
20 25 30

Tyr Asp Val Gln Trp Tyr Gln Gln Leu Pro Gly Thr Ala Pro Lys Leu
35 40 45

Leu Ile Phe Gly Asn Asn Asn Arg Pro Ser Gly Val Pro Asp Arg Phe
50 55 60

Ser Gly Ser Arg Ser Gly Thr Ser Ala Ser Leu Ala Ile Thr Gly Leu
65 70 75 80

Gln Ala Glu Asp Glu Ala Asn Tyr Tyr Cys Gln Ser Tyr Asp Arg Ser
85 90 95

Leu Ser Gly Ser Met Val Phe Gly Gly Gly Thr Lys Leu Thr Val Leu
100 105 110

Gly Gln Pro Lys Ala Ala Pro Ser Val Thr Leu Phe Pro Pro Ser Ser
115 120 125

Glu Glu Leu Gln Ala Asn Lys Ala Thr Leu Val Cys Leu Ile Ser Asp
130 135 140

Phe Tyr Pro Gly Ala Val Thr Val Ala Trp Lys Ala Asp Ser Ser Pro
145 150 155 160

Val Lys Ala Gly Val Glu Thr Thr Thr Pro Ser Lys Gln Ser Asn Asn
165 170 175

Lys Tyr Ala Ala Ser Ser Tyr Leu Ser Leu Thr Pro Glu Gln Trp Lys
180 185 190

Ser His Arg Ser Tyr Ser Cys Gln Val Thr His Glu Gly Ser Thr Val
195 200 205

Glu Lys Thr Val Ala Pro Thr Glu Cys Ser
210 215

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Gly Phe Thr Phe Ser Ser Tyr Ala Met Ser
1 5 10

<210> SEQ ID NO 59
<211> LENGTH: 17
<212> TYPE: PRT
<213> ORGANISM: Artificial Sequence
<220> FEATURE:
<223> OTHER INFORMATION: Synthetic Construct

<400> SEQUENCE: 59

Ala Ile Ser Gly Ser Gly Gly Ser Thr Tyr Tyr Ala Asp Ser Val Lys
1 5 10 15

Gly

<210> SEQ ID NO 60
<211> LENGTH: 9

<212> TYPE: PRT
<213> ORGANISM: Artificial Sequence
<220> FEATURE:
<223> OTHER INFORMATION: Synthetic Construct

<400> SEQUENCE: 60

Asn Gly Ala Ala Ala Ala Trp Asp Tyr
1               5

<210> SEQ ID NO 61
<211> LENGTH: 118
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Ala Ala Ala Ala Trp Asp Tyr Trp Gly Gln Gly Thr
            100                 105                 110

Leu Val Thr Val Ser Ser
        115

<210> SEQ ID NO 62
<211> LENGTH: 447
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Ala Ala Ala Ala Trp Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 63
<211> LENGTH: 120
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser
        115                 120


<210> SEQ ID NO 64
<211> LENGTH: 449
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 65
<211> LENGTH: 120
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Ala Thr Ser Leu Ser Ala Phe Asp Ile Trp Gly Gln
            100                 105                 110

Gly Thr Met Val Thr Val Ser Ser
        115                 120


<210> SEQ ID NO 66
<211> LENGTH: 449
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

-continued

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Ala Thr Ser Leu Ser Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 67
<211> LENGTH: 116
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Glu Ser Gly Gly Gly Leu Val Gln Pro Gly Arg
1               5                   10                  15

Ser Leu Arg Leu Ser Cys Ala Val Ser Gly Leu Thr Ile Asp Asn Tyr
            20                  25                  30

Ala Met Gln Trp Val Arg Gln Ala Pro Gly Lys Gly Leu Glu Trp Val
        35                  40                  45

Ser Gly Ile Ser Gly Asn Ser Arg Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Ile Phe Leu His Glu Ser Asp Tyr Trp Gly Gln Gly Thr Leu Val
            100                 105                 110

Thr Val Ser Ser
        115

<210> SEQ ID NO 68
<211> LENGTH: 445
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Glu Ser Gly Gly Gly Leu Val Gln Pro Gly Arg
1               5                   10                  15

Ser Leu Arg Leu Ser Cys Ala Val Ser Gly Leu Thr Ile Asp Asn Tyr
            20                  25                  30

Ala Met Gln Trp Val Arg Gln Ala Pro Gly Lys Gly Leu Glu Trp Val
        35                  40                  45

Ser Gly Ile Ser Gly Asn Ser Arg Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Ile Phe Leu His Glu Ser Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 69
<211> LENGTH: 116
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Val Glu Ser Gly Gly Gly Leu Val Gln Pro Gly Arg
1               5                   10                  15

Ser Leu Arg Leu Ser Cys Ala Ala Ser Gly Leu Thr Ile Asp Asn Tyr
            20                  25                  30

Ala Met Gln Trp Val Arg Gln Ala Pro Gly Lys Gly Leu Glu Trp Val
        35                  40                  45

Ser Gly Ile Ser Gly Asn Ser Arg Ser Ile Gly Tyr Ala Asp Ser Val
    50                  55                  60

Lys Gly Arg Leu Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95
```

Ala Ile Phe Leu His Glu Ser Asp Tyr Trp Gly Gln Gly Thr Leu Val
100 105 110

Thr Val Ser Ser
115

<210> SEQ ID NO 70
<211> LENGTH: 445
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Gln Pro Gly Arg
1 5 10 15

Ser Leu Arg Leu Ser Cys Ala Ala Ser Gly Leu Thr Ile Asp Asn Tyr
20 25 30

Ala Met Gln Trp Val Arg Gln Ala Pro Gly Lys Gly Leu Glu Trp Val
35 40 45

Ser Gly Ile Ser Gly Asn Ser Arg Ser Ile Gly Tyr Ala Asp Ser Val
50 55 60

Lys Gly Arg Leu Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Ile Phe Leu His Glu Ser Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Ala Ala Gly Ala Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

```
Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 71
<211> LENGTH: 111
<212> TYPE: PRT
<213> ORGANISM: Artificial Sequence
<220> FEATURE:
<223> OTHER INFORMATION: Synthetic Construct

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Met
            20                  25                  30

Tyr Val His Trp Tyr Gln His Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Leu Ala Trp Asp Asp Thr Leu
                85                  90                  95

Arg Ala Tyr Val Phe Gly Thr Gly Thr Lys Val Thr Val Leu Gly
            100                 105                 110


<210> SEQ ID NO 72
<211> LENGTH: 216
<212> TYPE: PRT
<213> ORGANISM: Artificial Sequence
<220> FEATURE:
<223> OTHER INFORMATION: Synthetic Construct

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Met
            20                  25                  30

Tyr Val His Trp Tyr Gln His Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Leu Ala Trp Asp Asp Thr Leu
```

```
                85                  90                  95

Arg Ala Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 73
<211> LENGTH: 111
<212> TYPE: PRT
<213> ORGANISM: Artificial Sequence
<220> FEATURE:
<223> OTHER INFORMATION: Synthetic Construct

<400> SEQUENCE: 73

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Met
            20                  25                  30

Tyr Val His Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Gly Ser Leu Ala Ile Ser Gly Leu Arg
65                  70                  75                  80

Ser Glu Asp Glu Ala Asp Tyr Tyr Cys Leu Ala Trp Asp Asp Thr Leu
                85                  90                  95

Arg Ala Tyr Val Phe Gly Thr Gly Thr Lys Val Thr Val Leu Gly
            100                 105                 110


<210> SEQ ID NO 74
<211> LENGTH: 216
<212> TYPE: PRT
<213> ORGANISM: Artificial Sequence
<220> FEATURE:
<223> OTHER INFORMATION: Synthetic Construct

<400> SEQUENCE: 74

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Met
            20                  25                  30

Tyr Val His Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60
```

Gly Ser Lys Ser Gly Thr Ser Gly Ser Leu Ala Ile Ser Gly Leu Arg
65 70 75 80

Ser Glu Asp Glu Ala Asp Tyr Tyr Cys Leu Ala Trp Asp Asp Thr Leu
85 90 95

Arg Ala Tyr Val Phe Gly Thr Gly Thr Lys Val Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 75
<211> LENGTH: 111
<212> TYPE: PRT
<213> ORGANISM: Artificial Sequence
<220> FEATURE:
<223> OTHER INFORMATION: Synthetic Construct

<400> SEQUENCE: 75

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Met
20 25 30

Tyr Val His Trp Tyr Gln His Leu Pro Gly Thr Ala Pro Lys Leu Leu
35 40 45

Ile Tyr Arg Asn Asn His Arg Pro Ser Gly Val Pro Asp Arg Phe Ser
50 55 60

Gly Ser Lys Ser Gly Thr Ser Gly Ser Leu Ala Ile Ser Gly Leu Arg
65 70 75 80

Ser Glu Asp Glu Ala Asp Tyr Tyr Cys Leu Ala Trp Asp Asp Thr Leu
85 90 95

Arg Ala Tyr Val Phe Gly Thr Gly Thr Lys Val Thr Val Leu Gly
100 105 110

<210> SEQ ID NO 76
<211> LENGTH: 216
<212> TYPE: PRT
<213> ORGANISM: Artificial Sequence
<220> FEATURE:
<223> OTHER INFORMATION: Synthetic Construct

<400> SEQUENCE: 76

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Met
20 25 30

Tyr Val His Trp Tyr Gln His Leu Pro Gly Thr Ala Pro Lys Leu Leu
35 40 45

```
Ile Tyr Arg Asn Asn His Arg Pro Ser Gly Val Pro Asp Arg Phe Ser
    50                  55                  60

Gly Ser Lys Ser Gly Thr Ser Gly Ser Leu Ala Ile Ser Gly Leu Arg
65                  70                  75                  80

Ser Glu Asp Glu Ala Asp Tyr Tyr Cys Leu Ala Trp Asp Asp Thr Leu
                85                  90                  95

Arg Ala Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 77
<211> LENGTH: 111
<212> TYPE: PRT
<213> ORGANISM: Artificial Sequence
<220> FEATURE:
<223> OTHER INFORMATION: Synthetic Construct

<400> SEQUENCE: 77

```
Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Met
            20                  25                  30

Tyr Val His Trp Tyr Gln Gln Leu Pro Gly Thr Ala Pro Lys Leu Leu
        35                  40                  45

Ile Tyr Arg Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Leu Ala Trp Asp Asp Thr Leu
                85                  90                  95

Arg Ala Tyr Val Phe Gly Thr Gly Thr Lys Val Thr Val Leu Gly
            100                 105                 110
```

<210> SEQ ID NO 78
<211> LENGTH: 216
<212> TYPE: PRT
<213> ORGANISM: Artificial Sequence
<220> FEATURE:
<223> OTHER INFORMATION: Synthetic Construct

<400> SEQUENCE: 78

```
Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Met
```

20 25 30

Tyr Val His Trp Tyr Gln Gln Leu Pro Gly Thr Ala Pro Lys Leu Leu
35 40 45

Ile Tyr Arg Asn Asn His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Leu Ala Trp Asp Asp Thr Leu
85 90 95

Arg Ala Tyr Val Phe Gly Thr Gly Thr Lys Val Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 79
<211> LENGTH: 116
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Val Glu Ser Gly Gly Gly Leu Val Gln Pro Gly Arg
1 5 10 15

Ser Leu Arg Leu Ser Cys Ala Val Ser Gly Leu Thr Ile Asp Asn Tyr
20 25 30

Ala Met Gln Trp Val Arg Gln Ala Pro Gly Lys Gly Leu Glu Trp Val
35 40 45

Ser Gly Ile Ser Gly Asn Ser Arg Ser Ile Gly Tyr Ala Asp Ser Val
50 55 60

Lys Gly Arg Leu Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Ile Phe Leu His Glu Ser Asp Tyr Trp Gly Gln Gly Thr Leu Val
100 105 110

Thr Val Ser Ser
115

<210> SEQ ID NO 80
<211> LENGTH: 445
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Gln Pro Gly Arg
1 5 10 15

Ser Leu Arg Leu Ser Cys Ala Val Ser Gly Leu Thr Ile Asp Asn Tyr
20 25 30

Ala Met Gln Trp Val Arg Gln Ala Pro Gly Lys Gly Leu Glu Trp Val
35 40 45

Ser Gly Ile Ser Gly Asn Ser Arg Ser Ile Gly Tyr Ala Asp Ser Val
50 55 60

Lys Gly Arg Leu Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Ile Phe Leu His Glu Ser Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Ala Ala Gly Ala Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp

```
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Lys Ala Ser Gln Asp Val His Thr Ala Val Ala
1               5                   10


<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Trp Ala Ser Thr Arg His Thr
1               5


<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

Gln Gln His Tyr Thr Thr Pro Tyr Thr
1               5


<210> SEQ ID NO 84
<211> LENGTH: 107
<212> TYPE: PRT
<213> ORGANISM: Artificial Sequence
<220> FEATURE:
<223> OTHER INFORMATION: Synthetic Construct

<400> SEQUENCE: 84

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val His Thr Ala
            20                  25                  30

Val Ala Trp Tyr Gln Gln Lys Pro Gly Gln Ser Pro Arg Leu Leu Ile
        35                  40                  45

Tyr Trp Ala Ser Thr Arg His Thr Gly Val Pro Asp Arg Phe Thr Gly
    50                  55                  60

Cys Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Tyr
                85                  90                  95

Thr Phe Gly Gly Gly Thr Lys Leu Glu Met Lys
            100                 105
```

<210> SEQ ID NO 85
<211> LENGTH: 106
<212> TYPE: PRT
<213> ORGANISM: Artificial Sequence
<220> FEATURE:
<223> OTHER INFORMATION: Synthetic Construct

<400> SEQUENCE: 85

Ala Asp Ala Ala Pro Thr Val Ser Ile Phe Pro Pro Ser Ser Glu Gln
1 5 10 15

Leu Thr Ser Gly Gly Ala Ser Val Val Cys Phe Leu Asn Asn Phe Tyr
20 25 30

Pro Lys Asp Ile Asn Val Lys Trp Lys Ile Asp Gly Ser Glu Arg Gln
35 40 45

Asn Gly Val Leu Asn Ser Trp Thr Asp Gln Asp Ser Lys Asp Ser Thr
50 55 60

Tyr Ser Met Ser Ser Thr Leu Thr Leu Thr Lys Asp Glu Tyr Glu Arg
65 70 75 80

His Asn Ser Tyr Thr Cys Glu Ala Thr His Lys Thr Ser Thr Ser Pro
85 90 95

Ile Val Lys Ser Phe Asn Arg Asn Glu Cys
100 105

<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Asp Ile Val Met Thr Gln Ser His Lys Phe Met Ser Thr Ser Val Gly
1 5 10 15

Asp Arg Val Ser Ile Thr Cys Lys Ala Ser Gln Asp Val His Thr Ala
20 25 30

Val Ala Trp Tyr Gln Gln Lys Pro Gly Gln Ser Pro Arg Leu Leu Ile
35 40 45

Tyr Trp Ala Ser Thr Arg His Thr Gly Val Pro Asp Arg Phe Thr Gly
50 55 60

Cys Gly Ser Gly Thr Asp Tyr Thr Leu Thr Ile Ser Ser Val Gln Ala
65 70 75 80

Glu Asp Leu Ala Leu Tyr Tyr Cys Gln Gln His Tyr Thr Thr Pro Tyr
85 90 95

Thr Phe Gly Gly Gly Thr Lys Leu Glu Met Lys Ala Asp Ala Ala Pro
100 105 110

Thr Val Ser Ile Phe Pro Pro Ser Ser Glu Gln Leu Thr Ser Gly Gly
115 120 125

Ala Ser Val Val Cys Phe Leu Asn Asn Phe Tyr Pro Lys Asp Ile Asn
130 135 140

Val Lys Trp Lys Ile Asp Gly Ser Glu Arg Gln Asn Gly Val Leu Asn
145 150 155 160

Ser Trp Thr Asp Gln Asp Ser Lys Asp Ser Thr Tyr Ser Met Ser Ser
165 170 175

Thr Leu Thr Leu Thr Lys Asp Glu Tyr Glu Arg His Asn Ser Tyr Thr
180 185 190

Cys Glu Ala Thr His Lys Thr Ser Thr Ser Pro Ile Val Lys Ser Phe
195 200 205

Asn Arg Asn Glu Cys
210

<210> SEQ ID NO 87
<211> LENGTH: 10
<212> TYPE: PRT
<213> ORGANISM: Artificial Sequence
<220> FEATURE:
<223> OTHER INFORMATION: Synthetic Construct

<400> SEQUENCE: 87

Gly Tyr Thr Phe Thr Asp Tyr Asn Leu Asp
1 5 10

<210> SEQ ID NO 88
<211> LENGTH: 17
<212> TYPE: PRT
<213> ORGANISM: Artificial Sequence
<220> FEATURE:
<223> OTHER INFORMATION: Synthetic Construct

<400> SEQUENCE: 88

Asp Ile Asn Pro Ile Asn Gly Ala Thr Leu Tyr Asn Gln Lys Phe Lys
1 5 10 15

Gly

<210> SEQ ID NO 89
<211> LENGTH: 10
<212> TYPE: PRT
<213> ORGANISM: Artificial Sequence
<220> FEATURE:
<223> OTHER INFORMATION: Synthetic Construct

<400> SEQUENCE: 89

Tyr Tyr Gly Asp Tyr Asp Ala Met Asp Tyr
1 5 10

<210> SEQ ID NO 90
<211> LENGTH: 119
<212> TYPE: PRT
<213> ORGANISM: Artificial Sequence
<220> FEATURE:
<223> OTHER INFORMATION: Synthetic Construct

<400> SEQUENCE: 90

Glu Val Leu Leu Gln Gln Ser Gly Pro Glu Leu Val Lys Pro Gly Ala
1 5 10 15

Ser Val Lys Ile Pro Cys Lys Ala Ser Gly Tyr Thr Phe Thr Asp Tyr
20 25 30

Asn Leu Asp Trp Val Lys Gln Ser His Gly Lys Ser Leu Glu Trp Ile
35 40 45

Gly Asp Ile Asn Pro Ile Asn Gly Ala Thr Leu Tyr Asn Gln Lys Phe
50 55 60

Lys Gly Lys Ala Thr Leu Thr Val Asp Gln Ser Ser Ser Thr Ala Tyr
65 70 75 80

Met Glu Leu Arg Ser Leu Thr Ser Glu Asp Thr Ala Val Tyr Tyr Cys
85 90 95

Ser Ile Tyr Tyr Gly Asp Tyr Asp Ala Met Asp Tyr Trp Gly Gln Gly
100 105 110

Ala Ser Val Thr Val Ser Ser
115

<210> SEQ ID NO 91
<211> LENGTH: 324
<212> TYPE: PRT
<213> ORGANISM: Artificial Sequence
<220> FEATURE:
<223> OTHER INFORMATION: Synthetic Construct

<400> SEQUENCE: 91

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 92
<211> LENGTH: 443
<212> TYPE: PRT
<213> ORGANISM: Artificial Sequence
<220> FEATURE:
<223> OTHER INFORMATION: Synthetic Construct

<400> SEQUENCE: 92

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Leu Asp Trp Val Lys Gln Ser His Gly Lys Ser Leu Glu Trp Ile
        35                  40                  45

Gly Asp Ile Asn Pro Ile Asn Gly Ala Thr Leu Tyr Asn Gln Lys Phe
    50                  55                  60

Lys Gly Lys Ala Thr Leu Thr Val Asp Gln Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ser Ile Tyr Tyr Gly Asp Tyr Asp Ala Met Asp Tyr Trp Gly Gln Gly
            100                 105                 110

Ala Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
420 425 430

Thr Glu Lys Ser Leu Ser His Ser Pro Gly Lys
435 440

<210> SEQ ID NO 93
<211> LENGTH: 214
<212> TYPE: PRT
<213> ORGANISM: Artificial Sequence
<220> FEATURE:
<223> OTHER INFORMATION: Synthetic Construct

<400> SEQUENCE: 93

Asp Ile Val Met Thr Gln Ser His Lys Phe Met Ser Thr Ser Val Gly
1 5 10 15

Asp Arg Val Ser Ile Thr Cys Lys Ala Ser Gln Asp Val His Thr Ala
20 25 30

Val Ala Trp Tyr Gln Gln Lys Pro Gly Gln Ser Pro Arg Leu Leu Ile
35 40 45

Tyr Trp Ala Ser Thr Arg His Thr Gly Val Pro Asp Arg Phe Thr Gly
50 55 60

Cys Gly Ser Gly Thr Asp Tyr Thr Leu Thr Ile Ser Ser Val Gln Ala
65 70 75 80

Glu Asp Leu Ala Leu Tyr Tyr Cys Gln Gln His Tyr Thr Thr Pro Tyr
85 90 95

Thr Phe Gly Gly Gly Thr Lys Leu Glu Met Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 94
<211> LENGTH: 448
<212> TYPE: PRT
<213> ORGANISM: Artificial Sequence
<220> FEATURE:
<223> OTHER INFORMATION: Synthetic Construct

<400> SEQUENCE: 94

Glu Val Leu Leu Gln Gln Ser Gly Pro Glu Leu Val Lys Pro Gly Ala
1 5 10 15

Ser Val Lys Ile Pro Cys Lys Ala Ser Gly Tyr Thr Phe Thr Asp Tyr
20 25 30

Asn Leu Asp Trp Val Lys Gln Ser His Gly Lys Ser Leu Glu Trp Ile
35 40 45

Gly Asp Ile Asn Pro Ile Asn Gly Ala Thr Leu Tyr Asn Gln Lys Phe

```
    50                  55                  60

Lys Gly Lys Ala Thr Leu Thr Val Asp Gln Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ser Ile Tyr Tyr Gly Asp Tyr Asp Ala Met Asp Tyr Trp Gly Gln Gly
            100                 105                 110

Ala Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 95
<211> LENGTH: 119
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser
        115

<210> SEQ ID NO 96
<211> LENGTH: 448
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys

```
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 97
<211> LENGTH: 119
<212> TYPE: PRT
<213> ORGANISM: Artificial Sequence
<220> FEATURE:
<223> OTHER INFORMATION: Synthetic Construct

<400> SEQUENCE: 97

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Gly Asp Ile Asn Pro Ile Asn Gly Ala Thr Leu Tyr Asn Gln Lys Phe
    50                  55                  60

Lys Gly Arg Ala Thr Ile Ser Val Asp Gln Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser
        115
```

<210> SEQ ID NO 98
<211> LENGTH: 448
<212> TYPE: PRT
<213> ORGANISM: Artificial Sequence
<220> FEATURE:
<223> OTHER INFORMATION: Synthetic Construct

<400> SEQUENCE: 98

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Gly Asp Ile Asn Pro Ile Asn Gly Ala Thr Leu Tyr Asn Gln Lys Phe
    50                  55                  60

Lys Gly Arg Ala Thr Ile Ser Val Asp Gln Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
```

```
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 99
<211> LENGTH: 119
<212> TYPE: PRT
<213> ORGANISM: Artificial Sequence
<220> FEATURE:
<223> OTHER INFORMATION: Synthetic Construct

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Gly Asp Ile Asn Pro Ile Asn Gly Ala Thr Leu Tyr Asn Gln Lys Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser
        115


<210> SEQ ID NO 100
<211> LENGTH: 448
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Gly Asp Ile Asn Pro Ile Asn Gly Ala Thr Leu Tyr Asn Gln Lys Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 101
<211> LENGTH: 119
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30
```

-continued

```
Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Ala Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser
        115


<210> SEQ ID NO 102
<211> LENGTH: 448
<212> TYPE: PRT
<213> ORGANISM: Artificial Sequence
<220> FEATURE:
<223> OTHER INFORMATION: Synthetic Construct

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Ala Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

-continued

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 103
<211> LENGTH: 119
<212> TYPE: PRT
<213> ORGANISM: Artificial Sequence
<220> FEATURE:
<223> OTHER INFORMATION: Synthetic Construct

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Phe Thr Ile Ser Arg Asp Gln Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser
        115


<210> SEQ ID NO 104
<211> LENGTH: 448
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Phe Thr Ile Ser Arg Asp Gln Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
        435                 440                 445


<210> SEQ ID NO 105
<211> LENGTH: 119
<212> TYPE: PRT
<213> ORGANISM: Artificial Sequence
<220> FEATURE:
<223> OTHER INFORMATION: Synthetic Construct

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Phe Thr Ile Ser Arg Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser
        115


<210> SEQ ID NO 106
<211> LENGTH: 448
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Ala Asp Ile Asn Pro Ile Asn Gly Ala Thr Leu Tyr Asn Gln Lys Phe
    50                  55                  60

Lys Gly Arg Phe Thr Ile Ser Arg Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Asp Tyr Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Ala Ala Gly Ala Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 107
<211> LENGTH: 119
<212> TYPE: PRT
<213> ORGANISM: Artificial Sequence
<220> FEATURE:
<223> OTHER INFORMATION: Synthetic Construct

<400> SEQUENCE: 107

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Asp Tyr
20 25 30

Asn Leu Asp Trp Val Arg Gln Ala Pro Gly Lys Gly Leu Glu Trp Val
35 40 45

Gly Asp Ile Asn Pro Ile Asn Gly Ala Thr Leu Tyr Asn Gln Lys Phe
50 55 60

Lys Gly Arg Ala Thr Ile Ser Val Asp Gln Ala Lys Asn Ser Ala Tyr
65 70 75 80

Leu Gln Met Asn Ser Leu Arg Ala Glu Asp Thr Ala Val Tyr Tyr Cys
85 90 95

```
Ser Ile Tyr Tyr Gly Asp Tyr Asp Ala Met Asp Tyr Trp Gly Gln Gly
            100                 105                 110

Thr Leu Val Thr Val Ser Ser
        115


<210> SEQ ID NO 108
<211> LENGTH: 448
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Asn Leu Asp Trp Val Arg Gln Ala Pro Gly Lys Gly Leu Glu Trp Val
        35                  40                  45

Gly Asp Ile Asn Pro Ile Asn Gly Ala Thr Leu Tyr Asn Gln Lys Phe
    50                  55                  60

Lys Gly Arg Ala Thr Ile Ser Val Asp Gln Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ser Ile Tyr Tyr Gly Asp Tyr Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 109
<211> LENGTH: 107
<212> TYPE: PRT
<213> ORGANISM: Artificial Sequence
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val His Thr Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Tyr
85 90 95

Thr Phe Gly Gln Gly Thr Lys Leu Glu Ile Lys
100 105

<210> SEQ ID NO 110
<211> LENGTH: 214
<212> TYPE: PRT
<213> ORGANISM: Artificial Sequence
<220> FEATURE:
<223> OTHER INFORMATION: Synthetic Construct

<400> SEQUENCE: 110

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val His Thr Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Tyr

```
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Thr Thr Pro Tyr
                85                  90                  95

Thr Phe Gly Gln Gly Thr Lys Leu Glu Ile Lys
            100                 105


<210> SEQ ID NO 112
<211> LENGTH: 214
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60
```

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln His Tyr Thr Thr Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 113
<211> LENGTH: 11
<212> TYPE: PRT
<213> ORGANISM: Artificial Sequence
<220> FEATURE:
<223> OTHER INFORMATION: Synthetic Construct

<400> SEQUENCE: 113

Lys Ala Ser Gln Asp Val Ile Thr Ala Val Ala
1 5 10

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 114

Trp Ala Ser Thr Arg His Thr
1 5

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct

<400> SEQUENCE: 115

Gln Gln His Tyr Ser Thr Pro Tyr Thr
1 5

<210> SEQ ID NO 116
<211> LENGTH: 107
<212> TYPE: PRT
<213> ORGANISM: Artificial Sequence
<220> FEATURE:
<223> OTHER INFORMATION: Synthetic Construct

<400> SEQUENCE: 116

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ile Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Val Arg Phe Thr Gly
    50                  55                  60

Ser Gly Ser Gly Thr Asp Tyr Thr Leu Thr Ile Ile Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105


<210> SEQ ID NO 117
<211> LENGTH: 213
<212> TYPE: PRT
<213> ORGANISM: Artificial Sequence
<220> FEATURE:
<223> OTHER INFORMATION: Synthetic Construct

<400> SEQUENCE: 117

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ile Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Val Arg Phe Thr Gly
    50                  55                  60

Ser Gly Ser Gly Thr Asp Tyr Thr Leu Thr Ile Ile Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 118
<211> LENGTH: 10
<212> TYPE: PRT
<213> ORGANISM: Artificial Sequence
<220> FEATURE:
```

<223> OTHER INFORMATION: Synthetic Construct

<400> SEQUENCE: 118

Gly Tyr Thr Phe Thr Asp Tyr Thr Met Asp
1 5 10

<210> SEQ ID NO 119
<211> LENGTH: 17
<212> TYPE: PRT
<213> ORGANISM: Artificial Sequence
<220> FEATURE:
<223> OTHER INFORMATION: Synthetic Construct

<400> SEQUENCE: 119

Asp Ile Asn Pro Ser Asn Gly Gly Ser Ile Tyr Asn Arg Lys Phe Lys
1 5 10 15

Gly

<210> SEQ ID NO 120
<211> LENGTH: 10
<212> TYPE: PRT
<213> ORGANISM: Artificial Sequence
<220> FEATURE:
<223> OTHER INFORMATION: Synthetic Construct

<400> SEQUENCE: 120

Met His Tyr Asn Tyr Asp Gly Phe Pro Tyr
1 5 10

<210> SEQ ID NO 121
<211> LENGTH: 119
<212> TYPE: PRT
<213> ORGANISM: Artificial Sequence
<220> FEATURE:
<223> OTHER INFORMATION: Synthetic Construct

<400> SEQUENCE: 121

Glu Val Leu Leu Gln Gln Ser Gly Pro Glu Leu Val Lys Pro Gly Ser
1 5 10 15

Ser Val Lys Ile Pro Cys Lys Ala Ser Gly Tyr Thr Phe Thr Asp Tyr
20 25 30

Thr Met Asp Trp Val Lys Gln Ser His Gly Lys Ser Leu Glu Trp Ile
35 40 45

Gly Asp Ile Asn Pro Ser Asn Gly Gly Ser Ile Tyr Asn Arg Lys Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Thr Ala Val Tyr Tyr Cys
85 90 95

Ala Arg Met His Tyr Asn Tyr Asp Gly Phe Pro Tyr Trp Gly Gln Gly
100 105 110

Thr Leu Val Thr Val Ser Ala
115

<210> SEQ ID NO 122
<211> LENGTH: 448
<212> TYPE: PRT
<213> ORGANISM: Artificial Sequence
<220> FEATURE:
<223> OTHER INFORMATION: Synthetic Construct

<400> SEQUENCE: 122

-continued

```
Glu Val Leu Leu Gln Gln Ser Gly Pro Glu Leu Val Lys Pro Gly Ser
1               5                   10                  15

Ser Val Lys Ile Pro Cys Lys Ala Ser Gly Tyr Thr Phe Thr Asp Tyr
            20                  25                  30

Thr Met Asp Trp Val Lys Gln Ser His Gly Lys Ser Leu Glu Trp Ile
        35                  40                  45

Gly Asp Ile Asn Pro Ser Asn Gly Gly Ser Ile Tyr Asn Arg Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Met His Tyr Asn Tyr Asp Gly Phe Pro Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

420 425 430

Ala Leu His Asn His Tyr Thr Gln Lys Ser Leu Ser Leu Ser Pro Gly
435 440 445

<210> SEQ ID NO 123
<211> LENGTH: 15
<212> TYPE: PRT
<213> ORGANISM: Artificial Sequence
<220> FEATURE:
<223> OTHER INFORMATION: Synthetic Construct

<400> SEQUENCE: 123

Arg Ala Ser Lys Ser Val Ser Thr Ser Gly Tyr Thr Tyr Met His
1 5 10 15

<210> SEQ ID NO 124
<211> LENGTH: 7
<212> TYPE: PRT
<213> ORGANISM: Artificial Sequence
<220> FEATURE:
<223> OTHER INFORMATION: Synthetic Construct

<400> SEQUENCE: 124

Leu Ala Ser Asn Leu Glu Ser
1 5

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gln His Ile Arg Glu Leu Pro Phe Thr
1 5

<210> SEQ ID NO 126
<211> LENGTH: 111
<212> TYPE: PRT
<213> ORGANISM: Artificial Sequence
<220> FEATURE:
<223> OTHER INFORMATION: Synthetic Construct

<400> SEQUENCE: 126

Asp Ile Val Leu Thr Gln Ser Pro Ala Ser Leu Ala Val Ser Leu Gly
1 5 10 15

Gln Arg Ala Thr Ile Ser Cys Arg Ala Ser Lys Ser Val Ser Thr Ser
20 25 30

Gly Tyr Thr Tyr Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Ala Tyr Tyr Cys Gln His Ile Arg
85 90 95

Glu Leu Pro Phe Thr Phe Gly Ser Gly Thr Lys Leu Glu Ile Lys
100 105 110

<210> SEQ ID NO 127
<211> LENGTH: 217
<212> TYPE: PRT

<213> ORGANISM: Artificial Sequence
<220> FEATURE:
<223> OTHER INFORMATION: Synthetic Construct

<400> SEQUENCE: 127

Asp Ile Val Leu Thr Gln Ser Pro Ala Ser Leu Ala Val Ser Leu Gly
1 5 10 15

Gln Arg Ala Thr Ile Ser Cys Arg Ala Ser Lys Ser Val Ser Thr Ser
20 25 30

Gly Tyr Thr Tyr Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Ala Tyr Tyr Cys Gln His Ile Arg
85 90 95

Glu Leu Pro Phe Thr Phe Gly Ser Gly Thr Lys Leu Glu Ile Lys Ala
100 105 110

Asp Ala Ala Pro Thr Val Ser Ile Phe Pro Pro Ser Ser Glu Gln Leu
115 120 125

Thr Ser Gly Gly Ala Ser Val Val Cys Phe Leu Asn Asn Phe Tyr Pro
130 135 140

Lys Asp Ile Asn Val Lys Trp Lys Ile Asp Gly Ser Glu Arg Gln Asn
145 150 155 160

Gly Val Leu Asn Ser Trp Thr Asp Gln Asp Ser Lys Asp Ser Thr Tyr
165 170 175

Ser Met Ser Ser Thr Leu Thr Leu Thr Lys Asp Glu Tyr Glu Arg His
180 185 190

Asn Ser Tyr Thr Cys Glu Ala Thr His Lys Thr Ser Thr Ser Pro Ile
195 200 205

Val Lys Ser Phe Asn Arg Asn Glu Cys
210 215

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Gly Tyr Thr Phe Thr Ser Tyr Val Met His
1 5 10

<210> SEQ ID NO 129
<211> LENGTH: 17
<212> TYPE: PRT
<213> ORGANISM: Artificial Sequence
<220> FEATURE:
<223> OTHER INFORMATION: Synthetic Construct

<400> SEQUENCE: 129

Tyr Leu Asn Pro Tyr Asn Asp Gly Thr Lys Tyr Asn Glu Lys Phe Lys
1 5 10 15

Gly

<210> SEQ ID NO 130
<211> LENGTH: 8

<212> TYPE: PRT
<213> ORGANISM: Artificial Sequence
<220> FEATURE:
<223> OTHER INFORMATION: Synthetic Construct

<400> SEQUENCE: 130

Thr Leu Leu Tyr Ala Met Asp Tyr
1 5

<210> SEQ ID NO 131
<211> LENGTH: 117
<212> TYPE: PRT
<213> ORGANISM: Artificial Sequence
<220> FEATURE:
<223> OTHER INFORMATION: Synthetic Construct

<400> SEQUENCE: 131

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Ser Tyr
20 25 30

Val Met His Trp Val Lys Gln Lys Pro Gly Gln Gly Leu Glu Trp Ile
35 40 45

Gly Tyr Leu Asn Pro Tyr Asn Asp Gly Thr Lys Tyr Asn Glu Lys Phe
50 55 60

Lys Gly Lys Ala Ser Leu Ile Ser Asp Lys Ser Ser Ser Thr Val Tyr
65 70 75 80

Met Glu Leu Ser Ser Leu Thr Ser Glu Asp Ser Ala Val Tyr Tyr Cys
85 90 95

Ala Thr Thr Leu Leu Tyr Ala Met Asp Tyr Trp Gly Gln Gly Ser Ser
100 105 110

Val Thr Val Ser Ser
115

<210> SEQ ID NO 132
<211> LENGTH: 358
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Ser Tyr
20 25 30

Val Met His Trp Val Lys Gln Lys Pro Gly Gln Gly Leu Glu Trp Ile
35 40 45

Gly Tyr Leu Asn Pro Tyr Asn Asp Gly Thr Lys Tyr Asn Glu Lys Phe
50 55 60

Lys Gly Lys Ala Ser Leu Ile Ser Asp Lys Ser Ser Ser Thr Val Tyr
65 70 75 80

Met Glu Leu Ser Ser Leu Thr Ser Glu Asp Ser Ala Val Tyr Tyr Cys
85 90 95

Ala Thr Thr Leu Leu Tyr Ala Met Asp Tyr Trp Gly Gln Gly Ser Ser
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys

```
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met
        355
```

<210> SEQ ID NO 133
<211> LENGTH: 11
<212> TYPE: PRT
<213> ORGANISM: Artificial Sequence
<220> FEATURE:
<223> OTHER INFORMATION: Synthetic Construct

<400> SEQUENCE: 133

```
Ser Gly Asp Asn Leu Arg Asn Tyr Tyr Ala His
1               5                   10
```

<210> SEQ ID NO 134
<211> LENGTH: 7
<212> TYPE: PRT
<213> ORGANISM: Artificial Sequence
<220> FEATURE:
<223> OTHER INFORMATION: Synthetic Construct

<400> SEQUENCE: 134

```
Tyr Asp Asn Asn Arg Pro Ser
1               5
```

<210> SEQ ID NO 135
<211> LENGTH: 9
<212> TYPE: PRT
<213> ORGANISM: Artificial Sequence
<220> FEATURE:
<223> OTHER INFORMATION: Synthetic Construct

<400> SEQUENCE: 135

```
Gln Ser Trp Asp Asp Gly Val Pro Val
1               5


<210> SEQ ID NO 136
<211> LENGTH: 107
<212> TYPE: PRT
<213> ORGANISM: Artificial Sequence
<220> FEATURE:
<223> OTHER INFORMATION: Synthetic Construct

<400> SEQUENCE: 136

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Tyr
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Asp Gly Val Pro Val
                85                  90                  95

Phe Gly Gly Gly Thr Lys Leu Thr Val Leu Gly
            100                 105


<210> SEQ ID NO 137
<211> LENGTH: 212
<212> TYPE: PRT
<213> ORGANISM: Artificial Sequence
<220> FEATURE:
<223> OTHER INFORMATION: Synthetic Construct

<400> SEQUENCE: 137

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Tyr
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Asp Gly Val Pro Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
```

-continued

```
            180                 185                 190

Cys Gln Val Thr His Glu Gly Ser Thr Val Glu Lys Thr Val Ala Pro
        195                 200                 205

Thr Glu Cys Ser
    210


<210> SEQ ID NO 138
<211> LENGTH: 10
<212> TYPE: PRT
<213> ORGANISM: Artificial Sequence
<220> FEATURE:
<223> OTHER INFORMATION: Synthetic Construct

<400> SEQUENCE: 138

Gly Phe Thr Phe Arg Ser Tyr Gly Met Ser
1               5                   10


<210> SEQ ID NO 139
<211> LENGTH: 17
<212> TYPE: PRT
<213> ORGANISM: Artificial Sequence
<220> FEATURE:
<223> OTHER INFORMATION: Synthetic Construct

<400> SEQUENCE: 139

Ser Ile Arg Gly Ser Ser Ser Ser Thr Tyr Tyr Ala Asp Ser Val Lys
1               5                   10                  15

Gly


<210> SEQ ID NO 140
<211> LENGTH: 8
<212> TYPE: PRT
<213> ORGANISM: Artificial Sequence
<220> FEATURE:
<223> OTHER INFORMATION: Synthetic Construct

<400> SEQUENCE: 140

Lys Tyr Arg Tyr Trp Phe Asp Tyr
1               5


<210> SEQ ID NO 141
<211> LENGTH: 117
<212> TYPE: PRT
<213> ORGANISM: Artificial Sequence
<220> FEATURE:
<223> OTHER INFORMATION: Synthetic Construct

<400> SEQUENCE: 141

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ser Ser Ile Arg Gly Ser Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Arg Tyr Trp Phe Asp Tyr Trp Gly Gln Gly Thr Leu
            100                 105                 110
```

```
Val Thr Val Ser Ser
        115


<210> SEQ ID NO 142
<211> LENGTH: 446
<212> TYPE: PRT
<213> ORGANISM: Artificial Sequence
<220> FEATURE:
<223> OTHER INFORMATION: Synthetic Construct

<400> SEQUENCE: 142

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ser Ser Ile Arg Gly Ser Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Arg Tyr Trp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 143
<211> LENGTH: 11
<212> TYPE: PRT
<213> ORGANISM: Artificial Sequence
<220> FEATURE:
<223> OTHER INFORMATION: Synthetic Construct

<400> SEQUENCE: 143

Ser Gly Asp Asn Leu Arg Asn Tyr Tyr Ala His
1 5 10

<210> SEQ ID NO 144
<211> LENGTH: 7
<212> TYPE: PRT
<213> ORGANISM: Artificial Sequence
<220> FEATURE:
<223> OTHER INFORMATION: Synthetic Construct

<400> SEQUENCE: 144

Tyr Asp Val Asn Arg Pro Ser
1 5

<210> SEQ ID NO 145
<211> LENGTH: 9
<212> TYPE: PRT
<213> ORGANISM: Artificial Sequence
<220> FEATURE:
<223> OTHER INFORMATION: Synthetic Construct

<400> SEQUENCE: 145

Gln Ser Trp Trp Asp Gly Val Pro Val
1 5

<210> SEQ ID NO 146
<211> LENGTH: 107
<212> TYPE: PRT
<213> ORGANISM: Artificial Sequence
<220> FEATURE:
<223> OTHER INFORMATION: Synthetic Construct

<400> SEQUENCE: 146

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Phe
35 40 45

Tyr Asp Val Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Trp Asp Gly Val Pro Val
85 90 95

Phe Gly Gly Gly Thr Lys Leu Thr Val Leu Gly
100 105

<210> SEQ ID NO 147
<211> LENGTH: 212
<212> TYPE: PRT
<213> ORGANISM: Artificial Sequence
<220> FEATURE:
<223> OTHER INFORMATION: Synthetic Construct

<400> SEQUENCE: 147

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Phe
35 40 45

Tyr Asp Val Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Trp Asp Gly Val Pro Val
85 90 95

Phe Gly Gly Gly Thr Lys Leu Thr Val Leu Gly Gln Pro Lys Ala Ala
100 105 110

Pro Ser Val Thr Leu Phe Pro Pro Ser Ser Glu Glu Leu Gln Ala Asn
115 120 125

Lys Ala Thr Leu Val Cys Leu Ile Ser Asp Phe Tyr Pro Gly Ala Val
130 135 140

Thr Val Ala Trp Lys Ala Asp Ser Ser Pro Val Lys Ala Gly Val Glu
145 150 155 160

Thr Thr Thr Pro Ser Lys Gln Ser Asn Asn Lys Tyr Ala Ala Ser Ser
165 170 175

Tyr Leu Ser Leu Thr Pro Glu Gln Trp Lys Ser His Arg Ser Tyr Ser
180 185 190

Cys Gln Val Thr His Glu Gly Ser Thr Val Glu Lys Thr Val Ala Pro
195 200 205

Thr Glu Cys Ser
210

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Gly Phe Thr Phe Arg Ser Tyr Gly Met Asp
1 5 10

<210> SEQ ID NO 149
<211> LENGTH: 17
<212> TYPE: PRT

<213> ORGANISM: Artificial Sequence
<220> FEATURE:
<223> OTHER INFORMATION: Synthetic Construct

<400> SEQUENCE: 149

Ser Ile Arg Gly Ser Arg Ser Ser Thr Tyr Tyr Ala Asp Ser Val Lys
1 5 10 15

Gly

<210> SEQ ID NO 150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 150

Leu Tyr Arg Tyr Trp Phe Asp Tyr
1 5

<210> SEQ ID NO 151
<211> LENGTH: 117
<212> TYPE: PRT
<213> ORGANISM: Artificial Sequence
<220> FEATURE:
<223> OTHER INFORMATION: Synthetic Construct

<400> SEQUENCE: 151

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser Tyr
20 25 30

Gly Met Asp Trp Val Arg Gln Ala Pro Gly Lys Gly Leu Glu Trp Val
35 40 45

Ser Ser Ile Arg Gly Ser Arg Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Tyr Arg Tyr Trp Phe Asp Tyr Trp Gly Gln Gly Thr Leu
100 105 110

Val Thr Val Ser Ser
115

<210> SEQ ID NO 152
<211> LENGTH: 446
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser Tyr
20 25 30

Gly Met Asp Trp Val Arg Gln Ala Pro Gly Lys Gly Leu Glu Trp Val
35 40 45

Ser Ser Ile Arg Gly Ser Arg Ser Ser Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 153
<211> LENGTH: 11
<212> TYPE: PRT
<213> ORGANISM: Artificial Sequence
<220> FEATURE:

<223> OTHER INFORMATION: Synthetic Construct

<400> SEQUENCE: 153

Ser Gly Asp Asn Leu Arg Asn Tyr Tyr Ala His
1 5 10

<210> SEQ ID NO 154
<211> LENGTH: 7
<212> TYPE: PRT
<213> ORGANISM: Artificial Sequence
<220> FEATURE:
<223> OTHER INFORMATION: Synthetic Construct

<400> SEQUENCE: 154

Tyr Asp Asn Asn Arg Pro Ser
1 5

<210> SEQ ID NO 155
<211> LENGTH: 9
<212> TYPE: PRT
<213> ORGANISM: Artificial Sequence
<220> FEATURE:
<223> OTHER INFORMATION: Synthetic Construct

<400> SEQUENCE: 155

Gln Ser Trp Asp Asp Gly Val Pro Val
1 5

<210> SEQ ID NO 156
<211> LENGTH: 107
<212> TYPE: PRT
<213> ORGANISM: Artificial Sequence
<220> FEATURE:
<223> OTHER INFORMATION: Synthetic Construct

<400> SEQUENCE: 156

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Tyr
35 40 45

Tyr Asp Asn Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Asp Asp Gly Val Pro Val
85 90 95

Phe Gly Gly Gly Thr Lys Leu Thr Val Leu Gly
100 105

<210> SEQ ID NO 157
<211> LENGTH: 105
<212> TYPE: PRT
<213> ORGANISM: Artificial Sequence
<220> FEATURE:
<223> OTHER INFORMATION: Synthetic Construct

<400> SEQUENCE: 157

Gln Pro Lys Ala Ala Pro Ser Val Thr Leu Phe Pro Pro Ser Ser Glu
1 5 10 15

Glu Leu Gln Ala Asn Lys Ala Thr Leu Val Cys Leu Ile Ser Asp Phe
20 25 30

```
Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 158
<211> LENGTH: 212
<212> TYPE: PRT
<213> ORGANISM: Artificial Sequence
<220> FEATURE:
<223> OTHER INFORMATION: Synthetic Construct

<400> SEQUENCE: 158

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Tyr
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Asp Gly Val Pro Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210


<210> SEQ ID NO 159
<211> LENGTH: 10
<212> TYPE: PRT
<213> ORGANISM: Artificial Sequence
<220> FEATURE:
<223> OTHER INFORMATION: Synthetic Construct

<400> SEQUENCE: 159

Gly Phe Thr Phe Ser Asn Tyr Ala Leu Ser
```

1 5 10

<210> SEQ ID NO 160
<211> LENGTH: 16
<212> TYPE: PRT
<213> ORGANISM: Artificial Sequence
<220> FEATURE:
<223> OTHER INFORMATION: Synthetic Construct

<400> SEQUENCE: 160

Ser Ile Ser Ser Gly Gly Ala Thr Tyr Tyr Pro Asp Ser Val Glu Gly
1 5 10 15

<210> SEQ ID NO 161
<211> LENGTH: 10
<212> TYPE: PRT
<213> ORGANISM: Artificial Sequence
<220> FEATURE:
<223> OTHER INFORMATION: Synthetic Construct

<400> SEQUENCE: 161

Gly Ala Tyr Gly Ser Asp Tyr Phe Asp Tyr
1 5 10

<210> SEQ ID NO 162
<211> LENGTH: 118
<212> TYPE: PRT
<213> ORGANISM: Artificial Sequence
<220> FEATURE:
<223> OTHER INFORMATION: Synthetic Construct

<400> SEQUENCE: 162

Glu Val Lys Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Tyr
20 25 30

Ala Leu Ser Trp Val Arg Gln Thr Pro Asp Lys Arg Leu Glu Trp Val
35 40 45

Ala Ser Ile Ser Ser Gly Gly Ala Thr Tyr Tyr Pro Asp Ser Val Glu
50 55 60

Gly Arg Phe Thr Ile Ser Arg Asp Asn Val Arg Asn Ile Leu Tyr Leu
65 70 75 80

Gln Met Ser Ser Leu Gln Ser Glu Asp Thr Ala Met Tyr Tyr Cys Thr
85 90 95

Arg Gly Ala Tyr Gly Ser Asp Tyr Phe Asp Tyr Trp Gly Gln Gly Thr
100 105 110

Thr Leu Thr Val Ser Ser
115

<210> SEQ ID NO 163
<211> LENGTH: 441
<212> TYPE: PRT
<213> ORGANISM: Artificial Sequence
<220> FEATURE:
<223> OTHER INFORMATION: Synthetic Construct

<400> SEQUENCE: 163

Glu Val Lys Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Tyr
20 25 30

Ala Leu Ser Trp Val Arg Gln Thr Pro Asp Lys Arg Leu Glu Trp Val

```
        35                  40                  45

Ala Ser Ile Ser Ser Gly Gly Ala Thr Tyr Tyr Pro Asp Ser Val Glu
    50                  55                  60

Gly Arg Phe Thr Ile Ser Arg Asp Asn Val Arg Asn Ile Leu Tyr Leu
65                  70                  75                  80

Gln Met Ser Ser Leu Gln Ser Glu Asp Thr Ala Met Tyr Tyr Cys Thr
                85                  90                  95

Arg Gly Ala Tyr Gly Ser Asp Tyr Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440
```

<210> SEQ ID NO 164

<211> LENGTH: 16
<212> TYPE: PRT
<213> ORGANISM: Artificial Sequence
<220> FEATURE:
<223> OTHER INFORMATION: Synthetic Construct

<400> SEQUENCE: 164

Lys Ser Ser Gln Ser Leu Leu Glu Ser Asp Gly Lys Thr Tyr Leu Asn
1 5 10 15

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 165

Leu Val Ser Ile Leu Asp Ser
1 5

<210> SEQ ID NO 166
<211> LENGTH: 9
<212> TYPE: PRT
<213> ORGANISM: Artificial Sequence
<220> FEATURE:
<223> OTHER INFORMATION: Synthetic Construct

<400> SEQUENCE: 166

Leu Gln Ala Thr His Phe Pro Gln Thr
1 5

<210> SEQ ID NO 167
<211> LENGTH: 112
<212> TYPE: PRT
<213> ORGANISM: Artificial Sequence
<220> FEATURE:
<223> OTHER INFORMATION: Synthetic Construct

<400> SEQUENCE: 167

Asp Ile Val Met Thr Gln Thr Pro Leu Ser Leu Ser Val Thr Pro Gly
1 5 10 15

Gln Pro Ala Ser Ile Ser Cys Lys Ser Ser Gln Ser Leu Leu Glu Ser
20 25 30

Asp Gly Lys Thr Tyr Leu Asn Trp Tyr Leu Gln Lys Pro Gly Gln Ser
35 40 45

Pro Gln Leu Leu Ile Tyr Leu Val Ser Ile Leu Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln Ala
85 90 95

Thr His Phe Pro Gln Thr Phe Gly Gly Gly Thr Lys Val Glu Ile Lys
100 105 110

<210> SEQ ID NO 168
<211> LENGTH: 219
<212> TYPE: PRT
<213> ORGANISM: Artificial Sequence
<220> FEATURE:
<223> OTHER INFORMATION: Synthetic Construct

<400> SEQUENCE: 168

Asp Ile Val Met Thr Gln Thr Pro Leu Ser Leu Ser Val Thr Pro Gly

```
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 169
<211> LENGTH: 10
<212> TYPE: PRT
<213> ORGANISM: Artificial Sequence
<220> FEATURE:
<223> OTHER INFORMATION: Synthetic Construct

<400> SEQUENCE: 169

Gly Phe Thr Phe Ser Asn Tyr Ala Met Ser
1               5                   10


<210> SEQ ID NO 170
<211> LENGTH: 17
<212> TYPE: PRT
<213> ORGANISM: Artificial Sequence
<220> FEATURE:
<223> OTHER INFORMATION: Synthetic Construct

<400> SEQUENCE: 170

Thr Ile Ser Arg Ser Gly Ser Tyr Ser Tyr Phe Pro Asp Ser Val Gln
1               5                   10                  15

Gly


<210> SEQ ID NO 171
<211> LENGTH: 12
<212> TYPE: PRT
<213> ORGANISM: Artificial Sequence
<220> FEATURE:
<223> OTHER INFORMATION: Synthetic Construct

<400> SEQUENCE: 171
```

```
Leu Gly Gly Tyr Asp Glu Gly Asp Ala Met Asp Ser
1               5                   10


<210> SEQ ID NO 172
<211> LENGTH: 121
<212> TYPE: PRT
<213> ORGANISM: Artificial Sequence
<220> FEATURE:
<223> OTHER INFORMATION: Synthetic Construct

<400> SEQUENCE: 172

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser
        115                 120


<210> SEQ ID NO 173
<211> LENGTH: 327
<212> TYPE: PRT
<213> ORGANISM: Artificial Sequence
<220> FEATURE:
<223> OTHER INFORMATION: Synthetic Construct

<400> SEQUENCE: 173

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 174
<211> LENGTH: 448
<212> TYPE: PRT
<213> ORGANISM: Artificial Sequence
<220> FEATURE:
<223> OTHER INFORMATION: Synthetic Construct

<400> SEQUENCE: 174

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205
```

```
Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 175
<211> LENGTH: 360
<212> TYPE: DNA
<213> ORGANISM: Artificial Sequence
<220> FEATURE:
<223> OTHER INFORMATION: Synthetic Construct

<400> SEQUENCE: 175

```
gaggtgcagc tgctggagtc tggcggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gattctggga    300

gctacttcgt tatcggcttt tgatatctgg ggccaaggga caatggtcac cgtctcgagc    360
```

<210> SEQ ID NO 176
<211> LENGTH: 336
<212> TYPE: DNA
<213> ORGANISM: Artificial Sequence
<220> FEATURE:
<223> OTHER INFORMATION: Synthetic Construct

<400> SEQUENCE: 176

```
cagtctgtgc tgacgcagcc gccctcagtg tctggggccc cagggcagag ggtcaccatc     60
```

tcctgcactg ggagcagctc caacatcggg gcaggttatg atgtacactg gtaccagcag 120
cttccaggaa cagcccccaa actcctcatc tatggtaaca gcaatcggcc ctcaggggtc 180
cctgaccgat tctctggctc caagtctggc acctcagcct ccctggccat cactgggctc 240
caggctgagg atgaggctga ttattactgc cagtcctatg acagcagcct gagtggttca 300
ggggtattcg gcggagggac caagctgacc gtccta 336

<210> SEQ ID NO 177
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 177
gaggtgcagc tgctggagtc tggcggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gattctggga 300
gctacttcgt tatcggcttt tgatatctgg ggccaaggga caatggtcac cgtctcgagc 360
gcgtcgacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaagc cgctggggca 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc cccgggt 1347

<210> SEQ ID NO 178
<211> LENGTH: 654
<212> TYPE: DNA
<213> ORGANISM: Artificial Sequence
<220> FEATURE:
<223> OTHER INFORMATION: Synthetic Construct

<400> SEQUENCE: 178
cagtctgtgc tgacgcagcc gccctcagtg tctggggccc cagggcagag ggtcaccatc 60

-continued

```
tcctgcactg ggagcagctc caacatcggg gcaggttatg atgtacactg gtaccagcag    120
cttccaggaa cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtggttca    300
ggggtattcg gcggagggac caagctgacc gtcctaggtc agcccaaggc tgccccctcg    360
gtcactctgt tcccgccctc ctctgaggag cttcaagcca acaaggccac actggtgtgt    420
ctcataagtg acttctaccc gggagccgtg acagtggcct ggaaggcaga tagcagcccc    480
gtcaaggcgg gagtggagac caccacaccc tccaaacaaa gcaacaacaa gtacgcggcc    540
agcagctatc tgagcctgac gcctgagcag tggaagtccc acagaagcta cagctgccag    600
gtcacgcatg aagggagcac cgtggagaag acagtggccc ctacagaatg ttca          654
```

TISSUE FACTOR PATHWAY INHIBITOR ANTIBODIES AND USES THEREOF

CROSS-REFERENCE TO RELATED APPLICATIONS

This application is a division of U.S. application Ser. No. 15/239,556, filed Aug. 17, 2016, which claims the benefit to U.S. Provisional Patent Application No. 62/207,229, filed on Aug. 19, 2015, and U.S. Provisional Patent Application No. 62/360,205, filed Jul. 8, 2016, which are hereby incorporated by reference herein in their entirety.

REFERENCE TO SEQUENCE LISTING

This application is being filed electronically via EFS-Web and includes an electronically submitted sequence listing in .txt format. The .txt file contains a sequence listing entitled "PC72096A_Sequence_Listing_ST25.txt" created on Aug. 10, 2016, and having a size of 224,226 bytes. The sequence listing contained in this .txt file is part of the specification and is hereby incorporated by reference herein in its entirety.

BACKGROUND OF THE INVENTION

Hemophilia A and B are X-linked genetic disorders resulting from functional deficiencies of the plasma proteins Factor VIII (FVIII) or Factor IX (FIX), respectively. Clinical severity of hemophilia is related to the residual level of clotting factor activity. Factor activity of <1% is associated with a severe phenotype, moderate hemophilia is associated with a factor activity of 2%-5% and mild with a factor activity 5%-40%.

The standard of care for these disorders is replacement of the missing coagulation factor through intravenous infusions. The replacement factor is commonly a recombinant protein, such as Xyntha (Factor VIII) or BeneFIX (FIX), but plasma derived products of various purity are still in use. Treatment with replacement factor can either be episodic, treating bleeds on demand as they occur, or prophylactic, preventing bleeds by maintaining factor levels in a protective range. Significant evidence exists that prophylactic treatment prevents bleeds and the associated joint damage that is the major morbidity in hemophilic patients. Effective prophylactic treatment requires intravenous injection of factor 3-4 times each week, which results in difficulties in compliance and reduced quality of life. The cost of treatment is also expensive due to the complexity of manufacture of coagulation factors. Furthermore, a significant number of patients, up to 32% of patients with severe Hemophilia A, develop neutralizing antibodies to the administered factors, which are seen as foreign proteins by patients who have mutations in these genes. These patients require alternative means of treatment such as the bypass factor, Factor VIIa (NovoSeven).

An alternative approach to therapy is to bypass the need for replacement factors by augmenting the intact extrinsic pathway. Patients with hemophilia have some ability to stop bleeds through their intact extrinsic pathway; however this is not sufficient to shut down major bleeds or to prevent spontaneous bleeds. The extrinsic pathway is insufficient to provide protection because it is rapidly shut down by Tissue Factor Pathway Inhibitor (TFPI).

Although WO 2010/017196 (Bayer), WO 2011/109452 (Bayer), WO 2014/144577 (Bayer), WO 2010/072687 (Novo Nordisk), WO 2012/001087 (Novo Nordisk), WO 2014/140240 (Novo Nordisk), and WO 2015/007880 (Novo Nordisk) disclose antibodies that bind to human TFPI, they do not provide the antibodies of the invention which have characteristics that make them novel potential therapeutics for hemophilia.

A product that would provide prophylactic protection while reducing the frequency of dosing of coagulation factors, reducing the quantity of use of factors, allowing alternative routes of delivery (e.g., subcutaneous) and having a lower risk of generating neutralizing antibodies, would fulfill a significant unmet need for patients with hemophilia.

BRIEF SUMMARY OF THE INVENTION

Disclosed and exemplified herein are antibodies (and antigen-binding fragments thereof) that bind to the Tissue Factor Pathway Inhibitor (TFPI).

Those skilled in the art will recognize, or be able to ascertain using no more than routine experimentation, many equivalents to the specific embodiments of the invention described herein. Such equivalents are intended to be encompassed by the following embodiments (E).

E1. An isolated antibody or antigen-binding fragment thereof, that specifically binds to an epitope in Kunitz Domain 2 (K2) of Tissue Factor Pathway Inhibitor (TFPI), wherein said epitope comprises residues Ile105, Arg107, and Leu131, according to the numbering of SEQ ID NO: 2.

E2. The antibody or antigen-binding fragment thereof of embodiment 1, wherein said antibody, or antigen-binding fragment thereof, does not bind to Kunitz Domain 1 (K1) of TFPI.

E3. The antibody or antigen-binding fragment thereof of embodiment 1 or 2, wherein said epitope further comprises one or more residues selected from the group consisting of: Cys106, Gly108, Cys130, Leu131, and Gly132, according to the numbering of SEQ ID NO: 2.

E4. The antibody or antigen-binding fragment thereof of any one of embodiments 1-3, wherein said epitope further comprises residues Cys106, Gly108, Cys130, Leu131, and Gly132, according to the numbering of SEQ ID NO: 2.

E5. The antibody or antigen-binding fragment thereof of any one of embodiments 1-4, wherein said epitope further comprises one or more residues selected from the group consisting of: Asp102, Arg112, Tyr127, Gly129, Met134, and Glu138, according to the numbering of SEQ ID NO: 2.

E6. The antibody or antigen-binding fragment thereof of any one of embodiments 1-5, wherein said epitope further comprises Asp102, Arg112, Tyr127, Gly129, Met134, and Glu138, according to the numbering of SEQ ID NO: 2.

E7. The antibody or antigen-binding fragment thereof of any one of embodiments 1-6, wherein said epitope does not comprise one or more residues selected from the group consisting of: E100, E101, P103, Y109, T111, Y113, F114, N116, Q118, Q121, C122, E123, R124, F125, K126, and L140, according to the numbering of SEQ ID NO: 2.

E8. The antibody or antigen-binding fragment thereof of any one of embodiments 1-7, wherein said epitope does not comprise: E100, E101, P103, Y109, T111, Y113, F114, N116, Q118, Q121, C122, E123, R124, F125, K126, and L140, according to the numbering of SEQ ID NO: 2.

E9. The antibody or antigen-binding fragment thereof of any one of embodiments 1-6, wherein said epitope does not comprise one or more residues selected from the group consisting of: D31, D32, P34, C35, K36, E100, E101, P103, Y109, K126, and G128, according to the numbering of SEQ ID NO: 2.

E10. The antibody or antigen-binding fragment thereof of any one of embodiments 1-6 and 9, wherein said epitope does not comprise: D31, D32, P34, C35, K36, E100, E101, P103, Y109, K126, and G128, according to the numbering of SEQ ID NO: 2.

E11. The antibody or antigen-binding fragment thereof of any one of embodiments 1-10, wherein said epitope comprises one or more residues selected from the group consisting of: Asp102, Gly104, Ile105, Cys106, Arg107, Gly108, Arg112, Tyr127, Gly129, Cys130, Leu131, Gly132, Asn133, Met134, and Glu138 (according to the numbering of SEQ ID NO: 2), wherein said epitope residue has a non-zero change in buried surface area (BSA) due to interaction with said antibody or antigen-binding fragment thereof.

E12. The antibody or antigen-binding fragment thereof of embodiment 11, wherein said epitope comprises: Asp102, Gly104, Ile105, Cys106, Arg107, Gly108, Arg112, Tyr127, Gly129, Cys130, Leu131, Gly132, Asn133, Met134, and Glu138 (according to the numbering of SEQ ID NO: 2).

E13. The antibody or antigen-binding fragment thereof of any one of embodiments 1-12, wherein said epitope comprises one or more residues selected from the group consisting of: Asp102, Arg107, Arg 112, Tyr127, and Leu131 (according to the numbering of SEQ ID NO: 2), wherein said epitope residue participates in a hydrogen bond with a residue from said antibody or antigen-binding fragment thereof.

E14. The antibody or antigen-binding fragment thereof of embodiment 13, wherein said epitope comprises: Asp102, Arg107, Arg 112, Tyr127, and Leu131 (according to the numbering of SEQ ID NO: 2).

E15. The antibody or antigen-binding fragment thereof of any one of embodiments 1-14, wherein said epitope comprises one or more contact residues selected from the group consisting of: Asp102, Gly104, Ile105, Cys106, Arg107, Gly108, Arg112, Tyr127, Gly129, Cys130, Leu131, Gly132, Met134, and Glu138 (according to the numbering of SEQ ID NO: 2).

E16. The antibody or antigen-binding fragment thereof of embodiment 15, wherein said epitope comprises: Asp102, Gly104, Ile105, Cys106, Arg107, Gly108, Arg112, Tyr127, Gly129, Cys130, Leu131, Gly132, Met134, and Glu138 (according to the numbering of SEQ ID NO: 2).

E17. The antibody or antigen-binding fragment thereof of any one of embodiments 1-16, comprising the following heavy (H) chain and light (L) chain paratope residues that have a non-zero change in BSA due to interaction with TFPI (numbering according to Kabat): H33 Ala, H58 Tyr, H95 Leu, H96 Gly, H97 Ala, H98 Thr, H99 Ser, H100 Leu, H100A Ser, L29 Ala, L31 Tyr, L91 Tyr, L95A Ser, and L95B Gly.

E18. The antibody or antigen-binding fragment thereof of any one of embodiments 1-17, comprising the following contact residues (numbering according to Kabat): (a) H47 is Trp or Tyr; (b) H58 is Tyr; and (c) L91 is Tyr or Arg; and optionally comprising: (d) L96 is Gly or Asn.

E19. The antibody or antigen-binding fragment thereof of any one of embodiments 1-18, comprising the following contact residues (numbering according to Kabat): (a) H33 is Ala, Asn, Gly, His, Lys, Met, Phe, Pro, Ser, Thr, Trp, or Val; (b) H47 is Trp or Tyr; (c) H50 is Ala, Arg, Gly, Lys, Met, Phe, Pro, Ser, Thr, Tyr, or Val; (d) H51 is Ile, Ala, Arg, Asn Asp, Gln, Glu, Gly, His, Leu, Lys, Met, Phe Pro, Ser, Thr, Trp, Tyr, or Val; (e) H52 is Ser, Ala, Arg, Asn, Asp, Gln, Glu, Gly His, Ile, Leu, Lys, Met, Phe, Pro, Ser, Trp, Tyr, or Val; (f) H56 is Ser, Arg, Gly, His, Ile, Leu, Lys, Met, Phe, Pro, Ser, Thr, Trp, Tyr, or Val; (g) H58 is Tyr; (h) H95 is Leu, Gln, Ile, Phe, or Tyr; (i) H96 is Gly, Ala, Arg, Asn Asp, Gln, Ile, Lys, Met, Phe, Pro, Ser, Thr, or Val; (j) H97 is Ala, Arg, Asn Asp, Gln, Glu, Gly, His, Leu, Lys, Met, Phe Pro, Ser, Thr, Trp, Tyr, or Val; (k) H98 is Thr, Ala, Arg, Asn Asp, Gln, Glu, Gly, His, Leu, Met, Phe Pro, Ser, Thr, Trp, Tyr, or Val; (l) H99 is Ser, Ala, Gly, Phe, or Pro; (m) H100 is Leu, Arg, His, Ile, Leu, Lys, Phe, Pro, Trp, Tyr, or Val; (n) H100A is Ser, Ala, Arg, Asn Asp, Gln, Glu, His, Leu, Lys, Met, Phe Pro, Ser, Thr, or Trp; (o) L29 is Ala, Arg, Asn Asp, Gln, Glu, Gly, His, Leu, Lys, Met, Phe Pro, Ser, Thr, or Trp, Tyr, Val; (p) L31 is Ala, Arg, Asn Asp, Gln, Glu, Gly, His, Leu, Lys, Met, Phe Pro, Ser, Thr, Trp, Tyr, or Val; (q) L91 is Tyr or Arg; (r) L95A is Ser, Ala, Arg, Asn Asp, Gln, Glu, Gly, His, Leu, Lys, Met, Phe Pro, Ser, Thr, Trp, Tyr, or Val; (s) L95B is Ser, Ala, Arg, Asn Asp, Gln, Glu, Gly, His, Leu, Lys, Met, Phe Pro, Ser, Thr, Trp, Tyr, or Val; and (t) L95C is Ser, Ala, Arg, Asn Asp, Gln, Glu, Gly, His, Leu, Lys, Met, Phe Pro, Ser, Thr, Trp, Tyr, or Val; and optionally comprising the following residues: (u) L93 is Tyr, Ala, Arg, Asn Asp, Gln, Glu, Gly, His, Leu, Lys, Met, Phe Pro, Ser, Thr, Trp, Tyr, or Val; and (v) L96 is Gly or Asn.

E20. The antibody or antigen-binding fragment thereof of any one of embodiments 1-18, comprising the following contact residues (numbering according to Kabat): (a) H33 is Ala or Val; (b) H47 is Trp; (c) H50 is Ala; (d) H51 is Ile; (e) H52 is Ser, Arg, Lys, Phe, or Tyr; (f) H56 is Ser, Arg, or Lys; (g) H58 is Tyr; (h) H95 is Leu; (i) H96 is Gly, Ala, Arg, Asn, Lys, Pro, Ser, or Val; (j) H97 is Ala; (k) H98 is Thr, His, Ile, Leu, Met, Phe, or Tyr; (l) H99 is Ser; (m) H100 is Leu, Phe, Trp, or Tyr; (n) H100A is Ser, Arg, Asn, Gln, Glu His, Leu, Lys, Met, Phe, Pro, or Trp; (o) L29 is Ala; (p) L31 is Tyr; (q) L91 is Tyr; (r) L95A is Ser, Phe, Trp, or Tyr; (s) L95B is Gly; and (t) L95C is Ser, Arg, Asn, Gln, Glu, Ile, Leu, Lys, Met, Phe, Trp, Tyr, or Val; and optionally comprising the following residues: (u) L93 is Ser; and (v) L96 is Gly.

E21. The antibody or antigen-binding fragment thereof of any one of embodiments 1-18, comprising the following contact residues (numbering according to Kabat): (a) H33 is Ala, Val, His, or Phe; (b) H47 is Trp or Tyr; (c) H50 is Ala, Thr, Ser, or Phe; (d) H51 is Ile, Arg, Lys, or Pro; (e) H52 is Ser, Phe, Arg, or Tyr; (f) H56 is Ser, Lys, Tyr, or Phe; (g) H58 is Tyr; (h) H95 is Leu, Ile, Gln, or Phe; (i) H96 is Gly, Arg, Asn, or Lys; (j) H97 is Ala, Leu, Tyr, or Ile; (k) H98 is Thr, Tyr, Phe, or His; (l) H99 is Ser, Pro, Ala, or Phe; (m) H100 is Leu, Tyr, Trp, or Phe; (n) H100A is Ser, Arg, Leu, or Trp; (o) L29 is Ala, Glu, Asp, or Gln; (p) L31 is Tyr, Glu, Asp, or Trp; (q) L91 is Ty or Arg; (r) L95A is Ser, Phe, Tyr, or His; (s) L95B is Gly, Glu, Asp, or Pro; and (t) L95C is Ser, Trp, Tyr, or Phe; and optionally comprising the following residues: (u) L93 is Ser, Glu, Asp, or His; and (v) L96 is Gly or Asn.

E22. The antibody or antigen-binding fragment thereof of any one of embodiments 1-18, comprising the following contact residues (numbering according to Kabat): H33 Ala, H47 Trp, H50 Ala, H51 Ile, H52 Ser, H56 Ser, H58 Tyr, H95 Leu, H96 Gly, H97 Ala, H98 Thr, H99 Ser, H100 Leu, H100A Ser, L29 Ala, L31 Tyr, L91 Tyr, L95A Ser, L95B Gly, and L95C Ser; and optionally comprising the following residues: L93 Ser and L96 Gly.

E23. The antibody or antigen-binding fragment thereof of any one of embodiments 1-22, comprising a heavy chain variable region (VH) that comprises:

(a) a VH complementarity determining region one (CDR-H1) comprising the amino acid sequence of SEQ ID NO: 38.

(b) a VH complementarity determining region two (CDR-H2) comprising the amino acid sequence of SEQ ID NO: 39; and (c) a VH complementarity determining region three (CDR-H3) comprising the amino acid sequence of SEQ ID NO: 40.

E24. The antibody or antigen-binding fragment thereof of any one of embodiments 1-22, comprising the CDR-H1, CDR-H2, and CDR-H3 sequences of SEQ ID NO: 41.

E25. The antibody or antigen-binding fragment thereof of any one of embodiments 1-24, comprising a human VH3 framework sequence.

E26. The antibody or antigen-binding fragment thereof of any one of embodiments 1-24, comprising a human VH1 framework sequence.

E27. The antibody or antigen-binding fragment thereof of any one of embodiments 1-24, comprising a human VH5 framework sequence.

E28. The antibody or antigen-binding fragment thereof of any one of embodiments 1-24, comprising the VH framework sequence of human germline IGHV3-23 or IGHV1-69.

E29. The antibody or antigen-binding fragment thereof of any one of embodiments 1-24, comprising the VH framework sequence of human germline IGHV3-7.

E30. The antibody or antigen-binding fragment thereof of any one of embodiments 1-24, comprising a human VH germline consensus framework sequence.

E31. The antibody or antigen-binding fragment thereof of any one of embodiments 1-30, comprising a VH that comprises an amino acid sequence at least 90% identical to an amino acid sequence selected from the group consisting of SEQ ID NOs: 41, 63, and 65.

E32. The antibody or antigen-binding fragment thereof of any one of embodiments 1-31, comprising a VH that comprises an amino acid sequence selected from the group consisting of SEQ ID NOs: 41, 63, and 65.

E33. The antibody or antigen-binding fragment thereof of any one of embodiments 1-32, comprising a VH that comprises the amino acid sequence of SEQ ID NO: 41.

E34. The antibody or antigen-binding fragment thereof of any one of embodiments 1-32, comprising a VH that comprises the amino acid sequence of SEQ ID NO: 63.

E35. The antibody or antigen-binding fragment thereof of any one of embodiments 1-32, comprising a VH that comprises the amino acid sequence of SEQ ID NO: 65.

E36. The antibody or antigen-binding fragment thereof of any one of embodiments 1-35, comprising a light chain variable region (VL) that comprises:

(a) a VL complementarity determining region one (CDR-L1) comprising the amino acid sequence of SEQ ID NO: 33.

(b) a VL complementarity determining region two (CDR-L2) comprising the amino acid sequence of SEQ ID NO: 34; and (c) a VL complementarity determining region three (CDR-L3) comprising the amino acid sequence of SEQ ID NO: 35.

E37. The antibody or antigen-binding fragment thereof of any one of embodiments 1-35, comprising the CDR-L1, CDR-L2, and CDR-L3 sequences of SEQ ID NO: 36.

E38. The antibody or antigen-binding fragment thereof of any one of embodiments 1-37, comprising a human $V_K$ framework sequence.

E39. The antibody or antigen-binding fragment thereof of any one of embodiments 1-37, comprising a human $V_\lambda$ framework sequence.

E40. The antibody or antigen-binding fragment thereof of any one of embodiments 1-37, comprising the VL framework sequence of human germline IGKV3-20.

E41. The antibody or antigen-binding fragment thereof of any one of embodiments 1-37, comprising the VL framework sequence of human germline IGKV1-39.

E42. The antibody or antigen-binding fragment thereof of any one of embodiments 1-37, comprising a human VL germline consensus framework sequence.

E43. The antibody or antigen-binding fragment thereof of any one of embodiments 1-42, comprising a VL that comprises an amino acid sequence at least 90% identical to SEQ ID NO:36.

E44. The antibody or antigen-binding fragment thereof of any one of embodiments 1-43, comprising a VL that comprises the amino acid sequence of SEQ ID NO:36.

E45. The antibody or antigen-binding fragment thereof of any one of embodiments 1-44, comprising a heavy chain constant region (CH) that comprises an amino acid sequence at least 90% identical to SEQ ID NO: 20.

E46. The antibody or antigen-binding fragment thereof of any one of embodiments 1-45, comprising a CH that comprises the amino acid sequence of SEQ ID NO: 20.

E47. The antibody or antigen-binding fragment thereof of any one of embodiments 1-46, comprising a light chain constant region (CL) that comprises an amino acid sequence at least 90% identical to SEQ ID NO: 26.

E48. The antibody or antigen-binding fragment thereof of any one of embodiments 1-47, comprising a CL that comprises the amino acid sequence of SEQ ID NO: 26.

E49. The antibody or antigen-binding fragment thereof of any one of embodiments 1-48, comprising an Fc domain.

E50. The antibody or antigen-binding fragment thereof of embodiment 49, wherein said Fc domain is the Fc domain of an IgA.

E51. The antibody or antigen-binding fragment thereof of embodiment 50, wherein said IgA is $IgA_1$ or $IgA_2$.

E52. The antibody or antigen-binding fragment thereof of embodiment 49, wherein said Fc domain is the Fc domain of an IgD.

E53. The antibody or antigen-binding fragment thereof of embodiment 49, wherein said Fc domain is the Fc domain of an IgE.

E54. The antibody or antigen-binding fragment thereof of embodiment 49, wherein said Fc domain is the Fc domain of an IgM.

E55. The antibody or antigen-binding fragment thereof of embodiment 49, wherein said Fc domain is the Fc domain of an IgG.

E56. The antibody or antigen-binding fragment thereof of embodiment 55, wherein said IgG is $IgG_1$, $IgG_2$, $IgG_3$, or $IgG_4$.

E57. The antibody or antigen-binding fragment thereof of any one of embodiments 1-56, comprising a heavy chain that comprises the amino acid sequence of SEQ ID NO: 42.

E58. The antibody or antigen-binding fragment thereof of any one of embodiments 1-56, comprising a heavy chain that comprises the amino acid sequence of SEQ ID NO: 64.

E59. The antibody or antigen-binding fragment thereof of any one of embodiments 1-56, comprising a heavy chain that comprises the amino acid sequence of SEQ ID NO: 66.

E60. The antibody or antigen-binding fragment thereof of any one of embodiments 1-59, comprising a light chain that comprises the amino acid sequence of SEQ ID NO: 37.

E61. The antibody or antigen-binding fragment thereof of any one of embodiments 1-60, comprising the VH sequence encoded by the insert present in the plasmid deposited under ATCC Accession No. PTA-122329.

E62. The antibody or antigen-binding fragment thereof of any one of embodiments 1-61, comprising the VL sequence encoded by the insert present in the plasmid deposited under ATCC Accession No. PTA-122328.

E63. The antibody or antigen-binding fragment thereof of any one of embodiments 1-4, wherein said epitope further comprises one or more residues selected from the group consisting of: Glu100, Glu101, Asp102, Gly104, and Tyr109, according to the numbering of SEQ ID NO: 2.

E64. The antibody or antigen-binding fragment thereof of any one of embodiments 1-4 and 63, wherein said epitope further comprises Glu100, Glu101, Asp102, Gly104, and Tyr109, according to the numbering of SEQ ID NO: 2.

E65. The antibody or antigen-binding fragment thereof of any one of embodiments 1-4 and 63-64, wherein said epitope does not comprise one or more residues selected from the group consisting of: P103, T111, Y113, F114, N116, Q118, Q121, C122, E123, R124, F125, K126, and L140 (numbering according to SEQ ID NO: 2).

E66. The antibody or antigen-binding fragment thereof of any one of embodiments 1-4 and 63-65, wherein said epitope does not comprise: P103, T111, Y113, F114, N116, Q118, Q121, C122, E123, R124, F125, K126, and L140 (numbering according to SEQ ID NO: 2).

E67. The antibody or antigen-binding fragment thereof of any one of embodiments 1-4 and 63-64, wherein said epitope does not comprise one or more residues selected from the group consisting of: D31, D32, P34, C35, K36, P103, K126, Y127, G128 (numbering according to SEQ ID NO: 2).

E68. The antibody or antigen-binding fragment thereof of any one of embodiments 1-4, 63-64, and 67, wherein said epitope does not comprise: D31, D32, P34, C35, K36, P103, K126, Y127, G128 (numbering according to SEQ ID NO: 2).

E69. The antibody or antigen-binding fragment thereof of any one of embodiments 1-4 and 63-68, comprising the following residues (numbering according to Kabat): H33 Ala, H35 Gln, H52 Ser, H53 Asn, H55 Arg, H56 Ser, H95 Phe, H96 Leu, H97 His, H99 Ser, H101 Asp, L31 Met, L32 Tyr, L34 His, L36 Tyr, L50 Arg, L91 Trp, and L96 Tyr.

E70. The antibody or antigen-binding fragment thereof of any one of embodiments 1-4 and 63-69, comprising a VH that comprises:

(a) a CDR-H1 comprising the amino acid sequence of SEQ ID NO: 48.

(b) a CDR-H2 comprising the amino acid sequence of SEQ ID NO: 49; and (c) a CDR-H3 comprising the amino acid sequence of SEQ ID NO: 50.

E71. The antibody or antigen-binding fragment thereof of any one of embodiments 1-4 and 63-69, comprising the CDR-H1, CDR-H2, and CDR-H3 sequences of SEQ ID NO: 51.

E72. The antibody or antigen-binding fragment thereof of any one of embodiments 1-4 and 63-71, comprising a human VH3, VH1, or VH5 framework sequence.

E73. The antibody or antigen-binding fragment thereof of any one of embodiments 1-4 and 63-72, comprising the VH framework sequence of human germline IGHV3-23 or IGHV1-69.

E74. The antibody or antigen-binding fragment thereof of any one of embodiments 1-4 and 63-72, comprising the VH framework sequence of human germline IGHV3-7.

E75. The antibody or antigen-binding fragment thereof of any one of embodiments 1-4 and 63-71, comprising a human VH germline consensus framework sequence.

E76. The antibody or antigen-binding fragment thereof of any one of embodiments 1-4 and 63-75, comprising a VH that comprises an amino acid sequence at least 90% identical to an amino acid sequence selected from the group consisting of SEQ ID NOs: 67, 69, 51, and 79.

E77. The antibody or antigen-binding fragment thereof of any one of embodiments 1-4 and 63-76, comprising a VH that comprises an amino acid sequence selected from the group consisting of SEQ ID NOs: 67, 69, 51, and 79.

E78. The antibody or antigen-binding fragment thereof of any one of embodiments 1-4 and 63-77, comprising a VH that comprises the amino acid sequence of SEQ ID NO: 67.

E79. The antibody or antigen-binding fragment thereof of any one of embodiments 1-4 and 63-77, comprising a VH that comprises the amino acid sequence of SEQ ID NO: 69.

E80. The antibody or antigen-binding fragment thereof of any one of embodiments 1-4 and 63-77, comprising a VH that comprises the amino acid sequence of SEQ ID NO: 51.

E81. The antibody or antigen-binding fragment thereof of any one of embodiments 1-4 and 63-77, comprising a heavy chain variable region (VH) that comprises the amino acid sequence of SEQ ID NO: 79.

E82. The antibody or antigen-binding fragment thereof according to any one of embodiments 1-4 and 63-81, comprising a VL that comprises:

(a) a CDR-L1 comprising the amino acid sequence of SEQ ID NO: 43.

(b) a CDR-L2 comprising the amino acid sequence of SEQ ID NO: 44; and (c) a CDR-L3 comprising the amino acid sequence of SEQ ID NO: 45.

E83. The antibody or antigen-binding fragment thereof of any one of embodiments 1-4 and 63-81, comprising the CDR-L1, CDR-L2, and CDR-L3 sequences of SEQ ID NO: 46.

E84. The antibody or antigen-binding fragment thereof of any one of embodiments 1-4 and 63-83, comprising a human $V_K$ or $V_\lambda$ framework sequence.

E85. The antibody or antigen-binding fragment thereof of any one of embodiments 1-4 and 63-84, comprising the VL framework sequence of human germline IGKV3-20 or IGKV1-39.

E86. The antibody or antigen-binding fragment thereof of any one of embodiments 1-4 and 63-83, comprising a human VL germline consensus framework sequence.

E87. The antibody or antigen-binding fragment thereof of any one of embodiments 1-4 and 63-86, comprising a VL that comprises an amino acid sequence at least 90% identical to a sequence selected from the group consisting of SEQ ID NOs: 46, 71, 73, 75, and 77.

E88. The antibody or antigen-binding fragment thereof of any one of embodiments 1-4 and 63-87, comprising a VL that comprises an amino acid sequence selected from the group consisting of SEQ ID NOs: 46, 71, 73, 75, and 77.

E89. The antibody or antigen-binding fragment thereof of any one of embodiments 1-4 and 63-88, comprising a VL that comprises the amino acid sequence of SEQ ID NO:46.

E90. The antibody or antigen-binding fragment thereof of any one of embodiments 1-4 and 63-88, comprising a VL that comprises the amino acid sequence of SEQ ID NO:71.

E91. The antibody or antigen-binding fragment thereof of any one of embodiments 1-4 and 63-88, comprising a VL that comprises the amino acid sequence of SEQ ID NO:73.

E92. The antibody or antigen-binding fragment thereof of any one of embodiments 1-4 and 63-88, comprising a VL that comprises the amino acid sequence of SEQ ID NO:75.

E93. The antibody or antigen-binding fragment thereof of any one of embodiments 1-4 and 63-88, comprising a VL that comprises the amino acid sequence of SEQ ID NO:77.

E94. The antibody or antigen-binding fragment thereof of any one of embodiments 1-4 and 63-93, comprising a CH that comprises an amino acid sequence at least 90% identical to SEQ ID NO: 20.

E95. The antibody or antigen-binding fragment thereof of any one of embodiments 1-4 and 63-94, comprising a CH that comprises the amino acid sequence of SEQ ID NO: 20.

E96. The antibody or antigen-binding fragment thereof of any one of embodiments 1-4 and 63-95, comprising a CL that comprises an amino acid sequence at least 90% identical to SEQ ID NO: 26.

E97. The antibody or antigen-binding fragment thereof of any one of embodiments 1-4 and 63-96, comprising a CL that comprises the amino acid sequence of SEQ ID NO: 26.

E98. The antibody or antigen-binding fragment thereof of any one of embodiments 1-4 and 63-97, comprising an Fc domain.

E99. The antibody or antigen-binding fragment thereof of embodiment 98, wherein said Fc domain is the Fc domain of an IgA.

E100. The antibody or antigen-binding fragment thereof of embodiment 99, wherein said IgA is $IgA_1$ or $IgA_2$.

E101. The antibody or antigen-binding fragment thereof of embodiment 98, wherein said Fc domain is the Fc domain of an IgD, IgE, or IgM.

E102. The antibody or antigen-binding fragment thereof of embodiment 98, wherein said Fc domain is the Fc domain of an IgG.

E103. The antibody or antigen-binding fragment thereof of embodiment 102, wherein said IgG is $IgG_1$, $IgG_2$, $IgG_3$, or $IgG_4$.

E104. The antibody or antigen-binding fragment thereof of any one of embodiments 1-4 and 63-103, comprising a heavy chain that comprises the amino acid sequence of SEQ ID NO: 52.

E105. The antibody or antigen-binding fragment thereof of any one of embodiments 1-4 and 63-103, comprising a heavy chain that comprises the amino acid sequence of SEQ ID NO: 68.

E106. The antibody or antigen-binding fragment thereof of any one of embodiments 1-4 and 63-103, comprising a heavy chain that comprises the amino acid sequence of SEQ ID NO: 70.

E107. The antibody or antigen-binding fragment thereof of any one of embodiments 1-4 and 63-103, comprising a heavy chain that comprises the amino acid sequence of SEQ ID NO: 80.

E108. The antibody or antigen-binding fragment thereof of any one of embodiments 1-4 and 63-107, comprising a light chain that comprises the amino acid sequence of SEQ ID NO: 47.

E109. The antibody or antigen-binding fragment thereof of any one of embodiments 1-4 and 63-107, comprising a light chain that comprises the amino acid sequence of SEQ ID NO: 72.

E110. The antibody or antigen-binding fragment thereof of any one of embodiments 1-4 and 63-107, comprising a light chain that comprises the amino acid sequence of SEQ ID NO: 74.

E111. The antibody or antigen-binding fragment thereof of any one of embodiments 1-4 and 63-107, comprising a light chain that comprises the amino acid sequence of SEQ ID NO: 76.

E112. The antibody or antigen-binding fragment thereof of any one of embodiments 1-4 and 63-107, comprising a light chain that comprises the amino acid sequence of SEQ ID NO: 78.

E113. An isolated antibody, or antigen-binding fragment thereof, that specifically binds to an epitope in Kunitz Domain 2 (K2) of Tissue Factor Pathway Inhibitor (TFPI), wherein said epitope comprises residues Glu101, Pro103, Tyr109, Thr111, Ser119, Gln121, Glu123, Arg124, Lys126, and Leu140, according to the numbering of SEQ ID NO: 2.

E114. The antibody or antigen-binding fragment thereof of embodiment 113, wherein said antibody, or antigen-binding fragment thereof, does not bind to Kunitz Domain 1 (K1) of TFPI.

E115. The antibody or antigen-binding fragment thereof of embodiment 113 or 114, wherein said epitope does not comprise one or more residues selected from the group consisting of: E100, D102, R107, Y113, F114, N116, Q118, and C122 (numbering according to SEQ ID NO: 2).

E116. The antibody or antigen-binding fragment thereof of any one of embodiments 113-115, wherein said epitope does not comprise: E100, D102, R107, Y113, F114, N116, Q118, and C122 (numbering according to SEQ ID NO: 2).

E117. The antibody or antigen-binding fragment thereof of embodiment 113 or 114, wherein said epitope does not comprise one or more residues selected from the group consisting of: D31, D32, P34, C35, K36, E100, 1105, R107, G108, Y127, and G128 (numbering according to SEQ ID NO: 2).

E118. The antibody or antigen-binding fragment thereof of any one of embodiments 113-114 and 117, wherein said epitope does not comprise: D31, D32, P34, C35, K36, E100, 1105, R107, G108, Y127, and G128 (numbering according to SEQ ID NO: 2).

E119. The antibody or antigen-binding fragment thereof of embodiment 113-118, comprising the following residues (according to Kabat numbering): H50 Asp, H57 Thr, H58 Leu, H59 Tyr, H61 Gln, H98 Asp, H99 Tyr, H100 Asp, L30 His, L50 Trp, L92 Tyr, L93 Thr, L94 Thr, and L96 Tyr.

E120. The antibody or antigen-binding fragment thereof of any one of embodiments 113-119, comprising a VH that comprises:

(a) a CDR-H1 comprising the amino acid sequence of SEQ ID NO: 87.

(b) a CDR-H2 comprising the amino acid sequence of SEQ ID NO: 88; and (c) a CDR-H3 comprising the amino acid sequence of SEQ ID NO: 89.

E121. The antibody or antigen-binding fragment thereof of any one of embodiments 113-119, comprising the CDR-H1, CDR-H2, and CDR-H3 sequences of SEQ ID NO: 90.

E122. The antibody or antigen-binding fragment thereof of any one of embodiments 113-121, comprising a human VH3, VH1, or VH5 framework sequence.

E123. The antibody or antigen-binding fragment thereof of any one of embodiments 113-122, comprising the VH framework sequence of human germline IGHV3-23, IGHV1-69, or IGHV3-7.

E124. The antibody or antigen-binding fragment thereof of any one of embodiments 113-121, comprising a human VH germline consensus framework sequence.

E125. The antibody or antigen-binding fragment thereof of any one of embodiments 113-124, comprising a VH that comprises an amino acid sequence at least 90% identical to an amino acid sequence selected from the group consisting of SEQ ID NOs: 90, 95, 97, 99, 101, 103, 105, and 107.

E126. The antibody or antigen-binding fragment thereof of any one of embodiments 113-125, comprising a VH that comprises an amino acid sequence selected from the group consisting of SEQ ID NOs: 90, 95, 97, 99, 101, 103, 105, and 107.

E127. The antibody or antigen-binding fragment thereof of any one of embodiments 113-126, comprising a VH that comprises the amino acid sequence of SEQ ID NO: 90.

E128. The antibody or antigen-binding fragment thereof of any one of embodiments 113-126, comprising a VH that comprises the amino acid sequence of SEQ ID NO: 95.

E129. The antibody or antigen-binding fragment thereof of any one of embodiments 113-126, comprising a VH that comprises the amino acid sequence of SEQ ID NO: 97.

E130. The antibody or antigen-binding fragment thereof of any one of embodiments 113-126, comprising a VH that comprises the amino acid sequence of SEQ ID NO: 99.

E131. The antibody or antigen-binding fragment thereof of any one of embodiments 113-126, comprising a VH that comprises the amino acid sequence of SEQ ID NO: 101.

E132. The antibody or antigen-binding fragment thereof of any one of embodiments 113-126, comprising a VH that comprises the amino acid sequence of SEQ ID NO: 103.

E133. The antibody or antigen-binding fragment thereof of any one of embodiments 113-126, comprising a VH that comprises the amino acid sequence of SEQ ID NO: 105.

E134. The antibody or antigen-binding fragment thereof of any one of embodiments 113-126, comprising a VH that comprises the amino acid sequence of SEQ ID NO: 107.

E135. The antibody or antigen-binding fragment thereof of any one of embodiments 113-134, comprising a VL that comprises:

(a) a CDR-L1 comprising the amino acid sequence of SEQ ID NO: 81.

(b) a CDR-L2 comprising the amino acid sequence of SEQ ID NO: 82; and (c) a CDR-L3 comprising the amino acid sequence of SEQ ID NO: 83.

E136. The antibody or antigen-binding fragment thereof of any one of embodiments 113-134, comprising the CDR-L1, CDR-L2, and CDR-L3 sequences of SEQ ID NO: 84.

E137. The antibody or antigen-binding fragment thereof of any one of embodiments 113-136, comprising a human $V_K$ or $V_\lambda$ framework sequence.

E138. The antibody or antigen-binding fragment thereof of any one of embodiments 113-137, comprising the VL framework sequence of human germline IGKV3-20 or IGKV1-39.

E139. The antibody or antigen-binding fragment thereof of any one of embodiments 113-136, comprising a human VL germline consensus framework sequence.

E140. The antibody or antigen-binding fragment thereof of any one of embodiments 113-139, comprising a VL that comprises an amino acid sequence at least 90% identical to an amino acid sequence selected from the group consisting of SEQ ID NOs: 84, 109, and 111.

E141. The antibody or antigen-binding fragment thereof of any one of embodiments 113-140, comprising a VL that comprises an amino acid sequence selected from the group consisting of SEQ ID NOs: 84, 109, and 111.

E142. The antibody or antigen-binding fragment thereof of any one of embodiments 113-141, comprising a VL that comprises the amino acid sequence of SEQ ID NO:84.

E143. The antibody or antigen-binding fragment thereof of any one of embodiments 113-141, comprising a VL that comprises the amino acid sequence of SEQ ID NO:109.

E144. The antibody or antigen-binding fragment thereof of any one of embodiments 113-141, comprising a VL that comprises the amino acid sequence of SEQ ID NO:111.

E145. The antibody or antigen-binding fragment thereof of any one of embodiments 113-144, comprising a CH that comprises an amino acid sequence at least 90% identical to SEQ ID NO: 20.

E146. The antibody or antigen-binding fragment thereof of any one of embodiments 113-145, comprising a CH that comprises the amino acid sequence of SEQ ID NO: 20.

E147. The antibody or antigen-binding fragment thereof of any one of embodiments 113-144, comprising a CH that comprises an amino acid sequence at least 90% identical to SEQ ID NO: 91.

E148. The antibody or antigen-binding fragment thereof of any one of embodiments 113-144 and 147, comprising a CH that comprises the amino acid sequence of SEQ ID NO: 91.

E149. The antibody or antigen-binding fragment thereof of any one of embodiments 113-148, comprising a CL that comprises an amino acid sequence at least 90% identical to SEQ ID NO: 14.

E150. The antibody or antigen-binding fragment thereof of any one of embodiments 113-149, comprising a CL that comprises the amino acid sequence of SEQ ID NO: 14.

E151. The antibody or antigen-binding fragment thereof of any one of embodiments 113-148, comprising a CL that comprises an amino acid sequence at least 90% identical to SEQ ID NO: 85.

E152. The antibody or antigen-binding fragment thereof of any one of embodiments 113-148 and 151, comprising a CL that comprises the amino acid sequence of SEQ ID NO: 85.

E153. The antibody or antigen-binding fragment thereof of any one of embodiments 113-152, comprising an Fc domain.

E154. The antibody or antigen-binding fragment thereof of embodiment 153, wherein said Fc domain is the Fc domain of an IgA (e.g., $IgA_1$ or $IgA_2$).

E155. The antibody or antigen-binding fragment thereof of embodiment 153, wherein said Fc domain is the Fc domain of an IgD, IgE, or IgM.

E156. The antibody or antigen-binding fragment thereof of embodiment 153, wherein said Fc domain is the Fc domain of an IgG.

E157. The antibody or antigen-binding fragment thereof of embodiment 156, wherein said IgG is $IgG_1$, $IgG_2$, $IgG_3$, or $IgG_4$.

E158. The antibody or antigen-binding fragment thereof of any one of embodiments 113-157, comprising a heavy chain that comprises the amino acid sequence of SEQ ID NO: 92.

E159. The antibody or antigen-binding fragment thereof of any one of embodiments 113-157, comprising a heavy chain that comprises the amino acid sequence of SEQ ID NO: 94.

E160. The antibody or antigen-binding fragment thereof of any one of embodiments 113-157, comprising a heavy chain that comprises the amino acid sequence of SEQ ID NO: 96.

E161. The antibody or antigen-binding fragment thereof of any one of embodiments 113-157, comprising a heavy chain that comprises the amino acid sequence of SEQ ID NO: 98.

E162. The antibody or antigen-binding fragment thereof of any one of embodiments 113-157, comprising a heavy chain that comprises the amino acid sequence of SEQ ID NO: 100.

E163. The antibody or antigen-binding fragment thereof of any one of embodiments 113-157, comprising a heavy chain that comprises the amino acid sequence of SEQ ID NO: 102.

E164. The antibody or antigen-binding fragment thereof of any one of embodiments 113-157, comprising a heavy chain that comprises the amino acid sequence of SEQ ID NO: 104.

E165. The antibody or antigen-binding fragment thereof of any one of embodiments 113-157, comprising a heavy chain that comprises the amino acid sequence of SEQ ID NO: 106.

E166. The antibody or antigen-binding fragment thereof of any one of embodiments 113-157, comprising a heavy chain that comprises the amino acid sequence of SEQ ID NO: 108.

E167. The antibody or antigen-binding fragment thereof of any one of embodiments 113-166, comprising a light chain that comprises the amino acid sequence of SEQ ID NO: 86.

E168. The antibody or antigen-binding fragment thereof of any one of embodiments 113-166, comprising a light chain that comprises the amino acid sequence of SEQ ID NO: 93.

E169. The antibody or antigen-binding fragment thereof of any one of embodiments 113-166, comprising a light chain that comprises the amino acid sequence of SEQ ID NO: 110.

E170. The antibody or antigen-binding fragment thereof of any one of embodiments 113-166, comprising a light chain that comprises the amino acid sequence of SEQ ID NO: 112.

E171. An isolated antibody, or antigen-binding fragment thereof, that specifically binds to the Kunitz Domain 2 (K2) of TFPI, comprising a VH that comprises:

(a) a CDR-H1 comprising the amino acid sequence of SEQ ID NO: 16.

(b) a CDR-H2 comprising the amino acid sequence of SEQ ID NO: 17; and (c) a CDR-H3 comprising the amino acid sequence of SEQ ID NO: 18.

E172. An isolated antibody, or antigen-binding fragment thereof, that specifically binds to the K2 Domain of TFPI, comprising the CDR-H1, CDR-H2, and CDR-H3 sequences of SEQ ID NO: 19.

E173. An isolated antibody, or antigen-binding fragment thereof, that specifically binds to the K2 Domain of TFPI, comprising a VL that comprises:

(a) a CDR-L1 comprising the amino acid sequence of SEQ ID NO: 10.

(b) a CDR-L2 comprising the amino acid sequence of SEQ ID NO: 11; and (c) a CDR-L3 comprising the amino acid sequence of SEQ ID NO: 12.

E174. An isolated antibody, or antigen-binding fragment thereof, that specifically binds to the K2 Domain of TFPI, comprising the CDR-L1, CDR-L2, and CDR-L3 sequences of SEQ ID NO: 13.

E175. An isolated antibody, or antigen-binding fragment thereof, that specifically binds to the K2 Domain of TFPI, comprising:

(i) a VH that comprises:

(a) a CDR-H1 comprising the amino acid sequence of SEQ ID NO: 16.

(b) a CDR-H2 comprising the amino acid sequence of SEQ ID NO: 17; and (c) a CDR-H3 comprising the amino acid sequence of SEQ ID NO: 18;

and (ii) a VL that comprises:

(a) a CDR-L1 comprising the amino acid sequence of SEQ ID NO: 10.

(b) a CDR-L2 comprising the amino acid sequence of SEQ ID NO: 11; and (c) a CDR-L3 comprising the amino acid sequence of SEQ ID NO: 12.

E176. An isolated antibody, or antigen-binding fragment thereof, that specifically binds to the K2 Domain of TFPI, comprising the CDR-H1, CDR-H2, and CDR-H3 sequences of SEQ ID NO: 19, and the CDR-L1, CDR-L2, and CDR-L3 sequences of SEQ ID NO: 13.

E177. The antibody or antigen-binding fragment thereof of any one of embodiments 171-176, comprising a human VH3, VH1, or VH5 framework sequence.

E178. The antibody or antigen-binding fragment thereof of any one of embodiments 171-177, comprising the VH framework sequence of human germline IGHV3-23, IGHV1-69, or IGHV3-7.

E179. The antibody or antigen-binding fragment thereof of any one of embodiments 171-176, comprising a human VH germline consensus framework sequence.

E180. The antibody or antigen-binding fragment thereof of any one of embodiments 171-179, comprising a VH that comprises an amino acid sequence at least 90% identical to SEQ ID NO: 19.

E181. The antibody or antigen-binding fragment thereof of any one of embodiments 171-180, comprising a VH that comprises the amino acid sequence of SEQ ID NO. 19.

E182. The antibody or antigen-binding fragment thereof of any one of embodiments 171-181, comprising a human $V_K$ or $V_\lambda$ framework sequence.

E183. The antibody or antigen-binding fragment thereof of any one of embodiments 171-182, comprising the VL framework sequence of human germline IGKV3-20 or IGKV1-39.

E184. The antibody or antigen-binding fragment thereof of any one of embodiments 171-181, comprising a human VL germline consensus framework sequence.

E185. The antibody or antigen-binding fragment thereof of any one of embodiments 171-184, comprising a VL that comprises an amino acid sequence at least 90% identical to SEQ ID NO: 13.

E186. The antibody or antigen-binding fragment thereof of any one of embodiments 171-185, comprising a VL that comprises the amino acid sequence of SEQ ID NO: 13.

E187. The antibody or antigen-binding fragment thereof of any one of embodiments 171-186, comprising a CH that comprises an amino acid sequence at least 90% identical to SEQ ID NO: 20.

E188. The antibody or antigen-binding fragment thereof of any one of embodiments 171-187, comprising a CH that comprises the amino acid sequence of SEQ ID NO: 20.

E189. The antibody or antigen-binding fragment thereof of any one of embodiments 171-188, comprising a CL that comprises an amino acid sequence at least 90% identical to SEQ ID NO: 14.

E190. The antibody or antigen-binding fragment thereof of any one of embodiments 171-189, comprising a CL that comprises the amino acid sequence of SEQ ID NO: 14.

E191. The antibody or antigen-binding fragment thereof of any one of embodiments 171-190, comprising an Fc domain.

E192. The antibody or antigen-binding fragment thereof of embodiment 191, wherein said Fc domain is the Fc domain of an IgA (e.g., $IgA_1$ or $IgA_2$), IgD, IgE, or IgM.

E193. The antibody or antigen-binding fragment thereof of embodiment 191, wherein said Fc domain is the Fc domain of an IgG.

E194. The antibody or antigen-binding fragment thereof of embodiment 193, wherein said IgG is $IgG_1$, $IgG_2$, $IgG_3$, or $IgG_4$.

E195. The antibody or antigen-binding fragment thereof of any one of embodiments 171-194, comprising a heavy chain that comprises the amino acid sequence of SEQ ID NO: 21.

E196. The antibody or antigen-binding fragment thereof of any one of embodiments 171-195, comprising a light chain that comprises the amino acid sequence of SEQ ID NO: 15.

E197. An isolated antibody, or antigen-binding fragment thereof, that specifically binds to the K2 Domain of TFPI, comprising a VH that comprises:

(a) a CDR-H1 comprising the amino acid sequence of SEQ ID NO: 28.

(b) a CDR-H2 comprising the amino acid sequence of SEQ ID NO: 29; and (c) a CDR-H3 comprising the amino acid sequence of SEQ ID NO: 30.

E198. An isolated antibody, or antigen-binding fragment thereof, that specifically binds to the K2 Domain of TFPI, comprising the CDR-H1, CDR-H2, and CDR-H3 sequences of SEQ ID NO: 31.

E199. An isolated antibody, or antigen-binding fragment thereof, that specifically binds to the K2 Domain of TFPI, comprising a VL that comprises:
- (a) a CDR-L1 comprising the amino acid sequence of SEQ ID NO: 22.
- (b) a CDR-L2 comprising the amino acid sequence of SEQ ID NO: 23; and
- (c) a CDR-L3 comprising the amino acid sequence of SEQ ID NO: 24.

E200. An isolated antibody, or antigen-binding fragment thereof, that specifically binds to the K2 Domain of TFPI, comprising the CDR-L1, CDR-L2, and CDR-L3 sequences of SEQ ID NO: 25.

E201. An isolated antibody, or antigen-binding fragment thereof, that specifically binds to the K2 Domain of TFPI, comprising:

(i) a VH that comprises:
- (a) a CDR-H1 comprising the amino acid sequence of SEQ ID NO: 28.
- (b) a CDR-H2 comprising the amino acid sequence of SEQ ID NO: 29; and
- (c) a CDR-H3 comprising the amino acid sequence of SEQ ID NO: 30;

and (ii) a VL that comprises:
- (a) a CDR-L1 comprising the amino acid sequence of SEQ ID NO: 22.
- (b) a CDR-L2 comprising the amino acid sequence of SEQ ID NO: 23; and
- (c) a CDR-L3 comprising the amino acid sequence of SEQ ID NO: 24.

E202. An isolated antibody, or antigen-binding fragment thereof, that specifically binds to the K2 Domain of TFPI, comprising the CDR-H1, CDR-H2, and CDR-H3 sequences of SEQ ID NO: 31, and the CDR-L1, CDR-L2, and CDR-L3 sequences of SEQ ID NO: 25.

E203. The antibody or antigen-binding fragment thereof of any one of embodiments 197-202, comprising a human VH3, VH1, or VH5 framework sequence.

E204. The antibody or antigen-binding fragment thereof of any one of embodiments 197-203, comprising the VH framework sequence of human germline IGHV3-23, IGHV1-69, or IGHV3-7.

E205. The antibody or antigen-binding fragment thereof of any one of embodiments 197-202, comprising a human VH germline consensus framework sequence.

E206. The antibody or antigen-binding fragment thereof of any one of embodiments 197-205, comprising a VH that comprises an amino acid sequence at least 90% identical to SEQ ID NO: 31.

E207. The antibody or antigen-binding fragment thereof of any one of embodiments 197-206, comprising a VH that comprises the amino acid sequence of SEQ ID NO. 31.

E208. The antibody or antigen-binding fragment thereof of any one of embodiments 197-207, comprising a human $V_K$ or $V_\lambda$ framework sequence.

E209. The antibody or antigen-binding fragment thereof of any one of embodiments 197-208, comprising the VL framework sequence of human germline IGKV3-20 or IGKV1-39.

E210. The antibody or antigen-binding fragment thereof of any one of embodiments 197-207, comprising a human VL germline consensus framework sequence.

E211. The antibody or antigen-binding fragment thereof of any one of embodiments 197-210, comprising a VL that comprises an amino acid sequence at least 90% identical to SEQ ID NO: 25.

E212. The antibody or antigen-binding fragment thereof of any one of embodiments 197-211, comprising a VL that comprises the amino acid sequence of SEQ ID NO: 25.

E213. The antibody or antigen-binding fragment thereof of any one of embodiments 197-212, comprising a CH that comprises an amino acid sequence at least 90% identical to SEQ ID NO: 20.

E214. The antibody or antigen-binding fragment thereof of any one of embodiments 197-213, comprising a CH that comprises the amino acid sequence of SEQ ID NO: 20.

E215. The antibody or antigen-binding fragment thereof of any one of embodiments 197-214, comprising a CL that comprises an amino acid sequence at least 90% identical to SEQ ID NO: 26.

E216. The antibody or antigen-binding fragment thereof of any one of embodiments 197-215, comprising a CL that comprises the amino acid sequence of SEQ ID NO: 26.

E217. The antibody or antigen-binding fragment thereof of any one of embodiments 197-216, comprising an Fc domain.

E218. The antibody or antigen-binding fragment thereof of embodiment 217, wherein said Fc domain is the Fc domain of an IgA (e.g., $IgA_1$ or $IgA_2$), IgD, IgE, or IgM.

E219. The antibody or antigen-binding fragment thereof of embodiment 217, wherein said Fc domain is the Fc domain of an IgG (e.g., $IgG_1$, $IgG_2$, $IgG_3$, or $IgG_4$).

E220. The antibody or antigen-binding fragment thereof of any one of embodiments 197-219, comprising a heavy chain that comprises the amino acid sequence of SEQ ID NO: 32.

E221. The antibody or antigen-binding fragment thereof of any one of embodiments 197-220, comprising a light chain that comprises the amino acid sequence of SEQ ID NO: 27.

E222. An isolated antibody, or antigen-binding fragment thereof, that specifically binds to the K2 Domain of TFPI, comprising a heavy chain variable region (VH) that comprises:
- (a) a CDR-H1 comprising the amino acid sequence of SEQ ID NO: 58.
- (b) a CDR-H2 comprising the amino acid sequence of SEQ ID NO: 59; and
- (c) a CDR-H3 comprising the amino acid sequence of SEQ ID NO: 60.

E223. An isolated antibody, or antigen-binding fragment thereof, that specifically binds to the K2 Domain of TFPI, comprising the CDR-H1, CDR-H2, and CDR-H3 sequences of SEQ ID NO: 61.

E224. An isolated antibody, or antigen-binding fragment thereof, that specifically binds to the K2 Domain of TFPI, comprising a VL that comprises:
- (a) a CDR-L1 comprising the amino acid sequence of SEQ ID NO: 53.
- (b) a CDR-L2 comprising the amino acid sequence of SEQ ID NO: 54; and
- (c) a CDR-L3 comprising the amino acid sequence of SEQ ID NO: 55.

E225. An isolated antibody, or antigen-binding fragment thereof, that specifically binds to the K2 Domain of TFPI, comprising the CDR-L1, CDR-L2, and CDR-L3 sequences of SEQ ID NO: 56.

E226. An isolated antibody, or antigen-binding fragment thereof, that specifically binds the K2 Domain of TFPI, comprising:

(i) a VH that comprises:
(a) a CDR-H1 comprising the amino acid sequence of SEQ ID NO: 58.
(b) a CDR-H2 comprising the amino acid sequence of SEQ ID NO: 59; and
(c) a CDR-H3 comprising the amino acid sequence of SEQ ID NO: 60;
and (ii) a VL that comprises:
(a) a CDR-L1 comprising the amino acid sequence of SEQ ID NO: 53.
(b) a CDR-L2 comprising the amino acid sequence of SEQ ID NO: 54; and
(c) a CDR-L3 comprising the amino acid sequence of SEQ ID NO: 55.

E227. An isolated antibody, or antigen-binding fragment thereof, that specifically binds to the K2 Domain of TFPI, comprising the CDR-H1, CDR-H2, and CDR-H3 sequences of SEQ ID NO: 61, and the CDR-L1, CDR-L2, and CDR-L3 sequences of SEQ ID NO: 56.

E228. The antibody or antigen-binding fragment thereof of any one of embodiments 222-227, comprising a human VH3, VH1, or VH5 framework sequence.

E229. The antibody or antigen-binding fragment thereof of any one of embodiments 222-228, comprising the VH framework sequence of human germline IGHV3-23, IGHV1-69, or IGHV3-7.

E230. The antibody or antigen-binding fragment thereof of any one of embodiments 222-227, comprising a human VH germline consensus framework sequence.

E231. The antibody or antigen-binding fragment thereof of any one of embodiments 222-230, comprising a VH that comprises an amino acid sequence at least 90% identical to SEQ ID NO: 61.

E232. The antibody or antigen-binding fragment thereof of any one of embodiments 222-231, comprising a VH that comprises the amino acid sequence of SEQ ID NO. 61.

E233. The antibody or antigen-binding fragment thereof of any one of embodiments 222-232, comprising a human $V_K$ or $V_\lambda$ framework sequence.

E234. The antibody or antigen-binding fragment thereof of any one of embodiments 222-233, comprising the VL framework sequence of human germline IGKV3-20 or IGKV1-39.

E235. The antibody or antigen-binding fragment thereof of any one of embodiments 222-232, comprising a human VL germline consensus framework sequence.

E236. The antibody or antigen-binding fragment thereof of any one of embodiments 222-235, comprising a VL that comprises an amino acid sequence at least 90% identical to SEQ ID NO: 56.

E237. The antibody or antigen-binding fragment thereof of any one of embodiments 222-236, comprising a VL that comprises the amino acid sequence of SEQ ID NO: 56.

E238. The antibody or antigen-binding fragment thereof of any one of embodiments 222-237, comprising a CH that comprises an amino acid sequence at least 90% identical to SEQ ID NO: 20.

E239. The antibody or antigen-binding fragment thereof of any one of embodiments 222-238, comprising a CH that comprises the amino acid sequence of SEQ ID NO: 20.

E240. The antibody or antigen-binding fragment thereof of any one of embodiments 222-239, comprising a CL that comprises an amino acid sequence at least 90% identical to SEQ ID NO: 26.

E241. The antibody or antigen-binding fragment thereof of any one of embodiments 222-240, comprising a CL that comprises the amino acid sequence of SEQ ID NO: 26.

E242. The antibody or antigen-binding fragment thereof of any one of embodiments 222-241, comprising an Fc domain.

E243. The antibody or antigen-binding fragment thereof of embodiment 242, wherein said Fc domain is the Fc domain of an IgA (e.g., $IgA_1$ or $IgA_2$), IgD, IgE, or IgM.

E244. The antibody or antigen-binding fragment thereof of embodiment 242, wherein said Fc domain is the Fc domain of an IgG (e.g., $IgG_1$, $IgG_2$, $IgG_3$, or $IgG_4$).

E245. The antibody or antigen-binding fragment thereof of any one of embodiments 222-244, comprising a heavy chain that comprises the amino acid sequence of SEQ ID NO: 62.

E246. The antibody or antigen-binding fragment thereof of any one of embodiments 222-245, comprising a light chain that comprises the amino acid sequence of SEQ ID NO: 57.

E247. An isolated antibody, or antigen-binding fragment thereof, that specifically binds to the K2 Domain of TFPI, comprising a VH that comprises:
(a) a CDR-H1 comprising the amino acid sequence of SEQ ID NO: 118.
(b) a CDR-H2 comprising the amino acid sequence of SEQ ID NO: 119; and
(c) a CDR-H3 comprising the amino acid sequence of SEQ ID NO: 120.

E248. An isolated antibody, or antigen-binding fragment thereof, that specifically binds to the K2 Domain of TFPI, comprising the CDR-H1, CDR-H2, and CDR-H3 sequences of SEQ ID NO: 121.

E249. An isolated antibody, or antigen-binding fragment thereof, that specifically binds to the K2 Domain of TFPI, comprising a VL that comprises:
(a) a CDR-L1 comprising the amino acid sequence of SEQ ID NO: 113.
(b) a CDR-L2 comprising the amino acid sequence of SEQ ID NO: 114; and
(c) a CDR-L3 comprising the amino acid sequence of SEQ ID NO: 115.

E250. An isolated antibody, or antigen-binding fragment thereof, that specifically binds to the K2 Domain of TFPI, comprising the CDR-L1, CDR-L2, and CDR-L3 sequences of SEQ ID NO: 116.

E251. An isolated antibody, or antigen-binding fragment thereof, that specifically binds to the K2 Domain of TFPI, comprising:
(i) a VH that comprises:
(a) a CDR-H1 comprising the amino acid sequence of SEQ ID NO: 118.
(b) a CDR-H2 comprising the amino acid sequence of SEQ ID NO: 119; and
(c) a CDR-H3 comprising the amino acid sequence of SEQ ID NO: 120;
and (ii) a VL that comprises:
(a) a CDR-L1 comprising the amino acid sequence of SEQ ID NO: 113.
(b) a CDR-L2 comprising the amino acid sequence of SEQ ID NO: 114; and
(c) a CDR-L3 comprising the amino acid sequence of SEQ ID NO: 115.

E252. An isolated antibody, or antigen-binding fragment thereof, that specifically binds to the K2 Domain of TFPI, comprising the CDR-H1, CDR-H2, and CDR-H3 sequences of SEQ ID NO: 121, and the CDR-L1, CDR-L2, and CDR-L3 sequences of SEQ ID NO: 116.

E253. The antibody or antigen-binding fragment thereof of any one of embodiments 247-252, comprising a human VH3, VH1, or VH5 framework sequence.

E254. The antibody or antigen-binding fragment thereof of any one of embodiments 247-253, comprising the VH framework sequence of human germline IGHV3-23, IGHV1-69, or IGHV3-7.

E255. The antibody or antigen-binding fragment thereof of any one of embodiments 247-252, comprising a human VH germline consensus framework sequence.

E256. The antibody or antigen-binding fragment thereof of any one of embodiments 247-255, comprising a VH that comprises an amino acid sequence at least 90% identical to SEQ ID NO: 121.

E257. The antibody or antigen-binding fragment thereof of any one of embodiments 247-256, comprising a VH that comprises the amino acid sequence of SEQ ID NO. 121.

E258. The antibody or antigen-binding fragment thereof of any one of embodiments 247-257, comprising a human $V_K$ or $V_\lambda$ framework sequence.

E259. The antibody or antigen-binding fragment thereof of any one of embodiments 247-258, comprising the VL framework sequence of human germline IGKV3-20 or IGKV1-39.

E260. The antibody or antigen-binding fragment thereof of any one of embodiments 247-257, comprising a human VL germline consensus framework sequence.

E261. The antibody or antigen-binding fragment thereof of any one of embodiments 247-260, comprising a VL that comprises an amino acid sequence at least 90% identical to SEQ ID NO: 116.

E262. The antibody or antigen-binding fragment thereof of any one of embodiments 247-261, comprising a VL that comprises the amino acid sequence of SEQ ID NO: 116.

E263. The antibody or antigen-binding fragment thereof of any one of embodiments 247-262, comprising a CH that comprises an amino acid sequence at least 90% identical to SEQ ID NO: 91.

E264. The antibody or antigen-binding fragment thereof of any one of embodiments 247-263, comprising a CH that comprises the amino acid sequence of SEQ ID NO: 91.

E265. The antibody or antigen-binding fragment thereof of any one of embodiments 247-264, comprising a CL that comprises an amino acid sequence at least 90% identical to SEQ ID NO: 85.

E266. The antibody or antigen-binding fragment thereof of any one of embodiments 247-265, comprising a CL that comprises the amino acid sequence of SEQ ID NO: 85.

E267. The antibody or antigen-binding fragment thereof of any one of embodiments 247-266, comprising an Fc domain.

E268. The antibody or antigen-binding fragment thereof of embodiment 267, wherein said Fc domain is the Fc domain of an IgA (e.g., $IgA_1$ or $IgA_2$), IgD, IgE, or IgM.

E269. The antibody or antigen-binding fragment thereof of embodiment 267, wherein said Fc domain is the Fc domain of an IgG (e.g., $IgG_1$, $IgG_2$, $IgG_3$, or $IgG_4$).

E270. The antibody or antigen-binding fragment thereof of any one of embodiments 247-269, comprising a heavy chain that comprises the amino acid sequence of SEQ ID NO: 122.

E271. The antibody or antigen-binding fragment thereof of any one of embodiments 247-270, comprising a light chain that comprises the amino acid sequence of SEQ ID NO: 117.

E272. An isolated antibody, or antigen-binding fragment thereof, that specifically binds to the K2 Domain of TFPI, comprising a VH that comprises:

(a) a CDR-H1 comprising the amino acid sequence of SEQ ID NO: 128.

(b) a CDR-H2 comprising the amino acid sequence of SEQ ID NO: 129; and (c) a CDR-H3 comprising the amino acid sequence of SEQ ID NO: 130.

E273. An isolated antibody, or antigen-binding fragment thereof, that specifically binds to the K2 Domain of TFPI, comprising the CDR-H1, CDR-H2, and CDR-H3 sequences of SEQ ID NO: 131.

E274. An isolated antibody, or antigen-binding fragment thereof, that specifically binds to the K2 Domain of TFPI, comprising a VL that comprises:

(a) a CDR-L1 comprising the amino acid sequence of SEQ ID NO: 123.

(b) a CDR-L2 comprising the amino acid sequence of SEQ ID NO: 124; and (c) a CDR-L3 comprising the amino acid sequence of SEQ ID NO: 125.

E275. An isolated antibody, or antigen-binding fragment thereof, that specifically binds to the K2 Domain of TFPI, comprising the CDR-L1, CDR-L2, and CDR-L3 sequences of SEQ ID NO: 126.

E276. An isolated antibody, or antigen-binding fragment thereof, that specifically binds to the K2 Domain of TFPI, comprising:

(i) a VH that comprises:

(a) a CDR-H1 comprising the amino acid sequence of SEQ ID NO: 128.

(b) a CDR-H2 comprising the amino acid sequence of SEQ ID NO: 129; and (c) a CDR-H3 comprising the amino acid sequence of SEQ ID NO: 130;

and (ii) a VL that comprises:

(a) a CDR-L1 comprising the amino acid sequence of SEQ ID NO: 123.

(b) a CDR-L2 comprising the amino acid sequence of SEQ ID NO: 124; and (c) a CDR-L3 comprising the amino acid sequence of SEQ ID NO: 125.

E277. An isolated antibody, or antigen-binding fragment thereof, that specifically binds to the K2 Domain of TFPI, comprising the CDR-H1, CDR-H2, and CDR-H3 sequences of SEQ ID NO: 131, and the CDR-L1, CDR-L2, and CDR-L3 sequences of SEQ ID NO: 126.

E278. The antibody or antigen-binding fragment thereof of any one of embodiments 272-277, comprising a human VH3, VH1, or VH5 framework sequence.

E279. The antibody or antigen-binding fragment thereof of any one of embodiments 272-278, comprising the VH framework sequence of human germline IGHV3-23, IGHV1-69, or IGHV3-7.

E280. The antibody or antigen-binding fragment thereof of any one of embodiments 272-277, comprising a human VH germline consensus framework sequence.

E281. The antibody or antigen-binding fragment thereof of any one of embodiments 272-280, comprising a VH that comprises an amino acid sequence at least 90% identical to SEQ ID NO: 131.

E282. The antibody or antigen-binding fragment thereof of any one of embodiments 272-281, comprising a VH that comprises the amino acid sequence of SEQ ID NO. 131.

E283. The antibody or antigen-binding fragment thereof of any one of embodiments 272-282, comprising a human $V_K$ or $V_\lambda$ framework sequence.

E284. The antibody or antigen-binding fragment thereof of any one of embodiments 272-283, comprising the VL framework sequence of human germline IGKV3-20 or IGKV1-39.

E285. The antibody or antigen-binding fragment thereof of any one of embodiments 272-282, comprising a human VL germline consensus framework sequence.

E286. The antibody or antigen-binding fragment thereof of any one of embodiments 272-285, comprising a VL that comprises an amino acid sequence at least 90% identical to SEQ ID NO: 126.

E287. The antibody or antigen-binding fragment thereof of any one of embodiments 272-286, comprising a VL that comprises the amino acid sequence of SEQ ID NO: 126.

E288. The antibody or antigen-binding fragment thereof of any one of embodiments 272-287, comprising a CH that comprises an amino acid sequence at least 90% identical to SEQ ID NO: 91.

E289. The antibody or antigen-binding fragment thereof of any one of embodiments 272-288, comprising a CH that comprises amino acid sequence of SEQ ID NO: 91.

E290. The antibody or antigen-binding fragment thereof of any one of embodiments 272-289, comprising a CL that comprises an amino acid sequence at least 90% identical to SEQ ID NO: 85.

E291. The antibody or antigen-binding fragment thereof of any one of embodiments 272-290, comprising a CL that comprises the amino acid sequence of SEQ ID NO: 85.

E292. The antibody or antigen-binding fragment thereof of any one of embodiments 272-291, comprising an Fc domain.

E293. The antibody or antigen-binding fragment thereof of embodiment 292, wherein said Fc domain is the Fc domain of an IgA (e.g., $IgA_1$ or $IgA_2$), IgD, IgE, or IgM.

E294. The antibody or antigen-binding fragment thereof of embodiment 292, wherein said Fc domain is the Fc domain of an IgG (e.g., $IgG_1$, $IgG_2$, $IgG_3$, or $IgG_4$).

E295. The antibody or antigen-binding fragment thereof of any one of embodiments 272-294, comprising a heavy chain that comprises the amino acid sequence of SEQ ID NO: 132.

E296. The antibody or antigen-binding fragment thereof of any one of embodiments 272-295, comprising a light chain that comprises the amino acid sequence of SEQ ID NO: 127.

E297. An antibody, or antigen-binding fragment thereof, that specifically binds to the K2 Domain of TFPI, wherein said antibody or antigen-binding fragment thereof competes for binding to TFPI with the antibody or antigen-binding fragment thereof of any one of embodiments 1-296.

E298. An antibody, or antigen-binding fragment thereof, that specifically binds to the K2 Domain of TFPI, wherein said antibody or antigen-binding fragment thereof competes for binding to TFPI with an antibody selected from the group consisting of: TFPI-3, TFPI-21, TFPI-23, TFPI-24, TFPI-26, TFPI-106, TFPI-107, TFPI-108, TFPI-109, TFPI-110, TFPI-111, TFPI-112, TFPI-113, TFPI-114, TFPI-115, TFPI-118, TFPI-119, TFPI-122, TFPI-123, TFPI-126, 4D8.b1, mu-hu 4D8 chimera, 4D8-Vk1.0×VH1.0, 4D8-Vk1.0×VH1.1, 4D8-Vk1.0×VH1.2, 4D8-Vk1.0×VH1.3, 4D8-Vk1.0×VH1.4, 4D8-Vk1.0×VH1.5, 4D8-Vk1.0×VH1.6, 4D8-Vk1.1×VH1.0, 4D8-Vk1.1×VH1.1, 4D8-Vk1.1×VH1.2, 4D8-Vk1.1×VH1.3, 4D8-Vk1.1×VH1.4, 4D8-Vk1.1×VH1.5, 4D8-Vk1.1×VH1.6, hz4D8, 6B7.c5, and 7A4.D9.

E299. An antibody, or antigen-binding fragment thereof, that specifically binds to the K2 Domain of TFPI, wherein said antibody or antigen-binding fragment thereof competes for binding to TFPI with an antibody selected from the group consisting of: TFPI-23, TFPI-24, TFPI-106, and TFPI-118.

E300. The antibody or antigen-binding fragment thereof of embodiment 299, wherein said antibody or antigen-binding fragment thereof competes for binding to TFPI with TFPI-23 or TFPI-106.

E301. The antibody or antigen-binding fragment thereof of embodiment 299, wherein said antibody or antigen-binding fragment thereof competes for binding to TFPI with TFPI-24 or TFPI-118.

E302. An antibody, or antigen-binding fragment thereof, that specifically binds to the K2 Domain of TFPI, wherein said antibody or antigen-binding fragment thereof competes for binding to TFPI with antibody 4D8.

E303. An antibody, or antigen-binding fragment thereof, that specifically binds to the K2 Domain of TFPI, wherein said antibody or antigen-binding fragment thereof binds to the same TFPI epitope as the antibody or antigen-binding fragment thereof of any one of embodiments 1-296.

E304. An antibody, or antigen-binding fragment thereof, that specifically binds to the K2 Domain of TFPI, wherein said antibody or antigen-binding fragment thereof binds to the same TFPI epitope as an antibody selected from the group consisting of: TFPI-3, TFPI-21, TFPI-23, TFPI-24, TFPI-26, TFPI-106, TFPI-107, TFPI-108, TFPI-109, TFPI-110, TFPI-111, TFPI-112, TFPI-113, TFPI-114, TFPI-115, TFPI-118, TFPI-119, TFPI-122, TFPI-123, TFPI-126, 4D8.b1, mu-hu 4D8 chimera, 4D8-Vk1.0×VH1.0, 4D8-Vk1.0×VH1.1, 4D8-Vk1.0×VH1.2, 4D8-Vk1.0×VH1.3, 4D8-Vk1.0×VH1.4, 4D8-Vk1.0×VH1.5, 4D8-Vk1.0×VH1.6, 4D8-Vk1.1×VH1.0, 4D8-Vk1.1×VH1.1, 4D8-Vk1.1×VH1.2, 4D8-Vk1.1×VH1.3, 4D8-Vk1.1×VH1.4, 4D8-Vk1.1×VH1.5, 4D8-Vk1.1×VH1.6, hz4D8, 6B7.c5, and 7A4.D9.

E305. An antibody, or antigen-binding fragment thereof, that specifically binds the K2 Domain of TFPI, wherein said antibody or antigen-binding fragment thereof binds to the same TFPI epitope as an antibody selected from the group consisting of: TFPI-23, TFPI-24, TFPI-106, and TFPI-118.

E306. The antibody or antigen-binding fragment thereof of embodiment 305, wherein said antibody or antigen-binding fragment thereof binds to the same TFPI epitope as TFPI-23 or TFPI-106.

E307. The antibody or antigen-binding fragment thereof of embodiment 305, wherein said antibody or antigen-binding fragment thereof binds to the same TFPI epitope as TFPI-24 or TFPI-118.

E308. An antibody, or antigen-binding fragment thereof, that specifically binds to the K2 Domain of TFPI, wherein said antibody or antigen-binding fragment thereof binds to the same TFPI epitope as antibody 4D8.

E309. The antibody or antigen-binding fragment thereof of any one of embodiments 297-308, wherein said antibody or antigen-binding fragment thereof does not bind to the K1 Domain of TFPI.

E310. The antibody or antigen-binding fragment thereof of any one of embodiments 1-309, wherein the antibody or antigen-binding fragment is an Fc fusion protein, a monobody, a maxibody, a bifunctional antibody, an scFab, an scFv, a peptibody, or an antigen-binding fragment of any of the foregoing.

E311. The antibody or antigen-binding fragment thereof of any one of embodiments 1-310, wherein said antibody or antigen-binding fragment binds to TFPI with a binding affinity (Kd) value from about $1\times10^{-7}$M to about $1\times10^{-12}$ M.

E312. The antibody or antigen-binding fragment thereof of any one of embodiments 1-311, wherein said antibody or antigen-binding fragment binds to TFPI with a binding affinity (Kd) value from about $5\times10^{-7}$M to about $5\times10^{-11}$ M.

E313. The antibody or antigen-binding fragment thereof of any one of embodiments 1-312, wherein said antibody or antigen-binding fragment binds to TFPI with a binding affinity (Kd) value of from about $1\times10^{-8}$M to about $1\times10^{-10}$ M.

E314. The antibody or antigen-binding fragment thereof of any one of embodiments 1-313, wherein said antibody or antigen-binding fragment: (i) decreases clotting time as measured in a plasma based dilute prothrombin time (dPT)

assay; (ii) reduces clotting time in whole blood as measured by thromboelastrography or rotational thromboelastometry; (iii) increases thrombin generation; (iv) increases FXa activity in the presence of TFPI; (v) enhance platelet accumulation in the presence of TFPI; (vi) increase fibrin generation in the presence of TFPI; or (vii) any combination thereof.

E315. The antibody or antigen-binding fragment thereof of embodiment 314, wherein said antibody or antigen-binding fragment decreases clotting time as measured in a plasma based dilute prothrombin time assay.

E316. The antibody or antigen-binding fragment thereof of embodiment 315, wherein said decrease in clotting time, as measured in a plasma based dilute prothrombin time assay, is dose-dependent.

E317. The antibody or antigen-binding fragment thereof of embodiment 314, wherein said antibody or antigen-binding fragment reduces clotting time in whole blood as measured by thromboelastrography or rotational thromboelastometry.

E318. The antibody or antigen-binding fragment thereof of embodiment 317, wherein said reduction in clotting time, as measured by thromboelastrography or rotational thromboelastometry, is dose-dependent.

E319. The antibody or antigen-binding fragment thereof of embodiment 314, wherein said antibody or antigen-binding fragment increases thrombin generation.

E320. The antibody or antigen-binding fragment thereof of embodiment 319, wherein said increase in thrombin generation, is dose-dependent.

E321. The antibody or antigen-binding fragment thereof of embodiment 314, wherein said antibody or antigen-binding fragment increases FXa activity in the presence of TFPI.

E322. The antibody or antigen-binding fragment thereof of embodiment 321, wherein said increase in FXa activity in the presence of TFPI, is dose-dependent.

E323. The antibody or antigen-binding fragment thereof of embodiment 322, wherein said antibody enhances platelet accumulation in the presence of TFPI.

E324. The antibody or antigen-binding fragment thereof of embodiment 323, wherein said enhancement of platelet accumulation in the presence of TFPI is dose-dependent.

E325. The antibody or antigen-binding fragment thereof of embodiment 324, wherein said antibody increases fibrin generation in the presence of TFPI.

E326. The antibody or antigen-binding fragment thereof of embodiment 325, wherein said increase in fibrin generation in the presence of TFPI is dose-dependent.

E327. The antibody or antigen-binding fragment thereof of embodiment 314, wherein the reduction in clotting time in whole blood is determined using whole blood obtained from a human patient having severe hemophilia A.

E328. The antibody or antigen-binding fragment thereof of embodiment 314, wherein the reduction in clotting time in whole blood is determined using whole blood obtained from a human patient having severe hemophilia A and inhibitory antibodies against human Factor VIII.

E329. The antibody or antigen-binding fragment thereof of embodiment 314, wherein the reduction in clotting time in whole blood is determined using whole blood obtained from a human patient having moderate hemophilia A.

E330. The antibody or antigen-binding fragment thereof of embodiment 314, wherein the reduction in clotting time in whole blood is determined using whole blood obtained from a human patient having severe hemophilia B.

E331. The antibody or antigen-binding fragment thereof of embodiment 314, wherein the reduction in clotting time in whole blood is determined using whole blood obtained from a human patient having severe hemophilia B and inhibitory antibodies against human Factor IX.

E332. The antibody or antigen-binding fragment thereof of embodiment 314, wherein the reduction in clotting time in whole blood is determined using whole blood obtained from a human patient having moderate hemophilia B.

E333. The antibody or antigen-binding fragment thereof of embodiment 314, wherein the reduction in clotting time as measured in a dPT assay is determined using plasma obtained from a human patient having severe hemophilia A.

E334. The antibody or antigen-binding fragment thereof of embodiment 314, wherein the reduction in clotting time as measured in a dPT assay is determined using plasma obtained from a human patient having severe hemophilia A and inhibitory antibodies against human Factor VIII.

E335. The antibody or antigen-binding fragment thereof of embodiment 314, wherein the reduction in clotting time as measured in a dPT assay is determined using plasma obtained from a human patient having moderate hemophilia A.

E336. The antibody or antigen-binding fragment thereof of embodiment 314, wherein the reduction in clotting time as measured in a dPT assay is determined using plasma obtained from a human patient having severe hemophilia B.

E337. The antibody or antigen-binding fragment thereof of embodiment 314, wherein the reduction in clotting time as measured in a dPT assay is determined using plasma obtained from a human patient having severe hemophilia B and inhibitory antibodies against human Factor IX.

E338. The antibody or antigen-binding fragment thereof of embodiment 314, wherein the reduction in clotting time as measured in a dPT assay is determined using plasma obtained from a human patient having moderate hemophilia B.

E339. The antibody or antigen-binding fragment thereof of embodiment 314, wherein the increase in thrombin generation is determined using plasma obtained from a human patient having severe hemophilia A.

E340. The antibody or antigen-binding fragment thereof of embodiment 314, wherein the increase in thrombin generation is determined using plasma obtained from a human patient having severe hemophilia A and inhibitory antibodies against human Factor VIII.

E341. The antibody or antigen-binding fragment thereof of embodiment 314, wherein the increase in thrombin generation is determined using plasma obtained from a human patient having moderate hemophilia A.

E342. The antibody or antigen-binding fragment thereof of embodiment 314, wherein the increase in thrombin generation is determined using plasma obtained from a human patient having severe hemophilia B.

E343. The antibody or antigen-binding fragment thereof of embodiment 314, wherein the increase in thrombin generation is determined using plasma obtained from a human patient having severe hemophilia B and inhibitory antibodies against human Factor IX.

E344. The antibody or antigen-binding fragment thereof of embodiment 314, wherein the increase in thrombin generation is determined using plasma obtained from a human patient having moderate hemophilia B.

E345. The antibody or antigen-binding fragment thereof of embodiment 314, wherein 100 nM of said antibody or antigen-binding fragment thereof is at least as effective in reducing clotting time of whole blood obtained from a human patient having severe hemophilia A as an amount of recombinant human Factor VIII that is sufficient to achieve 5% of normal clotting activity.

E346. The antibody or antigen-binding fragment thereof of embodiment 314, wherein 100 nM of said antibody or antigen-binding fragment thereof is at least as effective in increasing peak thrombin generation in platelet rich plasma obtained from a human patient having severe hemophilia A as an amount of recombinant human Factor VIII that is sufficient to achieve 5% of normal clotting activity.

E347. The antibody or antigen-binding fragment thereof of any one of embodiments 1-346, wherein said TFPI is human TFPI.

E348. The antibody or antigen-binding fragment thereof of any one of embodiments 1-347, wherein said TFPI comprises residues 91-147 SEQ ID NO: 2.

E349. An isolated nucleic acid molecule or nucleic acid molecules, comprising one or more nucleotide sequences encoding the antibody or antigen-binding fragment thereof of any one of embodiments 1-348.

E350. An isolated nucleic acid molecule encoding an antibody, or antigen-binding fragment thereof, that specifically binds TFPI, wherein said nucleic acid comprises a nucleic acid sequence selected from the group consisting of: the nucleic acid sequence of SEQ ID NO:175, the nucleic acid sequence of SEQ ID NO:176, the nucleic acid sequence of SEQ ID NO:177, the nucleic acid sequence of SEQ ID NO:178, the nucleic acid sequence of the insert of the vector deposited as mAb-TFPI-106 VL under ATCC Accession Number PTA-122328, and the nucleic acid sequence of the insert of the vector deposited as mAb-TFPI-106 VH under ATCC Accession Number PTA-122329.

E351. A vector comprising the nucleic acid molecule of embodiments 349 and 350.

E352. A host cell comprising the nucleic acid molecule of embodiment 349 or 350, or the vector of embodiment 351.

E353. The host cell of embodiment 352, wherein said cell is a mammalian cell.

E354. The host cell of embodiment 353, wherein said host cell is a CHO cell, a HEK-293 cell, or an Sp2.0 cell.

E355. A method of making an antibody or antigen-binding fragment thereof, comprising culturing the host cell of any one of embodiments 352-354, under a condition wherein said antibody or antigen-binding fragment is expressed by said host cell.

E356. The method of embodiment 355, further comprising isolating said antibody or antigen-binding fragment thereof.

E357. An antibody or antigen-binding fragment thereof obtained by the method of embodiment 355 or 356.

E358. A pharmaceutical composition comprising an antibody or antigen-binding fragment thereof of any one of embodiments 1-347 and 357, and a pharmaceutically acceptable carrier or excipient.

E359. A method of reducing the activity of Tissue Factor Pathway Inhibitor (TFPI), comprising administering to a subject in need thereof a therapeutically effective amount of the antibody or antigen-binding fragment thereof of any one of embodiments 1-347 and 357, or the pharmaceutical composition of embodiment 358.

E360. A method of shortening bleeding time, comprising administering to a subject in need thereof a therapeutically effective amount of the antibody or antigen-binding fragment thereof of any one of embodiments 1-347 and 357, or the pharmaceutical composition of embodiment 358.

E361. The method of embodiment 358 or 360, wherein said subject is a human.

E362. The method of any one of embodiments 359-361, wherein said subject suffers from or is susceptible to a deficiency in blood coagulation.

E363. The method of any one of embodiments 359-361, wherein said subject suffers from or is susceptible to a platelet disorder.

E364. The method of any one of embodiments 359-361, wherein said subject suffers from or is susceptible to hemophilia A, B or C.

E365. The method of any one of embodiments 359-361, wherein said subject suffers from or is susceptible to hemophilia A or B.

E366. The method of any one of embodiments 359-361, wherein said subject suffers from or is susceptible to von Willebrand Disease (vWD).

E367. The method of embodiment 360, further comprising administering a therapeutically effective amount of FVII.

E368. The method of embodiment 367, wherein said method increases the generation of thrombin in the presence of TFPI.

E369. The method of any one of embodiments 359-368, comprising administering said antibody or antigen-binding fragment thereof, or pharmaceutical composition, intravenously.

E370. The method of any one of embodiments 359-368, comprising administering said antibody or antigen-binding fragment thereof, or pharmaceutical composition, subcutaneously.

E371. The method of any one of embodiments 359-368, wherein said antibody or antigen-binding fragment thereof, or pharmaceutical composition, is administered once every 3 days, once every 4 days, once every 5 days, once every 6 days, once a week, or twice a week.

E372. The antibody or antigen-binding fragment thereof of any one of embodiments 1-347 and 357, or the pharmaceutical composition of embodiment 358, for use as a medicament.

E373. The antibody or antigen-binding fragment thereof of any one of embodiments 1-347 and 357, or the pharmaceutical composition of embodiment 358 for use in reducing the activity of TFPI in a subject.

E374. The antibody or antigen-binding fragment thereof of any one of embodiments 1-347 and 357, or the pharmaceutical composition of embodiment 357 for use in shortening bleeding time in a subject.

E375. The antibody or antigen-binding fragment, or pharmaceutical composition of any one of embodiments 372-374, wherein said subject is a human.

E376. The antibody or antigen-binding fragment, or pharmaceutical composition of any one of embodiments 372-375, wherein said subject suffers from or is susceptible to a deficiency in blood coagulation.

E377. The antibody or antigen-binding fragment, or pharmaceutical composition of any one of embodiments 372-375, wherein said subject suffers from or is susceptible to hemophilia A, B or C.

E378. The antibody or antigen-binding fragment, or pharmaceutical composition of any one of embodiments 372-375, wherein said subject suffers from or is susceptible to hemophilia A or B.

E379. The antibody or antigen-binding fragment, or pharmaceutical composition of any one of embodiments 372-375, wherein said subject suffers from or is susceptible to von Willebrand Disease (vWD).

E380. The antibody or antigen-binding fragment, or pharmaceutical composition of any one of embodiments 372-375, wherein said subject suffers from or is susceptible to a platelet disorder.

E381. Use of the antibody or antigen-binding fragment thereof of any one of embodiments 1-348 and 357, or the pharmaceutical composition of embodiment 358, for reducing the activity of TFPI in a subject.

E382. Use of the antibody or antigen-binding fragment thereof of any one of embodiments 1-348 and 357, or the pharmaceutical composition of embodiment 358, in the manufacture of a medicament for reducing the activity of TFPI in a subject.

E383. Use of the antibody or antigen-binding fragment thereof of any one of embodiments 1-348 and 357, or the pharmaceutical composition of embodiment 358, for shortening bleeding time in a subject.

E384. Use of the antibody or antigen-binding fragment thereof of any one of embodiments 1-348 and 357, or the pharmaceutical composition of embodiment 358, in the manufacture of a medicament for shortening bleeding time in a subject.

E385. The use of any one of embodiments 381-384, wherein said subject is a human.

E386. The use of any one of embodiments 381-384, wherein said subject suffers from or is susceptible to a deficiency in blood coagulation.

E387. The use of any one of embodiments 381-384, wherein said subject suffers from or is susceptible to hemophilia A, B or C.

E388. The use of any one of embodiments 381-384, wherein said subject suffers from or is susceptible to hemophilia A or B.

E389. The use of any one of embodiments 381-384, wherein said subject suffers from or is susceptible to von Willebrand Disease (vWD).

E390. The use of any one of embodiments 381-384, wherein said subject suffers from or is susceptible to a platelet disorder.

BRIEF DESCRIPTION OF THE DRAWINGS

FIGS. 3A and 3B show the duration in decreasing bleeding in Hemophilia A Factor VIII deficient (FVIII −/−) mice when 2A8-200 and 2A8 antibodies (used as reference antibodies in this study) were administered. FIG. 3C shows the duration of effect in Hemophilia A mice when TFPI 4D8 (control), TFPI-21, TFPI-23, and TFPI-24 antibodies were administered. FIGS. 3D and 3E show the duration of Hemophilia A mice when TFPI-106 and TFPI-118 antibodies were administered. Antibodies were administered to hemophilia A mice (FVIII −/−) by intravenous injection at 6 mg/kg at the indicated time points (hours (h)) before injury. Total volume of blood loss (μL) was then measured after tail transection. Vehicle (saline) treated hemophilia A mice served as a control. All measurements are presented as mean±SEM. *=P<0.05. FVIII+/+(wild-type) mice received saline. n=5/group.

FIG. 5, comprising panels A and B, each of which comprises six panels (FIG. 5A, 1 through 6 and FIG. 5B, 1 through 6) shows microphotographs of intravital microscopy (IVM) demonstrating that TFPI is detected in the platelet thrombus and along the endothelium in vivo at the site of vessel injury in a wild type mouse. FIG. 5B, panel 4 (60 seconds) shows strong green and red fluorescent signals (both light gray where red fluorescence can be seen to the left of the vessel injury site and green signal is primarily detected towards the right side of the injury site) demonstrating both platelet accumulation and TFPI are detected at the site of injury. FIG. 5B, panel 5, shows both red (platelets) and green (TFPI) fluorescence signals at the site of injury by 60 seconds where both signals are greater than at 30 seconds. FIG. 5B, panel 6, shows decreased red signal (platelets) and decreased green signal (TFPI) both still detectable at the site of injury at 120 seconds.

FIG. 6A shows the accumulation of platelets at the site of injury in wild type mice (WT) at 0.5 hours post-injury where the mice received only saline control compared with the lack of platelet accumulation in the hemophilia A mouse at 0.5 hours where saline was administered. Platelet accumulation was detected in hemophilia A mice at 0.5 hours where recombinant factor VIII (rFVIII) or TFPI-106 was administered. The thrombus accumulation effect was still detected at 168 hours in hemophilia A mice administered TFPI-106.

FIG. 6B shows the generation of fibrin at the site of injury in wild type mice (WT)

at 0.5 hours post-injury where the mice received only saline control compared with the lack of detectable fibrin generation in the hemophilia A mouse at 0.5 hours where saline was administered. Fibrin generation was detected in hemophilia A mice at 0.5 hours where recombinant factor VIII (rFVIII) or TFPI-106 was administered. The fibrin generation effect was still detected at 168 hours in hemophilia A mice administered TFPI-106.

Figure 7:
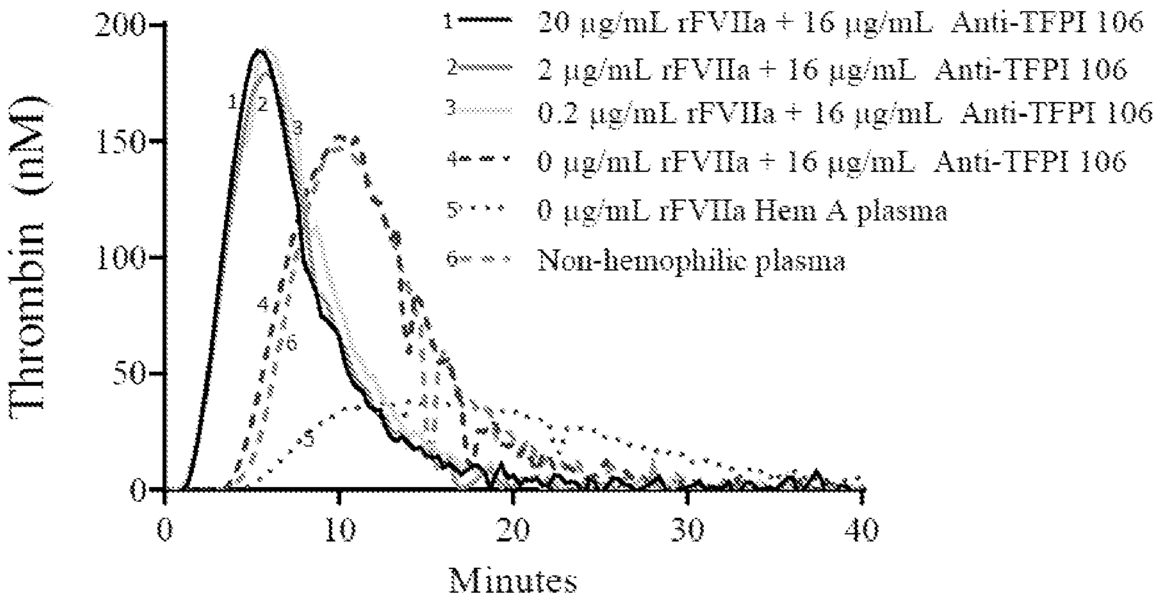

FIG. 7 depicts a graph showing the effect on a thrombin generation assay (TGA) of administration of TFPI-106 and recombinant factor VIIa (rFVIIa) in severe hemophilia A plasma in the presence of 1 pm tissue factor and 4 μM phospholipids. The graph shows the thrombograms for hemophilia A plasma with TFPI-106 alone (16 μg/ml) and in combination with rFVIIa (20 μg/ml; 2 μg/ml; or 0.2 μg/ml). Also shown are the thrombograms for hemophilic A plasma and non-hemophilic plasma with neither TFPI-106 nor rFVIIa.

Figure 8A:
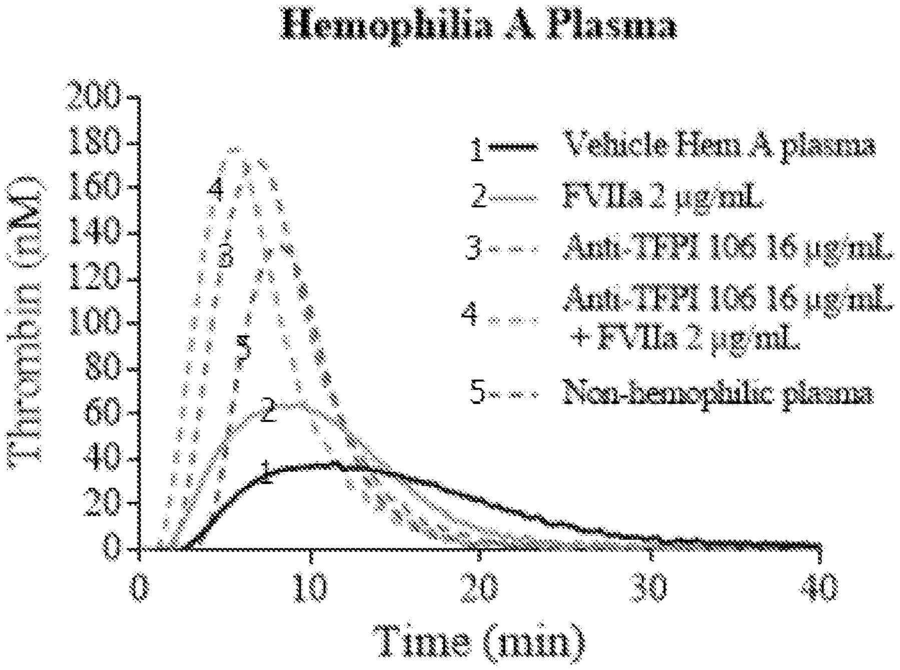

FIG. 8A depicts thrombograms showing the effect on thrombin generation in the presence of 1 pM tissue factor and 4 μM phospholipids in hemophilia A plasma in the presence of TFPI-106 with or without rFVIIa or in the presence of rFVIIa only. Non-hemophilic plasma is included as a control.

Figure 8B:
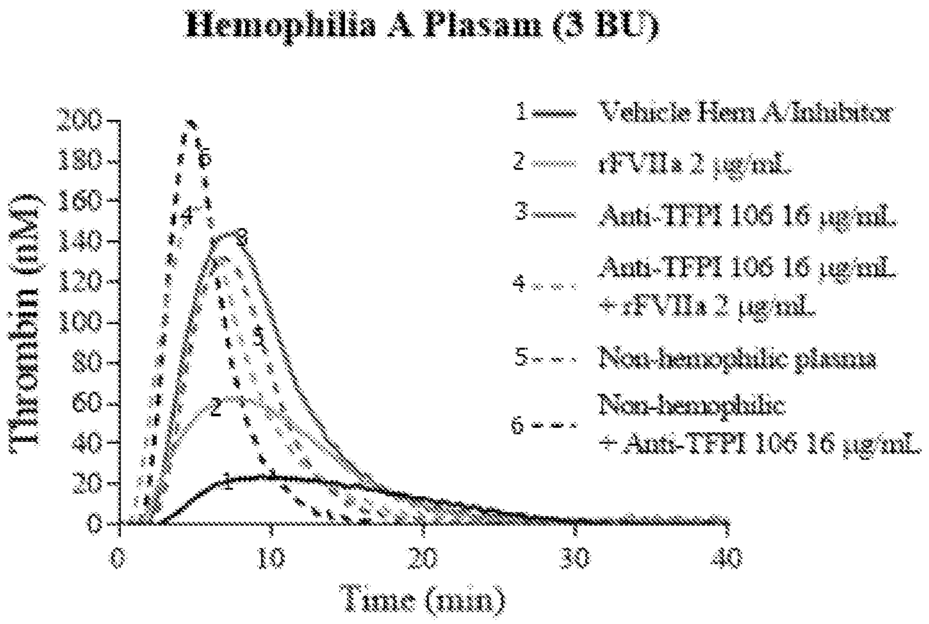

FIG. 8B depicts thrombograms showing the effect on thrombin generation in the presence of three Bethesda Units (3 BU) of an inhibitor in citrated platelet poor hemophilia A plasma in the presence of TFPI-106 with or without rFVIIa or in the presence of rFVIIa only. Non-hemophilic plasma is included as a control. Also included a control non-hemophilic plasma to which TFPI-106 (16 μg/ml) was added.

Figure 8C:
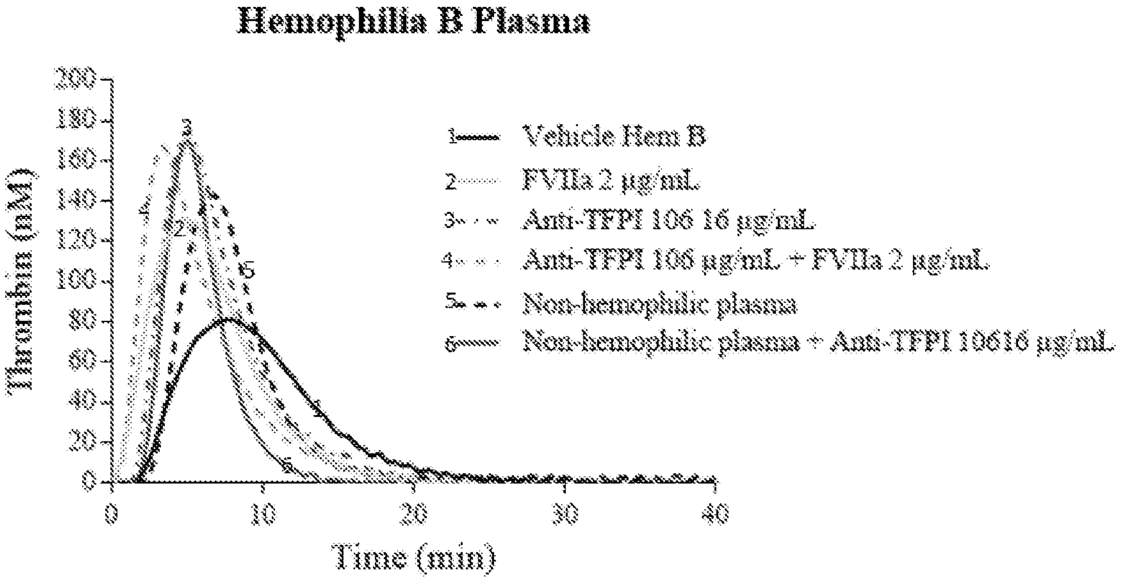

FIG. 8C depicts thrombograms showing the effect on thrombin generation in the presence of three Bethesda Units (3 BU) of an inhibitor in citrated platelet poor hemophilia B plasma in the presence of TFPI-106 with or without rFVIIa or in the presence of rFVIIa only. Non-hemophilic plasma is included as a control. Also included a control non-hemophilic plasma to which TFPI-106 (16 μg/ml) was added.

Figure 9A:
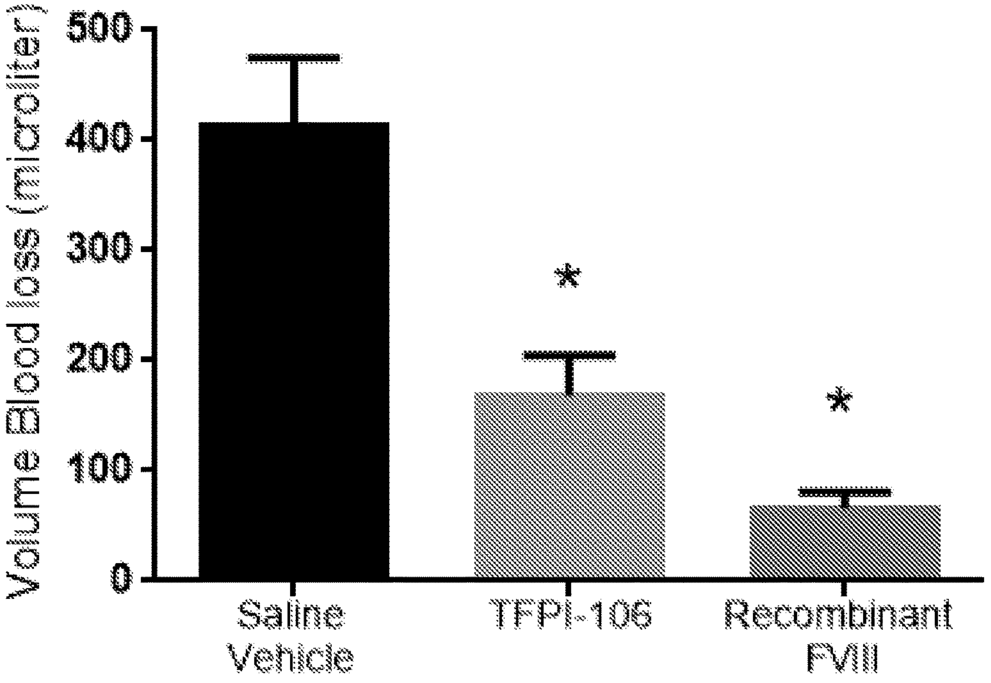
Figure 9B:
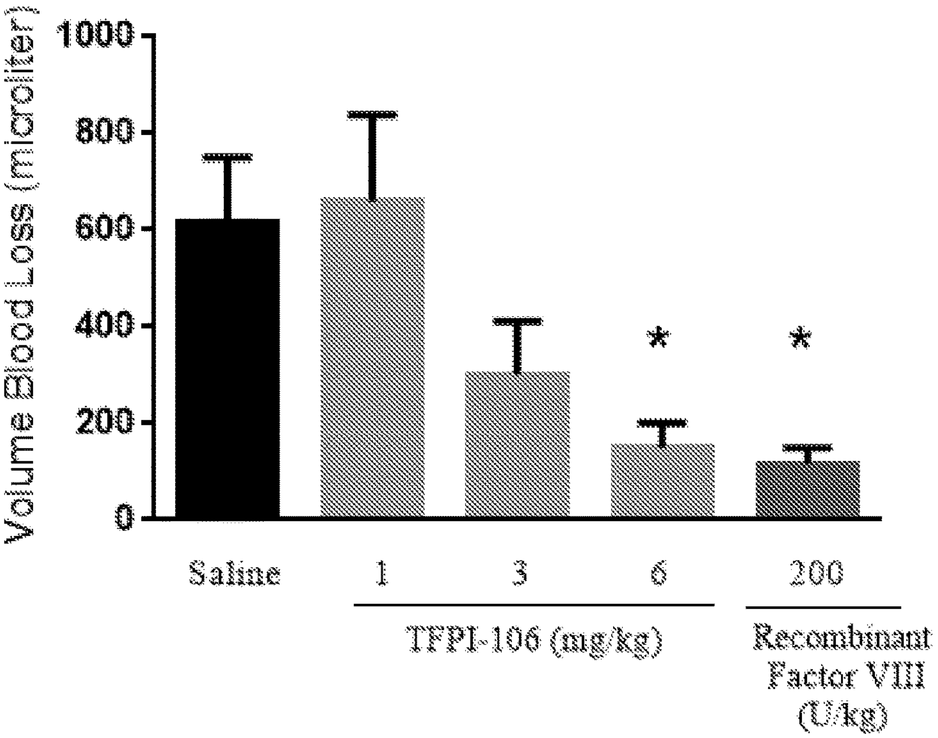

FIG. 9A shows the effect on blood loss compared to control of administering antibody TFPI-106 (6 mg/kg) and separately recombinant Factor VIII (200 units/kg) to hemophilia A mice immediately after tail transection. FIG. 9B shows the effect on blood loss compared to control of administering three different doses of antibody TFPI-106 (6 mg/kg) and separately recombinant Factor VIII (200 units/kg) to hemophilia A mice 2 minutes after tail transection.

Figure 10A:
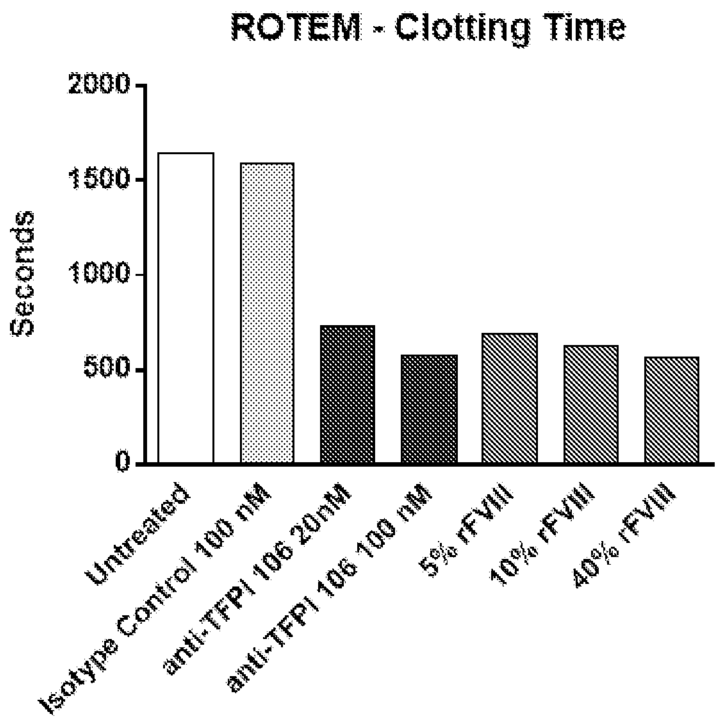
Figure 10B:
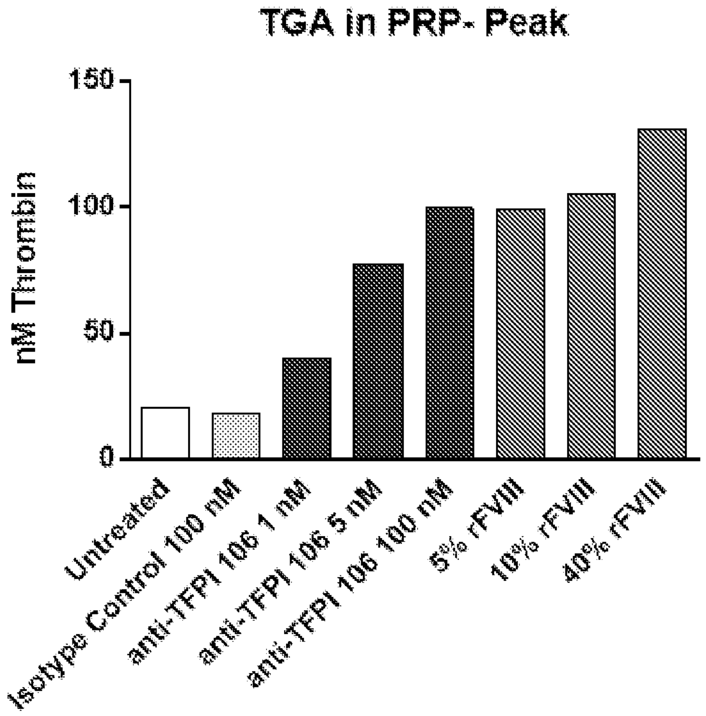

FIG. 10A shows the effect of different concentrations of TFPI 106 compared to recombinant Factor VIII on clotting time of whole blood from a human patient with severe hemophilia A. FIG. 10B shows the effect of different concentrations of TFPI 106 compared to recombinant Factor VIII on peak thrombin generation in platelet rich plasma from a human patient with severe hemophilia A.

Figure 11A:
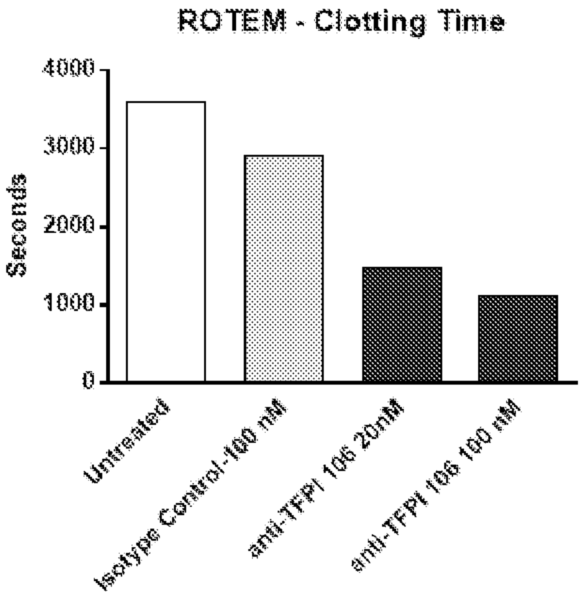
Figure 11B:
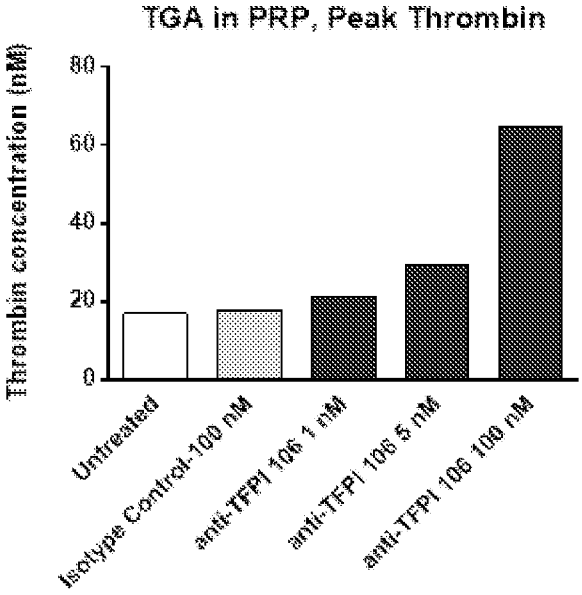
Figure 11C:
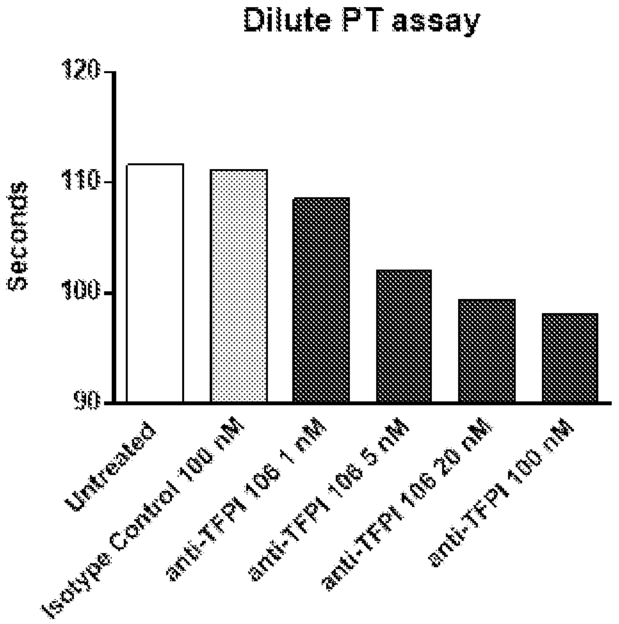

FIG. 11A shows the effect of different concentrations of TFPI 106 on clotting time of whole blood from a human patient with severe hemophilia A and inhibitors to FVIII. FIG. 11B shows the effect of different concentrations of TFPI 106 on peak thrombin generation in platelet rich plasma from a human patient with severe hemophilia A and inhibitors to FVIII. FIG. 11C shows the effect of different concentrations of TFPI 106 on clotting time of platelet poor plasma from a human patient with severe hemophilia A and inhibitors to FVIII.

Figure 12A:
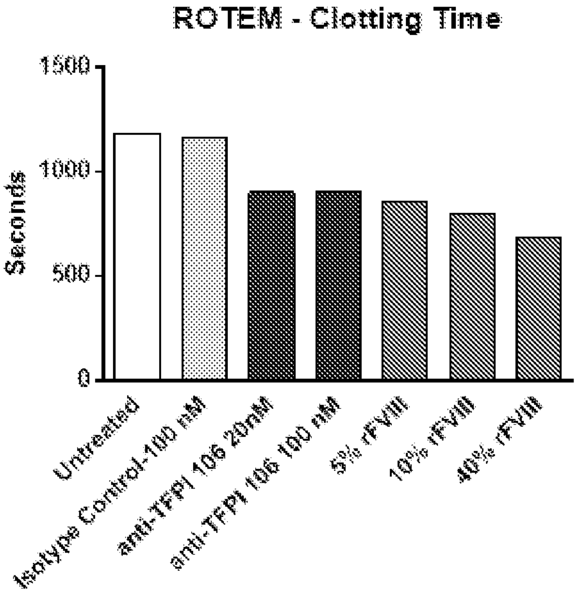
Figure 12B:
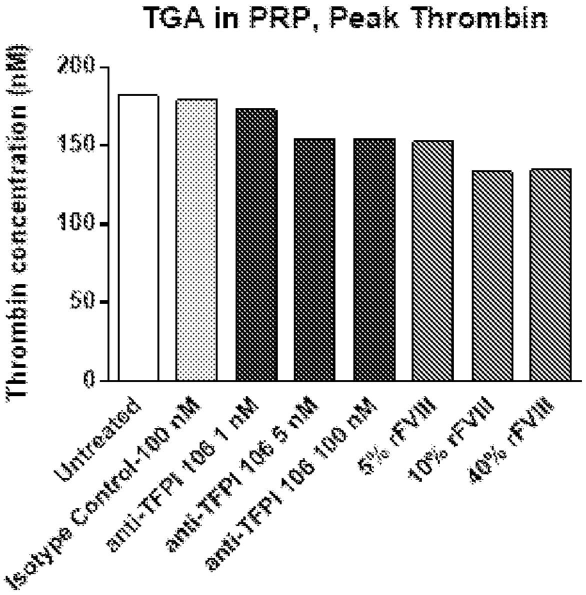
Figure 12C:
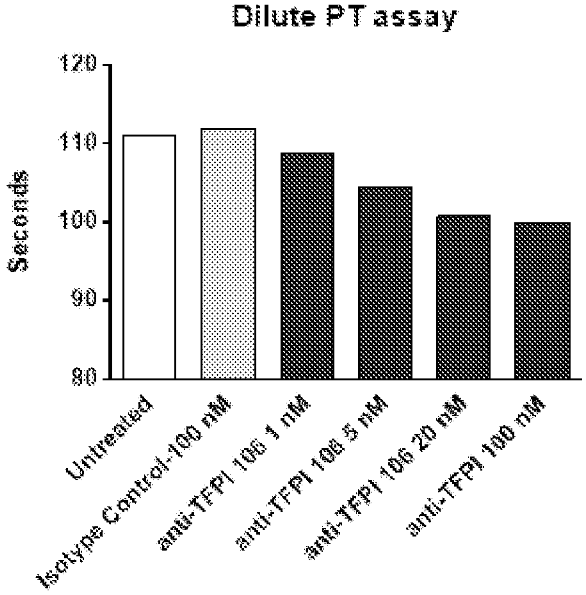

FIG. 12A shows the effect of different concentrations of TFPI 106 compared to recombinant Factor VIII on clotting time of whole blood from a human patient with moderate hemophilia A. FIG. 12B shows the effect of different concentrations of TFPI 106 compared to recombinant Factor VIII on peak thrombin generation in platelet rich plasma from a human patient with moderate hemophilia A. FIG. 12C shows the effect of different concentrations of TFPI 106 on clotting time of platelet poor plasma from a human patient with moderate hemophilia A.

Figure 13A:
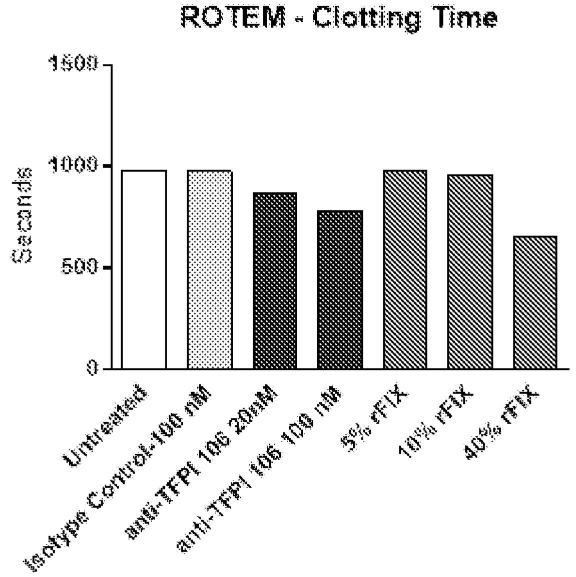
Figure 13B:
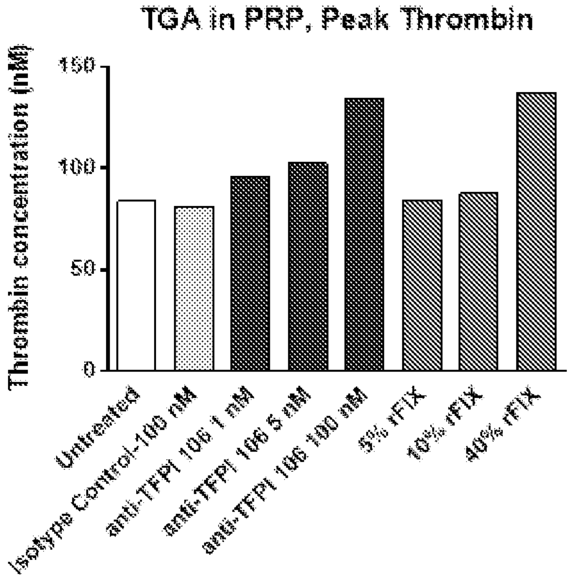

FIG. 13A shows the effect of different concentrations of TFPI 106 compared to recombinant Factor IX on clotting time of whole blood from a human patient with moderate hemophilia B. FIG. 13B shows the effect of different concentrations of TFPI 106 compared to recombinant Factor IX on peak thrombin generation in platelet rich plasma from a human patient with moderate hemophilia B.

Figure 13C:
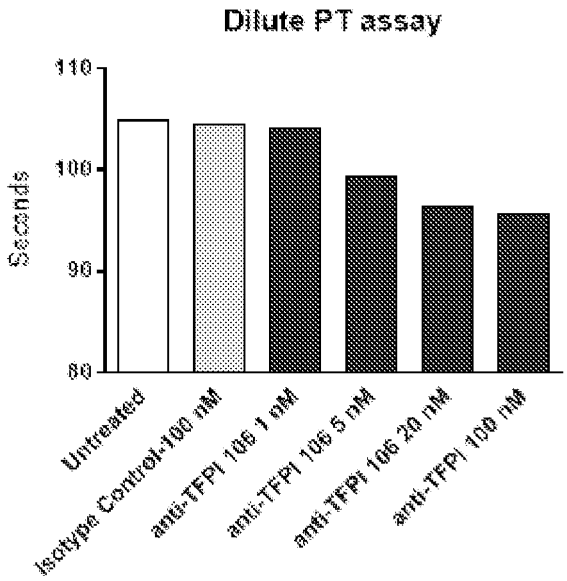

FIG. 13C shows the effect of different concentrations of TFPI 106 on clotting time of platelet poor plasma from a human patient with moderate hemophilia B.

Figure 14A:
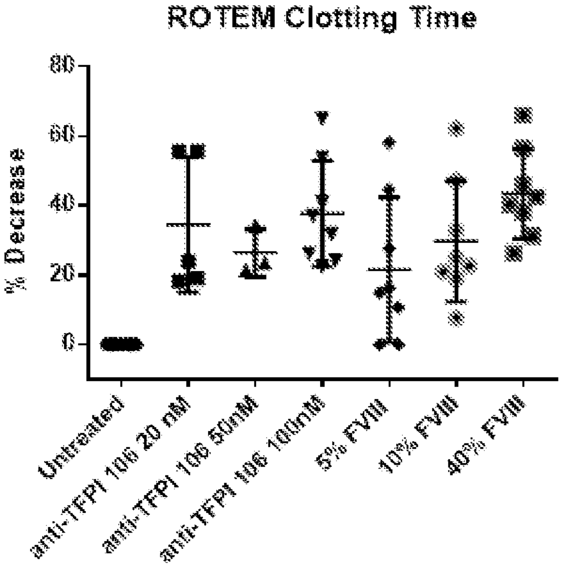
Figure 14B:
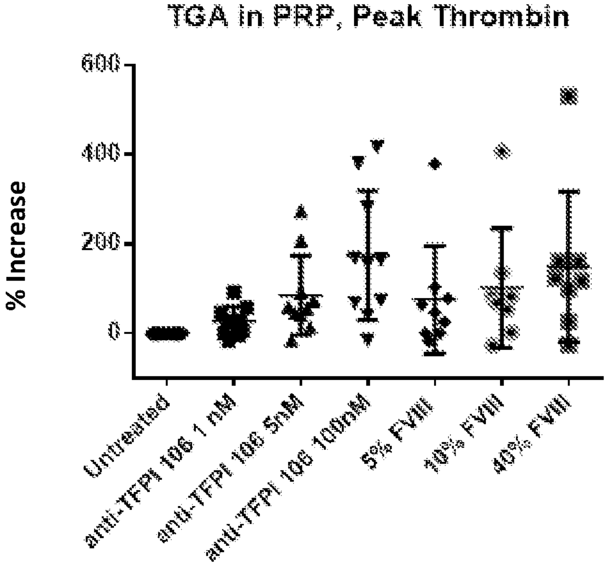
Figure 14C:
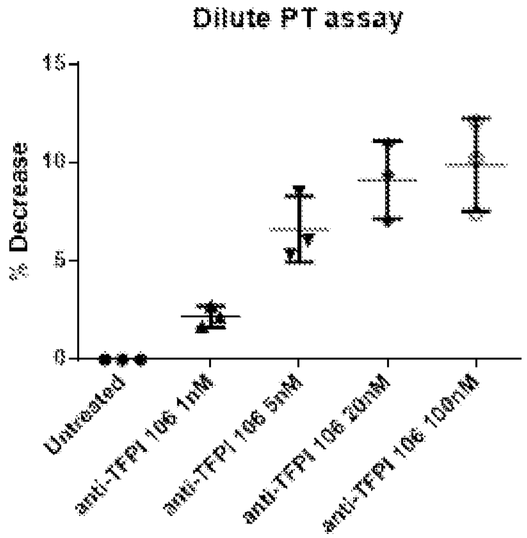

FIG. 14A shows the effect of different concentrations of TFPI 106 compared to recombinant Factor VIII on clotting time of whole blood from multiple human patients with hemophilia A. FIG. 14B shows the effect of different concentrations of TFPI 106 compared to recombinant Factor VIII on peak thrombin generation in platelet rich plasma from multiple human patients with hemophilia A. FIG. 14C shows the effect of different concentrations of TFPI 106 on clotting time of platelet poor plasma from multiple human patients with hemophilia B.

DETAILED DESCRIPTION OF THE INVENTION

1. Overview

As noted above, patients with hemophilia have some ability to stop bleeds through their intact extrinsic pathway; however the extrinsic pathway is insufficient to provide protection because it is rapidly shut down by the Tissue Factor Pathway Inhibitor (TFPI). Blocking/neutralizing TFPI inhibition in these patients can compensate for an inadequate FXa generation and normalize the bleeding diathesis. Accordingly, disclosed and exemplified herein are antibodies and antigen-binding fragments thereof that specifically bind to TFPI and inhibit the activity thereof.

2. Definitions

By "reducing the activity of TFPI" is meant that the antibody or antigen-binding fragment thereof can: (i) decrease clotting time when compared to the clotting time in the absence of the antibody as measured by, e.g., a plasma based dilute prothrombin time assay; (ii) reduce clotting time in whole blood as compared to the clotting time in the absence of the antibody as measured by, e.g., thromboelastrography or rotational thromboelastometry; (iii) increase thrombin generation; (iv) increase FXa activity in the presence of TFPI; (v) enhance platelet accumulation in the presence of TFPI; (vi) increase fibrin generation in the presence of TFPI; or (vii) any combination thereof. The inhibitory activities of an antibody or antigen-binding fragment can, but need not be dose-dependent (e.g., causing a dose-dependent decrease in clotting time as measured in a plasma based dilute prothrombin time assay).

Further, as disclosed and exemplified herein, co-crystal structures of anti-TFPI antibodies and the Kunitz Domain 2 (K2 domain) of TFPI were obtained. Structural analysis shows that the exemplary antibodies of the invention recognize unique epitopes of TFPI, as compared to other publicly disclosed TFPI antibodies (which were used as references antibodies in the Examples). For example, as shown in FIGS. 1A-1F and FIGS. 2A-2E, as compared to several reference TFPI antibodies (R&D (Mab2974) Fab, Novo2021 (also called hz4F36) Fab, 2A8 Fab), TFPI-23, TFPI-24, and 4D8 antibodies bind to non-overlapping sites in the K2 domain of TFPI.

Accordingly, in certain embodiments, the antibodies (and antigen-binding fragments) disclosed herein recognize a unique epitope of TFPI, located at the K2 domain of TFPI. Based on the co-crystal structure and computational alanine scan, this epitope comprises three residues that are important for antibody-antigen interactions: Ile105, Arg107, and Leu131 (according to the numbering of human TFPI as shown in SEQ ID NO: 2). Mutating these three residues to Alanine results in loss of antibody binding. For example, antibodies TFPI-23 and its variants (e.g., TFPI-106 and TFPI-107) all recognize this epitope.

In certain embodiments, the recognition of key epitope residues disclosed herein allows the antibodies (and antigen-binding fragments thereof) to reduce the activity of TFPI. In particular, the crystal structure shows that the K2 domain of TFPI adopts a cone-shaped structure, with the tip of the cone (especially Arg107) binding to FXa. TFPI-23 and TFPI-24 both recognize the tip of this cone-shaped region and block the binding of TFPI to FXa. Antibody 4D8 recognizes a different epitope in K2 domain. Although not interacting directly with residues at the tip of the cone, 4D8 nonetheless blocks the binding of TFPI to FXa. Table 16 summarizes the non-overlapping epitope residues recognized by the exemplary antibodies disclosed herein, as compared to other publicly known TFPI antibodies.

Further, in certain embodiments, antibodies and antigen-binding fragments thereof disclosed herein have demonstrated desirable pharmacological activities and pharmacokinetic properties for treatment of coagulation deficiencies (such as hemophilia) and for reducing bleeding time.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to a TFPI epitope is an antibody that binds this epitope with greater affinity, avidity, more readily, and/or with greater duration than it binds to other TFPI epitopes or non-TFPI epitopes. It is also understood by reading this definition, for example, that an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody or a peptide receptor which recognizes and binds to a cognate ligand or binding partner (e.g., an anti-TFPI antibody that binds TFPI) in a sample, but does not substantially recognize or bind other molecules in the sample, specifically binds to that cognate ligand or binding partner. Thus, under designated assay conditions, the specified binding moiety (e.g., an antibody or an antigen-binding portion thereof or a receptor or a ligand binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, Biacore™ (GE Healthcare, Piscataway, N.J.), KinExA, fluorescence-activated cell sorting (FACS), Octet™ (ForteBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. Also, an antibody is said to "specifically bind" an antigen when the equilibrium dissociation constant ($K_D$) is ≤7 nM.

The term "binding affinity" is herein used as a measure of the strength of a non-covalent interaction between two molecules, e.g., and antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA.

A competitive binding assay can be conducted in which the binding of the antibody to the antigen is compared to the binding of the target by another ligand of that target, such as another antibody or a soluble receptor that otherwise binds the target. The concentration at which 50% inhibition occurs is known as the K. Under ideal conditions, the $K_i$ is equivalent to $K_D$. The $K_i$ value will never be less than the $K_D$, so measurement of $K_i$ can conveniently be substituted to provide an upper limit for $K_D$.

Following the above definition, binding affinities associated with different molecular interactions, e.g., comparison of the binding affinity of different antibodies for a given antigen, may be compared by comparison of the $K_D$ values for the individual antibody/antigen complexes. $K_D$ values for antibodies or other binding partners can be determined using methods well established in the art. One method for determining the $K_D$ is by using surface plasmon resonance, typically using a biosensor system such as a Biacore® system.

Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind TFPI.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-TFPI molecule.

In general, a TFPI antibody needs to bind to TFPI with high affinity, in order to effectively reduce the activities of TFPI. However, when the binding affinity of an antibody is too high, the antibody can quickly get internalized and degraded by a host cell. This could potentially result in a short half-life and repeated injections. For example, antibody TFPI-23 shows a lower binding affinity (Kd) as compared to TFPI-24, and under certain circumstances, appears more desirable for clinical uses because it has a lower internalization rate and longer half-life. Accordingly, binding affinities (Kd) from $5\times10^{-7}$M to about $5\times10^{-11}$ M, in particular from about $1\times10^{-8}$M to about $1\times10^{-10}$ M, are generally desirable, especially for treating a chronic condition (e.g., hemophilia) that require repeated injections. Without wishing to be bound by any particular theory, this affinity range is believed to strike a balance between (i) binding affinities that are needed for effectively inhibiting the activities of TFPI, and (ii) a longer half-life and reduced antibody internalization.

Specific amino acid residue positions in TFPI are numbered according to SEQ ID NO: 2 (human TFPIα K1K2K3). However, the present invention is not limited to SEQ ID NO: 2. Corresponding residues from other TFPI homologs, isoforms, variants, or fragments can be identified according to sequence alignment or structural alignment that is known in the art. For example, alignments can be done by hand or by using well-known sequence alignment programs such as ClustalW2, or "BLAST 2 Sequences" using default parameters. For example, Arg107 of SEQ ID NO: 2 corresponds to Arg104 of Mouse TFPI K1K2 (SEQ ID NO: 4).

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al. Proc. Natl. Acad. Sci. USA 85:5879-5883 (1988)). Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al. Proc. Natl. Acad. Sci. USA 90:6444-6448 (1993); Poljak et al., 1994, Structure 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three complementarity determining regions (CDRs), and contribute to the formation of the antigen-binding site of antibodies.

Residues in a variable domain are numbered according Kabat, which is a numbering system used for heavy chain variable domains or light chain variable domains of the compilation of antibodies. See, Kabat et al., Sequences of Proteins of Immunological Interest, 5th Ed. Public Health Service, National Institutes of Health, Bethesda, Md. (1991)). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the 2012 release of Abysis (www.abysis.org) is used herein to assign Kabat numbering to variable regions unless otherwise noted.

Specific amino acid residue positions in an antibody (such as paratope residues disclosed herein) are also numbered according to Kabat.

"Complementarity Determining Regions" (CDRs) can be identified according to the definitions of the Kabat, Chothia, the accumulation of both Kabat and Chothia, AbM, contact, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). AbM definition of CDRs is a compromise between Kabat and Chothia and uses Oxford Molecular's AbM antibody modeling software (Accelrys®). The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, Journal of Biological Chemistry, 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches.

In the Examples (see Tables 3 and 4), the CDRs are defined as follows (numbering according to Kabat; H: heavy chain; L: light chain):

CDR-H1: H26-H35B; CDR-H2: H50-H65; CDR-H3: H95-H102

CDR-L1: L24-L34; CDR-L2: L50-L56; CDR-L3: L89-L97

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4. In the Examples (see Tables 3 and 4), FR residues include the following (numbering according to Kabat; H: heavy chain; L: light chain):

| | FR1 | FR2 | FR3 | FR4 |
|---|---|---|---|---|
| Heavy Chain | H1-H25 | H36-H49 | H66-H94 | H103-H113 |
| Light Chain | L1-L23 | L35-L49 | L57-L88 | L98-L107 |

An "epitope" refers to the area or region of an antigen (Ag) to which an antibody specifically binds, e.g., an area or region comprising residues that interacts with the antibody (Ab). Epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "epitope" as used herein, is defined as a portion of an antigen to which an antibody can specifically bind as determined by any method well known in the art, for example, by conventional immunoassays. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to TFPI. That is, the antibodies compete for binding to the antigen such that the antibodies compete for binding to the antigen-binding site of an anti-TFPI antibody of the disclosure.

The term "paratope" is derived from the above definition of "epitope" by reversing the perspective, and refers to the area or region of an antibody molecule which is involved in binding of an antigen, e.g., an area or region comprising residues that interacts with the antigen. A paratope may be linear or conformational (such as discontinuous residues in CDRs).

The epitope/paratope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen/deuterium exchange Mass Spectrometry (HX-MS) and various competition binding methods. As each method relies on a unique principle, the description of an epitope is intimately linked to the method by which it has been determined. Thus, the epitope/paratope for a given antibody/antigen pair will be defined differently depending on the mapping method employed.

At its most detailed level, the epitope/paratope for the interaction between the Ag and the Ab can be defined by the spatial coordinates defining the atomic contacts present in the Ag-Ab interaction, as well as information about their relative contributions to the binding thermodynamics. At one level, an epitope/paratope residue can be characterized by the spatial coordinates defining the atomic contacts between the Ag and Ab. In one aspect, the a epitope/paratope residue can be defined by a specific criterion, e.g., distance between atoms in the Ab and the Ag (e.g., a distance of equal to or less than 4 Å from a heavy atom of the cognate antibody and a heavy atom of the antigen ("contact" residues)). In another aspect, an epitope/paratope residue can be characterized as participating in a hydrogen bond interaction with the cognate antibody/antigen, or with a water molecule that is also hydrogen bonded to the cognate antibody/antigen (water-mediated hydrogen bonding). In another aspect, an epitope/paratope residue can be characterized as forming a salt bridge with a residue of the cognate antibody/antigen. In yet another aspect, an epitope/paratope residue can be characterized as a residue having a non-zero change in buried surface area (BSA) due to interaction with the cognate antibody/antigen. At a further less detailed level, epitope/paratope can be characterized through function, e.g., by competition binding with other Abs. The epitope/paratope can also be defined more generically as comprising amino acid residues for which substitution by another amino acid will alter the characteristics of the interaction between the Ab and Ag (e.g. alanine scanning).

In the context of an X-ray derived crystal structure defined by spatial coordinates of a complex between an antibody, e.g., a Fab fragment or two Fab fragments, and its antigen, unless otherwise specified, an epitope residue refers to a TFPI residue (i) having a heavy atom (i.e., a non-hydrogen atom) that is within a distance of 4 Å from a heavy atom of the cognate antibody (also called "contact" residues); (ii) participating in a hydrogen bond with a residue of the cognate antibody, or with a water molecule that is also hydrogen bonded to the cognate antibody (water-mediated hydrogen bonding), (iii) participating in a salt bridge to a residue of the cognate antibody, and/or (iv) having a non-zero change in buried surface area (BSA) due to interaction with the cognate antibody. In general, a cutoff is imposed for BSA to avoid inclusion of residues that have minimal interactions. Therefore, unless otherwise specified, epitope residues under category (iv) are selected if it has a BSA of 20 $Å^2$ or greater, or is involved in electrostatic interactions when the antibody binds to TFPI. Similarly, in the context of an X-ray derived crystal structure, unless otherwise specified or contradicted by context, a paratope residue, refers to an antibody residue (i) having a heavy atom (i.e., a non-hydrogen atom) that is within a distance of 4 Å from a heavy atom of TFPI (also called "contact" residues), (ii) participating in a hydrogen bond with a TFPI residue, or with a water molecule that is also hydrogen bonded to TFPI (water-mediated hydrogen bonding), (iii) participating in a salt bridge to a residue of TFPI, and/or (iv) having a non-zero change in buried surface area due to interaction with TFPI. Again, unless otherwise specified, paratope residues under category (iv) are selected if it has a BSA of 20 $Å^2$ or greater, or is involved in electrostatic interactions when antibody binds to TFPI.

From the fact that descriptions and definitions of epitopes, dependent on the epitope mapping method used, and obtained at different levels of detail, it follows that comparison of epitopes for different Abs on the same Ag can similarly be conducted at different levels of detail. For example, epitopes described on the amino acid level, e.g., determined from an X-ray structure, are said to be identical if they contain the same set of amino acid residues. Epitopes are said to be separate (unique) if no amino acid residue is shared by the epitopes. Epitopes characterized by competition binding are said to be overlapping if the binding of the corresponding antibodies are mutually exclusive, i.e., binding of one antibody excludes simultaneous or consecutive binding of the other antibody; and epitopes are said to be separate (unique) if the antigen is able to accommodate binding of both corresponding antibodies simultaneously.

The epitope and paratope for a given antibody/antigen pair may be identified by routine methods. For example, the general location of an epitope may be determined by assessing the ability of an antibody to bind to different fragments or variant TFPI polypeptides as more fully described previously elsewhere herein. Specific residues within TFPI that make contact with specific residues within an antibody may also be determined using routine methods, such as those described in the examples. For example, antibody/antigen complex may be crystallized. The crystal structure may be determined and used to identify specific sites of interaction between the antibody and antigen.

The term "compete", as used herein with regard to an antibody, means that binding of a first antibody, or an antigen-binding portion thereof, to an antigen reduces the subsequent binding of the same antigen by a second antibody or an antigen-binding portion thereof. In general, the binding a first antibody creates steric hindrance, conformational change, or binding to a common epitope (or portion thereof), such that the binding of the second antibody to the same antigen is reduced. Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach. Furthermore, a high throughput process for "binning" antibodies based upon their competition is described in International Patent Application No. WO2003/48731. Competition is present if one antibody (or fragment) reduces the binding of another antibody (or fragment) to TFPI. For example, a sequential binding competition assay may be used, with different antibodies being added sequentially. The first antibody may be added to reach binding that is close to saturation. Then, the second antibody is added. If the binding of second antibody to TFPI is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other. An exemplary antibody competition assay (and overlapping epitope analysis) by SPR is provided in Example 6.

An anti-TFPI antibody of the disclosure may have the ability to compete or cross-compete with another antibody of the disclosure for binding to TFPI as described herein. For example, an antibody of the disclosure may compete or cross-compete with antibodies described herein for binding to TFPI, or to a suitable fragment or variant of TFPI that is bound by the antibodies disclosed herein.

That is, if a first anti-TFPI antibody competes with a second antibody for binding to TFPI, but it does not compete where the second antibody is first bound to TFPI, it is deemed to "compete" with the second antibody (also referred to as unidirectional competition). Where an antibody competes with another antibody regardless of which antibody is first bound to TFPI, then the antibody "cross-competes" for binding to TFPI with the other antibody. Such competing or cross-competing antibodies can be identified based on their ability to compete/cross-compete with a known antibody of the disclosure in standard binding assays. For example, SPR, e.g., by using a Biacore™ system, ELISA assays or flow cytometry may be used to demonstrate competition/cross-competition. Such competition/cross-competition may suggest that the two antibodies bind to identical, overlapping or similar epitopes.

An anti-TFPI antibody of the disclosure may therefore be identified by a method that comprises a binding assay which assesses whether or not a test antibody is able to compete/cross-compete with a reference antibody of the disclosure (e.g., TFPI-3, TFPI-21, TFPI-23, TFPI-24, TFPI-26, TFPI-106, TFPI-107, TFPI-108, TFPI-109, TFPI-110, TFPI-111, TFPI-112, TFPI-113, TFPI-114, 4D8, 6B7.c5, 7A4.D9) for a binding site on the target molecule.

An "Fc fusion" protein is a protein wherein one or more polypeptides are operably linked to an Fc polypeptide. An Fc fusion combines the Fc region of an immunoglobulin with a fusion partner.

The binding affinity of an antibody can be expressed as Kd value, which refers to the dissociation rate of a particular antigen-antibody interaction. Kd is the ratio of the rate of dissociation, also called the "off-rate (koff)", to the association rate, or "on-rate (kon)". Thus, Kd equals koff/kon and is expressed as a molar concentration (M), and the smaller the Kd, the stronger the affinity of binding. Kd values for antibodies can be determined using methods well established in the art. One exemplary method for measuring Kd is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the Kd of an antibody is by using Bio-Layer Interferometry, typically using OCTET® technology (Octet QKe system, ForteBio).

Alternatively or in addition, a KinExA® (Kinetic Exclusion Assay) assay, available from Sapidyne Instruments (Boise, Id.) can also be used.

The term "therapeutically effective amount" means an amount of an anti-TFPI antibody or a fragment thereof, or a combination comprising such antibody or fragment thereof, that is of sufficient quantity to achieve the intended purpose, such as an increase in coagulation, or in the case of hemophilia, a decrease in clotting time, or otherwise causing a measurable benefit in vivo to a subject in need. The precise amount will depend upon numerous factors, including, but not limited to the components and physical characteristics of the therapeutic composition, intended patient population, individual patient considerations, and the like, and can be determined by one skilled in the art.

By the term "synergistic therapeutic effective amount," is meant an amount of an anti-TFPI antibody or an antigen-binding fragment thereof that when provided with a second therapeutic agent, e.g., factor VIIa (FVIIa), provides a measurable benefit (e.g., decreased clotting time, decreased bleeding time, increased fibrin generation, enhanced platelet accumulation, and the like) that is greater than the additive measurable effect of each therapeutic agent or antibody administered alone.

The term "treatment" includes prophylactic and/or therapeutic treatments. If it is administered prior to clinical manifestation of a condition, the treatment is considered prophylactic. Therapeutic treatment includes, e.g., ameliorating or reducing the severity of a disease, or shortening the length of the disease.

The term "about", as used here, refers to +/−10% of a value.

3. Anti-TFPI Antibodies

Disclosed and exemplified herein are antibodies (and antigen-binding fragments thereof) that bind to the Tissue Factor Pathway Inhibitor (TFPI). The antibodies and antibody fragments bind to unique epitopes of TFPI. In certain embodiments, the recognition of certain epitope residues in TFPI allows the antibodies (and antigen-binding fragments thereof) to reduce the activity of TFPI. Further, in certain embodiments, antibodies (and antigen-binding fragments thereof) disclosed herein have demonstrated desirable pharmacological activities and pharmacokinetic properties for treatment of coagulation deficiencies and reducing bleeding time.

A. Tissue Factor Pathway Inhibitor (TFPI)

TFPI is a multi-valent Kunitz domain containing protease inhibitor. Exemplary sequences of human, mouse, cynomolgus monkey, rabbit, and rat TFPI are provided in Table 2.

Human TFPI is an extracellular glycoprotein with two predominant forms, TFPI-alpha and TFPI-beta. TFPI alpha, which is a 276 amino acid glycosylated protein (MW 43 kD) is the largest form of TFPI and consists of three Kunitz like domains and a basic carboxy terminal region.

Alternative splicing produces TFPI-beta, which contains Kunitz Domain 1 (K1) and Kunitz Domain 2 (K2), but contains an alternative C-terminal portion lacking Kunitz domain 3 (K3) and the basic region. TFPI-beta is anchored to cell membranes through post-translational modification with a glycosylphosphatidylinositol (GPI) anchor.

The primary targets of TFPI are the proteases Factor Xa (FXa) and Factor VIIa (FVIIa), which are key factors in the initiation stage of the coagulation cascade. Biochemical analysis has revealed that K2 is the inhibitor of FXa, while K1 inhibits FVIIa-Tissue Factor complex. The role of K3 is unclear as it does not seem to have direct protease inhibitory activity, but may serve as a recognition site for the co-factor Protein S. The C-terminal domain, unique to TFPI-alpha, may be involved in the recognition of prothrombinase on the platelet surface.

Kunitz domain 1 (K1) corresponds to amino acid residues 26-76 of SEQ ID NO: 2, and Kunitz domain 2 (K2) corresponds to residues 91 to 147 of SEQ ID NO: 2. The K1 and K2 domains from other TFPI homologs, isoforms, variants, or fragments can be identified by sequence alignment or structural alignment against SEQ ID NO: 2.

The TFPI of the instant disclosure includes any naturally occurring form of TFPI which may be derived from any suitable organism. For example, TFPI may be a mammalian TFPI, such as human, mouse, rat, non-human primate, bovine, ovine, canine, feline, or porcine TFPI. In certain embodiments, the TFPI is human TFPI. The TFPI may be a mature form of TFPI (i.e., a TFPI protein that has undergone post-translational processing within a suitable cell). Such a mature TFPI protein may, for example, be glycosylated.

The TFPI of the instant disclosure includes any functional fragments or variants derived from a naturally occurring TFPI. A functional fragment of TFPI can be any part or portion of TFPI that retains the activity of a TFPI, such as the ability to inhibit Factor Xa (FXa), to inhibit the activity of FVIIa-tissue factor complex, and/or to function as a negative regulator of coagulation or hemostasis. For example, a functional fragment may comprise a Kunitz domain, such as the K1 domain, K2 domain, or both K1 and K2 domains of TFPI.

A functional variant can comprise one or more mutations as compared to a naturally occurring TFPI, and still retain the activity of a naturally occurring TFPI, such as the ability to inhibit Factor Xa (FXa), or the ability to inhibit the activity of FVIIa-tissue factor complex. For example, a variant may have various degrees of sequence identity to SEQ ID NOs: 1, 2, 3, 4, 5, 6, or 7, such as at least 60%, 70%, 80%, 85%, 90%, 91%, 92%, 93%, 94%, 95%, 96%, 97%, 98% or 99% identical to the sequence recited in SEQ ID NO: 1, SEQ ID NO: 2, SEQ ID NO: 3, SEQ ID NO: 4, SEQ ID NO: 5, SEQ ID NO: 6, or SEQ ID NO: 7.

The TPFI fragments, variants, isoforms and homologs of the invention should maintain important epitope residues (such as Ile105, Arg107, and Leu131, if TFPI-23 and TFPI-24 antibodies are used) as described herein. In addition, the TFPI may comprise five or more, eight or more, ten or more, twelve or more or fifteen or more surface accessible residues of the K2 domain of TFPI. A surface accessible residue is a residue having more than 40% relative accessibility.

For example, for the K2 domain of TFPI (see, e.g., SEQ ID NO: 2), the following amino acid residues have a greater than 40% relative accessibility: 94-95, 98, 100-110, 118-121, 123-124, 131, 134, 138-142 and 144-145. The TFPI may comprise five or more, eight or more, ten or more, twelve or more or fifteen or more of these residues, such as a fragment of TFPI that includes five or more, eight or more, ten or more, twelve or more or fifteen or more of these residues.

B. Anti-TFPI Antibodies

The antibody or antigen-binding fragment thereof of the invention specifically binds the K2 domain of TFPI, and can inhibit its interaction with FXa and/or reduce the activities of TFPI.

TFPI-23 and Variants

In one aspect, the invention includes antibody TFPI-23, and variants of TFPI-23 that were made to increase the content of human framework germline residues ("germlining"). For example, TFPI-106 comprises H1Q to E and H5V to L mutations (Kabat numbering) and TFPI-107 comprises H1Q to E, H5V to L and H941 to K mutations (Kabat numbering). For purposes of this invention, TFPI-23 parental antibody and TFPI-106 germline variant are interchangeable in their epitope residue and paratope residue interactions.

In one aspect, the invention provides an isolated antibody, or antigen-binding fragment thereof, that specifically binds to an epitope in Kunitz Domain 2 (K2) of Tissue Factor Pathway Inhibitor (TFPI), wherein said epitope comprises residues Ile105, Arg107, and Leu131, according to the numbering of SEQ ID NO: 2. In certain embodiments, the antibody or antigen-binding fragment thereof does not bind to Kunitz Domain 1 (K1) of TFPI.

As disclosed and exemplified herein, based on the co-crystal structure and computational alanine scan, unique epitopes in the K2 domain of TFPI have been discovered. In particular, the crystal structure shows that the K2 domain of TFPI adopts a cone-shaped structure, with the tip of the cone (especially Arg107) binding to FXa. TFPI-23, TFPI-24, and their variants all recognize residues near the tip of this cone-shaped region, and block the binding of TFPI to FXa. Therefore, antibodies recognizing epitope residues located near the tip of the cone are particularly useful for inhibiting TFPI activities.

In certain embodiments, the invention discloses TFPI epitopes that comprise three residues that are important for antibody-antigen interaction: Ile105, Arg107, and Leu131 (according to the numbering of human TFPI, as shown in SEQ ID NO: 2). Mutating these three residues to Alanine results in loss of binding by TFPI-23, TFPI-24, and their variants. See Table 28, which summarizes the alanine scan results.

Additional TPFI residues have also been identified as involved in antibody binding, but these residues can be mutated to Alanine without a significant destabilizing effect. See Table 28. Accordingly, in certain embodiments, the TFPI epitopes further comprise one or more residues selected from the group consisting of: Cys106, Gly108, Cys130, Gly132 (according to the numbering of SEQ ID NO: 2), and any combination thereof. These epitope residues are recognized by TFPI-23, TFPI-24, and their variants. See Table 27, which shows the common epitopes residues shared by TFPI-23 and TFPI-24.

In certain embodiments, the epitope further comprises one or more residues selected from the group consisting of: Asp102, Arg112, Tyr127, Gly129, Met134, Glu138 (according to the numbering of SEQ ID NO: 2), and any combination thereof. These epitopes residues are recognized by TFPI-23 and its variants (e.g., TFPI-106, TFPI-107), but not by TFPI-24 (and its variants). See Table 27.

In certain embodiments, the epitope does not comprise one or more residues selected from the group consisting of: E100, E101, P103, Y109, T111, Y113, F114, N116, Q118, Q121, C122, E123, R124, F125, K126, L140 (numbering according to SEQ ID NO: 2), and any combination thereof. See, Table 27. According to WO201007269 (Novo Nordisk), reference antibody 4F36 recognizes an epitope comprising E100, E101, P103, Y109, T111, Y113, F114, N116, Q118, Q121, C122, E123, R124, F125, K126, and L140.

In certain embodiments, the epitope does not comprise one or more residues selected from the group consisting of: D31, D32, P34, C35, K36, E100, E101, P103, Y109, K126, G128 (numbering according to SEQ ID NO: 2), and any combination thereof. See, Table 27. According to Table 27, reference antibodies 2A8 and 2A8-200 recognize an epitope comprising D31, D32, P34, C35, K36, E100, E101, P103, Y109, K126, and G128.

In certain embodiments, the epitope may refer to one or more TFPI "contact" residues (having a heavy atom (i.e., a non-hydrogen atom) that is within a distance of 4 Å from a heavy atom of the cognate antibody), and comprises one or more residues selected from the group consisting of: Asp102, Gly104, Ile105, Cys106, Arg107, Gly108, Arg112, Tyr127, Gly129, Cys130, Leu131, Gly132, Met134, Glu138 (according to the numbering of SEQ ID NO: 2), and any combination thereof. See, Table 29B.

In certain embodiments, the epitope may refer to one or more TFPI residues participating in a hydrogen bond with a residue of the antibody, or with a water molecule that is also hydrogen bonded to the cognate antibody (water-mediated hydrogen bonding), and comprises one or more residues selected from the group consisting of: Asp102, Arg107, Arg 112, Tyr127, and Leu131 (according to the numbering of SEQ ID NO: 2), and any combination thereof. These epitope residues participate in a hydrogen bond with the cognate antibody. See, Table 29B.

In certain embodiments, the epitope may refer to residues having a non-zero change in buried surface area (BSA) due to interaction with the cognate antibody, and comprises one or more residues selected from the group consisting of: Asp102, Gly104, Ile105, Cys106, Arg107, Gly108, Arg112, Tyr127, Gly129, Cys130, Leu131, Gly132, Asn133, Met134, Glu138 (according to the numbering of SEQ ID NO: 2), and any combination thereof. These. See, Table 29B.

Any combination of these different categories of epitope residues are also encompassed by the invention.

In certain embodiments, the epitope comprises at least 1, at least 2, at least 3, at least 4, at least 5, at least 6, at least 7, at least 8, at least 9, at least 10, at least 11, at least 12, at least 13, or all of epitope residues described above, or any combination of the various categories of epitope residues described above.

Paratope residues of TFPI-23 (and variants) may refer to contact residues (within 4 Å of a TFPI epitope residue) as follows: H33 Ala, H47 Trp, H50 Ala, H51 Ile, H52 Ser, H56 Ser, H58 Tyr, H95 Leu, H96 Gly, H97 Ala, H98 Thr, H99 Ser, H100 Leu, H100A Ser, L29 Ala, L31 Tyr, L91 Tyr, L95A Ser, L95B Gly, and L95C Ser; and optionally L93 Ser and L96 Gly (numbering according to Kabat). L93 Ser (4.07 Å) and L96 Gly (4.03 Å) are optional because the distances marginally exceed 4 Å, but are close enough to be rounded to 4 Å.

Note that the above contact residues are original residues from TFPI-23 antibody. However, based on the structural analysis and alanine scanning, it is believed that a number of contact residues in TFPI-23 can be substituted with another residue without significantly affect antigen-binding. For example, Table 29 Å shows that a number of contact residues in TFPI-23 can be substituted with other residues and only results in <0.5 kcal/mol effect on binding or stability ("<0.5 kcal/mol" means that a substitution has a neutral effect on binding). In particular, as shown in Table 29A, column 4, three CDR positions and 1 framework position: H47, H58, L91, and L96 (numbering according to Kabat) only tolerate one or two residues: (a) H47 is Trp or Tyr; (b) H58 is Tyr; (c) L91 is Tyr or Arg; and (d) L96 is Gly or Asn. Other CDR positions can accommodated more substitutions as summarized in Table 29A, column 4.

Accordingly, in certain embodiments, the antibody or antigen-binding fragment thereof described herein comprises the following residues (numbering according to Kabat):

(a) H33 is Ala, Asn, Gly, His, Lys, Met, Phe, Pro, Ser, Thr, Trp, or Val;
(b) H47 is Trp or Tyr;
(c) H50 is Ala, Arg, Gly, Lys, Met, Phe, Pro, Ser, Thr, Tyr, or Val;
(d) H51 is Ile, Ala, Arg, Asn Asp, Gln, Glu, Gly, His, Leu, Lys, Met, Phe Pro, Ser, Thr, Trp, Tyr, or Val;
(e) H52 is Ser, Ala, Arg, Asn, Asp, Gln, Glu, Gly His, Ile, Leu, Lys, Met, Phe, Pro, Ser, Trp, Tyr, or Val;
(f) H56 is Ser, Arg, Gly, His, Ile, Leu, Lys, Met, Phe, Pro, Ser, Thr, Trp, Tyr, or Val;
(g) H58 is Tyr;
(h) H95 is Leu, Gln, Ile, Phe, or Tyr;
(i) H96 is Gly, Ala, Arg, Asn Asp, Gln, Ile, Lys, Met, Phe, Pro, Ser, Thr, or Val;
(j) H97 is Ala, Arg, Asn Asp, Gln, Glu, Gly, His, Leu, Lys, Met, Phe Pro, Ser, Thr, Trp, Tyr, or Val;
(k) H98 is Thr, Ala, Arg, Asn Asp, Gln, Glu, Gly, His, Leu, Met, Phe Pro, Ser, Thr, Trp, Tyr, or Val;
(l) H99 is Ser, Ala, Gly, Phe, or Pro;
(m) H100 is Leu, Arg, His, Ile, Leu, Lys, Phe, Pro, Trp, Tyr, or Val;
(n) H100A is Ser, Ala, Arg, Asn Asp, Gln, Glu, His, Leu, Lys, Met, Phe Pro, Ser, Thr, or Trp;
(o) L29 is Ala, Arg, Asn Asp, Gln, Glu, Gly, His, Leu, Lys, Met, Phe Pro, Ser, Thr, Trp, Tyr, or Val;
(p) L31 is Ala, Arg, Asn Asp, Gln, Glu, Gly, His, Leu, Lys, Met, Phe Pro, Ser, Thr, Trp, Tyr, or Val;
(q) L91 is Tyr or Arg;
(r) L95A is Ser, Ala, Arg, Asn Asp, Gln, Glu, Gly, His, Leu, Lys, Met, Phe Pro, Ser, Thr, Trp, Tyr, or Val;
(s) L95B is Ser, Ala, Arg, Asn Asp, Gln, Glu, Gly, His, Leu, Lys, Met, Phe Pro, Ser, Thr, Trp, Tyr, or Val; and
(t) L95C is Ser, Ala, Arg, Asn Asp, Gln, Glu, Gly, His, Leu, Lys, Met, Phe Pro, Ser, Thr, Trp, Tyr, or Val;

and optionally comprises (u) L93 is Tyr, Ala, Arg, Asn Asp, Gln, Glu, Gly, His, Leu, Lys, Met, Phe Pro, Ser, Thr, Trp, Tyr, or Val; and
(v) L96 is Gly or Asn.

Among these residues, H47 is a framework residue; all others are CDR residues.

When a more stringent substitution criterion is imposed—substitution must result in <−0.5 kcal/mol affinity, meaning that the substitution must have a positive (neutral/stabilizing) effect—contact residues are as follows (numbering according to Kabat) (Table 29A, col. 5):

(a) H33 is Ala or Val;
(b) H47 is Trp;
(c) H50 is Ala;
(d) H51 is Ile;
(e) H52 is Ser, Arg, Lys, Phe, or Tyr;
(f) H56 is Ser, Arg, or Lys;
(g) H58 is Tyr;
(h) H95 is Leu;
(i) H96 is Gly, Ala, Arg, Asn, Lys, Pro, Ser, or Val;
(j) H97 is Ala;
(k) H98 is Thr, His, Ile, Leu, Met, Phe, or Tyr;
(l) H99 is Ser;
(m) H100 is Leu, Phe, Trp, or Tyr;
(n) H100A is Ser, Arg, Asn, Gln, Glu His, Leu, Lys, Met, Phe, Pro, or Trp;
(o) L29 is Ala;
(p) L31 is Tyr;
(q) L91 is Tyr;
(r) L95A is Ser, Phe, Trp, or Tyr;
(s) L95B is Gly; and
(t) L95C is Ser, Arg, Asn, Gln, Glu, Ile, Leu, Lys, Met, Phe, Trp, Tyr, or Val;

and optionally: (u) L93 is Ser; and
(v) L96 is Gly.

Alternatively or in addition, the selection of acceptable substitutions can be based on column 6 of Table 29A, where top 3 residues are selected based on their impact on affinity (i.e., top 3 predicted sites with the most stabilizing effect on affinity). Under this criteria, contact residues are as follows (numbering according to Kabat):

(a) H33 is Ala, Val, His, or Phe;
(b) H47 is Trp or Tyr;
(c) H50 is Ala, Thr, Ser, or Phe;
(d) H51 is Ile, Arg, Lys, or Pro;
(e) H52 is Ser, Phe, Arg, or Tyr;
(f) H56 is Ser, Lys, Tyr, or Phe;
(g) H58 is Tyr;
(h) H95 is Leu, Ile, Gln, or Phe;
(i) H96 is Gly, Arg, Asn, or Lys;
(j) H97 is Ala, Leu, Tyr, or Ile;
(k) H98 is Thr, Tyr, Phe, or His;
(l) H99 is Ser, Pro, Ala, or Phe;
(m) H100 is Leu, Tyr, Trp, or Phe;
(n) H100A is Ser, Arg, Leu, or Trp;
(o) L29 is Ala, Glu, Asp, or Gln;
(p) L31 is Tyr, Glu, Asp, or Trp;
(q) L91 is Ty or Arg;
(r) L95A is Ser, Phe, Tyr, or His;
(s) L95B is Gly, Glu, Asp, or Pro; and
(t) L95C is Ser, Trp, Tyr, or Phe;

and optionally: (u) L93 is Ser, Glu, Asp, or His;
(v) L96 is Gly or Asn.

Paratope residues of TFPI-23 (and variants) may also refer to residues participating in a hydrogen bond with a residue of TFPI, or with a water molecule that is also hydrogen bonded to TFPI, and include the following: H58 Tyr, H96 Gly, H97 Ala, H98 Thr, H99 Ser, H100 Leu, L29 Ala, L31 Tyr, and L95B Gl (numbering according to Kabat). See, Table 29B.

Paratope residues of TFPI-23 (and variants) may also refer to residues having a non-zero change in BSA due to interaction with TFPI, and include the following (numbering according to Kabat): H33 Ala, H58 Tyr, H95 Leu, H96 Gly, H97 Ala, H98 Thr, H99 Ser, H100 Leu, H100A Ser, L29 Ala, L31 Tyr, L91 Tyr, L93 Ser, L95A Ser, and L95B Gly. A cutoff (BSA of 20 $Å^2$ or greater, or involved in electrostatic interaction) is applied to avoid inclusion of residues that have minimal interactions. See Table 29B.

If no cutoff of BSA is applied, paratope residues include the following: H33 Ala, H34 Met, H47 Trp, H50 Ala, H51 Ile, H52 Ser, H56 Ser, H58 Tyr; H95 Leu, H96 Gly, H97 Ala, H98 Thr, H99 Ser, H100 Leu, H100A Ser, L28 Gly, L29 Ala, L31 Tyr, L91 Tyr, L93 Ser, L94 Ser, L95A Ser, L95B Gly, L95C Ser, and L96 Gly. See Table 29C.

An antibody or antigen-binding fragment thereof of the invention may bind to the same epitope or domain of TFPI as the antibodies that are specifically exemplified herein. For example, an antibody or antigen-binding fragment thereof may be identified by comparing their binding to TFPI with that of TFPI-23 or germlined variants (e.g., TFPI-106 and TFPI-107); or by comparing the function of these antibodies with TFPI-23 and its variants. Analyses and assays that may be used for the purpose of such identification include assays assessing the competitions for binding of TFPI and are exemplified in the Examples.

In one embodiment, an antibody or antigen-binding fragment thereof of the invention may bind to the same epitope or region as the antibodies described herein, such as TFPI-23 and its variants. This may include it being in contact with a particular TFPI residue as described above. For example, an antibody or antigen-binding fragment of the invention may bind to TFPI in such a way that it is in contact (within 4 Å) with a residue selected from the group consisting of: Asp102, Gly104, Ile105, Cys106, Arg107, Gly108, Arg112, Tyr127, Gly129, Cys130, Leu131, Gly132, Met134, Glu138 (according to the numbering of SEQ ID NO: 2), and any combination thereof. An antibody or antigen-binding fragment of the invention may be capable of binding an epitope comprising one or more residues selected from the group consisting of Asp102, Gly104, Ile105, Cys106, Arg107, Gly108, Arg112, Tyr127, Gly129, Cys130, Leu131, Gly132, Met134, Glu138 (according to the numbering of SEQ ID NO: 2), and any combination thereof.

An antibody antigen-binding fragment thereof can comprise at least one paratope residue (numbering according to Kabat) which is within 4.0 Å of at least one epitope residue on TFPI (numbering according to SEQ ID NO:2), as follows: epitope residue 102 Asp is within 4.0 Å of paratope residue H58 Tyr; epitope residue 104 Gly is within 4.0 Å of paratope residue H58 Tyr; epitope residue 105 Ile is within 4.0 Å of paratope residues H33 Ala, H50 Ala, H51 Ile, H52 Ser, H56 Ser, H58 Tyr, H95 Leu; epitope residue 106 Cys is within 4.0 Å of paratope residues H100 Leu, H100A Ser; epitope residue 107 Arg is within 4.0 Å of paratope residue H96 Gly, H97 Ala, H98 Thr, H99 Ser, H100 Leu; epitope residue 108 Gly is within 4.0 Å of paratope residue H100 Leu; epitope residue 112 Arg is within 4.0 Å of paratope residue L29 Ala, L31 Tyr; epitope residue 127 Tyr is within 4.0 Å of paratope residue L31 Tyr; epitope residue 129 Gly is within 4.0 Å of paratope residue L31 Tyr; epitope residue 130 Cys is within 4.0 Å of paratope residue L91 Tyr, L95B Gly; epitope residue 131 Leu is within 4.0 Å of paratope residue H47 Trp, H50 Ala, H58 Tyr, L95A Ser, L95B Gly, L95C Ser; epitope residue 132 Gly is within 4.0 Å of paratope residue H58 Tyr, L95A Ser; H58 Tyr, L95A Ser; epitope residue 134 Met is within 4.0 Å of paratope residue L95A Ser; and epitope residue 138 Glu is within 4.0 Å of paratope residue L29 Ala. See Tables 29 Å and 29B An antibody or an antigen-binding fragment thereof can also comprise at least one paratope residue (numbering according to Kabat) which can form a hydrogen bond with an epitope residue of TFIP (numbering according to SEQ ID NO:2) as follows: epitope residue 102 Asp can form a hydrogen bond with paratope residue H58 Tyr; epitope residue 107 Arg can form a hydrogen bond with at least one paratope residue selected from the group consisting of H96 Gly, H97 Ala, H98 Thr, H99 Ser, and H100 Leu; epitope residue 112 Arg can form a hydrogen bond with paratope residue L29 Ala; epitope residue 127 Tyr can form a hydrogen bond with paratope residue L31 Tyr; and epitope residue 131 Leu can form a hydrogen bond with paratope residue L95B Gly. See Table 29B.

An antibody or an antigen-binding fragment thereof can also comprise at least one paratope residue (numbering according to Kabat) having a non-zero change in BSA due to interaction with an epitope residue (numbering according to SEQ ID NO:2) as follows: epitope residue 102 Asp interacts with paratope residue H58 Tyr; epitope residue 104 Gly interacts with paratope residue H58 Tyr; epitope residue 105 Ile interacts with at least one paratope residue selected from the group consisting of H33 Ala, H34 Met, H50 Ala, H51 Ile, H52 Ser, H56 Ser, H58 Tyr, and H95 Leu; epitope residue 106 Cys interacts with at least one paratope residue selected from the group consisting of H95 Leu, H100 Leu, H100A Ser, and L91 Tyr; epitope residue 107 Arg interacts with at least one paratope residue selected from the group consisting of H96 Gly, H97 Ala, H98 Thr, H99 Ser, and H100 Leu; epitope residue 108 Gly interacts with paratope residue H100 Leu; epitope residue 112 Arg interacts with at least one paratope residue selected from the group consisting of L29 Ala, L31 Tyr, and L93 Ser; epitope residue 127 Tyr interacts with at least one paratope residue selected from the group consisting of L31 Tyr, and L95B Gly; epitope residue 129 Gly interacts with at least one paratope residue selected from the group consisting of H100A Ser, L31 Tyr, and L91 Tyr; epitope residue 130 Cys interacts with at least one paratope residue selected from the group consisting of H95 Leu, H100A Ser, L31 Tyr, L91 Tyr, and L95B Gly; epitope residue 131 Leu interacts with at least one paratope residue selected from the group consisting of H47 Trp, H50 Ala, H58 Tyr, H95 Leu, L31 Tyr, L91 Tyr, L95A Ser, L95B Gly, L95C Ser, and L96 Gly; epitope residue 132 Gly interacts with at least one paratope residue selected from the group consisting of H58 Tyr, and L95A Ser; epitope residue 133 Asn interacts with paratope residue L95A Ser; epitope residue 134 Met interacts with at least one paratope residue selected from the group consisting of L93 Ser, L94 Ser, and L95A Ser; and epitope residue 138 Glu interacts with at least one paratope residue selected from the group consisting of L28 Gly, L29 Ala, and L93 Ser.

An antibody or an antigen-binding fragment thereof of the invention can be any antibody or antigen-binding fragment that comprises any of the paratope residues above which interacts with at least one epitope residue listed above.

In certain embodiments, the antibody or antigen-binding fragment thereof described herein comprises at least 1, at least 2, at least 3, at least 4, at least 5, at least 6, at least 7, at least 8, at least 9, at least 10, at least 11, at least 12, at least 13, or all of paratope residues described above, or any combination of the various categories of paratope residues described above. Further, conservative substitutions may be introduced to these paratope residues. For example, the antibody or antigen binding fragment thereof may comprise 1, 2, 3, 4, 5, 6, 7, or 8 conservative substitutions according to Table 34.

TABLE 34

Conservative Substitutions

| Residue | Conservative substitution | Residue | Conservative substitution |
|---|---|---|---|
| Ala | Ser | Leu | Ile, Val |
| Arg | Lys | Lys | Arg, Gln |
| Asn | Gln; His | Met | Leu, Ile |
| Asp | Glu | Phe | Met, Leu, Tyr |
| Cys | Ser | Ser | Thr; Gly |
| Gln | Asn | Thr | Ser, Val |
| Glu | Asp | Trp | Tyr |
| Gly | Pro | Tyr | Trp, Phe |
| His | Asn, Gln | Val | Ile, Leu |
| Ile | Leu, Val | Pro | — |

An antibody of the invention may have the ability to compete with another antibody for binding to TFPI as described herein. For example, an antibody of the invention may cross-compete with TFPI-23 and its variants thereof described herein for binding to TFPI, or to a suitable fragment or variant of TFPI that is bound by the TFPI-23 antibodies. Such cross-competing antibodies can be identified based on their ability to cross-compete with an exemplified antibody of the invention in standard binding assays. For example, SPR (e.g., by using a Biacore™ system), ELISA assays or flow cytometry may be used to demonstrate cross-competition. Such cross-competition may suggest that the two antibodies bind to identical, overlapping or similar epitopes.

An antibody of the invention may therefore be identified by a method that comprises a binding assay which assesses whether or not a test antibody is able to compete with an exemplified antibody of the invention (such as TFPI-23, or any variant or fragment thereof as described herein) for a binding site on the target molecule.

In certain embodiments, the antibody or antigen-binding fragment thereof described herein comprises the following heavy chain CDR sequences: (i) CDR-H1 comprising SEQ ID NO: 38, CDR-H2 comprising SEQ ID NO: 39, and CDR-H3 comprising SEQ ID NO: 40; and/or (ii) the following light chain CDR sequences: CDR-L1 comprising SEQ ID NO: 33, CDR-L2 comprising SEQ ID NO: 34, and CDR-L3 comprising SEQ ID NO: 35. In certain embodiments, the antibody or antigen-binding fragment thereof described herein comprises following heavy chain CDR sequences: (i) a CDR-H1 at least 85%, at least 90%, or at least 95% identical to SEQ ID NO: 38, a CDR-H2 at least 85%, at least 90%, or at least 95% identical to SEQ ID NO: 39, and a CDR-H3 at least 85%, at least 90%, or at least 95% identical to SEQ ID NO: 40; and/or (ii) the following light chain CDR sequences: a CDR-L1 at least 85%, at least 90%, or at least 95% identical to SEQ ID NO: 33, a CDR-L2 at least 85%, at least 90%, or at least 95% identical to SEQ ID NO: 34, and a CDR-L3 at least 85%, at least 90%, or at least 95% identical to SEQ ID NO: 35. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 38, 39, 40, 33, 34, and 35, respectively. In certain embodiments, the substitution is a conservative substation according to Table 34. In certain embodiments, the substitution is according to Table 29A, column 4, column 5, or column 6.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline. Preferred human germline heavy chain frameworks are frameworks derived from VH1, VH3, or VH5 germlines. For example, VH frameworks from the following germlines may be used: IGHV3-23, IGHV3-7, or IGHV1-69 (germline names are based on IMGT germline definition). Preferred human germline light chain frameworks are frameworks derived from VK or Vλ germlines. For example, VL frameworks from the following germlines may be used: IGKV1-39 or IGKV3-20 (germline names are based on IMGT germline definition). Alternatively or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence.

Sequences of human germline frameworks are available from various public databases, such as V-base, IMGT, NCBI, or Abysis.

In certain embodiments, the antibody or antigen-binding fragment thereof described herein comprises: (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to an amino acid sequence selected from the group consisting of SEQ ID NOs: 41, 63, and 65; and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:36. Any combination of these VL and VH sequences is also encompassed by the invention.

In certain embodiments, the antibody or antigen-binding fragment thereof described herein comprises: (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 20; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 26. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises: (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 42, SEQ ID NO: 64, or SEQ ID NO: 66; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 37. Any combination of these heavy chain and light chain sequences is also encompassed by the invention.

TFPI-24 and Variants

The co-crystal structures show that TFPI-24 (and its variants) share a number of epitope residues with TFPI-23. Among these, Ile105, Arg107, and Leu131 (according to the numbering of human TFPI, as shown in SEQ ID NO: 2) are believed to be important for antibody-antigen interaction. Other shared epitope residues include: Cys106, Gly108, C130, L131, and G132, (according to the numbering of SEQ ID NO: 2).

Epitope residues that are specific for TFPI-24 (and its variants) include: Glu100, Glu101, Asp102, Gly104, and Tyr109. TFPI-23 and its variants do not bind to these residues. See Table 27. Accordingly, the invention provides an isolated antibody, or antigen-binding fragment thereof, that specifically binds to an epitope in K2 of TFPI, wherein said epitope (i) comprises residues Ile105, Arg107, and Leu131; (ii) optionally comprises one or more residues selected from the group consisting of: Cys106, Gly108, Cys130, Leu131, and Gly132; and (iii) further optionally comprises one or more residues selected from the group consisting of: Glu100, Glu101, Asp102, Gly104, and Tyr109 (according to the numbering of SEQ ID NO: 2).

In certain embodiments, the epitope does not comprise one or more residues selected from the group consisting of: P103, T111, Y113, F114, N116, Q118, Q121, C122, E123, R124, F125, K126, L140 (numbering according to SEQ ID NO: 2), and any combination thereof. See, Table 27. According to WO201007269 (Novo Nordisk), reference antibody 4F36 recognizes an epitope comprising P103, T111, Y113, F114, N116, Q118, Q121, C122, E123, R124, F125, K126, and L140.

In certain embodiments, the epitope does not comprise one or more residues selected from the group consisting of: D31, D32, P34, C35, K36, P103, K126, Y127, G128 (numbering according to SEQ ID NO: 2), and any combination thereof. See, Table 27. According to Table 27, reference antibodies 2A8 and 2A8-200 recognize an epitope comprising D31, D32, P34, C35, K36, P103, K126, Y127, and G128.

Paratope residues from TFPI-24 (based on BSA) have also been characterized (see Table 24) and include the following: H33 Ala, H35 Gln, H52 Ser, H53 Asn, H55 Arg, H56 Ser, H95 Phe, H96 Leu, H97 His, H99 Ser, H101 Asp, L31 Met, L32 Tyr, L34 His, L36 Tyr, L50 Arg, L91 Trp, and L96 Tyr. In certain embodiments, the antibody or antigen-binding fragment thereof described herein comprises at least 8, at least 9, at least 10, at least 11, at least 12, at least 13, at least 14, at least 15, at least 16, at least 17, or all of these paratope residues. Further, conservative substitutions may be introduced to these paratope residues. For example, the antibody or antigen binding fragment thereof may comprise 1, 2, 3, 4, 5, 6, 7, or 8 conservative substitutions according to Table 34.

In certain embodiments, the antibody or antigen-binding fragment thereof described herein comprises the following heavy chain CDR sequences: (i) CDR-H1 comprising SEQ ID NO: 48, CDR-H2 comprising SEQ ID NO: 49, and CDR-H3 comprising SEQ ID NO: 50; and/or (ii) the following light chain CDR sequences: CDR-L1 comprising SEQ ID NO: 43, CDR-L2 comprising SEQ ID NO: 44, and CDR-L3 comprising SEQ ID NO: 45. In certain embodiments, the antibody or antigen-binding fragment thereof described herein comprises following heavy chain CDR sequences: (i) a CDR-H1 at least 85%, at least 90%, or at least 95% identical to SEQ ID NO: 48, a CDR-H2 at least 85%, at least 90%, or at least 95% identical to SEQ ID NO: 49, and a CDR-H3 at least 85%, at least 90%, or at least 95% identical to SEQ ID NO: 50; and/or (ii) the following light chain CDR sequences: a CDR-L1 at least 85%, at least 90%, or at least 95% identical to SEQ ID NO: 43, a CDR-L2 at least 85%, at least 90%, or at least 95% identical to SEQ ID NO: 44, and a CDR-L3 at least 85%, at least 90%, or at least 95% identical to SEQ ID NO: 45. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 48, 49, 50, 43, 44, and 45, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to an amino acid sequence selected from the group consisting of SEQ ID NOs: 67, 69, 51, and 79; and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to an amino acid sequence selected from the group consisting of SEQ ID NOs: 46, 71, 73, 75, and 77. Any combination of these VL and VH sequences is also encompassed by the invention.

In certain embodiments, the antibody or antigen-binding fragment thereof described herein comprises: (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 20; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 26. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises: (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 52, SEQ ID NO: 68, SEQ ID NO: 70, or SEQ ID NO: 80; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 47, SEQ ID NO: 72, SEQ ID NO: 74, SEQ ID NO: 76, or SEQ ID NO: 78. Any combination of these heavy chain and light chain sequences is also encompassed by the invention.

4D8 and Variants

Co-crystal structures also reveal the epitope and paratope information for antibody 4D8 and variants. Epitope residues for 4D8 and its variants include: Glu101, Pro103, Tyr109, Thr111, Ser119, Gln121, Glu123, Arg124, Lys126, and Leu140, according to the numbering of SEQ ID NO: 2.

In certain embodiments, the epitope does not comprise one or more residues selected from the group consisting of: E100, D102, R107, Y113, F114, N116, Q118, C122 (numbering according to SEQ ID NO: 2), and any combination thereof. See, Table 27. According to WO201007269 (Novo Nordisk), reference antibody 4F36 recognizes an epitope comprising E100, D102, R107, Y113, F114, N116, Q118, and C122.

In certain embodiments, the epitope does not comprise one or more residues selected from the group consisting of: D31, D32, P34, C35, K36, E100, 1105, R107, G108, Y127, G128 (numbering according to SEQ ID NO: 2), and any combination thereof. See, Table 27. According to Table 27, reference antibodies 2A8 and 2A8-200 recognize an epitope comprising D31, D32, P34, C35, K36, E100, 1105, R107, G108, Y127, and G128.

Paratope residues from 4D8 (based on BSA) have also been characterized (see Table 20) and include the following: H50 Asp, H57 Thr, H58 Leu, H59 Tyr, H61 Gln, H98 Asp, H99 Tyr, H100 Asp, L30 His, L50 Trp, L92 Tyr, L93 Thr, L94 Thr, and L96 Tyr. In certain embodiments, the antibody or antigen-binding fragment thereof described herein comprises at least 8, at least 9, at least 10, at least 11, at least 12, at least 13, or all of these paratope residues. Further, conservative substitutions may be introduced to these paratope residues. For example, the antibody or antigen binding fragment thereof may comprise 1, 2, 3, 4, 5, 6, 7, or 8 conservative substitutions according to Table 34.

In certain embodiments, the antibody or antigen-binding fragment thereof described herein comprises the following heavy chain CDR sequences: (i) CDR-H1 comprising SEQ ID NO: 87, CDR-H2 comprising SEQ ID NO: 88, and CDR-H3 comprising SEQ ID NO: 89; and/or (ii) the following light chain CDR sequences: CDR-L1 comprising SEQ ID NO: 81, CDR-L2 comprising SEQ ID NO: 82, and CDR-L3 comprising SEQ ID NO: 83. In certain embodiments, the antibody or antigen-binding fragment thereof described herein comprises following heavy chain CDR sequences: (i) a CDR-H1 at least 85%, at least 90%, or at least 95% identical to SEQ ID NO: 87, a CDR-H2 at least 85%, at least 90%, or at least 95% identical to SEQ ID NO: 88, and a CDR-H3 at least 85%, at least 90%, or at least 95% identical to SEQ ID NO: 89; and/or (ii) the following light chain CDR sequences: a CDR-L1 at least 85%, at least 90%, or at least 95% identical to SEQ ID NO: 81, a CDR-L2 at least 85%, at least 90%, or at least 95% identical to SEQ ID NO: 82, and a CDR-L3 at least 85%, at least 90%, or at least 95% identical to SEQ ID NO: 83. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 87, 88, 89, 81, 82, and 83, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to an amino acid sequence selected from the group consisting of SEQ ID NOs: 90, 95, 97, 99, 101, 103, 105, and 107; and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to an amino acid sequence selected from the group consisting of SEQ ID NOs: 84, 109, and 111. Any combination of these VL and VH sequences is also encompassed by the invention.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 20, and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91 or SEQ ID NO: 85. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_r$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 86, SEQ ID NO: 93, SEQ ID NO: 110, or SEQ ID NO: 112. Any combination of these heavy chain and light chain sequences is also encompassed by the invention.

TFPI-3 and Variants

Also provided herein are TFPI-3 and its variants. Accordingly, the antibody or antigen-binding fragment thereof based on TFPI-3 comprises the following heavy chain CDR sequences: (i) CDR-H1 comprising SEQ ID NO: 16, CDR-H2 comprising SEQ ID NO: 17, and CDR-H3 comprising SEQ ID NO: 18; and/or (ii) the following light chain CDR sequences: CDR-L1 comprising SEQ ID NO: 10, CDR-L2 comprising SEQ ID NO: 11, and CDR-L3 comprising SEQ ID NO: 12. In certain embodiments, the antibody or antigen-binding fragment thereof described herein comprises following heavy chain CDR sequences: (i) a CDR-H1 at least 85%, at least 90%, or at least 95% identical to SEQ ID NO: 16, a CDR-H2 at least 85%, at least 90%, or at least 95% identical to SEQ ID NO: 17, and a CDR-H3 at least 85%, at least 90%, or at least 95% identical to SEQ ID NO: 18; and/or (ii) the following light chain CDR sequences: a CDR-L1 at least 85%, at least 90%, or at least 95% identical to SEQ ID NO: 10, a CDR-L2 at least 85%, at least 90%, or at least 95% identical to SEQ ID NO: 11, and a CDR-L3 at least 85%, at least 90%, or at least 95% identical to SEQ ID NO: 12. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 16, 17, 18, 10, 11, and 12, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 19, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 13. Any combination of these VL and VH sequences is also encompassed by the invention.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 20; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91 or SEQ ID NO: 14. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 21; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 15. Any combination of these heavy chain and light chain sequences is also encompassed by the invention.

TFPI-21 and Variants

Also provided herein are TFPI-21 and its variants. Accordingly, the antibody or antigen-binding fragment thereof based on TFPI-21 comprises the following heavy chain CDR sequences: (i) CDR-H1 comprising SEQ ID NO: 28, CDR-H2 comprising SEQ ID NO: 29, and CDR-H3 comprising SEQ ID NO: 30; and/or (ii) the following light chain CDR sequences: CDR-L1 comprising SEQ ID NO: 22, CDR-L2 comprising SEQ ID NO: 23, and CDR-L3 comprising SEQ ID NO: 24. In certain embodiments, the antibody or antigen-binding fragment thereof described herein comprises following heavy chain CDR sequences: (i) a CDR-H1 at least 85%, at least 90%, or at least 95% identical to SEQ ID NO: 28, a CDR-H2 at least 85%, at least 90%, or at least 95% identical to SEQ ID NO: 29, and a CDR-H3 at least 85%, at least 90%, or at least 95% identical to SEQ ID NO: 30; and/or (ii) the following light chain CDR sequences: a CDR-L1 at least 85%, at least 90%, or at least 95% identical to SEQ ID NO: 22, a CDR-L2 at least 85%, at least 90%, or at least 95% identical to SEQ ID NO: 23, and a CDR-L3 at least 85%, at least 90%, or at least 95% identical to SEQ ID NO: 24. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 28, 29, 30, 22, 23, and 24, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 31, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 25. Any combination of these VL and VH sequences is also encompassed by the invention.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 20; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91 or SEQ ID NO: 26. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_t$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 32, and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 27. Any combination of these heavy chain and light chain sequences is also encompassed by the invention.

TFPI-26 and Variants

Also provided herein are TFPI-26 and its variants. Accordingly, the antibody or antigen-binding fragment thereof based on TFPI-26 comprises the following heavy chain CDR sequences: (i) CDR-H1 comprising SEQ ID NO: 58, CDR-H2 comprising SEQ ID NO: 59, and CDR-H3 comprising SEQ ID NO: 60; and/or (ii) the following light chain CDR sequences: CDR-L1 comprising SEQ ID NO: 53, CDR-L2 comprising SEQ ID NO: 54, and CDR-L3 comprising SEQ ID NO: 55. In certain embodiments, the antibody or antigen-binding fragment thereof described herein comprises following heavy chain CDR sequences: (i) a CDR-H1 at least 85%, at least 90%, or at least 95% identical to SEQ ID NO: 58, a CDR-H2 at least 85%, at least 90%, or at least 95% identical to SEQ ID NO: 59, and a CDR-H3 at least 85%, at least 90%, or at least 95% identical to SEQ ID NO: 60; and/or (ii) the following light chain CDR sequences: a CDR-L1 at least 85%, at least 90%, or at least 95% identical to SEQ ID NO: 53, a CDR-L2 at least 85%, at least 90%, or at least 95% identical to SEQ ID NO: 54, and a CDR-L3 at least 85%, at least 90%, or at least 95% identical to SEQ ID NO: 55. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 58, 59, 60, 53, 54, and 55, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 61, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 56. Any combination of these VL and VH sequences is also encompassed by the invention.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 20; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 26. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_t$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 62; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 57. Any combination of these heavy chain and light chain sequences is also encompassed by the invention.

6B7.c5 and Variants

Also provided herein are 6B7.c5 and its variants. Accordingly, the antibody or antigen-binding fragment thereof based on 6B7.c5 comprises the following heavy chain CDR sequences: (i) CDR-H1 comprising SEQ ID NO: 118, CDR-H2 comprising SEQ ID NO: 119, and CDR-H3 comprising SEQ ID NO: 120; and/or (ii) the following light chain CDR sequences: CDR-L1 comprising SEQ ID NO: 113, CDR-L2 comprising SEQ ID NO: 114, and CDR-L3 comprising SEQ ID NO: 115. In certain embodiments, the antibody or antigen-binding fragment thereof described herein comprises following heavy chain CDR sequences: (i) a CDR-H1 at least 85%, at least 90%, or at least 95% identical to SEQ ID NO: 118, a CDR-H2 at least 85%, at least 90%, or at least 95% identical to SEQ ID NO: 119, and a CDR-H3 at least 85%, at least 90%, or at least 95% identical to SEQ ID NO: 120; and/or (ii) the following light chain CDR sequences: a CDR-L1 at least 85%, at least 90%, or at least 95% identical to SEQ ID NO: 113, a CDR-L2 at least 85%, at least 90%, or at least 95% identical to SEQ ID NO: 114, and a CDR-L3 at least 85%, at least 90%, or at least 95% identical to SEQ ID NO: 115. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 118, 119, 120, 113, 114, and 115, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 121, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 116. Any combination of these VL and VH sequences is also encompassed by the invention.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91, and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91 or SEQ ID NO: 85. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 122; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 117. Any combination of these heavy chain and light chain sequences is also encompassed by the invention.

7A4.D9 and Variants

Also provided herein are TFPI-3 and its variants. Accordingly, the antibody or antigen-binding fragment thereof based on TFPI-3 comprises the following heavy chain CDR sequences: (i) CDR-H1 comprising SEQ ID NO: 128, CDR-H2 comprising SEQ ID NO: 129, and CDR-H3 comprising SEQ ID NO: 130; and/or (ii) the following light chain CDR sequences: CDR-L1 comprising SEQ ID NO: 123, CDR-L2 comprising SEQ ID NO: 124, and CDR-L3 comprising SEQ ID NO: 125. In certain embodiments, the antibody or antigen-binding fragment thereof described herein comprises following heavy chain CDR sequences: (i) a CDR-H1 at least 85%, at least 90%, or at least 95% identical to SEQ ID NO: 128, a CDR-H2 at least 85%, at least 90%, or at least 95% identical to SEQ ID NO: 129, and a CDR-H3 at least 85%, at least 90%, or at least 95% identical to SEQ ID NO: 130; and/or (ii) the following light chain CDR sequences: a CDR-L1 at least 85%, at least 90%, or at least 95% identical to SEQ ID NO: 123, a CDR-L2 at least 85%, at least 90%, or at least 95% identical to SEQ ID NO: 124, and a CDR-L3 at least 85%, at least 90%, or at least 95% identical to SEQ ID NO: 125. In certain embodiments, no more than 10, no more than 9, no more than 8, no more than 7, no more than 6, no more than 5, no more than 4, no more than 3, no more than 3, no more than 2, or no more than one substitution is made in each CDR, relative to SEQ ID NOs. 128, 129, 130, 123, 124, and 125, respectively. In certain embodiments, the substitution is a conservative substation according to Table 34.

In certain embodiments, the antibody or antigen-binding fragment thereof described herein comprises a human framework sequence. For example, heavy chain framework sequence can be from a human VH3 germline, a VH1 germline, a VH5 germline, or a VH4 germline, as described above. Preferred human germline light chain frameworks are frameworks derived from VK or Vλ germlines, as described above. Consensus human germline framework sequences may also be used as described above.

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 131, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 126. Any combination of these VL and VH sequences is also encompassed by the invention.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 91 or SEQ ID NO: 85. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 132; and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 127. Any combination of these heavy chain and light chain sequences is also encompassed by the invention.

Also disclosed is an antibody, or antigen-binding fragment thereof, that specifically binds to the K2 Domain of TFPI, and competes for binding to TFPI with any of the antibody or antigen-binding fragment thereof described herein, such as any one of the antibodies listed in Table 3 (or antigen-binding fragment thereof). For example, if the binding of an antibody, or an antigen-binding portion thereof, to TFPI hinders the subsequent binding to TFPI by TFPI-23 or TFPI-106, the antibody or an antigen-binding portion thereof competes with TFPI-23 or TFPI-106 for TFPI binding.

Also disclosed is an antibody, or antigen-binding fragment thereof, that specifically binds to the K2 Domain of TFPI, and binds to the same TFPI epitope as any of the antibody or antigen-binding fragment thereof described herein, such as any one of the antibodies listed in Table 3 or antigen-binding fragment thereof.

An exemplary antibody competition assay (and overlapping epitope analysis) by SPR is provided in Example 6.

The antibodies and antigen-binding fragments disclosed herein include monoclonal antibodies, polyclonal antibodies, antibody fragments (e.g., Fab, Fab', $F(ab)_2$, Fv, Fc, etc.), chimeric antibodies, bispecific antibodies, heteroconjugate antibodies, single chain (ScFv), mutants thereof, fusion proteins comprising an antibody portion, domain antibodies (dAbs), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a human antibody. In certain embodiments, the antibody is a humanized antibody.

In certain embodiments, the antibody or antigen-binding fragment thereof disclosed herein has an affinity (Kd) value of no more than about $1\times10^{-3}$M, such as no more than about $5\times10^{-4}$M, no more than about $4\times10^{-4}$ M, no more than about $3\times10^{-4}$ M, no more than about $2\times10^{-4}$ M, no more than about $1\times10^{-4}$ M, no more than about $9\times10^{-5}$ M, no more than about $8\times10^{-5}$ M, no more than about $7\times10^{-5}$ M, no more than about $6\times10^{-5}$M, no more than about $5\times10^{-5}$M, no more than about $4\times10^{-5}$ M, no more than about $3\times10^{-5}$ M, no more than about $2\times10^{-5}$ M, no more than about $1\times10^{-5}$M, no more than about $9\times10^{-6}$M, no more than about $8\times10^{-6}$ M, no more than about $7\times10^{-6}$M, no more than about $6\times10^{-6}$ M, no more than about $5\times10^{-6}$ M, no more than about $4\times10^{-6}$ M, no more than about $3\times10^{-6}$ M, no more than about $2\times10^{-6}$M, no more than about $1\times10^{-6}$M, no more than about $9\times10^{-7}$M, no more than about $8\times10^{-7}$M, no more than about $7\times10^{-7}$M, no more than about $6\times10^{-7}$M, no more than about $5\times10^{-7}$M, no more than about $4\times10^{-7}$M, no more than about $3\times10^{-7}$M, no more than about $2\times10^{-7}$ M, no more than about $1\times10^{-7}$ M, no more than about $9\times10^{-8}$ M, no more than about $8\times10^{-8}$M, no more than about $7\times10^{-8}$M, no more than about $6\times10^{-8}$M, no more than about $5\times10^{-8}$ M, no more than about $4\times10^{-8}$ M, no more than about $3\times10^{-8}$ M, no more than about $2\times10^{-8}$M, no more than about $1\times10^{-8}$M, no more than about $9\times10^{-9}$ M, no more than about $8\times10^{-9}$M, no more than about $7\times10^{-9}$ M, no more than about $6\times10^{-9}$ M, no more than about $5\times10^{-9}$ M, no more than about $4\times10^{-9}$ M, no more than about $3\times10^{-9}$M, no more than about $2\times10^{-9}$M, no more than about $1\times10^{-9}$M, from about $1\times10^{-3}$M to about $1\times10^{-13}$M, $1\times10^{-4}$M to about $1\times10^{-13}$M, $1\times10^{-5}$M to about $1\times10^{-13}$M, from about $1\times10^{-6}$M to about $1\times10^{-13}$M, from about $1\times10^{-7}$M to about $1\times10^{-13}$ M, from about $1\times10^{-8}$M to about $1\times10^{-13}$M, from about $1\times10^{-9}$M to about $1\times10^{-13}$M, $1\times10^{-3}$M to about $1\times10^{-12}$ M $1\times10^{-4}$M to about $1\times10^{-12}$M, from about $1\times10^{-5}$M to about $1\times10^{-12}$M, from about $1\times10^{-6}$M to about $1\times10^{-12}$ M, from about $1\times10^{-7}$M to about $1\times10^{-12}$M, from about $1\times10^{-8}$ M to about $1\times10^{-12}$ M, from about $1\times10^{-9}$M to about $1\times10^{-12}$M, $1\times10^{-3}$M to about $1\times10^{-11}$M, $1\times10^{-4}$M to about $1\times10^{-11}$M, from about $1\times10^{-5}$M to about $1\times10^{-11}$M, from about $1\times10^{-6}$M to about $1\times10^{-11}$ M, from about $1\times10^{-7}$M to about $1\times10^{-11}$ M, from about $1\times10^{-8}$M to about $1\times10^{-11}$ M, from about $1\times10^{-9}$M to about $1\times10^{-11}$ M, $1\times10^{-3}$M to about $1\times10^{-10}$ M, $1\times10^{-4}$M to about $1\times10^{-10}$ M, from about $1\times10^{-5}$M to about $1\times10^{-10}$ M, from about $1\times10^{-6}$M to about $1\times10^{-10}$ M, from about $1\times10^{-7}$M to about $1\times10^{-10}$ M, from about $1\times10^{-8}$M to about $1\times10^{-19}$M, or from about $1\times10^{-9}$M to about $1\times10^{-19}$M.

In certain embodiments, the dissociation constant is measured using surface plasmon resonance (SPR) method (Biacore). Surface plasmon resonance refers to an optical phenomenon that allows for the analysis of real-time biospecific interactions by detection of alterations in protein concentrations within a biosensor matrix, for example using the BIACORE™ system. In certain embodiments, the SPR measurement is conducted using a Biacore T100 or T200 instrument.

For example, a standard assay condition for surface plasmon resonance can be based on ligand immobilization of approximately 100 Response Units (RU) of IgG on the SPR chip. Purified target proteins are diluted in buffer to a range of final concentrations and injected at a requisite flow rate (e.g. 10-100 μl/min) to allow the calculation of Ka. Dissociation is allowed to proceed to establish off-rate (Kd), followed by a 5 sec pulse of 3M $MgCl_2$ (or 20 mM NaOH) for regeneration of the chip surface. Sensorgrams are then analyzed using a kinetics evaluation software package.

In an exemplary embodiment, the SPR assay is according to the conditions as set forth in Example 1, under the subheading "Surface plasmon resonance (SPR)."

In certain embodiments, the dissociation constant is measured using solution-based kinetic exclusion assay (KinExA™). In a particular embodiment, the KinExA measurement is conducted using a KinExA™ 3200 instrument (Sapidyne). The Kinetic Exclusion Assay (KinExA™) is a general purpose immunoassay platform (basically a flow spectrofluorimeter) that is capable of measuring equilibrium dissociation constants, and association and dissociation rate constants for antigen/antibody interactions. Since KinExA™ is performed after equilibrium has been obtained it is an advantageous technique to use for measuring the Kd of high affinity interactions where the off-rate of the interaction may be very slow. The KinExA™ methodology can be conducted generally as described in Drake et al (2004) Analytical Biochemistry 328, 35-43.

In general, a TFPI antibody needs to bind to TFPI with high affinity, in order to effectively block the activities of TFPI. However, because TFPI is also expressed on cell surface, when the binding affinity of an antibody is too high, the antibody can quickly get internalized and degraded by a host cell. This could potentially result in a short half-life and repeated injections. For example, antibody TFPI-23 shows a lower binding affinity (Kd) as compared to TFPI-24, and under certain circumstances, is more desirable because it has a lower internalization rate and longer half-life. Accordingly, binding affinities (Kd) from $5\times10^{-7}$M to about $5\times10^{-11}$ M, in particular from about $1\times10^{-8}$ M to about $1\times10^{-19}$ M (0.1 nM to 10 nM), are generally desirable if longer half-life is desired. This range is believed to strike a balance between (i) binding affinities that are needed for effectively inhibiting the activities of TFPI, and (ii) a longer half-life and reduced antibody internalization.

In particular, it is believed that to maintain weekly subcutaneous dosing at 3 mg/kg, Kd value from about $1\times10^{-8}$M to about $1\times10^{-10}$ M (0.1 nM to 10 nM) is desired.

Whether an antibody or antigen-binding fragment thereof reduces the activity of TFPI, or reduces the binding of TFPI to a physiological substrate (e.g., FXa) can be determined by measuring the decrease in the binding affinity of TFPI to said physiological substrate, for example by comparing (i) the binding affinity of TFPI to its substrate in the presence of the anti-TFPI antibody (or antigen-binding fragment thereof), with (ii) the binding affinity of TFPI to the same substrate in the absence of the anti-TFPI antibody. The reduction in binding of TFPI to a physiological substrate (e.g., FXa) can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the anti-TFPI antibody (or antigen-binding fragment thereof). The expected binding of TFPI to its physiological substrate in the absence of the antibody (or fragment) can be set as 100%.

The TFPI inhibitory activities, also referred to herein as "reducing the activity of TFPI," of an anti-TFPI antibody or antigen-binding fragment thereof can also be assessed in an in vivo model and/or in vitro using, e.g., plasmatic systems. For example, inhibitory activities (or the level of reducing an activity of TFPI) of an antibody can be assessed by: (i) a decrease in clotting time as measured in a plasma based dilute prothrombin time assay; (ii) a reduction in clotting time in whole blood as measured by thromboelastrography; (iii) an increase in thrombin generation; (iv) an increase in FXa activity in the presence of TFPI; (v) enhanced platelet accumulation in the presence of TFPI; (vi) increased fibrin generation in the presence of TFPI; or (vii) any combination thereof. The inhibitory activities of an antibody or antigen-binding fragment can be dose-dependent (e.g., causing a dose-dependent decrease in clotting time as measured in a plasma based dilute prothrombin time assay).

Several exemplary assays for assessing the TFPI inhibitory activity of an antibody are described in detail in the Examples. For example, the plasma dilute Prothrombin Time (PT) assay is a modified PT assay using diluted thromboplastin or Tissue Factor to prolong the clotting time and dynamic range of the assay. An inhibitory/neutralizing anti-TFPI antibody should decrease the dilute prothrombin time.

Another exemplary model system for determining TFPI-inhibitory activity is the extrinsic tenase assay, which tests the ability of antibody or antigen-binding fragment thereof to restore extrinsic complex-mediated FX activation in the presence of TFPI. Another model system for characterizing TFPI-inhibitory activity is the FXa inhibition assay, wherein FXa activity is measured in the presence of TFPI (see Sprecher et al., Proc. Nat. Acad. Sci. USA 91:3353-3357 (1994)).

The inhibitory activities of an antibody or antigen-binding fragment thereof can also be assessed in a plasma-based assay. Thrombin formation can be triggered in plasma substantially lacking FVIII or FIX activity (e.g., the residual coagulation factor activity is lower than 1%) in the presence of an anti-TFPI antibody or antigen-binding fragment thereof. Thrombin formation can be detected using a fluorogenic or chromogenic substrate. Prothrombin conversion can be measured using, e.g., a Thrombograph™ (Thermo Scientific, Waltham, Mass.), and the resulting data can be compiled into a Calibrated Automatic Thrombogram generated by Thrombinoscope™ software available from Thrombinoscope BV.

For example, an antibody or antigen-binding fragment may improve TFPI-regulated thrombin generation in the absence of FVIII (e.g., in FVIII-depleted plasma) to at least 1% of the level of TFPI-dependent thrombin generation in normal plasma. Generally, normal (unafflicted) plasma contains about 0.5 U/mL to about 2 U/mL Factor VIII. Accordingly, in some instances, an antibody or antigen-binding fragment of the invention will enhance thrombin formation in the absence of FVIII to at least about 1% of that observed in the presence of 0.5 U/mL to 2 U/mL FVIII. In further embodiments, the antibody (or antigen-binding fragment thereof) enhances thrombin formation in the absence of Factor VIII to at least about 2%, at least about 3%, at least about 5%, at least about 7%, or at least about 10% of the level of thrombin formation in normal plasma, i.e., in the presence of physiological levels of Factor VIII.

The antibody or antigen-binding fragment may also be administered to an animal model of thrombin deficiency or hemophilia to characterize TFPI inhibitory activity in vivo. Such in vivo models are known in the art and include for example, mice administered anti-FVIII antibodies to induce hemophilia A (Tranholm et al., Blood, 102, 3615-3620 (2003)); coagulation factor knock-out models such as, but not limited to, FVIII knock-out mice (Bi et al., Nat. Genet., 10(1), 119-121 (1995)) and FIX knock-out mice (Wang et al., Proc. Nat. Acad. Sci. USA 94(21):11563-11566 (1997)); induced hemophilia-A in rabbits (Shen et al., Blood, 42(4): 509-521 (1973)); and Chapel Hill HA dogs (Lozier et al., Proc. Nat. Acad. Sci. USA 99:12991-12996 (2002)).

In certain embodiments, the antibodies (or antigen-binding fragments) disclosed herein enhances FXa activity in the presence of TFPI, with a half maximal effective concentration ($EC_{50}$) of no more than $1\times10^{-4}$ M, no more than $1\times10^{-5}$ M, no more than $1\times10^{-6}$ M, no more than $1\times10^{-7}$ M, no more than $1\times10^{-8}$ M, no more than $1\times10^{-9}$ M, no more than $1\times10^{-10}$ M, no more than $1\times10^{-11}$ M, or no more than $1\times10^{-12}$ M. Preferably the $EC_{50}$ is from about $5\times10^{-7}$ M to $1\times10^{-11}$ M, such as from about $1\times10^{-7}$ M to $5\times10^{-10}$ M, from about $1\times10^{-7}$ M to $1\times10^{-10}$ M, $1\times10^{-7}$ M to $5\times10^{-9}$ M, $5\times10^{-7}$ M to $5\times10^{-10}$ M, from about $5\times10^{-7}$ M to $1\times10^{-10}$ M, or from about $5\times10^{-7}$ M to $5\times10^{-9}$ M.

In certain embodiments, the antibodies (or antigen-binding fragments) disclosed herein neutralizes the TFPI inhibition of the FVIIa/TF mediated FX activation, with a half maximal effective concentration ($EC_{50}$) of no more than $1\times10^{-4}$ M, no more than $1\times10^{-5}$ M, no more than $1\times10^{-6}$ M, no more than $1\times10^{-7}$ M, no more than $1\times10^{-8}$ M, no more than $1\times10^{-9}$ M, no more than $1\times10^{-10}$ M, no more than $1\times10^{-11}$ M, or no more than $1\times10^{-12}$ M. Preferably the $EC_{50}$ is from about $5\times10^{-7}$ M to $1\times10^{-11}$ M, such as from about $1\times10^{-7}$ M to $5\times10^{-10}$ M, from about $1\times10^{-7}$ M to $1\times10^{-10}$ M, $1\times10^{-7}$ M to $5\times10^{-9}$ M, $5\times10^{-7}$ M to $5\times10^{-10}$ M, from about $5\times10^{-7}$ M to $1\times10^{-10}$ M, or from about $5\times10^{-7}$ M to $5\times10^{-9}$ M.

In certain embodiments, the antibodies (or antigen-binding fragments) disclosed herein decreases the clotting time as measured in a plasma based dilute prothrombin time assay, with a half maximal effective concentration ($EC_{50}$) of no more than $1\times10^{-4}$ M, no more than $1\times10^{-5}$ M, no more than $1\times10^{-6}$ M, no more than $1\times10^{-7}$ M, no more than $1\times10^{-8}$ M, no more than $1\times10^{-9}$ M, no more than $1\times10^{-10}$ M, no more than $1\times10^{-11}$ M, or no more than $1\times10^{-12}$ M. Preferably the $EC_{50}$ is from about $5\times10^{-7}$ M to $1\times10^{-11}$ M, such as from about $1\times10^{-7}$ M to $5\times10^{-10}$ M, from about $1\times10^{-7}$ M to $1\times10^{-10}$ M, $1\times10^{-7}$ to $5\times10^{-9}$ M, $5\times10^{-7}$ to $5\times10^{-10}$ M from about $5\times10^{-7}$ M to $1\times10^{-10}$ M, or from about $5\times10^{-7}$ M to $5\times10^{-9}$ M.

In certain embodiments, the antibodies (or antigen-binding fragments) disclosed herein increases thrombin generation velocity index, with a half maximal effective concentration ($EC_{50}$) of no more than $1\times10^{-4}$ M, no more than $1\times10^{-5}$ M, no more than $1\times10^{-6}$ M, no more than $1\times10^{-7}$ M, no more than $1\times10^{-8}$ M, no more than $1\times10^{-9}$ M, no more than $1\times10^{-10}$ M, no more than $1\times10^{-11}$ M, or no more than $1\times10^{-12}$ M. Preferably the $EC_{50}$ is from about $5\times10^{-7}$ M to $1\times10^{-11}$ M, such as from about $1\times10^{-7}$ M to $5\times10^{-10}$ M, from about $1\times10^{-7}$ M to $1\times10^{-10}$ M, $1\times10^{-7}$ M to $5\times10^{-9}$ M, $5\times10^{-7}$ M to $5\times10^{-10}$ M, from about $5\times10^{-7}$ M to $1\times10^{-10}$ M, or from about $5\times10^{-7}$ M to $5\times10^{-9}$ M.

In certain embodiments, the antibody and antibody fragments disclosed herein may also be further assessed by other biological activity assays, e.g., in order to evaluate its potency, pharmacological activity, and potential efficacy as a therapeutic agent. Such assays are known in the art and depend on the target antigen and intended use for the antibody. Examples include e.g., tumor cell growth inhibition assays; antibody-dependent cellular cytotoxicity (ADCC) and complement-mediated cytotoxicity (CDC) assays; agonistic activity or antagonist activity assays.

C. Polynucleotides, Vectors, and Host Cells

The invention also provides polynucleotides encoding any of the TFPI binding antibodies of the disclosure, including antibody fragments and modified antibodies described herein, such as, e.g., antibodies having impaired Fc effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the TFPI antibodies and antigen-binding fragments thereof of the invention.

In one embodiment, the VH and VL domains, or antigen-binding fragment thereof, or full length HC or LC, are encoded by separate polynucleotides. Alternatively, both VH and VL, or antigen-binding fragment thereof, or HC and LC, are encoded by a single polynucleotide.

The invention provides polynucleotides, or compositions comprising the polynucleotides, encoding any of the TFPI antibodies and antigen-binding fragments thereof of the invention, including, but not limited to, TFPI-23, TFPI-24, TFPI-106, TFPI-107, and 4D8, wherein the sequence of the polynucleotide encompasses the sequence of SEQ ID NO:175 (encoding TFPI-106 VH region), SEQ ID NO:176 (encoding TFPI-106 VL region), SEQ ID NO:177 (encoding TFPI-106 Heavy Chain), and SEQ ID NO:178 (encoding TFPI-106 Light Chain).

In another aspect, the invention provides an isolated nucleic acid encoding the VH region of an antibody, or an antigen-binding portion thereof, that specifically binds TFPI, comprising the nucleic acid sequence of the insert present in the plasmid deposited as ATCC Accession No. PTA-122329.

In another aspect, the invention provides an isolated nucleic acid encoding the VL region of an antibody, or an antigen-binding portion thereof, that specifically binds TFPI, comprising the nucleic acid sequence of the insert present in the plasmid deposited as ATCC Accession No. PTA-122328.

In another aspect, the invention provides polynucleotides and variants thereof encoding a TFPI antibody, or portion thereof, wherein such variant polynucleotides comprise a nucleic acid sequence sharing at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. The degree of sequence identity over any length of nucleotide sequence can be calculated using methods familiar to those of ordinary skill in the art. In one non-limiting embodiment, percent sequence identity between two or more related nucleotide sequences can be determined using the nucleotide BLAST server available from the National Library of Medicine (http://blast.ncbi.nlm.nih.gov/). This software provides different settings that one of ordinary skill can use to optimize sequence comparisons depending on such factors as length, complexity, and other factors.

The invention provides a nucleic acid molecule comprising a nucleotide sequence encoding an amino acid sequence of any TFPI antibody, and antigen-biding fragment thereof, of the invention, including, but not limited to, an amino acid sequence of an antibody, or antigen-binding fragment thereof, provided in Table 33 (e.g., an amino acid sequence of SEQ ID NOs:21-174), and any antibody that binds the same epitope as and/or competes for binding of TFPI with an antibody of the invention.

In another aspect, the invention provides polynucleotides and variants thereof encoding a TFPI antibody, wherein such variant polynucleotides encode an amino acid sequence sharing at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any TFPI antibody amino acid sequence disclosed herein.

In other embodiments, the degree of relatedness between nucleic acids comprising a variant polynucleotide sequence encoding a TFPI antibody, or portion thereof, and any of the specific nucleotide sequences disclosed herein can be determined by testing if the variant sequence (or complement thereto) can hybridize with a specific nucleotide sequence (or complement thereto) under moderate or highly stringent conditions in a Northern blot or Southern blot assay format. Exemplary and non-limiting "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Exemplary and non-limiting, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like. One of ordinary skill in the art will also be familiar with standard techniques for conducting a Northern blot or Southern blot assay to detect the degree of relatedness between variant a nucleotide sequence and a specific nucleotide sequence of the disclosure.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include hnRNA molecules, which contain introns and correspond to a DNA molecule in a one-to-one manner, and mRNA molecules, which do not contain introns. Additional coding or non-coding sequences may, but need not, be present within a polynucleotide of the present invention.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

It will be appreciated by those of ordinary skill in the art that, as a result of the degeneracy of the genetic code, there are many nucleotide sequences capable of encoding any of the TFPI antibodies, or portions thereof, disclosed herein. Some of these polynucleotides may bear a relatively low degree of sequence identity to any of the specific nucleotide sequences for TFPI antibodies provided herein, while encoding the same amino acid sequence. Nonetheless, polynucleotides that vary due to differences in codon usage are specifically contemplated by the present invention.

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells can be transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to simian COS, human HeLa, human embryonic kidney (HEK) 293, Sp2.0 and Chinese hamster ovary (CHO) cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Screening for host cells expressing a TFPI antibody, or antigen binding portion thereof, can be detected using an immune-binding assay, such as ELISA, FACS, or other assay familiar to those of ordinary skill in the art.

Thus, the antibody (or antigen-binding fragment thereof) of the invention may be recombinantly produced using a suitable host cell. Nucleic acid encoding the antibody or antigen-binding fragment thereof can be cloned into an expression vector, which can then be introduced into a host cell, such as *E. coli* cell, a yeast cell, an insect cell, a COS cell, a CHO cell, or a myeloma cell that do not otherwise produce immunoglobulin protein, to obtain the synthesis of monoclonal antibodies in the recombinant host cells. Exemplary host cells include CHO cell, HEK 293, and Sp2.0 cells.

An expression vector can be used to direct expression of a TFPI antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. According to certain non-limiting embodiments, the expression vector is administered directly to the liver, skeletal muscles, bone marrow, or other tissues.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

The sequence of a desired antibody (or antigen-binding fragment thereof), and nucleic acid encoding such antibody (or antigen-binding fragment thereof), can be determined using standard sequencing techniques. Nucleic acid sequence encoding a desired antibody (or fragments) may be inserted into other vectors (such as cloning and expression vectors) for recombinant production and characterization. Heavy chain (or a fragment of the heavy chain) and light chain (or a fragment of the light chain) can be cloned in the same vector, or different vectors.

Suitable cloning and expression vectors can include a variety of components, such as promoter, enhancer, and other transcriptional regulatory sequences. The vector may also be constructed to allow for movement of antibody variable domain between different vectors.

Antibody fragments can be produced by proteolytic or other degradation of the antibodies, by recombinant methods, or by chemical synthesis. Polypeptides of the antibodies, especially shorter polypeptides up to about 50 amino acids, are conveniently made by chemical synthesis. Methods of chemical synthesis are known in the art and are commercially available.

The antibody or antigen-binding fragment thereof disclosed herein may be affinity-matured. For example, affinity matured antibodies can be produced by procedures known in the art (Marks et al., 1992, Bio/Technology, 10:779-783; Barbas et al., 1994, Proc. Nat. Acad. Sci. USA 91:3809-3813; Schier et al., 1995, Gene, 169:147-155; Yelton et al., 1995, J. Immunol., 155:1994-2004; Jackson et al., 1995, J. Immunol., 154(7):3310-3319; Hawkins et al., 1992, J. Mol. Biol., 226:889-896; and WO2004/058184).

4. Formulations and Uses

Antibodies or antigen-binding fragments described herein can be formulated as pharmaceutical formulations. The pharmaceutical formulation may further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The antibodies or antigen-binding fragments described herein can be used for various therapeutic or diagnostic purposes. For example, the antibody or antigen-binding fragment thereof may be used as an affinity purification agents (e.g., for in vitro purification of TFPI), as a diagnostic agent (e.g., for detecting expression of TFPI in specific cells, tissues, or serum).

Exemplary therapeutic uses of the antibody and antibody fragments of the invention include treating thrombocytopenia, platelet disorders (disorders of platelet function or number), and bleeding disorders (e.g., hemophilia A, hemophilia B and hemophilia C). The antibodies and antibody fragments may also be used for treating uncontrolled bleeding in indications such as trauma and hemorrhagic stroke. The antibodies and antibody fragments may also be used in prophylactic treatment (e.g., before surgeries).

In particular, antibodies or antigen-binding fragments described herein can be used to treat deficiencies or defects in coagulation. For example, the antibodies or antigen-binding fragments described herein may be used to reduce or inhibit the interaction of TFPI with FXa, or to reduce TFPI-dependent inhibition of the TF/FVIIa/FXa activity.

For therapeutic applications, antibodies or antigen-binding fragments described herein can be administered to a mammal, especially a human by conventional techniques, such as intravenously (as a bolus or by continuous infusion over a period of time), intramuscularly, intraperitoneally, intra-cerebrospinally, subcutaneously, intra-articularly, intrasynovially, intrathecally, orally, topically, or by inhalation. The antibodies or antigen-binding fragments also are suitably administered by intra-tumoral, peri-tumoral, intralesional, or peri-lesional routes.

Accordingly, in one aspect, the invention provides a method of reducing the activity of Tissue Factor Pathway Inhibitor (TFPI), comprising administering to a subject in need thereof a therapeutically effective amount of the antibodies or antigen-binding fragments described herein. In another aspect, the invention provides a method of shortening bleeding time, comprising administering to a subject in need thereof a therapeutically effective amount of the antibodies or antigen-binding fragments described herein.

In certain embodiments, the subject is a human.

In certain embodiments, the subject suffers from or is susceptible to a deficiency in blood coagulation. Deficiency in blood coagulation includes, e.g., von Willebrand disease (vWD), hemophilia A, B, or C, and other platelet disorders (such as congenital platelet defects, congenital and acquired storage pool deficiency, prolonged bleeding time).

In certain embodiments, the antibodies or antigen-binding fragments described herein is administered subcutaneously.

In certain embodiments, the antibodies or antigen-binding fragments described herein is administered intravenously.

The pharmaceutical compositions may be administered to a subject in need thereof at a frequency that may vary with the severity of the bleeding episode or, in the case of prophylactic therapy, may vary with the severity of the patient's clotting deficiency.

The compositions may be administered to patients in need as a bolus or by continuous infusion. For example, a bolus administration of an antibody present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, an antibody present as an Fab fragment may be administered at 0.001 to 100 mg/kg body weight/minute, 0.0125 to 1.25 mg/kg/min, 0.010 to 0.75 mg/kg/min, 0.010 to 1.0 mg/kg/min. or 0.10-0.50 mg/kg/min for a period of 1-24 hours, 1-12 hours, 2-12 hours, 6-12 hours, 2-8 hours, or 1-2 hours.

For administration of an antibody present as a full-length antibody (with full constant regions), dosage amounts may be from about 1 mg/kg to about 10 mg/kg, from about 2 mg/kg to about 10 mg/kg, from about 3 mg/kg to about 10 mg/kg, from about 4 mg/kg to about 10 mg/kg, from about 5 mg/kg to about 10 mg/kg, from about 1 mg/kg to about 20 mg/kg, from about 2 mg/kg to about 20 mg/kg, from about 3 mg/kg to about 20 mg/kg, from about 4 mg/kg to about 20 mg/kg, from about 5 mg/kg to about 20 mg/kg, about 1 mg/kg or more, about 2 mg/kg or more, about 3 mg/kg or more, about 4 mg/kg or more, about 5 mg/kg or more, about 6 mg/kg or more, about 7 mg/kg or more, about 8 mg/kg or more, about 9 mg/kg or more, about 10 mg/kg or more, about 11 mg/kg or more, about 12 mg/kg or more, about 13 mg/kg or more, about 14 mg/kg or more, about 15 mg/kg or more, about 16 mg/kg or more, about 17 mg/kg or more, about 19 mg/kg or more, or about 20 mg/kg or more. The frequency of the administration would depend upon the severity of the condition. Frequency could range from three times per week to once every two or three weeks.

Additionally, the compositions may be administered to patients via subcutaneous injection. For example, a dose of 1 to 100 mg anti-TFPI antibody can be administered to patients via subcutaneous injection once every day, once every 2 days, once every 3 days, once every 4 days, once every 5 days, once every 6 days, twice a week, weekly, biweekly, or monthly.

In certain embodiments, the pharmaceutical composition is administered subcutaneous by a weekly schedule, with a dose from about 0.1 mg/kg to about 10 mg/kg, from about 0.5 mg/kg to about 10 mg/kg, from about 1 mg/kg to about 10 mg/kg, from about 1.5 mg/kg to about 10 mg/kg, from about 2 mg/kg to about 10 mg/kg, from about 0.1 mg/kg to about 8 mg/kg, from about 0.5 mg/kg to about 8 mg/kg, from about 1 mg/kg to about 8 mg/kg, from about 1.5 mg/kg to about 8 mg/kg, from about 2 mg/kg to about 8 mg/kg, from about 0.1 mg/kg to about 5 mg/kg, from about 0.5 mg/kg to about 5 mg/kg, from about 1 mg/kg to about 5 mg/kg, from about 1.5 mg/kg to about 5 mg/kg, from about 2 mg/kg to about 5 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10.0 mg/kg.

In certain embodiments, the pharmaceutical composition is administered subcutaneous by a weekly schedule, with a dose of about 2.0 mg/kg. In certain embodiments, the pharmaceutical composition is administered subcutaneous by a weekly schedule, with a dose of about 3.0 mg/kg.

The antibodies and antibody fragments described herein can be used as monotherapy or in combination with other therapies to address a hemostatic disorder. For example, co-administration of one or more antibodies (or antibody fragments) of the invention with a clotting agent such as factor Vila, factor VIII, factor IX or tranexamic acid may be useful for treating hemophilia.

In one embodiment, provided is a method for treating a deficiency in coagulation or shortening bleeding time, comprising administering (a) a first amount of the antibody or antigen-binding fragment of the invention, and (b) a second amount of factor VIII or factor IX. Optionally, factor VII is not co-administered. In another embodiment, provided is a method for treating a deficiency in coagulation or shortening bleed time, comprising administering (a) a first amount of the antibody or antigen-binding fragment of the invention and (b) a second amount of factor VIII or factor IX. Optionally, factor VII is not co-administered. One skilled in the art would appreciate that in treating a deficiency in coagulation, a shortening in bleeding time can also be referred to as a shortening in clotting time.

The invention also includes a pharmaceutical composition comprising a therapeutically effective amount of the combination of an antibody (or antibody fragment) of the invention and factor VIII or factor IX, wherein the composition does not comprise factor VII. “Factor VII” includes factor VII and factor VIIa.

Biological Deposit

Representative materials of the present invention were deposited in the American Type Culture Collection, 10801 University Boulevard, Manassas, Va. 20110-2209, USA, on Jul. 22, 2015. Plasmid vector mAb-TFPI-106 VH having ATCC Accession No. PTA-122329 comprises a DNA insert encoding the heavy chain variable region of antibody TFPI-106, and plasmid vector mAb-TFPI-106 VL having ATCC Accession No. PTA-122328 comprises a DNA insert encoding the light chain variable region of antibody TFPI-106. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner’s rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1. Experimental Materials and Methods

1. TFPI Protein Reagents

Protein reagents used for immunization, phage display selection and characterization of anti-TFPI antibodies are listed in Table 1, and their sequence IDs are listed in Table 2.

The TFPI constructs (pSMED2 vector) were expressed transiently in HEK293F cells and conditioned media was harvested 120 hours post transfection. The protein of interest was captured from conditioned media using Nickel Sepharose HP and further purified by size exclusion chromatography. Factor Xa and Factor X were obtained from Haematologic Technologies, Inc. The chromogenic substrate for the for the amidolytic assay of Factor Xa, Spectrozyme®FXa was obtained from Sekisui Diagnostics.

TABLE 1

Protein reagents used for immunization, phage display selection and identification of anti-TFPI antibodies

| | | SeqID (see table 2) | | |
|---|---|---|---|---|
| Protein Reagent | Species | Secretory Leader | TFPI | C-terminal tag |
| humTFPI K1K2 | human | 9 | 1 | 8 |
| humTFPI K1K2K3 | human | 9 | 2 | 8 |
| humTFPI2 K1K2K3 | human | 9 | 3 | 8 |
| murTFPI K1K2 | mouse | 9 | 4 | 8 |
| cynTFPI K1K2 | cynomolgus monkey | 9 | 5 | 8 |
| rabTFPI K1K2 | rabbit | 9 | 6 | 8 |
| ratTFPI K1K2 | rat | 9 | 7 | 8 |

TABLE 2

TFPI reagent sequence identification numbers, descriptions and sequences

| Seq ID | Description | Sequence |
|---|---|---|
| 1 | Human TFPIα K1K2 (Accession #P10646, residues 29-177) | DSEEDEEHTI ITDTELPPLK LMHSFCAFKA DDGPCKAIMK RFFFNIFTRQ CEEFIYGGCE GNQNRFESLE ECKKMCTRDN ANRIIKTTLQ QEKPDFCFLE EDPGICRGYI TRYFYNNQTK QCERFKYGGC LGNMNNFETL EECKNICED |

TABLE 2-continued

TFPI reagent sequence identification numbers, descriptions and sequences

| Seq ID | Description | Sequence |
|---|---|---|
| 2 | Human TFPIα K1K2K3 (Accession #P10646, residues 29-282) | DSEEDEEHTI ITDTELPPLK LMHSFCAFKA DDGPCKAIMK RFFFNIFTRQ CEEFIYGGCE GNQNRFESLE ECKKMCTRDN ANRIIKTTLQ QEKPDFCFLE EDPGICRGYI TRYFYNNQTK QCERFKYGGC LGNMNNFETL EECKNICEDG PNGFQVDNYG TQLNAVNNSL TPQSTKVPSL FEFHGPSWCL TPADRGLCRA NENRFYYNSV IGKCRPFKYS GCGGNENNFT SKQECLRACK KGFIQRISKG GLIK |
| 3 | Human TFPI2 K1K2K3 (Accession #P10646, residues 23-211) | DAAQEPTGNN AEICLLPLDY GPCRALLLRY YYDRYTQSCR QFLYGGCEGN ANNFYTWEAC DDACWRIEKV PKVCRLQVSV DDQCEGSTEK YFFNLSSMTC EKFFSGGCHR NRIENRFPDE ATCMGFCAPK KIPSFCYSPK DEGLCSANVT RYYFNPRYRT CDAFTYTGCG GNDNNFVSRE DCKRACAKA |
| 4 | Mouse TFPI K1K2 (Accession #O54819, residues 29-174) | LSEEADDTDS ELGSMKPLHT FCAMKADDGP CKAMIRSYFF NMYTHQCEEF IYGGCEGNEN RFDTLEECKK TCIPGYEKTA VKAASGAERP DFCFLEEDPG LCRGYMKRYL YNNQTKQCER FVYGGCLGNR NNFETLDECK KICENP |
| 5 | Cynomolgus Monkey TFPI K1K2 (Accession #Q2PFV4, residues 29-177) | DSEEDEEYTI ITDTELPPLK LMHSFCAFKP DDGPCKAIMK RFFFNIFTRQ CEEFIYGGCG GNQNRFESME ECKKVCTRDN VNRIIQTALQ KEKPDFCFLE EDPGICRGYI TRYFYNNQSK QCERFKYGGC LGNMNNFETL EECKNTCED |
| 6 | Rabbit TFPI K1K2 (Accession #P19761, residues 29-177) | AAEEDEEFTN ITDIKPPLQK PTHSFCAMKV DDGPCRAYIK RFFFNILTHQ CEEFIYGGCE GNENRFESLE ECKEKCARDY PKMTTKLTFQ KGKPDFCFLE EDPGICRGYI TRYFYNNQSK QCERFKYGGC LGNLNNFESL EECKNTCEN |
| 7 | Rat TFPI K1K2 (Accession #Q02445, residues 29-176) | LPEEDDDTIN TDSELRPMKP LHTFCAMKAE DGPCKAMIRS YYFNMNSHQC EEFIYGGCRG NKNRFDTLEE CRKTCIPGYK KTTIKTTSGA EKPDFCFLEE DPGICRGFMT RYFYNNQSKQ CEQFKYGGCL GNSNNFETLE ECRNTCED |
| 8 | Spacer residues in italics, AviTag ™ is underlined, His-8 tag in bold | *GGGSGG*GLND IFEAQKIEWH E*GGPP* **HHHHH HHHHH** |
| 9 | Mouse Ig kappa secretory leader (Accession #P01661, residues 1-20) | METDTLLLWV LLLWVPGSTG |

2. Antibody Reagents

The monoclonal antibodies used for comparative purposes (reference antibodies 2A8, 2A8-200, 3F18, hz4F36) are listed in Table 3. The antibody descriptions, sources and sequences are listed in Table 4 (FIG. 5). The light chain and heavy chain sequences were cloned into the appropriate vectors and were expressed transiently in Human Embryonic Kidney-293 (HEK-293) cells, and purified by Protein A Sepharose and size exclusion chromatography. Mab 2974 was obtained from R&D Systems (catalog #MAB2974).

TABLE 3

| | Light Chain SeqID (See Table 4) | | | | | | Heavy Chain SeqID (See Table 4) | | | | | |
|---|---|---|---|---|---|---|---|---|---|---|---|---|
| Antibody | LC CDR1 | LC CDR2 | LC CDR3 | VL | CL | LC | HC CDR1 | HC CDR2 | HC CDR3 | VH | CH | HC |
| TFPI-3 | 10 | 11 | 12 | 13 | 14 | 15 | 16 | 17 | 18 | 19 | 20 | 21 |
| TFPI-21 | 22 | 23 | 24 | 25 | 26 | 27 | 28 | 29 | 30 | 31 | 20 | 32 |
| TFPI-23 | 33 | 34 | 35 | 36 | 26 | 37 | 38 | 39 | 40 | 41 | 20 | 42 |
| TFPI-24 | 43 | 44 | 45 | 46 | 26 | 47 | 48 | 49 | 50 | 51 | 20 | 52 |
| TFPI-26 | 53 | 54 | 55 | 56 | 26 | 57 | 58 | 59 | 60 | 61 | 20 | 62 |
| TFPI-106 | 33 | 34 | 35 | 36 | 26 | 37 | 38 | 39 | 40 | 63 | 20 | 64 |
| TFPI-107 | 33 | 34 | 35 | 36 | 26 | 37 | 38 | 39 | 40 | 65 | 20 | 66 |
| TFPI-108 | 43 | 44 | 45 | 46 | 26 | 47 | 48 | 49 | 50 | 67 | 20 | 68 |
| TFPI-109 | 43 | 44 | 45 | 46 | 26 | 47 | 48 | 49 | 50 | 69 | 20 | 70 |
| TFPI-110 | 43 | 44 | 45 | 71 | 26 | 72 | 48 | 49 | 50 | 51 | 20 | 52 |
| TFPI-111 | 43 | 44 | 45 | 73 | 26 | 74 | 48 | 49 | 50 | 51 | 20 | 52 |
| TFPI-112 | 43 | 44 | 45 | 75 | 26 | 76 | 48 | 49 | 50 | 51 | 20 | 52 |
| TFPI-113 | 43 | 44 | 45 | 77 | 26 | 78 | 48 | 49 | 50 | 51 | 20 | 52 |
| TFPI-114 | 43 | 44 | 45 | 46 | 26 | 47 | 48 | 49 | 50 | 79 | 20 | 80 |

TABLE 3-continued

| | Light Chain SeqID (See Table 4) | | | | | | Heavy Chain SeqID (See Table 4) | | | | | |
|---|---|---|---|---|---|---|---|---|---|---|---|---|
| Antibody | LC CDR1 | LC CDR2 | LC CDR3 | VL | CL | LC | HC CDR1 | HC CDR2 | HC CDR3 | VH | CH | HC |
| TFPI-115 | 43 | 44 | 45 | 71 | 26 | 72 | 48 | 49 | 50 | 67 | 20 | 68 |
| TFPI-118 | 43 | 44 | 45 | 77 | 26 | 78 | 48 | 49 | 50 | 67 | 20 | 68 |
| TFPI-119 | 43 | 44 | 45 | 71 | 26 | 72 | 48 | 49 | 50 | 69 | 20 | 70 |
| TFPI-122 | 43 | 44 | 45 | 77 | 26 | 78 | 48 | 49 | 50 | 69 | 20 | 70 |
| TFPI-123 | 43 | 44 | 45 | 71 | 26 | 72 | 48 | 49 | 50 | 51 | 20 | 52 |
| TFPI-126 | 43 | 44 | 45 | 77 | 26 | 78 | 48 | 49 | 50 | 51 | 20 | 52 |
| 4D8.b1 | 81 | 82 | 83 | 84 | 85 | 86 | 87 | 88 | 89 | 90 | 91 | 92 |
| mu-hu 4D8 chimera | 81 | 82 | 83 | 84 | 14 | 93 | 87 | 88 | 89 | 90 | 20 | 94 |
| 4D8-$V_k1.0 \times V_H1.0$ | 81 | 82 | 83 | 109 | 14 | 110 | 87 | 88 | 89 | 95 | 20 | 96 |
| 4D8-$V_k1.0 \times V_H1.1$ | 81 | 82 | 83 | 109 | 14 | 110 | 87 | 88 | 89 | 97 | 20 | 98 |
| 4D8-$V_k1.0 \times V_H1.2$ | 81 | 82 | 83 | 109 | 14 | 110 | 87 | 88 | 89 | 99 | 20 | 100 |
| 4D8-$V_k1.0 \times V_H1.3$ | 81 | 82 | 83 | 109 | 14 | 110 | 87 | 88 | 89 | 101 | 20 | 102 |
| 4D8-$V_k1.0 \times V_H1.4$ | 81 | 82 | 83 | 109 | 14 | 110 | 87 | 88 | 89 | 103 | 20 | 104 |
| 4D8-$V_k1.0 \times V_H1.5$ | 81 | 82 | 83 | 109 | 14 | 110 | 87 | 88 | 89 | 105 | 20 | 106 |
| 4D8-$V_k1.0 \times V_H1.6$ | 81 | 82 | 83 | 109 | 14 | 110 | 87 | 88 | 89 | 107 | 20 | 108 |
| 4D8-$V_k1.1 \times V_H1.0$ | 81 | 82 | 83 | 111 | 14 | 112 | 87 | 88 | 89 | 95 | 20 | 96 |
| 4D8-$V_k1.1 \times V_H1.1$ | 81 | 82 | 83 | 111 | 14 | 112 | 87 | 88 | 89 | 97 | 20 | 98 |
| 4D8-$V_k1.1 \times V_H1.2$ | 81 | 82 | 83 | 111 | 14 | 112 | 87 | 88 | 89 | 99 | 20 | 100 |
| 4D8-$V_k1.1 \times V_H1.3$ | 81 | 82 | 83 | 111 | 14 | 112 | 87 | 88 | 89 | 101 | 20 | 102 |
| 4D8-$V_k1.1 \times V_H1.4$ | 81 | 82 | 83 | 111 | 14 | 112 | 87 | 88 | 89 | 103 | 20 | 104 |
| 4D8-$V_k1.1 \times V_H1.5$ | 81 | 82 | 83 | 111 | 14 | 112 | 87 | 88 | 89 | 105 | 20 | 106 |
| 4D8-$V_k1.1 \times V_H1.6$ | 81 | 82 | 83 | 111 | 14 | 112 | 87 | 88 | 89 | 107 | 20 | 108 |
| hz4D8 | 81 | 82 | 83 | 111 | 14 | 112 | 87 | 88 | 89 | 103 | 20 | 104 |
| 6B7.c5 | 113 | 114 | 115 | 116 | 85 | 117 | 118 | 119 | 120 | 121 | 91 | 122 |
| 7A4.D9 | 123 | 124 | 125 | 126 | 85 | 127 | 128 | 129 | 130 | 131 | 91 | 132 |
| 2A8 | 133 | 134 | 135 | 136 | 26 | 137 | 138 | 139 | 140 | 141 | 20 | 142 |
| 2A8-200 | 143 | 144 | 145 | 146 | 26 | 147 | 148 | 149 | 150 | 151 | 20 | 152 |
| 3F18 | 153 | 154 | 155 | 156 | 157 | 158 | 159 | 160 | 161 | 162 | 81 | 163 |
| hz4F36 | 164 | 165 | 166 | 167 | 14 | 168 | 169 | 170 | 171 | 172 | 173 | 174 |

Antibody sequence identification numbers (SeqID) for light chain (LC) CDR1,2,3, variable light (VL), constant light (CL), light chain (LC), heavy chain (HC) CDR1,2,3, variable heavy (VH), constant heavy (CH) and heavy chain (HC) regions.
Sequence compositions for SeqID numbers are in Table 4.

3. TFPI binding ELISA

Recombinant humTFPI K1K2, murTFPI K1K2, cynTFPI K1K2, ratTFPI K1K2, rabTFPI K1K2 or TFPI2 was biotinylated using the AviTag™ system and captured onto Greiner streptavidin-coated 96 well plates at a concentration of $1\times10^{-8}$ M in ELISA assay buffer. Purified anti-TFPI antibodies were diluted to 1 ug/ml in ELISA assay buffer, then serially diluted three-fold to generate an eight-point dilution series. The diluted antibodies were added at a volume of 100 uL per well. The plates were incubated at room temperature for 2 hours. After washing the plates with PBS/0.05% Tween 20, the plates were incubated with a goat anti-mouse IgG-Fc polyclonal antibody conjugated with horseradish peroxidase (Pierce) at 1:10,000 dilution. After 1 hour of incubation, bound antibody was detected with the addition of a TMB substrate solution. Absorbances were read a 450 nm, and the data were analyzed by GraphPad Prism software.

4. Surface Plasmon Resonance (SPR)

An anti-human Fc sensor chip was prepared by amine coupling anti-human IgG antibody (catalogue number BR-1008-39, GE Healthcare) to all four flow cells of a carboxymethylated dextran coated sensor chip (CM5) (catalogue number BR100530, GE Healthcare). The flow cells were activated by injecting a 1:1 mixture of 400 mM 1-Ethyl-3-(3-dimethylaminopropyl) carbodiimide hydrochloride (EDC) and N-hydroxysuccinimide (NHS) for 7 minutes at a flow rate of 10 μl/minute. Anti-human IgG antibody was diluted to 25 μg/ml in 10 mM Sodium Acetate pH 5.0 and injected over all flow cells for 7 minutes at 10 ul/minute. All flow cells were blocked with 1M Ethanolamine-HCL (ETH) for 7 minutes at 10 μl/minute. Final immobilization level of the capture antibody was approximately 10,000 resonance units (RU). The running buffer for immobilization and kinetics was 10 mM HEPES pH 7.4, 150 mM NaCl, 3 mM EDTA, 0.05% (v/v) Tween-20 (HBS-EP+). To characterize the binding of anti-TFPI antibodies to human TFPI, the antibodies were diluted to 0.5 μg/mL in HBS-EP+ and captured by the anti-human IgG immobilized on flow cells 2, 3 and 4 for 30 seconds to 1 minute at a flow rate of 5 μL/minute to achieve a capture level of 70 to 300 RU. Flow cell 1 was used as a reference surface. After antibody capture, the flow rate was increased to 50 μL/minute and buffer or human TFPI ranging in concentration from 0.2 nM to 200 nM in HBS-EP+ was injected over all flow cells for a 1.0 minute association and allowed to dissociate for 10 to 15 minutes. Buffer cycles collected for each captured antibody were used for double-referencing (Myszka, D. G. J. Mol. Recognit. 12, 279-284 (1999)). At the end of each cycle, the entire anti-IgG surface was regenerated by a 60 second pulse of 3M MgCl2. Kinetic assays were conducted at 25° C. at a collection rate of 10 Hz on a BIAcore T200 instrument (GE Healthcare). Rate constants and affinities were determined by fitting the data to a 1:1 model in BIAcore T200 Evaluation software version 1.0 (GE).

5. Factor Xa TFPI Inhibition Reversal Assay

The ability of purified anti-TFPI antibodies to restore Factor Xa activity in the presence of inhibitory concentrations of TFPI was assessed in vitro. Anti-TFPI antibodies diluted in PBS at concentrations ranging from 1 nM-500 nM were pre-incubated with 10 nM recombinant human TFPI K1K2 or 10 nM rabbit TFPI K1K2 proteins in activity buffer (20 mM HEPES, pH 8.0, 150 mM NaCl, 5 mM $CaCl_2$, 0.5 mg/mL BSA) for 30 minutes at 37° C. 2 nM human plasma-derived Factor Xa was added and the reactions were incubated at 37° C. for 30 minutes. The chromogenic substrate Spectrozyme Xa was added to a final concentration of 500 uM for a final reaction volume of 100 uL. Control reactions included reactions without Factor Xa to control for assay background, without TFPI, allowing for maximal generation of FXa (100% activity) or without anti-TFPI antibody (PBS alone). Absorbances of the reactions were immediately read on a SpectraMax M5e multi-mode plate reader at a wavelength of 405 nm at 2 minute intervals over a period of 60 minutes. $EC_{50}$s were calculated with Prism Graph Pad software.

6. Two-Stage TF-FVIIa-FX Inhibition Reversal Assay

The ability of purified anti-TFPI antibodies to restore Factor Vila-Tissue Factor activity in the presence of inhibitory concentrations of TFPI was assessed in vitro. Anti-TFPI antibodies at concentrations ranging from 1 nm-500 nM were pre-incubated with 10 nM recombinant TFPI proteins in activity buffer for 30 minutes at 37° C. Approximately 1 μM lipidated tissue factor and 1 nM recombinant Factor VIIa (NovoSeven) were added to the reactions and incubated at 37° C. for 5 minutes. 150 nM Human Factor X was introduced into the reactions. The chromogenic substrate Spectrozyme Xa was added to a final concentration of 500 uM to each well for a final reaction volume of 100 uL. Control reactions included reactions without Factor Vila, without Tissue Factor, without Factor X, without TFPI or without anti-TFPI antibody (PBS alone). Absorbances of the reactions were immediately read on a SpectraMax M5e multi-mode plate reader at a wavelength of 405 nm at a 2 minute intervals over a period of 60 minutes. $EC_{50}$s were calculated with Prism Graph Pad software.

7. Thrombin Generation Assay (TGA)

The ability of purified anti-TFPI antibodies to restore thrombin generation in plasma with attenuated Factor VIII activity was assessed in thrombin generation assays using the Calibrated Automated Thrombogram (CAT) system. Anti-TFPI antibodies at concentrations of 1 nm-500 nm diluted in PBS were introduced into reactions containing human Factor VIII deficient plasma and PPP-Low reagent, containing 4 uM phospholipid and 1 μM Tissue Factor. Control reactions used PBS without antibody. Reactions were triggered with addition of Fluca buffer containing a fluorogenic thrombin substrate and $CaCl_2$. Fluorescence of each reaction was immediately read using a Fluoroskan Ascent plate reader using Thrombinoscope software at a 20 second interval for 60 minutes. Each reaction was compared to a calibrator control well containing PBS, thrombin calibrator, FVIII deficient plasma and FLUCA buffer. Thrombinoscope Thrombin generation curves (nM thrombin versus time) were analyzed to extract lag time, peak height, time to peak and the area under the curve or endogenous thrombin potential (ETP) using the Thrombinoscope software (Thrombinoscope BV version). The data were used to calculate velocity index (Peak thrombin concentration/Time to Peak−Lag Time).

The ability of purified anti-TFPI antibodies to restore thrombin generation in rabbit plasma with attenuated FVIIIa activity was also assessed. Normal New Zealand white rabbit plasma were treated with anti-FVIII antibody (GM-8015) at a final concentration of 100 ug/ml or control mouse anti-human IgG2a at 100 ug/mL for 60 minutes at 37° C. Immediately prior to addition into reaction wells, rabbit plasma was diluted 1:3 into buffer (20 mM HEPES, 140 mM NaCl). Thrombin generation assays with the FVIII neutralized rabbit plasma were performed as described above.

8. Generation of Cynomolgus TFPI K2 Domain for Structural Studies

Cynomolgus (cyno) TFPI K1K2 (Table 1) was expressed in HEK293 cells and conditioned media was harvested 120 hours post transfection. Purified Cyno TFPI K1K2 was incubated with human neutrophil elastase (HNE) at 1:70 (molar ratio HNE:TFPI) for 120 min at RT for cleavage to occur. Separation of cyno K1 from cyno K2 was performed using anion exchange chromatography on HQ50 (Poros). Size exclusion chromatography using Superdex 75 was performed as the final purification step. Endoproteinase AspN was used to trim the residual AviTag from the C-terminus of the cyno K2 domain.

9. Generation of Antibody Fab/Cyno TFPI K2 Complexes for Structural Studies

Anti-TFPI antibodies 4D8.b1, TFPI-23, TFPI-24, 2A8-200 (Table 3) and Mab 2974 (R&D systems) were digested with immobilized Papain per manufacturer's protocol (Thermo/Pierce). MabSelect SuRe was used to purify the Fabs from the digest, which were then used for complex formation with cyno TFPI K2. The Fab/cyno TFPI K2 complexes were then concentrated to approximately 16 mg/ml. The concentrated complexes were then used to screen for protein crystallization conditions.

Example 2. Generation of Mouse Anti-TFPI Antibodies

1. Mouse Immunization and Hybridoma Generation

A cohort of five BALB/c mice were each immunized subcutaneously with a mixture of 5 ug humTFPI K1K2 and 5 ug murTFPI K1K2 protein emulsified in Complete Freund's Adjuvant. The mice were subsequently immunized twice per week with the protein mixture alternately emulsified in Incomplete Freund's Adjuvant or diluted in PBS. Blood samples were taken on day 17 and day 27 (after the fifth and seventh immunizations, respectively), and sera were tested for the presence of circulating anti-TFPI antibodies by ELISA. By day 27, each mouse received a final boost of protein mixture (10 ug) intraperitoneally. Four days later, draining lymph nodes (axillary, inguinal and popliteal) were harvested, and pooled lymph node cells were mixed at a 1:1 ratio with the P3X63.Ag8.653 cells and subjected to electro-cell fusion. Fused cells were plated in RPM11640 media supplemented with FBS (25%), NCTC-109 (12.5%), Glutamax (1%), Penicillin-Streptomycin (1%), Hybridoma Cloning Supplement (5%) and HAT ($1\times10^{-4}$M hypoxanthine, $4\times10^{-7}$M aminopterin, and $1.6\times10^{-5}$M thymidine). Fourteen days after the fusion hybridoma culture supernatants were tested for binding to humTFPI K1K2 by ELISA. Based upon their binding activity and their efficacy in functional assays, antibodies from three hybridomas, 4D8, 6B7 and 7A4, were selected for further characterization.

2. Cloning and Sequencing of Hybridoma-Derived Anti-TFPI Antibodies

RNA from hybridomas 4D8, 6B7 and 7A4 was prepared and the variable region DNA sequences from the expressed antibodies were obtained by RT-PCR cloning. The PCR products were cloned into the TOPO-TA cloning vector, then sequenced by conventional methods. One heavy chain and light chain cDNA pair was detected from hybridomas 6B7 and 7A4. Two heavy chain and light chain cDNAs were detected from 4D8.

Example 3. Characterization of Mouse Hybridoma Anti-TFPI Antibodies

Parental hybridomas 4D8, 6B7 and 7A4 were subcloned by limiting dilution to obtain monoclonal hybridoma cell lines. Positive subclones were identified by ELISA screening for reactivity with humTFPI K1K2 and expanded. Purified antibodies from one subclone of each hybridoma were characterized further.

1. TFPI Binding

Purified anti-TFPI antibodies 4D8.B1, 6B7.C5 and 7A4.D9 were tested for binding to recombinant human and rabbit TFPI proteins by protein-binding ELISA. The EC50 values of each antibody for both humTFPI K1K2-aviHis10 and rabTFPI K1K2 are shown in Table 5.

TABLE 5

EC50 (nM) values of mouse anti-TFPI MAbs for human and rabbit TFPI

| Antibody | EC50 (nM) humTFPI K1K2 | EC50 (nM) rabTFPI K1K2 |
|---|---|---|
| 4D8.B1 | 0.0959 | 0.0976 |
| 6B7.C5 | 0.1209 | 0.1289 |
| 7A4.D9 | 0.0887 | 0.0887 |

Surface plasmon resonance experiments were carried out to assess the affinity of the purified mouse anti-TFPI antibodies for human and rabbit TFPI K1K2 proteins. The $k_a$, $k_d$ and $K_D$ values for each antibody binding to human and rabbit TFPI K1K2 are shown in Table 6.

TABLE 6

Kinetic measurements for anti-TFPI mouse hybridoma clones binding to human and rabbit TFPI

| Analyte | Ligand | $k_a$ (1/Ms) | $k_d$(1/s) | $K_D$ (nM) |
|---|---|---|---|---|
| humTFPI K1K2 | 4D8.B1 | $9.58 \times 10^5$ | $1.14 \times 10^{-3}$ | 1.19 |
| humTFPI K1K2 | 6B7.C5 | $5.52 \times 10^5$ | $3.63 \times 10^{-3}$ | 6.58 |
| humTFPI K1K2 | 7A4.D9 | $1.48 \times 10^6$ | $9.21 \times 10^{-3}$ | 6.22 |
| rabTFPI K1K2 | 4D8.B1 | $2.01 \times 10^6$ | $1.26 \times 10^{-3}$ | 0.63 |
| rabTFPI K1K2 | 6B7.C5 | $1.14 \times 10^6$ | $5.64 \times 10^{-3}$ | 4.95 |
| rabTFPI K1K2 | 7A4.D9 | $5.30 \times 10^6$ | $1.88 \times 10^{-2}$ | 3.55 |

2. In Vitro Activity Assays

The anti-TFPI murine monoclonal antibodies were tested for activity in the FXa and TF-FXa-FVIIa inhibition reversal assays and the thrombin generation assay (TGA). The most potent antibody, 4D8.B1, was chosen to move forward for further studies.

TABLE 7

Activity of anti-TFPI murine monoclonal antibodies in the FXa and TF-FXa-FVIIa inhibition reversal assays and the thrombin generation assay (TGA)

| Antibody | FXa EC50 (nM) | FXa-FVIIa EC50 (nM) | TGA Velocity Index at 20 nM |
|---|---|---|---|
| 4D8.B1 | 5.9 | 6.67 | 26.3 |
| 6B7.C5 | 13.9 | 12.13 | 23.5 |
| 7A4.D9 | 22.3 | 9.35 | 23.3 |

Example 4. Generation of Chimeric and Humanized Antibodies from Clone 4D8

1. Generation of Mouse Human Chimeric Antibody 4D8

Variable region cDNAs derived from hybridoma 4D8 were subcloned into mammalian expression vectors to generate chimeric antibodies in which the mouse heavy chain variable region was fused in frame to human IgG1 3M (SEQ 20, Table 4), and the mouse light chain variable region was fused in frame to the human Ig kappa constant region (SEQ 62, Table 4). The chimeric constructs were transiently transfected into HEK293 cells. To identify the correct heavy and light chain pair from hybridoma 4D8 a total of four transient transfections were carried out with all possible heavy and light chain combinations. Antibody generated from one of the transfections was termed hu-mu 4D8 chimera (Tables 3 and 4).

2. Characterization of Mouse-Human Chimeric Antibody 4D8 (Mu-Hu 4D8)

Mu-hu 4D8 chimera was tested for its ability to bind both human and rabbit TFPI K1K2 proteins by protein binding ELISA (Table 8) and SPR (Table 9). The KD and EC50 values were closely comparable to those measured with purified mouse MAb 4D8.B1, demonstrating that grafting of the mouse variable regions grafted onto the human IgG1 background retained binding activity.

TABLE 8

EC50 (nM) values of mu-hu 4D8 chimera for human and rabbit TFPI

| Antibody | EC50 (nM) humTFPI K1K2 | EC50 (nM) rabTFPI K1K2 |
|---|---|---|
| mu-hu 4D8 chimera | 0.0577 | 0.0680 |

TABLE 9

Kinetic measurements for mu-hu 4D8 chimera binding to human and rabbit TFPI

| Analyte | Ligand | $k_a$ (1/MS) | $k_d$(1/s) | $K_D$ (nM) |
|---|---|---|---|---|
| humTFPI K1K2 | mu-hu 4D8 chimera | $9.58 \times 10^5$ | $1.14 \times 10^{-3}$ | 1.19 |
| rabTFPI K1K2 | mu-hu 4D8 chimera | $2.01 \times 10^6$ | $1.26 \times 10^{-3}$ | 0.63 |

3. Humanization of Hu-Mu 4D8 Chimera

The hu-mu 4D8 chimera sequence was humanized by CDR grafting onto human acceptor framework sequences. DP54 framework and DPK9 framework were chosen. Combinations of the heavy and light chain constructs (see Table 3) were then expressed. The antibodies were tested for human and rabbit TFPI binding in an ELISA binding assay (Table 10) and human TFPI binding in an SPR binding assay (Table 11).

TABLE 10

EC50 (nM) values of humanized 4D8 antibodies binding to human and rabbit TFPI K1K2 proteins

| Antibody | EC50 (nM) humTFPI K1K2 | EC50 (nM) rabTFPI K1K2 |
|---|---|---|
| 4D8 $V_k$ 1.0 × $V_H$ 1.0 | 0.0772 | 0.0785 |

TABLE 10-continued

| EC50 (nM) values of humanized 4D8 antibodies binding to human and rabbit TFPI K1K2 proteins | | |
|---|---|---|
| Antibody | EC50 (nM) humTFPI K1K2 | EC50 (nM) rabTFPI K1K2 |
| 4D8 $V_k$ 1.0 × $V_H$ 1.1 | 0.0884 | 0.0705 |
| 4D8 $V_k$ 1.0 × $V_H$ 1.2 | 0.0758 | 0.0422 |
| 4D8 $V_k$ 1.0 × $V_H$ 1.3 | 0.0822 | 0.0556 |
| 4D8 $V_k$ 1.0 × $V_H$ 1.4 | 0.0560 | 0.0426 |
| 4D8 $V_k$ 1.1 × $V_H$ 1.0 | 0.0429 | 0.0451 |
| 4D8 $V_k$ 1.1 × $V_H$ 1.1 | 0.0818 | 0.0788 |
| 4D8 $V_k$ 1.1 × $V_H$ 1.2 | 0.0590 | 0.0783 |
| 4D8 $V_k$ 1.1 × $V_H$ 1.3 | 0.0651 | 0.0511 |
| 4D8 $V_k$ 1.1 × $V_H$ 1.4 | 0.0493 | 0.0716 |

TABLE 11

| SPR analysis of humanized 4D8 antibodies binding to humTFPI K1K2 protein | | | |
|---|---|---|---|
| Antibody | $k_a$ (1/Ms) | $K_d$ (1/s) | $K_D$, nM |
| 4D8 $V_k$ 1.0 × $V_H$ 1.0 | $6.77 \times 10^4$ | $4.70 \times 10^{-4}$ | $6.94 \times 10^{-9}$ |
| 4D8 $V_k$ 1.0 × $V_H$ 1.1 | $6.06 \times 10^4$ | $1.54 \times 10^{-3}$ | $2.54 \times 10^{-8}$ |
| 4D8 $V_k$ 1.0 × $V_H$ 1.2 | $2.38 \times 10^5$ | $1.65 \times 10^{-4}$ | $6.95 \times 10^{-10}$ |
| 4D8 $V_k$ 1.0 × $V_H$ 1.3 | $7.95 \times 10^4$ | $5.71 \times 10^{-4}$ | $7.19 \times 10^{-9}$ |
| 4D8 $V_k$ 1.0 × $V_H$ 1.4 | $7.55 \times 10^4$ | $8.35 \times 10^{-4}$ | $1.11 \times 10^{-8}$ |
| 4D8 $V_k$ 1.1 × $V_H$ 1.0 | $1.25 \times 10^5$ | $8.35 \times 10^{-4}$ | $5.50 \times 10^{-10}$ |
| 4D8 $V_k$ 1.1 × $V_H$ 1.1 | $1.93 \times 10^5$ | $1.61 \times 10^{-4}$ | $8.32 \times 10^{-10}$ |
| 4D8 $V_k$ 1.1 × $V_H$ 1.2 | $1.51 \times 10^5$ | $9.49 \times 10^{-5}$ | $6.27 \times 10^{-10}$ |
| 4D8 $V_k$ 1.1 × $V_H$ 1.3 | $1.59 \times 10^5$ | $1.31 \times 10^{-4}$ | $8.23 \times 10^{-10}$ |
| 4D8 $V_k$ 1.1 × $V_H$ 1.4 | $2.21 \times 10^5$ | $5.28 \times 10^{-5}$ | $2.93 \times 10^{-10}$ |

Based upon these data, 4D8 Vk1.1×VH 1.4 was selected for further characterization and designated hz4D8 (Table 3). The humanized anti-TFPI antibody (hz4D8) was compared with the murine 4D8.B1 for activity in the FXa inhibition reversal assay, the two-stage TF-FVIIa-FX inhibition assay, and the thrombin generation assay. The data in Table 12 show that the humanized antibody had improved activity in all three assays compared with the mouse antibody, indicating that TFPI binding activity was fully retained in the humanized antibody.

TABLE 12

| Comparison of 4D8.B1 and hz4D8 antibodies in the FXa and FXa-FVIIa inhibition reversal assays and the thrombin generation assay (TGA) | | | |
|---|---|---|---|
| Antibody | FXa EC50 (nM) | FXa-FVIIa EC50 (nM) | TGA Velocity Index at 20 nM |
| 4D8.B1 | 4.15 | 3.5 | 13.5 |
| Hz4D8 | 1.87 | 1.57 | 15.7 |

Example 5. Generation of Additional Anti-TFPI Antibodies by Phage Display

1. Selection of Anti-TFPI Antibodies by Phage Display

Single chain fragment variable (scFv) antibodies that bind to the recombinant human and mouse TFPI K1K2 were identified following four rounds of selection using a phage display library of scFv antibody fragments derived from non-immunized human donors. Phage selections were performed in solution using streptavidin beads. Bound phage were eluted by incubation with 140 mM triethanolamine (TEA) pH 11.5 or 50 mM MES pH 5.5 for 10 min at room temperature on a rotary shaker and neutralized with 1M Tris-HCl, pH7.5.

The eluted phage pool was used to infect 10 mL of an *E. coli* ER2738 culture that had been grown to mid-logarithmic phase (corresponding to an $OD_{600}$ of approximately 0.5). Bacteria were infected with phage for 30 minutes at 37° C. without shaking, concentrated by centrifugation and plated, followed by overnight growth at 30° C. For the next round of selection, phages were rescued by inoculating 25 mL 2×TYAG/Tetracycline to an $OD_{600}$ of ~0.1, grown at 37° C. to an OD600 of 0.3-0.5. Cells were super-infected with MK13K07 helper phage at 1:20 cell/helper phage ratio, and incubated at 37° C. without shaking for 30 minutes then shaking at 150 rpm for 60 minutes. The cells were then centrifuged and the pellet re-suspended in a kanamycin/non-glucose containing medium. This culture was grown overnight at 25° C. Phage were harvested in the supernatant following centrifugation and used in the next round of selection.

2. Preparation of Crude Periplasmic Material for Use in ELISA Assay.

ScFv antibody fragments can be expressed either on the surface of a phage particle or in solution in the bacterial periplasmic space, depending upon the growth conditions used. To induce release of scFv antibody fragments into the periplasm, 96-deepwell plates containing 2×TY media with 0.1% glucose/100 μg/mL ampicillin were inoculated from thawed glycerol stocks and grown at 37° C. for approximately 4 hours. The contents of the bacterial periplasm (peripreps) were released by osmotic shock. Plates were centrifuged and the scFv-containing supernatant was harvested.

3. ELISA to Measure Binding of scFvs Expressed in the Periplasm to Human and Mouse TFPI K1K2.

A total of 1984 clones were picked randomly from rounds 2, 3 and 4 of all the branch selections. TFPI scFv binders were identified by the periplasmic preparation (periprep) binding ELISA. Biotinylated human and mouse TFPI K1K2 were coated on 384-well Nunc Maxisorp streptavidin plates at a concentration of 1 μg/mL in PBS. The TFPI K1K2 solutions were removed and plates were blocked for 1 hour at room temperature in 0.05% Tween 20/1% BSA/PBS. Peripreps were prepared and blocked for 1 hour at room temperature in an equal volume of 6% milk/1% BSA. 20 μl/well of blocked periplasmic scFv and control antibodies were transferred to the appropriate plates and incubated for 1 hour at room temperature. A 1:2,000 dilution of anti-myc horseradish peroxidase (HRP) or a 1:10,000 dilution of goat anti-human-HRP secondary antibody was added to detect bound scFv or anti-TFPI control antibodies. The signal was developed using 3,3',5,5'-Tetramethylbenzidine, with absorbance read at 450 nm on an Envision plate reader (Perkin Elmer). A total of 883 scFV clones were identified as TFPI binders. The 883 TFPI binding scFVs were sequenced to identify unique clones. 288 unique clones were chosen to test for TFPI/FXa competitive binding.

4. ELISA to Identify scFvs that Compete with FXa Binding to Human and Mouse TFPI K1K2.

A total of 288 unique clones were tested in an FXa/TFPI competitive binding ELISA. Human FXa was coated overnight on 384-well Nunc Maxisorp plates at a concentration of 1 μg/mL in PBS. The FXa solution was removed and the plate surface was blocked for 1 hour at room temperature in 0.05% Tween20/1% BSA/PBS. Peripreps were prepared and blocked for 1 hour at room temperature in an equal volume of 6% milk/1% BSA. 20 μl/well of blocked periplasmic scFv and control antibodies were mixed with biotinylated humTFPI K1K2 and allowed to incubate for 1 hour at room temperature. The mixture was transferred to the FXa coated plates and incubated for 1 hour at room temperature. A 1:2000 dilution of streptavidin-horseradish peroxidase was added to detect bound TFPI. The signal was developed using 3,3',5,5'-Tetramethylbenzidine, with absorbance read at 450 nm on an Envision plate reader. A total of 48 scFV antibodies were classified as competitive inhibitors of TFPI/FXa binding.

5. ScFv Conversion to Human IgG.

A total of 48 ScFv antibodies with unique sequences that demonstrated binding to TFPI and inhibition in a TFPI/FXa competition ELISA were selected for sub-cloning into human IgG-3M cloning vectors. Briefly, fragments were amplified by standard PCR. The VH or VL fragments were gel purified and ligated into a mammalian expression vector containing either the human IgG1-3M (VH) or Kappa or Lambda constant region (VK/VL). The VH and VK/VL paired expression vectors were then used for transient mammalian expression and purification in HEK 293 cells.

6. Characterization of Human IgG-3M Anti-TFPI Antibodies 48 anti-TFPI antibodies were ranked in various assays including FXa and TF/FVIIa/FXa inhibition reversal assays. TFPI-3, TFPI-21, TFPI-23, TFPI-24 and TFPI-26 had the desirable properties such as TFPI cross species, low or no binding to humTFPI2 K1K2K3 (Table 13). The FXa and TF/FVIIa/FXa inhibition reversal assay data for these same 5 antibodies are shown in Table 14 and SPR binding data in Table 15.

TABLE 13

TFPI antibodies that showed binding to multiple TFPI species (human, monkey, murine, rabbit and rat) and no or weak binding to human TFPI2

| Antibody | humTFPI K1K2 | cynTFPI K1K2 | murTFPI K1K2 | rabTFPI K1K2 | ratTFPI K1K2 | humTFPI2 K1K2K3 |
|---|---|---|---|---|---|---|
| TFPI-3 | ++ | ++ | ++ | ++ | − | − |
| TFPI-21 | ++ | ++ | ++ | ++ | ++ | − |
| TFPI-23 | ++ | ++ | ++ | ++ | ++ | − |
| TFPI-24 | ++ | ++ | ++ | ++ | ++ | +/− |
| TFPI-26 | ++ | ++ | ++ | ++ | ++ | − |

TABLE 14

TFPI antibody activity in FXa, TF/FVIIa/FXa inhibition reversal and thrombin generation assays

| Antibody | FXa EC50 (nM) | FXa-FVIIa EC50 (nM) | TGA Velocity Index at 20 nM |
|---|---|---|---|
| TFPI-3 | 207.9 | 37.4 | NT |
| TFPI-21 | 80.64 | 54.1 | 24.71 |
| TFPI-23 | 46 | 32.2 | 23.28 |
| TFPI-24 | 23 | 9.3 | 23.21 |
| TFPI-26 | 12.8 | 9.6 | 18.65 |

TABLE 15

TFPI antibody SPR binding kinetics to human and mouse TFPI

| Analyte | Ligand | $k_a$ (1/Ms) | $k_d$(1/s) | $K_D$ (nM) |
|---|---|---|---|---|
| humTFPI K1K2 | TFPI-3 | $6.25 \times 10^4$ | $1.7 \times 10^{-3}$ | 27.05 |
| humTFPI K1K2 | TFPI-21 | $7.85 \times 10^5$ | $3.47 \times 10^{-2}$ | 43.95 |
| humTFPI K1K2 | TFPI-23 | $9.18 \times 10^5$ | $9.71 \times 10^{-3}$ | 9.89 |
| humTFPI K1K2 | TFPI-24 | $1.59 \times 10^5$ | $8.62 \times 10^{-4}$ | 5.46 |
| humTFPI K1K2 | TFPI-26 | $2.05 \times 10^5$ | $1.18 \times 10^{-3}$ | 5.79 |
| murTFPI K1K2 | TFPI-3 | $2.15 \times 10^5$ | $8.24 \times 10^{-4}$ | 3.81 |
| murTFPI K1K2 | TFPI-21 | $1.73 \times 10^6$ | $7.71 \times 10^{-3}$ | 4.54 |
| murTFPI K1K2 | TFPI-23 | $1.69 \times 10^6$ | $2.48 \times 10^{-3}$ | 1.46 |
| murTFPI K1K2 | TFPI-24 | $2.48 \times 10^5$ | $5.96 \times 10^{-3}$ | 24.1 |
| murTFPI K1K2 | TFPI-26 | $1.29 \times 10^6$ | $4.76 \times 10^{-3}$ | 3.68 |

Example 6. Epitope Mapping of Anti-TFPI Antibodies by SPR

A sandwich SPR assay was used to map the epitopes of the anti-TFPI antibodies discovered and disclosed in this document (TFPI-21, TFPI-23, TFPI-24, 4D8, 6B7.c5 and 7A4.D9). Other known reference antibodies (hz4F36, 2A8-200 and Mab2974) were also included in the epitope mapping experiment. Antibody 1 was immobilized on a CM5 biacore chip using NHS chemistry. Human TFPI (humTFPI K1K2) was initially injected onto the chip until binding was near apparent equilibrium. Immediately after stopping human TFPI injection, antibody 2 was injected over the chip. If antibody 2 binds the complex of antibody 1 and human TFPI on the surface of the CM5 chip, then antibody 2 has a distinct and non-overlapping TFPI binding epitope versus antibody 1 (scored as +). If antibody 2 shows no binding, then it is scored as as a significantly overlapping epitope (negative (−)) versus antibody 1. If antibody 2 shows weak binding then antibodies 1 and 2 are deemed to have some partial overlap in TFPI epitopes (scored as +/−). As shown in Table 16, TFPI-21 and TFPI-23 have similar epitopes and the data also show that TFPI-21 and TFPI-23 have epitopes that are completely distinct from mab2974 and hz4F36.

sequence. Three TFPI-24 VH variants were made (TFPI-108, TFPI-109, TFPI-114) were made and paired with the TFPI-24 VL sequence. Based on these data, the best VL variant, TFPI-113, and the best VH variant, TFPI-108 were paired to produce antibody TFPI-118. TFPI-118 and TFPI-24 were tested for binding to human TFPI by SPR and the results in Table 18 show comparable binding kinetics.

TABLE 16

Epitope mapping of anti-TFPI antibodies using an SPR sandwhich assay

| | Antibody 2 | | | | | | | | |
|---|---|---|---|---|---|---|---|---|---|
| Antibody 1 | TFPI-21 | TFPI-23 | TFPI-24 | hz4F36 | 2A8-200 | Mab2479 | 4D8.b1 | 6B7.c5 | 7A4.D9 |
| TFPI-21 | − | − | − | + | − | + | + | + | − |
| TFPI-23 | − | − | − | + | − | + | + | + | − |
| TFPI-24 | − | − | − | − | − | − | − | − | − |
| hz4F36 | + | + | − | − | − | − | − | − | − |
| 2A8-200 | − | − | − | − | − | − | − | − | − |
| Mab2479 | + | + | − | − | − | − | − | − | +/− |
| 4D8.b1 | + | + | − | − | − | − | − | − | + |
| 6B7.c5 | + | + | − | − | − | − | − | − | + |
| 7A4.D9 | − | − | − | − | − | +/− | + | + | − |

Antibody 1 was immobilized on the surface of a CM5 chip.
Human TFPI (humTFPI K1K2) was then injected onto the surface until the measurement was close to apparent equilibrium.
Immediately after stopping TFPI injection, antibody 2 was injected to measure the binding to the antibody 1/TFPI complex.
A "+" score is given to antibody 1 and 2 parings that have completely distinct epitopes.
A "−" score is given to antibody pairings that have strongly overlapping epitopes.
If antibody 2 shows weak binding then antibodies 1 and 2 are deemed to have some partial overlap in TFPI epitopes (scored as +/−).

Example 7. Germlining Human Frameworks of TFPI-23 Antibody

Two variants of TFPI-23 were made to increase the content of human framework germline residues. TFPI-106 contains H1Q to E and H5V to L mutations (Kabat numbering) and TFPI-107 (Tables 3 and 4), contained H1Q to E, H5V to L and H941 to K mutations (Kabat numbering). TFPI-106, TFPI-107, and TFPI-23, were expressed, purified, and tested for binding to humTFPI K1K2 by SPR. The data in Table 17 show that when compared to the TFPI-23 parental antibody, TFPI-106 germline variant retained full binding affinity.

TABLE 17

TFPI-23 human frameworks germline variants SPR binding kinetics to human TFPI

| Analyte | Ligand | $k_a$ (1/Ms) | $k_d$(1/s) | $K_D$ (nM) |
|---|---|---|---|---|
| humTFPI K1K2 | TFPI-23 | $9.18 \times 10^5$ | $9.71 \times 10^{-3}$ | 9.89 |
| humTFPI K1K2 | TFPI-106 | $2.72 \times 10^6$ | $9.74 \times 10^{-3}$ | 3.7 |
| humTFPI K1K2 | TFPI-107 | — | — | No binding |

TFPI-106 showed a modest improvement in binding when compared to the parental TFPI-23 antibody.

Example 8. Germlining Human Frameworks of TFPI-24 Antibody

Four TFPI-24 VL variants were made (TFPI-110, TFPI-111, TFPI-112, TFPI-113) and paired with the TFPI-24 VH

TABLE 18

The binding kenetics of TFPI-24 and human frameworks variant TFPI-118 to human TFPI were compared using SPR

| Analyte | Ligand | $k_a$ (1/Ms) | $k_d$(1/s) | $K_D$ (nM) |
|---|---|---|---|---|
| humTFPI K1K2 | TFPI-24 | $9.18 \times 10^5$ | $9.71 \times 10^{-3}$ | 3.68 |
| humTFPI K1K2 | TFPI-118 | $1.25 \times 10^5$ | $1.19 \times 10^{-3}$ | 9.61 |

TFPI-118 showed comparable binding kinetics to the parental TFPI-23 antibody.

Example 9. SPR Binding Kinetics of Anti-TFPI Antibodies to TFPI from Various Species Anti-TFPI antibodies (TFPI-106, TFPI-118, and hz4F36) were analysed by SPR to determine the binding kinetics to TFPI from different animal species (human (huTFPI K1K2), cynomolgus monkey (cynTFPI K1K2), rabbit (rabTFPI K1K2), mouse (murTFPI K1K2) and rat (ratTFPI K1K2); Table 1). Three comparitor antibodies (hz4F36, 2A8 and 2A8-200) were also included in this experiment.

TABLE 19

Anti-TFPI antibody SPR binding kinetics to human, cyno, rabbit, rat and mouse TFPI (The $K_d$ values are means from 2 experiments)

| Analyte | Ligand | $k_a$ (1/Ms) | $k_d$(1/s) | $K_D$ (nM) |
|---|---|---|---|---|
| humTFPI K1K2 | TFPI-106 | $2.72 \times 10^6$ | $9.74 \times 10^{-3}$ | 3.7 |
| humTFPI K1K2 | TFPI-118 | $1.25 \times 10^5$ | $1.19 \times 10^{-3}$ | 9.61 |
| humTFPI K1K2 | hz4D8 | $3.16 \times 10^6$ | $1.32 \times 10^{-3}$ | 0.42 |
| humTFPI K1K2 | hz4F36 | $1.89 \times 10^6$ | $9.30 \times 10^{-4}$ | 0.49 |
| humTFPI K1K2 | 2A8 | $3.55 \times 10^5$ | $3.77 \times 10^{-3}$ | 10.6 |
| humTFPI K1K2 | 2A8-200 | $1.16 \times 10^6$ | $3.81 \times 10^{-3}$ | 0.327 |
| cynTFPI K1K2 | TFPI-106 | $6.55 \times 10^6$ | $8.01 \times 10^{-3}$ | 1.22 |
| cynTFPI K1K2 | TFPI-118 | $7.21 \times 10^5$ | $1.27 \times 10^{-3}$ | 1.8 |
| cynTFPI K1K2 | hz4D8 | $2.93 \times 10^7$ | $1.95 \times 10^{-3}$ | 0.067 |

TABLE 19-continued

Anti-TFPI antibody SPR binding kinetics to human, cyno, rabbit, rat and mouse TFPI (The $K_d$ values are means from 2 experiments)

| Analyte | Ligand | $k_a$ (1/Ms) | $k_d$(1/s) | $K_D$ (nM) |
|---|---|---|---|---|
| cynTFPI K1K2 | hz4F36 | $6.86 \times 10^6$ | $2.88 \times 10^{-3}$ | 0.425 |
| cynTFPI K1K2 | 2A8 | $2.37 \times 10^5$ | $3.06 \times 10^{-2}$ | 13.25 |
| cynTFPI K1K2 | 2A8-200 | $1.25 \times 10^6$ | $8.09 \times 10^{-4}$ | 0.637 |
| rabTFPI K1K2 | TFPI-106 | $3.66 \times 10^6$ | $1.55 \times 10^{-2}$ | 4.25 |
| rabTFPI K1K2 | TFPI-118 | $2.01 \times 10^5$ | $1.55 \times 10^{-2}$ | 5.79 |
| rabTFPI K1K2 | hz4D8 | $3.16 \times 10^6$ | $2.9 \times 10^{-3}$ | 0.502 |
| rabTFPI K1K2 | hz4F36 | $4.2 \times 10^6$ | $7.6 \times 10^{-3}$ | 1.81 |
| rabTFPI K1K2 | 2A8 | $7.3 \times 10^5$ | $1.23 \times 10^{-3}$ | 1.69 |
| rabTFPI K1K2 | 2A8-200 | $1.92 \times 10^6$ | $2.77 \times 10^{-4}$ | 0.145 |
| murTFPI K1K2 | TFPI-106 | $4.05 \times 10^6$ | $2.32 \times 10^{-3}$ | 0.575 |
| murTFPI K1K2 | TFPI-118 | $2.19 \times 10^5$ | $9.82 \times 10^{-3}$ | 45.6 |
| murTFPI K1K2 | hz4D8 | — | — | No binding |
| murTFPI K1K2 | hz4F36 | — | — | No binding |
| murTFPI K1K2 | 2A8 | $1.91 \times 10^5$ | $6.32 \times 10^{-3}$ | 33.65 |
| murTFPI K1K2 | 2A8-200 | $2.54 \times 10^6$ | $1.17 \times 10^{-3}$ | 0.455 |
| ratTFPI K1K2 | TFPI-106 | $3.01 \times 10^6$ | $4.71 \times 10^{-3}$ | 1.57 |
| ratTFPI K1K2 | TFPI-118 | $4.83 \times 10^5$ | $1.75 \times 10^{-3}$ | 3.65 |
| ratTFPI K1K2 | hz4D8 | — | — | No binding |
| ratTFPI K1K2 | hz4F36 | — | — | No binding |
| ratTFPI K1K2 | 2A8 | — | — | Not tested |
| ratTFPI K1K2 | 2A8-200 | — | — | Not tested |

Example 10. Anti-TFPI Antibody/TFPI Complex Structures 1. 4D8.b1 Fab/Cyno TFPI K2 Complex Structure The 4D8.b1 Fab and cyno TFPI K2 were mixed at a 1:1 molar ratio to form the complex. Final purification was performed using a Superdex 200 column. The complex was concentrated to 12.6 mg/ml for structural studies. Crystals of the TFPI K2+4D8 Fab complex were obtained in 100 mM Tris-HCl pH8.5, 20% PEG10000. It yielded rod-shaped crystals that diffracted to 2.9 Å. Crystals were transiently cryo-protected and synchrotron data collection was performed remotely at Advanced Photon Source. Image frames were processed using software AutoPROC (Global Phasing Ltd). The data belongs to space group P212121, with unit cells as follows: a=62.102 Å, b=82.284 Å, c=103.628 Å, α=β=γ=90°, with one complex per asymmetric unit. Molecular Replacement searches using homology models of 4D8 Fab as well as publicly available structures (RSCB Protein Data Bank; PDB codes 1TFX and 4DTG) of TFPI K2 domains yielded convincing solutions of each component. Refinement was performed using software autoBUSTER (Global Phasing Ltd), and the final R/Rfree factors at 2.9 Å are 0.1707 and 0.2424, respectively, with RMSD of bond 0.010 Å, RMSD of angles 1.26°. Based on buried surface area (BSA) and percent BSA (% BSA) for residues at the Fab/TFPI K2 interface, the epitope and paratope of the 4D8 Fab were determined. The following residues in K2 domain of TFPI are involved in direct contact with 4D8 Fab (epitope according to BSA): E101, P103, Y109, I110, T111, Y113, F114, S119, Q121, C122, E123, R124, F125, K126, and L140. The following residues in heavy chain of 4D8 Fab comprise the heavy chain paratope: D50, T57, L58, Y59, Q61, K64, D98, Y99, and D100. The following residues in light chain of 4D8 Fab comprise the light chain paratope: H30, W50, H91, Y92, T93, T94, P95, and Y96. The BSA and % BSA values for the epitope and paratope residues are shown in table 20.

TABLE 20

Anti-TFPI antibody 4D8.b1 epitope and paratope residues as defined by buried surface area (BSA) and percent BSA (% BSA) of the interface residues in the 4D8.b1 Fab/cyno TFPI K2 complex structure (Antibody lightchain (LC) and heavy chain (HC) residues are numbered using Kabat definitions). A cutoff (BSA of 20 $Å^2$ or greater, or involved in electrostatic interaction) is applied in BSA analysis.

| Residue | Chain | Residue # | Classification | BSA | % BSA |
|---|---|---|---|---|---|
| GLU | TFPIK2 | 101 | epitope | 33.93 | 48.73 |
| PRO | TFPIK2 | 103 | epitope | 34.91 | 74.82 |
| TYR | TFPIK2 | 109 | epitope | 71.54 | 55.15 |
| THR | TFPIK2 | 111 | epitope | 41.72 | 66.65 |
| SER | TFPIK2 | 119 | epitope | 32.89 | 65.61 |
| GLN | TFPIK2 | 121 | epitope | 67.99 | 86.51 |
| GLU | TFPIK2 | 123 | epitope | 63.53 | 99.15 |
| ARG | TFPIK2 | 124 | epitope | 147.09 | 97.31 |
| LYS | TFPIK2 | 126 | epitope | 114.72 | 95.85 |
| LEU | TFPIK2 | 140 | epitope | 41.62 | 60.14 |
| ASP | 4D8.b1 HC | 50 | paratope | 5.98 | 52.56 |
| THR | 4D8.b1 HC | 57 | paratope | 26.48 | 42.04 |
| LEU | 4D8.b1 HC | 58 | paratope | 72.95 | 93.41 |
| TYR | 4D8.b1 HC | 59 | paratope | 15.75 | 33.75 |
| GLN | 4D8.b1 HC | 61 | paratope | 59.14 | 45.41 |
| ASP | 4D8.b1 HC | 98 | paratope | 62.87 | 50.71 |
| TYR | 4D8.b1 HC | 99 | paratope | 44.28 | 59.06 |
| ASP | 4D8.b1 HC | 100 | paratope | 5.83 | 27.84 |
| HIS | 4D8.b1 LC | 30 | paratope | 53.18 | 56.60 |
| TRP | 4D8.b1 LC | 50 | paratope | 53.41 | 51.52 |
| TYR | 4D8.b1 LC | 92 | paratope | 97.99 | 96.61 |
| THR | 4D8.b1 LC | 93 | paratope | 39.89 | 73.42 |
| THR | 4D8.b1 LC | 94 | paratope | 48.00 | 95.74 |
| TYR | 4D8.b1 LC | 96 | paratope | 15.49 | 72.23 |

2. 2A8 & 2A8-200 Fab/Cyno K1K2 Complex Structures

The 2A8 Fab and cyno TFPI K1K2 were mixed at a 1:1 molar ratio to form the complex. Final purification was performed using a Superdex 200 column. The complex was concentrated to 10.8 mg/ml for structural studies. Crystals of the complex containing 2A8 Fab and TFPI K1K2 were obtained in the following two conditions: (1) 100 mM HEPES pH7.5, 12.5% PEG8000, which yielded needle-shaped crystals that diffracted to 3.0 Å; (2) 100 mM HEPES pH 7.5, 1600 mM Ammonium Sulfate, 2% PEG1000, which yielded block-shaped crystals that diffracted to 3.3 Å. Crystals were transiently cryo-protected and synchrotron data collection was performed remotely at Advanced Photon Source. Image frames were processed using software AutoPROC (Global Phasing Ltd). The data belongs to space group P3221, with unit cells as follows: a=b=196.146 Å, c=41.262 Å, α=β=90°, γ=120°, with one complex per asymmetric unit. Molecular Replacement searches using homology models of 2A8 Fab as well as publicly available structures (RSCB Protein Data Bank; PDB codes 1TFX and 4DTG) of TFPI K2 domains yielded convincing solutions of each component. Refinement was performed using software PHENIX, and the final R/Rfree factors at 3.0 Å are 0.1667 and 0.2088, respectively, with RMSD of bond 0.011 Å, RMSD of angles 1.474°. Based on buried surface area (BSA) and percent BSA (% BSA) for residues at the Fab TFPI K1K2 interface, the epitope and paratope of the complex were determined. The following residues in TFPI K1K2 domains of TFPI are involved in direct contact with 2A8 Fab (epitope according to BSA): D31, D32, G33, P34, C35, K36, E100, E101, P103, G104, 1105, C106, R107, G108, Y109, E123, K126, Y127 and G128. The following residues in heavy chain of 4D8 Fab comprise the heavy chain paratope: G26, T28, S31, Y32, Y96, R97, Y98, W99 and D101 (Kabat numbering). The following residues in the light chain of 2A8 Fab comprise the light chain paratope: L28, R29, N30, Y31, Y32, Y49, Y50, D51 and N66 (Kabat numbering). The BSA and % BSA values for the epitope and paratope residues are shown in table 21. The very closely related antibody, 2A8-200, was also solved in complex with TFPI K1K2 using essentially identical methods. The epitope and paratope of this antibody was identical to that of 2A8.

TABLE 21

Anti-TFPI antibody 2A8 epitope and paratope residues as defined by buried surface area (BSA) and percent BSA (% BSA) of the interface residues in the 2A8 Fab/cyno TFPI K2 complex structure (Antibody light chain (LC) and heavy chain (HC) residues are numbered using Kabat definitions). A cutoff (BSA of 20 Å$^2$ or greater, or involved in electrostatic interaction) is applied in BSA analysis.

| Residue | Chain | Residue # | Classification | BSA | % BSA |
|---|---|---|---|---|---|
| ASP | TFPI K1K2 | 31 | epitope | 41.9 | 59.8 |
| ASP | TFPI K1K2 | 32 | epitope | 4.9 | 44.0 |
| PRO | TFPI K1K2 | 34 | epitope | 98.8 | 88.7 |
| CYS | TFPI K1K2 | 35 | epitope | 40.5 | 91.8 |
| LYS | TFPI K1K2 | 36 | epitope | 143.6 | 73.4 |
| GLU | TFPI K1K2 | 100 | epitope | 47.6 | 35.6 |
| GLU | TFPI K1K2 | 101 | epitope | 90.2 | 90.7 |
| PRO | TFPI K1K2 | 103 | epitope | 56.8 | 79.2 |
| ILE | TFPI K1K2 | 105 | epitope | 9.3 | 39.1 |
| ARG | TFPI K1K2 | 107 | epitope | 111.0 | 71.3 |
| GLY | TFPI K1K2 | 108 | epitope | 20.5 | 55.8 |
| TYR | TFPI K1K2 | 109 | epitope | 128.1 | 79.1 |
| GLU | TFPI K1K2 | 123 | epitope | 26.5 | 43.0 |
| LYS | TFPI K1K2 | 126 | epitope | 49.3 | 60.2 |
| TYR | TFPI K1K2 | 127 | epitope | 1.5 | 9.0 |
| GLY | TFPI K1K2 | 128 | epitope | 3.2 | 47.7 |
| GLY | 2A8 HC | 26 | paratope | 29.3 | 46.5 |
| THR | 2A8 HC | 28 | paratope | 61.6 | 74.1 |
| SER | 2A8 HC | 31 | paratope | 46.5 | 56.7 |
| TYR | 2A8 HC | 32 | paratope | 54.2 | 85.6 |
| TYR | 2A8 HC | 96 | paratope | 85.7 | 99.1 |
| ARG | 2A8 HC | 97 | paratope | 104.4 | 78.6 |
| TYR | 2A8 HC | 98 | paratope | 89.3 | 81.3 |
| TRP | 2A8 HC | 99 | paratope | 20.0 | 96.7 |
| ASP | 2A8 HC | 101 | paratope | 16.5 | 51.6 |
| LEU | 2A8 LC | 28 | paratope | 7.4 | 67.0 |
| ASN | 2A8 LC | 30 | paratope | 43.4 | 38.7 |
| TYR | 2A8 LC | 31 | paratope | 49.6 | 58.2 |
| TYR | 2A8 LC | 32 | paratope | 94.8 | 72.8 |
| TYR | 2A8 LC | 49 | paratope | 43.0 | 79.4 |
| TYR | 2A8 LC | 50 | paratope | 41.2 | 92.9 |
| ASP | 2A8 LC | 51 | paratope | 15.7 | 64.4 |

3. Mab 2974 Fab/TFPI K2 Complex Structure

The Mab 2974 (R&D Systems) Fab and cyno TFPI K2 were mixed at a 1:1.2 molar ratio to form the complex. Final purification was performed using a Superdex 200 column. The complex was concentrated to 17.5 mg/ml for structural studies. Crystals of the complex containing Mab 2974 Fab and TFPI K2 were obtained in 100 mM Sodium Citrate pH 5.6, 20% isopropanol, 20% PEG4000, which yielded block-shaped crystals that diffracted to 2.15 Å. Crystals were transiently cryo-protected and synchrotron data collection was performed remotely at Advanced Photon Source. Image frames were processed using software AutoPROC (Global Phasing Ltd). The data of the complex belongs to space group P212121, with unit cells as follows: a=82.075 Å b=117.829 Å, c=170.945 Å, α=β=γ=90°, with three complexes per asymmetric unit. Since the sequence of Mab 2947 Fab was not available, a high-resolution data set of the Fab alone (1.63 Å) was collected, along with bioinformatics analysis, to decipher the protein sequence. Molecular Replacement searches using the structure of Mab 2974 Fab as well as publicly available structures (RSCB Protein Data Bank; PDB codes 1TFX and 4DTG) of TFPI K2 domains yielded convincing solutions of each component. Refinement was performed using software autoBUSTER, and the final R/Rfree factors at 2.15 Å are 0.1702 and 0.2161, respectively, with RMSD of bond 0.010 Å, RMSD of angles 1.13°. Based on buried surface area (BSA) and percent BSA (% BSA) for residues at the Fab TFPI K2 interface, the epitope of the complex was determined. The following residues in TFPI K2 domain of TFPI are involved in direct contact with Mab 2974 Fab (epitope according to BSA): E100, E101, P103, R107, Y109, T111, N116, Q118, S119, Q121, E123, R124, F125 and K126. The BSA and % BSA values for the epitope residues are shown in table 22.

TABLE 22

Anti-TFPI antibody Mab 2974 epitope residues as defined by buried surface area (BSA) and percent BSA (% BSA) of the interface residues in the Mab 2974 Fab/cyno TFPI K2 complex structure. A cutoff (BSA of 20 Å$^2$ or greater, or involved in electrostatic interaction) is applied in BSA analysis.

| Residue | Chain | Residue # | Classification | BSA | % BSA |
|---|---|---|---|---|---|
| GLU | TFPI K2 | 100 | epitope | 25.9 | 16.8 |
| GLU | TFPI K2 | 101 | epitope | 42.2 | 54.7 |
| PRO | TFPI K2 | 103 | epitope | 26.8 | 58.5 |
| ARG | TFPI K2 | 107 | epitope | 32.3 | 16.4 |
| TYR | TFPI K2 | 109 | epitope | 83.1 | 62.9 |
| THR | TFPI K2 | 111 | epitope | 13.8 | 18.9 |
| ASN | TFPI K2 | 116 | epitope | 23.9 | 71.9 |
| GLN | TFPI K2 | 118 | epitope | 107.0 | 62.7 |
| SER | TFPI K2 | 119 | epitope | 48.4 | 87.6 |
| GLN | TFPI K2 | 121 | epitope | 51.6 | 53.3 |
| GLU | TFPI K2 | 123 | epitope | 61.6 | 79.8 |
| ARG | TFPI K2 | 124 | epitope | 56.0 | 33.2 |
| LYS | TFPI K2 | 126 | epitope | 114.8 | 91.8 |

4. TFPI-23 Fab/Cyno TFPI K2 Complex Structure

The TFPI-23 Fab and cyno TFPI K2 were mixed at a 1:2 molar ratio to form the complex. Final purification was performed using a Superdex 200 column. The complex was concentrated to 12.4 mg/ml for structural studies. Crystals of the TFPI K2+4D8 Fab complex were obtained in 100 mM Bis-Tris pH6.5, 20% PEGMME5000. It yielded fiber-shaped crystals that diffracted to 2.9 Å. Crystals were transiently cryo-protected and synchrotron data collection was performed remotely at Advanced Photon Source. Image frames were processed using software AutoPROC (Global Phasing Ltd). The data belongs to space group P1, with unit cells as follows: a=74.669 Å, b=101.372 Å, c=119.275 Å, a=101.83, β=92.27°, γ=96.78°, with six copies of complex per asymmetric unit. Molecular Replacement searches using homology models of TFPI-23 Fab as well as publicly available structures (RSCB Protein Data Bank; PDB codes 1TFX and 4DTG) of TFPI K2 domains yielded convincing solutions of each component. Refinement was performed using software autoBUSTER, and the final R/Rfree factors at 2.9 Å are 0.1961 and 0.2344, respectively, with RMSD of bond 0.010

Å, RMSD of angles 1.22°. Based on BSA and percent BSA (% BSA) for residues at the Fab TFPI K2 interface, the epitope and paratope of the complex were determined. The following residues in K2 domain of TFPI are involved in direct contact with the TFPI-23 Fab (epitope according to BSA): D102, 1105, C106, R107, G108, R112, Y127, G129, C130, L131, G132, M134 and E138. The following residues in heavy chain of 4D8 Fab comprise the heavy chain paratope: A33, W47, A50, I51, S52, S56, Y58, L95, G96, A97, T98, S99, L100 and S100A. The following residues in light chain of 4D8 Fab comprise the light chain paratope: A29, Y31, Y91, S95 Å, G95B and S95C. The BSA and % BSA values for the epitope and paratope residues are shown in table 23.

TABLE 23

Anti-TFPI antibody TFPI-23 epitope and paratope residues as defined by buried surface area (BSA) and percent BSA (% BSA) of the interface residues in the TFPI-23 Fab/cyno TFPI K2 complex structure (Antibody light chain (LC) and heavy chain (HC) residues are numbered using Kabat definitions). A cutoff (BSA of 20 Å$^2$ or greater, or involved in electrostatic interaction) is applied in BSA analysis.

| Residue | Chain | Residue # | Classification | BSA | % BSA |
|---|---|---|---|---|---|
| ASP | TFPI K2 | 102 | epitope | 27.4 | 49.2 |
| ILE | TFPI K2 | 105 | epitope | 116.0 | 81.9 |
| CYS | TFPI K2 | 106 | epitope | 46.8 | 97.0 |
| ARG | TFPI K2 | 107 | epitope | 99.9 | 49.5 |
| GLY | TFPI K2 | 108 | epitope | 23.1 | 45.7 |
| ARG | TFPI K2 | 112 | epitope | 42.8 | 70.4 |
| TYR | TFPI K2 | 127 | epitope | 18.7 | 92.6 |
| GLY | TFPI K2 | 129 | epitope | 36.7 | 69.5 |
| CYS | TFPI K2 | 130 | epitope | 26.7 | 100.0 |
| LEU | TFPI K2 | 131 | epitope | 120.8 | 97.5 |
| GLY | TFPI K2 | 132 | epitope | 29.3 | 77.8 |
| MET | TFPI K2 | 134 | epitope | 48.7 | 38.2 |
| GLU | TFPI K2 | 138 | epitope | 43.8 | 31.7 |
| ALA | TFPI-23 HC | 33 | paratope | 20.3 | 70.5 |
| TYR | TFPI-23 HC | 58 | paratope | 107.0 | 82.7 |
| LEU | TFPI-23 HC | 95 | paratope | 31.6 | 93.4 |
| GLY | TFPI-23 HC | 96 | paratope | 20.8 | 73.1 |
| ALA | TFPI-23 HC | 97 | paratope | 12.1 | 34.0 |
| THR | TFPI-23 HC | 98 | paratope | 5.6 | 4.9 |
| SER | TFPI-23 HC | 99 | paratope | 2.4 | 80.7 |
| LEU | TFPI-23 HC | 100 | paratope | 87.0 | 55.9 |
| SER | TFPI-23 HC | 100A | paratope | 24.7 | 83.8 |
| ALA | TFPI-23 LC | 29 | paratope | 38.7 | 86.9 |
| TYR | TFPI-23 LC | 31 | paratope | 60.8 | 86.0 |
| TYR | TFPI-23 LC | 91 | paratope | 27.0 | 94.3 |
| SER | TFPI-23 LC | 95A | paratope | 71.4 | 64.9 |
| GLY | TFPI-23 LC | 95B | paratope | 25.3 | 96.5 |

5. TFPI-24 Fab/Cyno TFPI K2 Complex Structure

The TFPI-24 Fab and cyno TFPI K2 were mixed at a 1:2 molar ratio to form the complex. Final purification was performed using a Superdex 200 column. The complex was concentrated to 12.2 mg/ml for structural studies. Crystals of the TFPI K2/TFPI-24 Fab complex were obtained in 20% PEG3350, 200 mM Ammonium Nitrate. It yielded crystals that diffracted to 1.75 Å. Crystals were transiently cryo-protected and synchrotron data collection was performed remotely at Advanced Photon Source. Image frames were processed using software AutoPROC. The data belongs to space group P212121, with unit cells as follows: a=42.817 Å, b=71.362 Å, c=148.729 Å, α=β=γ=90°, with one complex per asymmetric unit. Molecular Replacement searches using homology models of TFPI-24 Fab as well as publicly available structures (RSCB Protein Data Bank; PDB codes 1TFX and 4DTG) of TFPI K2 domains yielded convincing solutions of each component. Refinement was performed using software autoBUSTER, and the final R/Rfree factors at 1.75 Å are 0.1900 and 0.2269, respectively, with RMSD of bond 0.010 Å, RMSD of angles 1.18°. Based on buried surface area (BSA) and percent BSA (% BSA) for residues at the Fab/TFPI K2 interface, the epitope and paratope of the complex were determined. The following residues in K2 domain of TFPI are involved in direct contact with the TFPI-24 Fab (epitope according to BSA): E100, E101, D102, G104, 1105, C106, R107, G108, Y109, 1110, G129, C130, L131 and G132. The following residues in heavy chain of TFPI-24 Fab comprise the heavy chain paratope: A33, Q35, W47, G50, 151, S52, N53, R55, S56, I57, G58, F95, L96, H97, S99 and D101. The following residues in light chain of TFPI-24 Fab comprise the light chain paratope: M31, Y32, H34, Y36, L46, R50, W91 and Y96. The BSA and % BSA values for the epitope and paratope residues are shown in table 24.

TABLE 24

Anti-TFPI antibody TFPI-24 epitope and paratope residues as defined by buried surface area (BSA) and percent BSA (% BSA) of the interface residues in the TFPI-24 Fab/cyno TFPI K2 complex structure (Antibody light chain (LC) and heavy chain (HC) residues are numbered using Kabat definitions). A cutoff (BSA of 20 Å$^2$ or greater, or involved in electrostatic interaction) is applied in BSA analysis.

| Residue | Chain | Residue # | Classification | BSA | % BSA |
|---|---|---|---|---|---|
| GLU | TFPI K2 | 100 | epitope | 44.1 | 30.0 |
| GLU | TFPI K2 | 101 | epitope | 12.3 | 13.7 |
| ASP | TFPI K2 | 102 | epitope | 57.1 | 93.5 |
| GLY | TFPI K2 | 104 | epitope | 22.0 | 84.1 |
| ILE | TFPI K2 | 105 | epitope | 137.7 | 99.1 |
| CYS | TFPI K2 | 106 | epitope | 45.2 | 91.5 |
| ARG | TFPI K2 | 107 | epitope | 202.7 | 99.7 |
| GLY | TFPI K2 | 108 | epitope | 33.1 | 79.3 |
| TYR | TFPI K2 | 109 | epitope | 106.1 | 76.3 |
| CYS | TFPI K2 | 130 | epitope | 25.1 | 83.9 |
| LEU | TFPI K2 | 131 | epitope | 66.8 | 54.9 |
| GLY | TFPI K2 | 132 | epitope | 4.7 | 14.4 |
| ALA | TFPI-24 HC | 33 | paratope | 33.1 | 74.0 |
| GLN | TFPI-24 HC | 35 | paratope | 14.3 | 95.5 |
| SER | TFPI-24 HC | 52 | paratope | 26.3 | 99.3 |
| ASN | TFPI-24 HC | 53 | paratope | 54.6 | 52.6 |
| ARG | TFPI-24 HC | 55 | paratope | 22.0 | 11.0 |
| SER | TFPI-24 HC | 56 | paratope | 68.7 | 93.5 |
| PHE | TFPI-24 HC | 95 | paratope | 47.2 | 92.9 |
| LEU | TFPI-24 HC | 96 | paratope | 18.4 | 41.5 |
| HIS | TFPI-24 HC | 97 | paratope | 70.9 | 44.2 |
| SER | TFPI-24 HC | 99 | paratope | 1.0 | 2.1 |
| ASP | TFPI-24 HC | 101 | paratope | 3.7 | 11.6 |
| MET | TFPI-24 LC | 31 | paratope | 30.9 | 46.0 |
| TYR | TFPI-24 LC | 32 | paratope | 23.3 | 22.5 |
| HIS | TFPI-24 LC | 34 | paratope | 23.7 | 85.2 |
| TYR | TFPI-24 LC | 36 | paratope | 4.3 | 96.5 |
| ARG | TFPI-24 LC | 50 | paratope | 62.5 | 60.1 |
| TRP | TFPI-24 LC | 91 | paratope | 58.3 | 85.6 |
| TYR | TFPI-24 LC | 96 | paratope | 43.2 | 78.5 |

6. Epitope Analysis of hz4F36

The structure of the hz4F36 fab in complex with the human TFPI K2 domain is available at the Protein Data Bank (PDB accession code 4DTG). Based on BSA and percent BSA (% BSA) of the interface residues in the hz4F36/TFPI K2 complex structure the epitope residues were defined as shown in Table 25.

TABLE 25

| Anti-TFPI antibody hz4F36 epitope residues as defined by buried surface area (BSA) and percent BSA (% BSA) of the interface residues in the hz4F36 Fab/cyno TFPI K2 complex structure (PDB accession code 4DTG). A cutoff (BSA of 20 Å$^2$ or greater, or involved in electrostatic interaction) is applied in BSA analysis. | | | | | |
|---|---|---|---|---|---|
| Residue | Chain | Residue # | Classification | BSA | % BSA |
| GLU | TFPI K2 | 100 | epitope | 103.9 | 72.9 |
| GLU | TFPI K2 | 101 | epitope | 44.4 | 68.0 |
| ASP | TFPI K2 | 102 | epitope | 31.9 | 55.3 |
| PRO | TFPI K2 | 103 | epitope | 45.7 | 91.7 |
| ARG | TFPI K2 | 107 | epitope | 105.0 | 55.8 |
| TYR | TFPI K2 | 109 | epitope | 75.9 | 67.4 |
| THR | TFPI K2 | 111 | epitope | 24.1 | 51.5 |
| TYR | TFPI K2 | 113 | epitope | 51.9 | 100.0 |
| ASN | TFPI K2 | 116 | epitope | 17.6 | 63.0 |
| GLN | TFPI K2 | 118 | epitope | 76.6 | 34.8 |
| GLN | TFPI K2 | 121 | epitope | 43.5 | 50.3 |
| GLU | TFPI K2 | 123 | epitope | 27.3 | 63.6 |

TABLE 25-continued

| Anti-TFPI antibody hz4F36 epitope residues as defined by buried surface area (BSA) and percent BSA (% BSA) of the interface residues in the hz4F36 Fab/cyno TFPI K2 complex structure (PDB accession code 4DTG). A cutoff (BSA of 20 Å$^2$ or greater, or involved in electrostatic interaction) is applied in BSA analysis. | | | | | |
|---|---|---|---|---|---|
| Residue | Chain | Residue # | Classification | BSA | % BSA |
| ARG | TFPI K2 | 124 | epitope | 129.9 | 80.9 |
| LYS | TFPI K2 | 126 | epitope | 60.8 | 63.6 |
| LEU | TFPI K2 | 140 | epitope | 33.4 | 61.9 |

7. Comparison of Anti-TFPI Antibody Epitopes

The anti-TFPI antibody epitopes shown in Tables 20-25 are compared in Tables 26 and 27. Table 26 shows the epitopes of antibodies that are specific for the TFPI K2 domain. Table 27 includes 2 additional antibodies (2A8 and 2A8-200) that bind both K1 and K2 domains.

TABLE 26

| Anti-TFPI antibody epitope residues based on the data in Tables 20, 22-25 | | | | | | |
|---|---|---|---|---|---|---|
| Human TFPI residues | TFPI domain | TFPI-24 | TFPI-23 | 4D8.b1 | hz4F36 | Mab 2974 |
| E100 | K2 | X | | | X | X |
| E101 | K2 | X | | X | X | X |
| D102 | K2 | X | X | | X | |
| P103 | K2 | | | X | X | X |
| G104 | K2 | **X** | | | | |
| I105 | K2 | **X** | **X** | | | |
| C106 | K2 | **X** | **X** | | | |
| R107 | K2 | X | X | | X | X |
| G108 | K2 | **X** | **X** | | | |
| Y109 | K2 | X | | X | X | X |
| I110 | K2 | | | | | |
| T111 | K2 | | | X | X | X |
| R112 | K2 | | **X** | | | |
| Y113 | K2 | | | | X | |
| F114 | K2 | | | | | |
| Y115 | K2 | | | | | |
| N116 | K2 | | | | X | X |
| N117 | K2 | | | | | |
| Q118 | K2 | | | | X | X |
| S119 | K2 | | | X | | X |
| K120 | K2 | | | | | |
| Q121 | K2 | | | X | X | X |
| C122 | K2 | | | | | |
| E123 | K2 | | | X | X | X |
| R124 | K2 | | | X | X | X |
| F125 | K2 | | | | | |
| K126 | K2 | | | X | X | X |
| Y127 | K2 | | **X** | | | |
| G128 | K2 | | | | | |
| G129 | K2 | | **X** | | | |
| C130 | K2 | **X** | **X** | | | |
| L131 | K2 | **X** | **X** | | | |
| G132 | K2 | **X** | **X** | | | |
| N133 | K2 | | | | | |
| M134 | K2 | | **X** | | | |
| N135 | K2 | | | | | |
| N136 | K2 | | | | | |
| F137 | K2 | | | | | |

TABLE 26-continued

Anti-TFPI antibody epitope residues based on the data in Tables 20, 22-25

| Human TFPI residues | TFPI domain | TFPI-24 | TFPI-23 | 4D8.b1 | hz4F36 | Mab 2974 |
|---|---|---|---|---|---|---|
| E138 | K2 | | **X** | | | |
| T139 | K2 | | | | | |
| L140 | K2 | | | X | X | |
| E141 | K2 | | | | | |

X denotes TFPI amino acid residues that are part of the epitope.

X (bold) denotes novel epitope residues for antibodies disclosed in this invention.

Note that TFPI-23 does not compete for binding TFPI with hz4F36, 4D8 or mab2974 but does compete with TFPI-24 for binding to TFPI.

Antibodies 2A8 and 2A8-200 are not included in this table since they require both K1 & K2 domains for binding and do not bind K2 domain alone.

TABLE 27

A comparison of anti-TFPI antibody epitope residues based on the data shown in Tables 20-25

| Human TFPI residues | TFPI domain | TFPI-24 | TFPI-23 | 4D8 | hz4F36 | R&D2974 | 2A8 | 2A8-200 |
|---|---|---|---|---|---|---|---|---|
| D31 | K1 | | | | | | X | X |
| D32 | K1 | | | | | | X | X |
| G33 | K1 | | | | | | | |
| P34 | K1 | | | | | | X | X |
| C35 | K1 | | | | | | X | X |
| K36 | K1 | | | | | | X | X |
| C59 | K1 | | | | | | | |
| E100 | K2 | X | | | X | X | X | X |
| E101 | K2 | X | | X | X | X | X | X |
| D102 | K2 | X | X | | X | | | |
| P103 | K2 | | | X | X | X | X | X |
| G104 | K2 | **X** | | | | | | |
| I105 | K2 | X | X | | | | X | X |
| C106 | K2 | **X** | **X** | | | | | |
| R107 | K2 | X | X | | X | X | X | X |
| G108 | K2 | X | X | | | | X | X |
| Y109 | K2 | X | | X | X | X | X | X |
| I110 | K2 | | | | | | | |
| T111 | K2 | | | X | X | X | | |
| R112 | K2 | | **X** | | | | | |
| Y113 | K2 | | | | X | | | |
| F114 | K2 | | | | | | | |
| Y115 | K2 | | | | | | | |
| N116 | K2 | | | | X | X | | |
| N117 | K2 | | | | | | | |
| Q118 | K2 | | | | X | X | | |
| S119 | K2 | | | X | | X | | |
| K120 | K2 | | | | | | | |
| Q121 | K2 | | | X | X | X | | |
| C122 | K2 | | | | | | | |
| E123 | K2 | | | X | X | X | | |
| R124 | K2 | | | X | X | X | | |
| F125 | K2 | | | | | | | |
| K126 | K2 | | | X | X | X | X | X |
| Y127 | K2 | | X | | | | X | X |
| G128 | K2 | | | | | | X | X |
| G129 | K2 | | **X** | | | | | |
| C130 | K2 | **X** | **X** | | | | | |
| L131 | K2 | **X** | **X** | | | | | |
| G132 | K2 | **X** | **X** | | | | | |
| N133 | K2 | | | | | | | |
| M134 | K2 | | **X** | | | | | |
| N135 | K2 | | | | | | | |
| N136 | K2 | | | | | | | |
| F137 | K2 | | | | | | | |
| E138 | K2 | | **X** | | | | | |
| T139 | K2 | | | | | | | |
| L140 | K2 | | | X | X | | | |
| E141 | K2 | | | | | | | |

X denotes TFPI amino acid residues that are part of the epitope.

X (bold) denotes novel epitope residues for antibodies disclosed in this invention.

Antibodies 2A8 and 2A8-200 require both K1 & K2 domains for binding and do not bind K2 or K1 domain alone.

TABLE 28

Prediction of key TFPI epitope residues for TFPI-23 by alanine scanning using computational methods (Accelrys Discovery Studio 4.1)

| Epitope Mutation | Mutation Energy (kcal/mol) | Effect of Mutation | VDW Term | Electrostatic Term | Entropy Term |
|---|---|---|---|---|---|
| ASP102 > ALA | 0.73 | NEUTRAL | 1.56 | 0.37 | −0.3 |
| GLY104 > ALA | −0.19 | NEUTRAL | −0.25 | −0.13 | 0 |
| ILE105 > ALA | 2.19 | DESTABILIZING | 5.28 | −0.05 | −0.53 |
| CYS106 > ALA | 0.43 | NEUTRAL | 0.96 | −0.01 | −0.05 |
| ARG107 > ALA | 2.63 | DESTABILIZING | 7.35 | 0.35 | −1.52 |
| GLY108 > ALA | 0.3 | NEUTRAL | 0.74 | −0.02 | −0.08 |
| ARG112 > ALA | −0.07 | NEUTRAL | 0.05 | −0.18 | 0 |
| TYR127 > ALA | 0.12 | NEUTRAL | 0.18 | 0.07 | 0 |
| GLY129 > ALA | −0.33 | NEUTRAL | −0.35 | −0.19 | −0.08 |
| CYS130 > ALA | 0.06 | NEUTRAL | 0.26 | −0.08 | −0.04 |
| LEU131 > ALA | 2.12 | DESTABILIZING | 4.15 | 0.03 | 0.04 |
| GLY132 > ALA | −0.06 | NEUTRAL | −0.08 | −0.04 | 0 |
| MET134 > ALA | 0.02 | NEUTRAL | 0.05 | −0.01 | 0 |
| GLU138 > ALA | 0.07 | NEUTRAL | 0.02 | 0.13 | 0 |

Based on an arbitrary threshold of >1 kcal/mol, 3 TFPI residues (Ile105, Arg107 and Leu131), when mutated to alanine, are predicted to contribute significantly to binding of TFPI-23 to TFPI.

TABLE 29A

TFPI-23 CDR and framework residues within 4 angstroms of the TFPI K2 epitope

| Column 1 | Column 2 TFPI-23 | Column 3 | Column 4 | Column 5 | Column 6 |
|---|---|---|---|---|---|
| | | | Potential Substitutions | | |
| Corresponding TFPI residues | CDR/paratope residues | CDR/ Frameworks | <0.5 kcal/ mol affinity | <−0.5 kcal/ mol affinity | Top 3 |
| 105 Ile | H33 Ala | VH1 | Asn, Gly, His, Lys, Met, Phe, Pro, Ser, Thr, Trp, Val | Val | Val, His, Phe |
| 131 Leu | H47 Trp | HFR2 | Tyr | none | Tyr |
| 105 Ile, 131 Leu | H50 Ala | VH2 | Arg, Gly, Lys, Met, Phe, Pro, Ser, Thr, Tyr, Val | none | Thr, Ser, Phe |
| 105 Ile | H51 lie | VH2 | Ala, Arg, Asn Asp, Gln, Glu, Gly, His, Leu, Lys, Met, Phe Pro, Ser, Thr, Trp, Tyr, Val | none | Arg, Lys, Pro |
| 105 Ile | H52 Ser | VH2 | Ala, Arg, Asn, Asp, Gln, Glu, Gly His, Ile, Leu, Lys, Met, Phe, Pro, Ser, Trp, Tyr, Val | Arg, Lys, Phe, Tyr | Phe, Arg, Tyr |
| 105 Ile | H56 Ser | VH2 | Arg, Gly, His, Ile, Leu, Lys, Met, Phe, Pro, Ser, Thr, Trp, Tyr, Val | Arg, Lys | Lys, Tyr, Phe |
| 102 Asp, 104 Gly, 105 Ile, 131 Leu, 132 Gly | H58 Tyr | VH2 | none | none | none |
| 105 Ile | H95 Leu | VH3 | Gin, Ile, Phe, Tyr | none | Ile, Gln, Phe |
| 107 Arg | H96 Gly | VH3 | Ala, Arg, Asn Asp, Gln, Ile, Lys, Met, Phe, Pro, Ser, Thr, Val | Ala, Arg, Asn, Lys, Pro, Ser, Val | Arg, Asn, Lys |
| 107 Arg | H97 Ala | VH3 | Ala, Arg, Asn Asp, Gln, Glu, Gly, His, Leu, Lys, Met, Phe Pro, Ser, Thr, Trp, Tyr, Val | None | Leu, Tyr, Ile |

TABLE 29A-continued

TFPI-23 CDR and framework residues within 4 angstroms of the TFPI K2 epitope

| Column 1 | Column 2 TFPI-23 | Column 3 | Column 4 Potential Substitutions | Column 5 | Column 6 |
|---|---|---|---|---|---|
| Corresponding TFPI residues | CDR/paratope residues | CDR/ Frameworks | <0.5 kcal/ mol affinity | <−0.5 kcal/ mol affinity | Top 3 |
| 107 Arg | H98 Thr | VH3 | Ala, Arg, Asn Asp, Gln, Glu, Gly, His, Leu, Met, Phe Pro, Ser, Thr, Trp, Tyr, Val | His, Ile, Leu, Met, Phe, Tyr | Tyr, Phe, His |
| 107 Arg | H99 Ser | VH3 | Ala, Gly, Phe, Pro | None | Pro, Ala, Phe |
| 106 Cys, 107 Arg, 108 Gly | H100 Leu | VH3 | Arg, His, Ile, Leu, Lys, Phe, Pro, Trp, Tyr, Val | Phe, Trp, Tyr | Tyr, Trp, Phe |
| 106 Cys | H100A Ser | VH3 | Ala, Arg, Asn Asp, Gln, Glu, His, Leu, Lys, Met, Phe Pro, Ser, Thr, Trp | Arg, Asn, Gln, Glu His, Leu, Lys, Met, Phe, Pro, Trp | Arg, Leu, Trp |
| 112 Arg, 138 Gly | L29 Ala | VL1 | Ala, Arg, Asn Asp, Gln, Glu, Gly, His, Leu, Lys, Met, Phe Pro, Ser, Thr, Trp, Tyr, Val | none | Glu, Asp, Gin |
| 112 Arg, 127 Tyr, 129 Gly | L31 Tyr | VL1 | Ala, Arg, Asn Asp, Gln, Glu, Gly, His, Leu, Lys, Met, Phe Pro, Ser, Thr, Trp, Tyr, Val | None | Glu, Asp, Trp |
| 130 Cys | L91 Tyr | VL3 | Arg | None | Arg |
| 131 Leu, 132 Gly, 134 Met | L95A Ser | VL3 | Ala, Arg, Asn Asp, Gln, Glu, Gly, His, Leu, Lys, Met, Phe Pro, Ser, Thr, Trp, Tyr, Val | Phe, Trp, Tyr | Phe, Tyr, His |
| 130 Cys, 131 Leu | L95B Gly | VL3 | Ala, Arg, Asn Asp, Gln, Glu, Gly, His, Leu, Lys, Met, Phe Pro, Ser, Thr, Trp, Tyr, Val | None | Glu, Asp, Pro |
| 131 Leu | L95C Ser | VL3 | Ala, Arg, Asn Asp, Gln, Glu, Gly, His, Leu, Lys, Met, Phe Pro, Ser, Thr, Trp, Tyr, Val | Arg, Asn, Gln, Glu, Ile, Leu, Lys, Met, Phe, Trp, Tyr, Val | Trp, Tyr, Phe |
| *138 Glu (4.07 Å) | L93 Ser | VL3 | Ala, Arg, Asn Asp, Gln, Glu, Gly, His, Leu, Lys, Met, Phe Pro, Ser, Thr, Trp, Tyr, Val | None | Glu, Asp, His |
| *131 Leu (4.03 Å) | L96 Gly | VL3 | Asn | none | Asn |

Using computational prediction methods (Accelrys Discovery Studio 4.1), possible amino acid substitutions are also shown for each CDR/paratope residue that are predicted to not negatively affect the stability of TFPI-23 or the affinity to TFPI (<0.5 kcal/mol, columns 4-6). These are categorized into three groups: (1) those with at least a neutral effect on binding (<0.5 kcal/mol affinity, col. 4), (2) those that have a neutral/stabilizing effect on binding (<−0.5 kcal/mol affinity, col. 5) and (3) the top 3 predicted sites with the most stabilizing effect on affinity. Kabat numbering is used for all residues (col. 6). 138Glu/L93Ser and 131Leu/L96Gly are included as optional contact residues because the distance marginally exceeds 4Å (4.07 Å and 4.03 Å, respectively), but is close enough to be rounded to 4Å.

TABLE 29B

| TFPI epitope residues and corresponding TFPI-23 paratope residues | |
|---|---|
| TFPI epitope residue | TFPI-23 paratope residue |
| TFPI residues within 4.0 Å of residues on antibody TFPI-23 | |
| 102 Asp | H58 Tyr |
| 104 Gly | H58 Tyr |
| 105 Ile | H33 Ala, H50 Ala, H51 Ile, H52 Ser, H56 Ser, H58 Tyr, H95 Leu |
| 106 Cys | H100 Leu, H100A Ser |
| 107 Arg | H96 Gly, H97 Ala, H98 Thr, H99 Ser, H100 Leu |
| 108 Gly | H100 Leu |
| 112 Arg | L29 Ala, L31 Tyr |
| 127 Tyr | L31 Tyr |
| 129 Gly | L31 Tyr |
| 130 Cys | L91 Tyr, L95B Gly |
| 131 Leu | H47 Trp, H50 Ala, H58 Tyr, L95A Ser, L95B Gly, L95C Ser |
| 132 Gly | H58 Tyr, L95A Ser |
| 134 Met | L95A Ser |
| 138 Glu | L29 Ala |
| Hydrogen Bonded Residue Pairs | |
| 102 Asp | H58 Tyr |
| 107 Arg | H100 Leu |
| 107 Arg | H96 Gly |
| 107 Arg | H99 Ser |
| 107 Arg | H97 Ala |
| 107 Arg | H98 Thr |
| 112 Arg | L29 Ala |
| 127 Tyr | L31 Tyr |
| 131 Leu | L95B Gly |
| a non-zero change in buried surface area due to interaction with the cognate antigen/antibody A cutoff (BSA of 20 Å$^2$ or greater, or involved in electrostatic interaction) is applied | |
| 102 Asp | H58 Tyr |
| 105 Ile | H33 Ala, H58 Tyr, H95 Leu |
| 106 Cys | H95 Leu, H100 Leu, H100A Ser, L91 Tyr |
| 107 Arg | H96 Gly, H97 Ala, H98 Thr, H99 Ser, H100 Leu |
| 108 Gly | H100 Leu |
| 112 Arg | L29 Ala, L31 Tyr |
| 127 Tyr | L31 Tyr, L95B Gly |
| 129 Gly | H100A Ser, L31 Tyr, L91 Tyr |
| 130 Cys | H95 Leu, H100A Ser, L31 Tyr, L91 Tyr, L95B Gly |
| 131 Leu | H58 Tyr, H95 Leu, L31 Tyr, L91 Tyr, L95A Ser, L95B Gly |
| 132 Gly | H58 Tyr, L95A Ser |
| 134 Met | L95A Ser |
| 138 Glu | L29 Ala |

TABLE 29C

| TFPI epitope residues and corresponding TFPI-23 paratope residues by BSA (no cutoff of minimal BSA applied) a non-zero change in buried surface area due to interaction with the cognate antigen/antibody | |
|---|---|
| TFPI epitope residue | TFPI-23 paratope residue |
| 102 Asp | H56 Ser, H58 Tyr |
| 104 Gly | H58 Tyr |
| 105 Ile | H33 Ala, H34 Met, H50 Ala, H51 Ile, H52 Ser, H56 Ser, H58 Tyr, H95 Leu |
| 106 Cys | H95 Leu, H100 Leu, H100A Ser, L91 Tyr |

TABLE 29C-continued

| TFPI epitope residues and corresponding TFPI-23 paratope residues by BSA (no cutoff of minimal BSA applied) a non-zero change in buried surface area due to interaction with the cognate antigen/antibody | |
|---|---|
| TFPI epitope residue | TFPI-23 paratope residue |
| 107 Arg | H96 Gly, H97 Ala, H98 Thr, H99 Ser, H100 Leu |
| 108 Gly | H100 Leu |
| 112 Arg | L29 Ala, L31 Tyr, L93 Ser |
| 127 Tyr | L31 Tyr, L95B Gly |
| 129 Gly | H100A Ser, L31 Tyr, L91 Tyr |
| 130 Cys | H95 Leu, H100A Ser, L31 Tyr, L91 Tyr, L95B Gly |
| 131 Leu | H47 Trp, H50 Ala, H58 Tyr, H95 Leu, L31 Tyr, L91 Tyr, L95A Ser, L95B Gly, L95C Ser, L96 Gly |
| 132 Gly | H58 Tyr, L95A Ser |
| 133 Asn | L95A Ser |
| 134 Met | L93 Ser, L94 Ser, L95A Ser |
| 138 Glu | L28 Gly, L29 Ala, L93 Ser |

Example 11. Dilute Prothrombin Time (dPT)

The ability of the anti-TFPI antibodies to inhibit endogenous TFPI in human FVIII deficient plasma (Hemophilia A) was studied using a dilute prothrombin time (PT) assay. The dilute PT is a modified PT assay using diluted Tissue Factor (Innovin) to prolong the clotting time.

For the dPT analysis in humanFVIII deficient plasma (George King Biomedical), the Innovin® reagent was diluted 1:3000 in a dilution buffer (Imidazole 50 mM, sodium chloride 0.1 M, BSA 1 mg/mL, calcium chloride 8.34 mM, pH 7.4) and preincubated to 37° C. Plasma was thawed in a 37° C. water bath for 5 minutes immediately before assay. Dilutions of anti-TFPI antibodies were prepared in PBS and added to plasma and the plasma was incubated for 20 minutes at room temperature. Following this incubation, 50 μL of the plasma was incubated for 1 minute at 37° C. and the clotting reaction was initiated immediately with the addition of 50 μL of 1:3000 dilution of Innovin® reagent warmed to 37° C. The time to clot was performed at 37° C. using a STart®4 Coagulation Analyzer. Data points were collected in duplicate, entered into Microsoft excel and the Effective concentration (EC50) at 50% was estimated using GraphPad Prism®. The results are shown in Table 30.

TFPI down regulates the extrinsic FVIIa/TF/FXa pathway of coagulation, decreasing the generation of FXa and ultimately thrombin. The dPT measures the effects on the extrinsic pathway of coagulation. The data show that the addition of the anti-TFPI antibodies to hemophilia A plasma dose-dependently shortened the clotting time. Control IgG at 300 nM had no effect on the clotting time.

TABLE 30

| | Anti-TFPI-23 | Anti-TFPI-106 | Anti-TFPI-24 | Anti-TFPI-118 | Anti-TFPI-4F36 | Anti-TFPI-h4D8 |
|---|---|---|---|---|---|---|
| EC50 (nM) | 0.98 | 1.24 | 0.57 | 1.16 | 0.44 | 0.47 |

Example 12. Thromboelastography (TEG)

Thromboelastography (TEG) is a global hemostatic assay that measures the kinetics of clot formation in whole blood. Whole blood was isolated from healthy human donors drawn into plastic blood collection tubes containing 3.2% sodium citrate, and to minimize introduction of coagulation activators, such as tissue factor, the first drawn tube of blood was discarded. The citrated whole blood was treated for one hour with a control mouse-anti human IgG2 (100 mcg/mL) or with an inhibitory FVIII antibody (GM1805 (Green Mountain), 100 mcg/mL) to inhibit endogenous FVIII, inducing a hemophilia A-like phenotype. The whole blood (320 μL) dosed with anti-TFPI antibodies or IgG1 control antibody was added to a TEG® reaction cup containing 20 μL of 0.2 M calcium chloride and 20 μL of lipidated tissue factor (Innovin®) diluted in 20 mM HEPES, 150 mM sodium chloride, pH 7.4 resulting in a final lipidated tissue factor dilution of 1:200,000 in each reaction. Reactions were run in duplicate and immediately commenced upon addition of whole blood to the TEG cup. Analysis was performed on TEG® 5000 Hemostasis analyzers using TEG® software according to the manufacturer's instructions following calibration with Level I and Level II controls (Haemonetics). The reactions were performed at 37° C. for 60 minutes. See Table 31.

TABLE 31

TEG Parameters in Antibody Induced Hemophilia A (HA) Blood Treated with Anti-TFPI Antibodies

| | TEG Parameters | | | |
|---|---|---|---|---|
| Group | R-Value min | K Value min | Alpha angle degrees | MA mm |
| Hemophilia A Blood | 41.45 ± 2.33 | 6 ± 0.7 | 33.75 ± 1.6 | 59.8 ± 4.67 |
| Anti-TFPI-4F36 (100 nM) | 23 ± 0.14 | 4.65 ± 0.21 | 41.4 ± 1.8 | 60.4 ± 0.14 |
| Anti-TFPI-4F36 (300 nM) | 24.05 ± 0.07 | 7.0 ± 0.42 | 28.35 ± 2.9 | 56.45 ± 0.49 |
| Anti-TFPI-2A8-200 (100 nM) | 26.85 ± 0.92 | 8.3 ± 0.14 | 24.5 ± 0.14 | 50.75 ± 0.49 |
| Anti-TFPI-2A8-200 (300 nM) | 20.4 ± 0.84 | 6.25 ± 0.77 | 31.7 ± 5.09 | 54.05 ± 1.9 |
| Anti-TFPI-106 (100 nM) | 25.25 ± 0.92 | 5.35 ± 0.07 | 38.3 ± 1.2 | 67.6 ± 0.98 |
| Anti-TFPI-106 (300 nM) | 17.85 ± 0.07 | 4.65 ± 0.21 | 40.85 ± 1.2 | 59.15 ± 1.34 |
| Normal Blood | 10 ± 0.28 | 2.2 | 60.2 ± 0.56 | 62.8 ± 1.98 |

Table 31 shows that treatment of the whole blood with the FVIII antibody significantly prolonged the TEG-R value to 41.5 minutes. In the presence of whole blood anti-TFPI 106 showed a favorable profile relative to 2A8-200 and 4F36. The addition of TFPI-106, 2A8-200, or 4F36 (300 nM) resulted in a shortening of TEG-R value to 17.85 minutes, 20.4 minutes and 24.05 minutes, respectively. Anti-TFPI 106 promoted clotting in hemophilia blood as exhibited by the decrease in the TEG-R-Value and the increase observed in the TEG-alpha angle.

Example 13. Neutralization of TFPI and Thrombin Generation

The neutralization of TFPI by TFPI antibodies was measured using two chromogenic assays, a direct Factor Xa activity assay and a two-stage FVIIa/TF/FXa assay based on TFPI inhibition of FXa generation by TF-FVIIa. In the first assay, TFPI-106, TFPI-118, hz4D8, and two reference antibodies, 4F36 or 2A8-200, were preincubated at various concentrations (0-500 nM) with a fixed concentration of human recombinant TFPI K1K2 and FXa to allow the complex to form. FXa activity was evaluated using a chromogenic FXa substrate. The addition of TFPI antibodies of the invention caused a dose-dependent increase in FXa activity in this assay (see Table 32, Xa Inhibition Assay, $EC_{50}$ values).

In vivo, the two predominant forms of TFPI are TFPI-alpha (K1K2K3) and TFPI-beta (K1K2). The ability of TFPI antibodies to inhibit recombinant TFPI K1K2 or TFPI K1K2K3 was assessed in the two-stage FVIIa/TF/FXa assay. This assay measures the combined effects of neutralization of the TFPI inhibition of both FXa and FVIIa/TF/FXa. Antibodies were incubated at increasing concentrations (0-500 nM) with TFPI, added to the assay with FVIIa/TF/FX and FXa activity was measured using an FXa chromogenic substrate. TFPI antibodies of the invention neutralized the TFPI K1K2 inhibition of the FVIIa/TF mediated FX activation (See, Table 32, FVIIa/TF/Xa $EC_{50}$ values). Exemplary antibodies of the invention were also effective at inhibiting TFPI K1K2K3 ($EC_{50}$ for TFPI-106 is 8.47 nM for neutralization of FVIIa/TF/FXa Inhibition by TFPI K1K2K3). The data demonstrates inhibition of full length and truncated TFPI.

Clinical severity of hemophilia is related to the residual level of clotting factor activity. Factor activity of <1% is associated with a severe phenotype, moderate hemophilia is associated with a factor activity or 2-5% and mild with a factor activity of >5%-<40%). The defects in the intrinsic coagulation pathway in hemophilia result in the inadequate generation of thrombin. The thrombin generation assay (TGA) was utilized to examine inhibition of endogenous TFPI in platelet poor hemophilic plasma. The TGA assay measures the initiation phase, activation phase and inactivation phase of thrombin generation. The abilities of TFPI antibodies to restore thrombin generation in platelet poor hemophilia plasma were tested using a Calibrated Automated Thrombin (CAT) generation assay. TFPI-106, TFPI-118, hz4D8, and two reference antibodies, 4F36 or 2A8-200 (0-500 nM) were incubated in hemophilia plasma to neutralize TFPI prior to the addition to the assay. Compared to normal human pooled plasma, thrombin generation is markedly reduced in human hemophilic plasma. A dose-dependent response was observed when a normal control, FACT, which is standardized at 1 U/mL FVIII was spiked into the hemophilia A plasma. Similarly, the addition of B-domain deleted FVIII at 200 ng/mL (1 U/ml) restored thrombin generation to 100 nM. Over the 60 minute time course of the assay, minimal thrombin generation was observed in hemophilic plasma. Incubation of the plasma with antibodies of the invention resulted in dose-dependent increase in peak thrombin, endogenous thrombin potential and velocity index. References antibodies 2A8-200 and 4F36 were also assayed for comparison (Table 32, TGA Velocity $EC_{50}$ values).

Example 14. In Vivo Efficacy in Hemophilia Mouse Models

Efficacy of certain anti-TFPI antibodies as procoagulants was tested using the acute tail transection assay in hemophilic mice. In the assay, the distal portion of the tail was amputated resulting in substantial blood loss, which can be reduced if a hemostatic agent is administered before or shortly after the transection is made. Hemophilic mice received a single intravenous (IV) dose in a volume of 4 ml/kg via the tail vein of anti-TFPI antibodies (6 mg/kg), a non-specific IgG control (6 mg/kg), or saline vehicle. At different times after dosing, the effect of the antibodies on bleeding was assessed as follows.

Mice were anesthetized with Ketamine/Xylazine cocktail intraperitoneally. The tails were immersed in 50 mL of prewarmed phosphate buffered saline (PBS) at 37° C. for 2 minutes. A 3 mm tail transection was made and blood was collected into PBS for a 10 minute period. Volume of blood loss was then quantified by measuring the hemoglobin content of the PBS using the following technique. Tubes were centrifuged to collect erythrocytes, resuspended in 5 mL of lysis buffer (8.3 g/l ammonium chloride, 1.0 g/l potassium bicarbonate, and 0.037 g/l EDTA), and the absorbance at 575 nM of the samples measured by spectrophotometer. Absorbance values were converted to total blood loss (4) using a standard curve. The statistical significance of the difference between means was assessed by the analysis of variance (ANOVA) followed by Dunnett's multiple comparison test using GraphPad Prism software. Results are expressed as mean±standard error of the mean (SEM). In the figures described below, statistical significance is defined as a P value<0.05, and is indicated by an asterisk above the data.

Figure 1A:
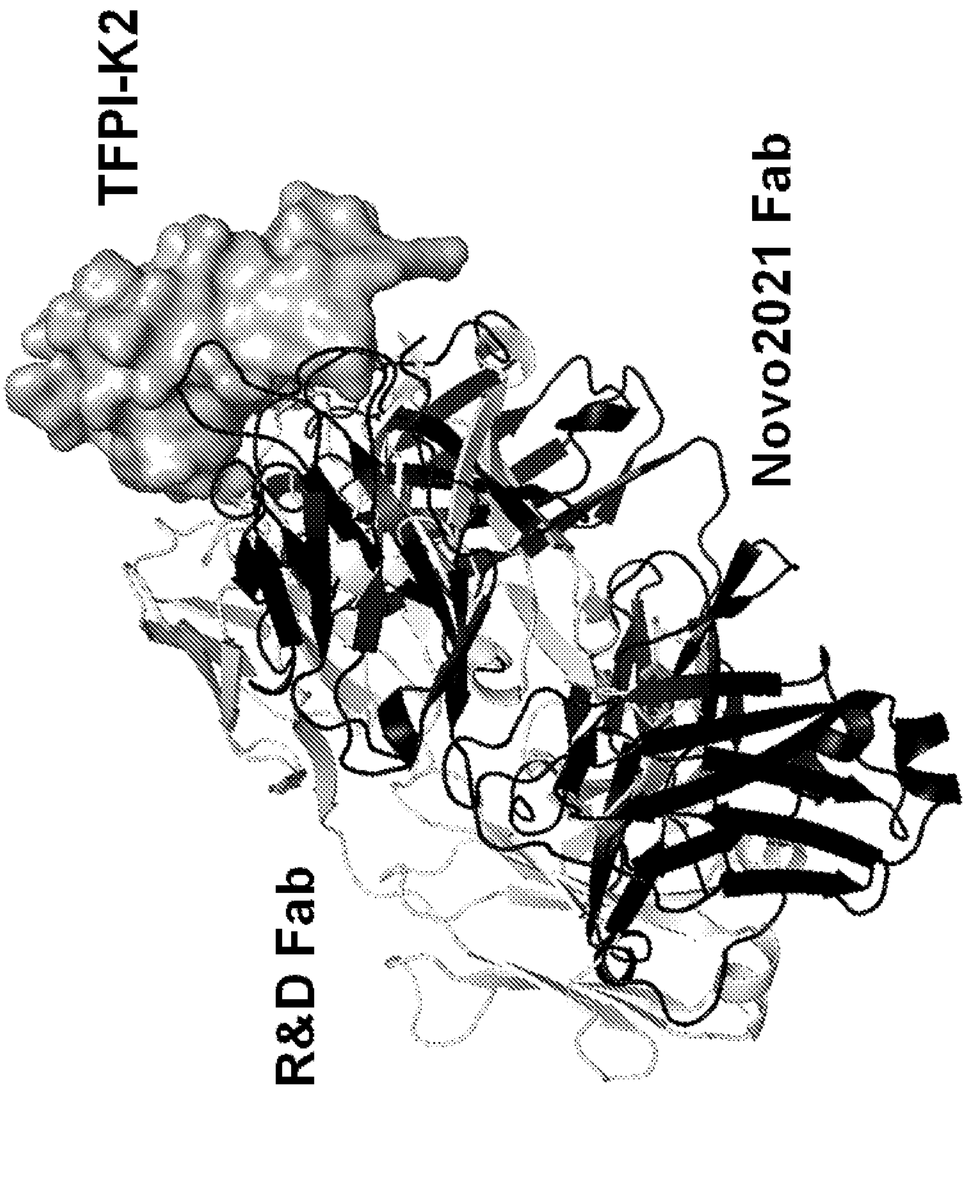
FIGS. 1A-1F are drawings showing the co-crystal structures of various anti-TFPI antibodies and the K2 domain of TFPI. In particular, as shown in FIG. 1F, exemplary antibodies disclosed herein, TFPI-23, TFPI-24, and 4D8, all bind to non-overlapping epitopes of the K2 domain as compared to other reference antibodies. TFPI-106 binds to the same site as TFPI-23, and TFPI-118 bind to the same site as TFPI-24. “R&D” or “R&D Fab” refers to antibody Mab 2974 from R&D Systems. Novo2021 antibody is also called “hz4F36.” “Clone 23” refers to TFPI-23; “clone 24” refers to TFPI-24.
Figure 1B:
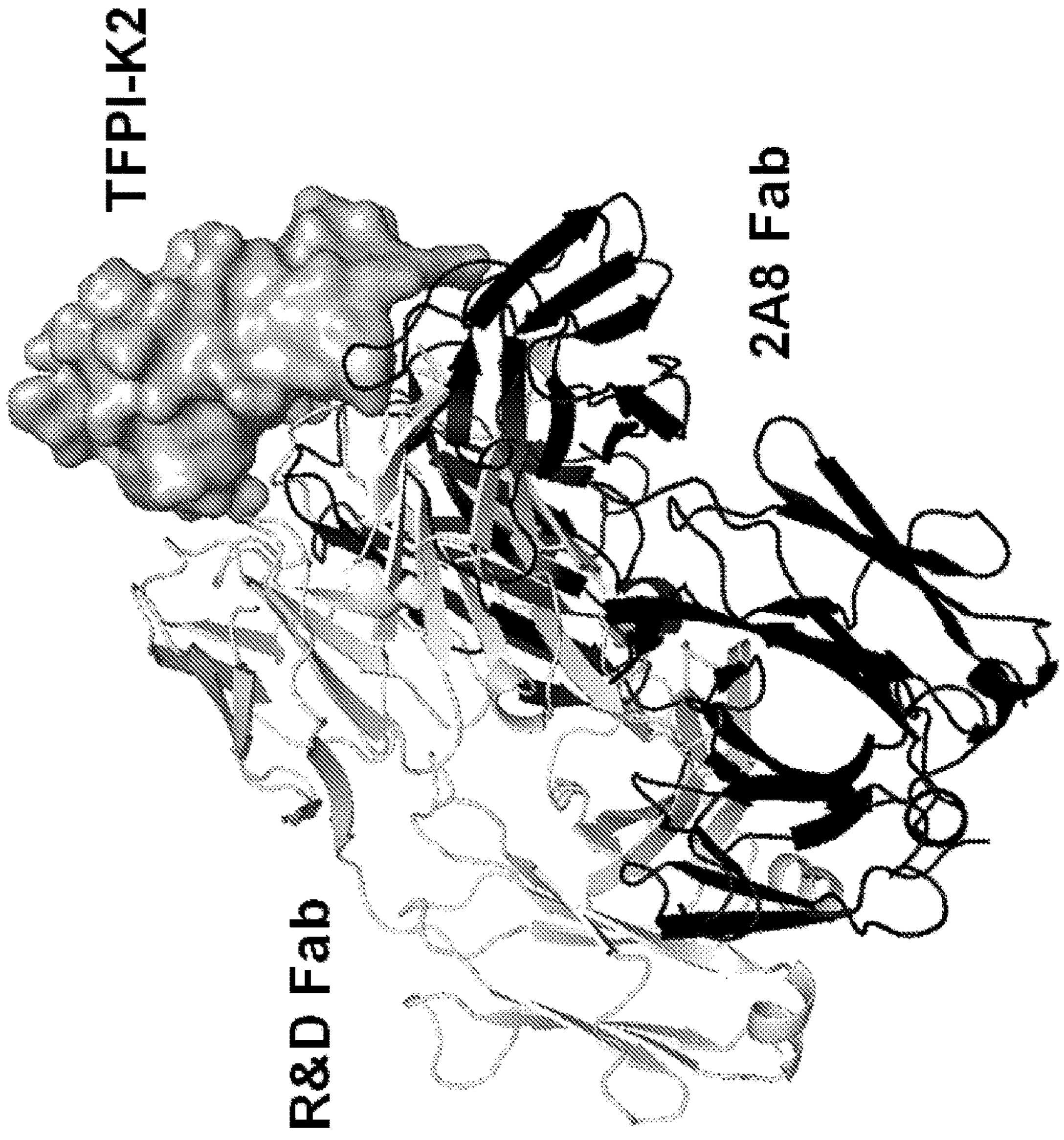
Figure 1C:
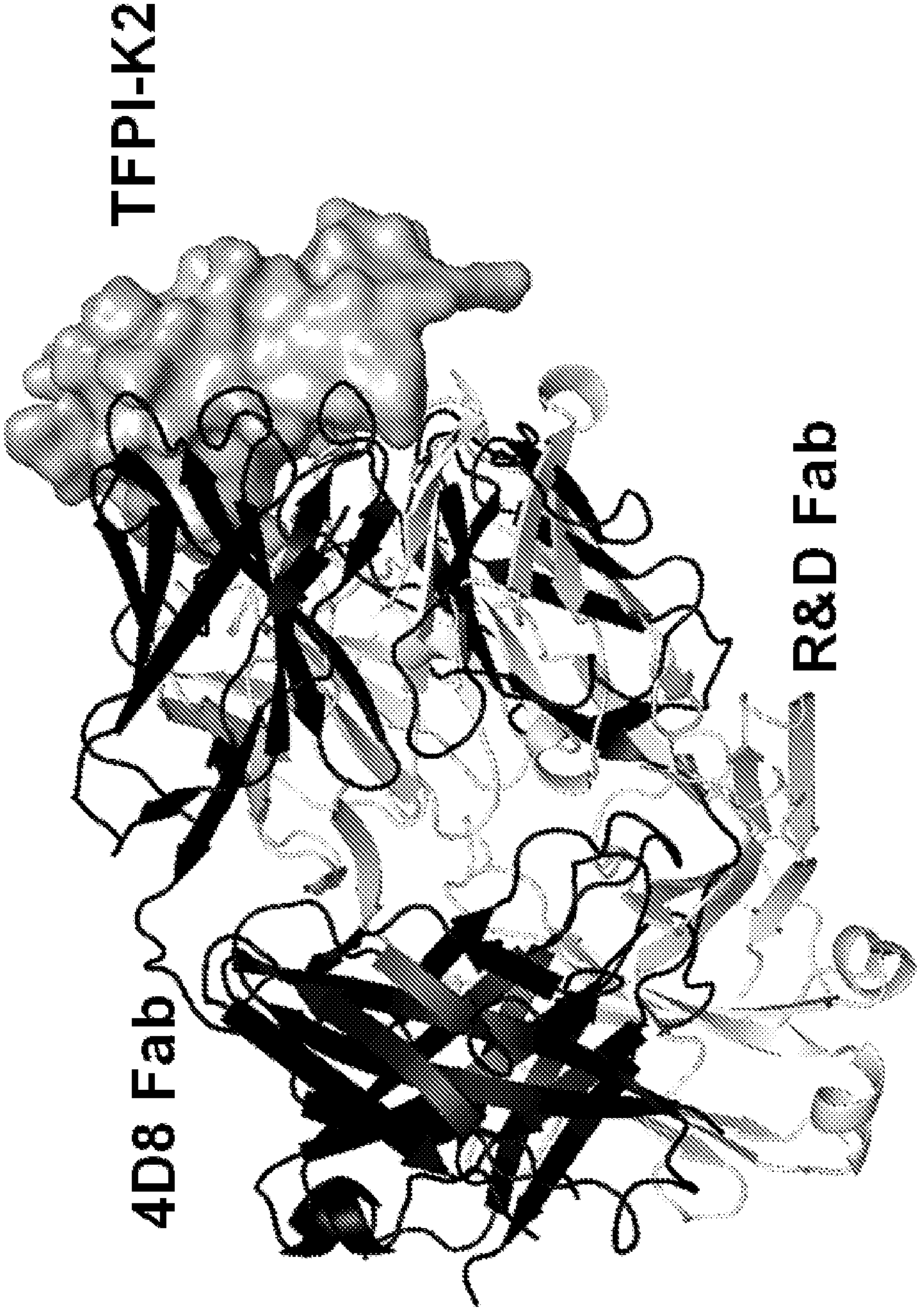
Figure 1D:
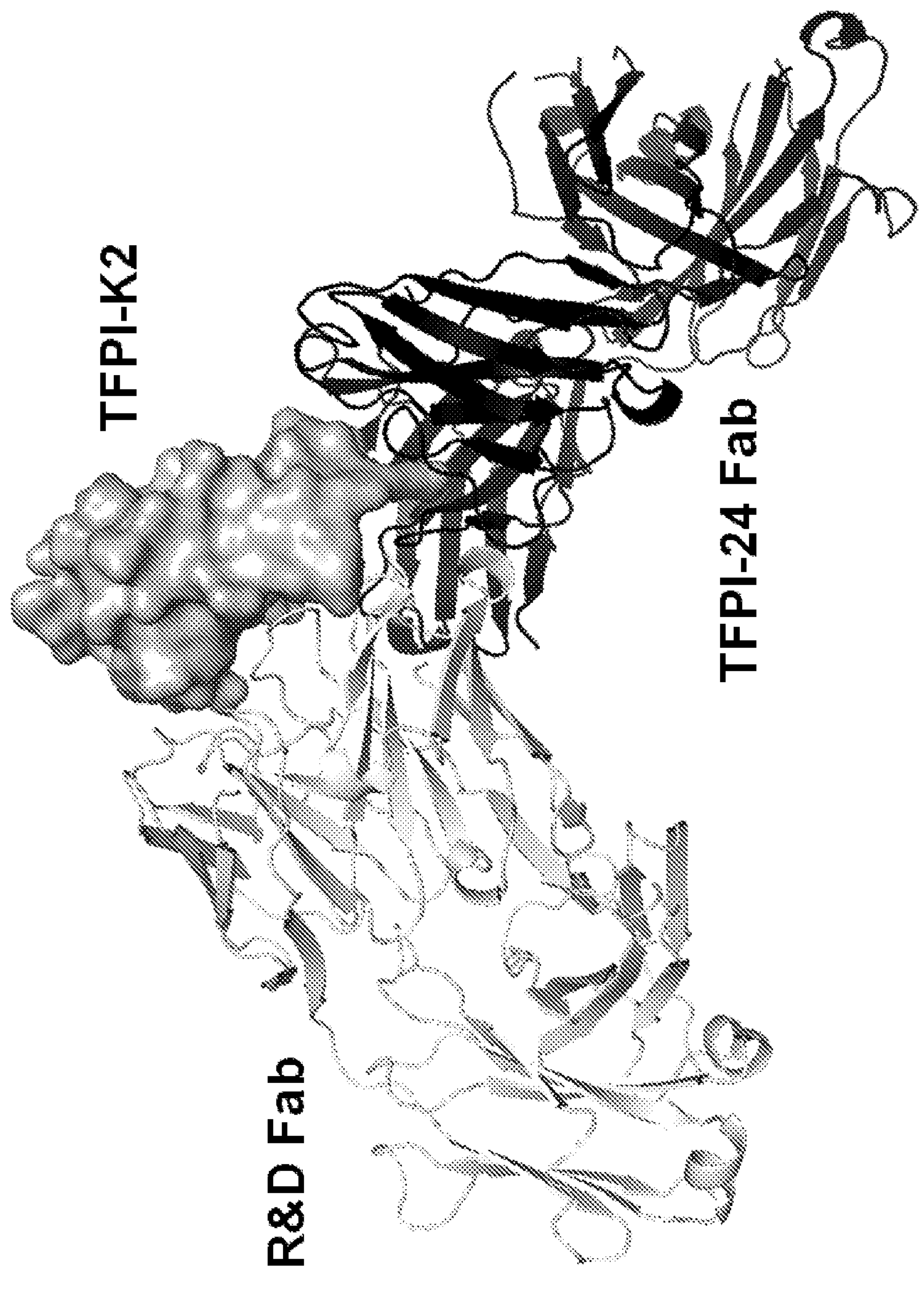
Figure 1E:
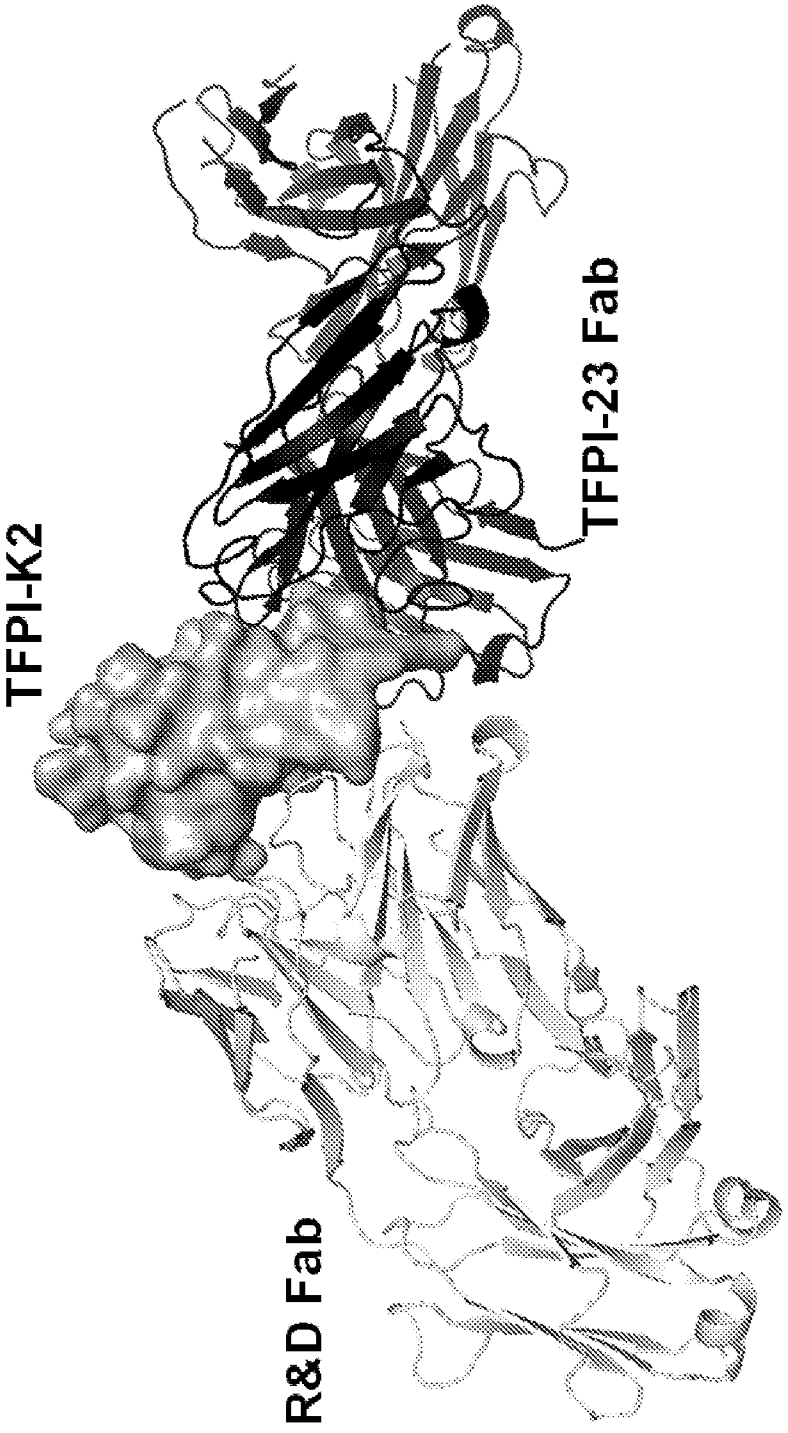
Figure 1F:
Figure 2A:
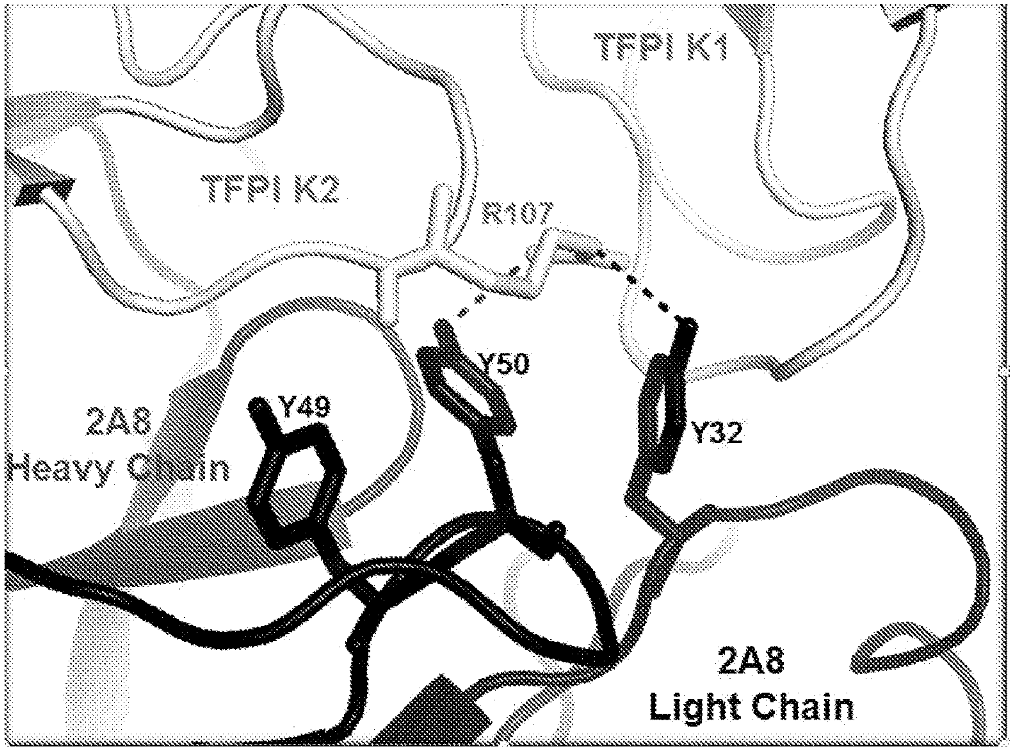
FIGS. 2A-2E are diagrams showing the interactions between epitopes residues within the K2 domain of TFPI and paratope residues from various anti-TFPI antibodies. “R&D” or “R&D Fab” refers to Mab 2974 from R&D Systems. “Clone 23” refers to TFPI-23; “clone 24” refers to TFPI-24.
Figure 2B:
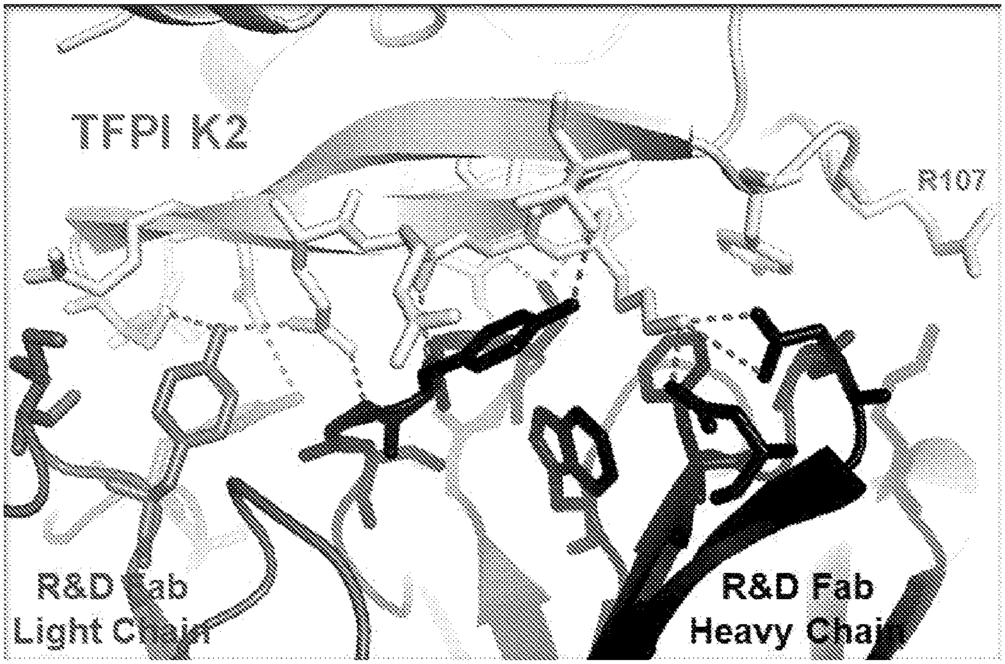
Figure 2C:
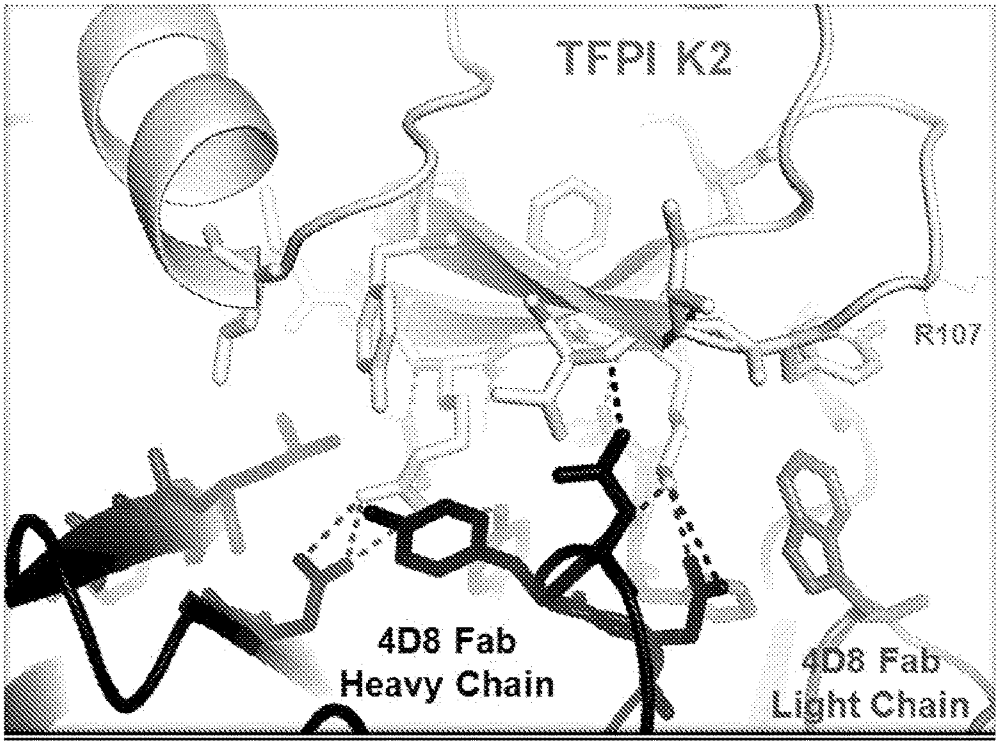
Figure 2D:
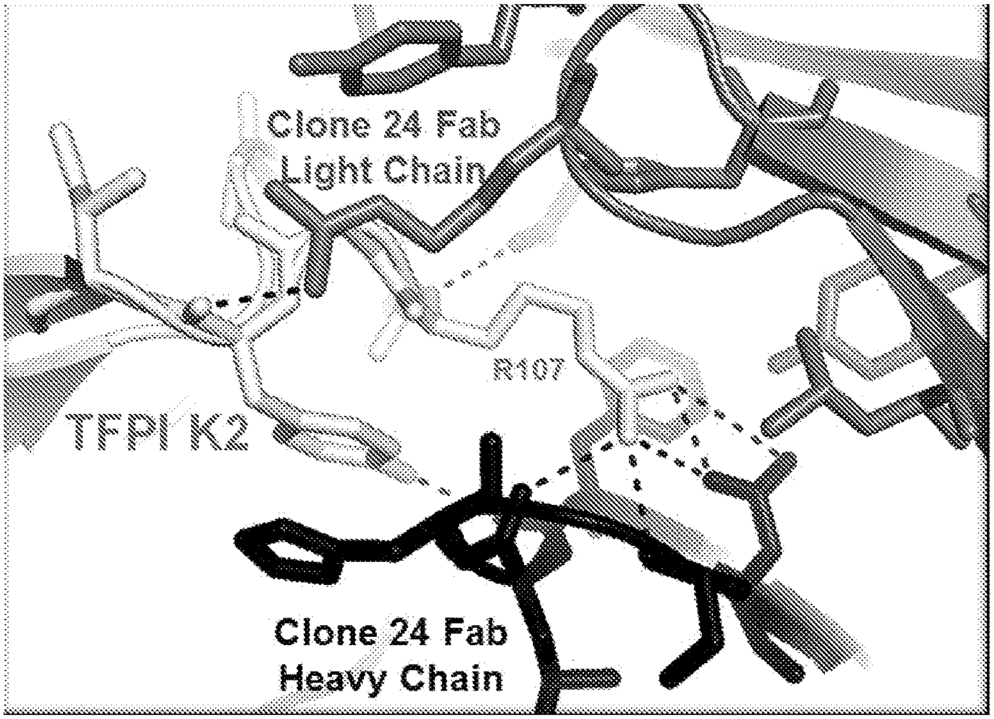
Figure 2E:
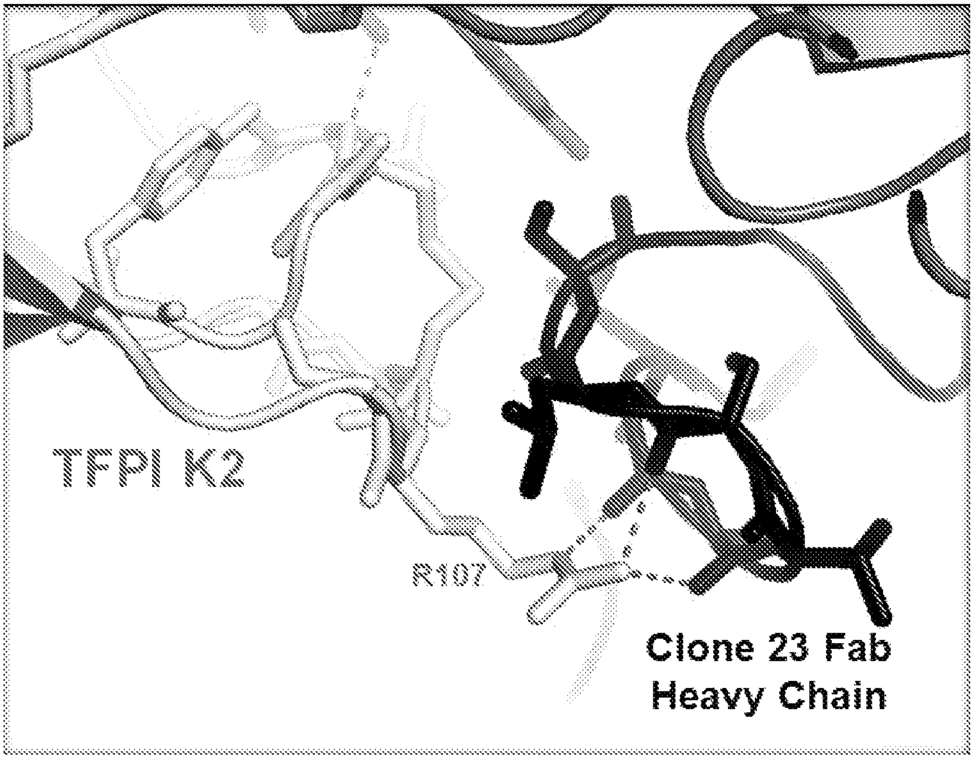
Figure 3A:
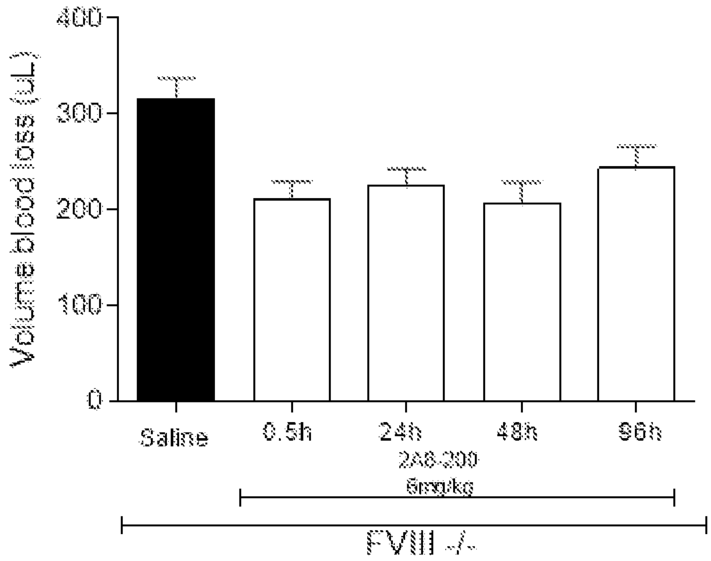
FIGS. 3A-3E show the in vivo efficacies of various anti-TFPI antibodies in a mouse injury model.
Figure 3B:
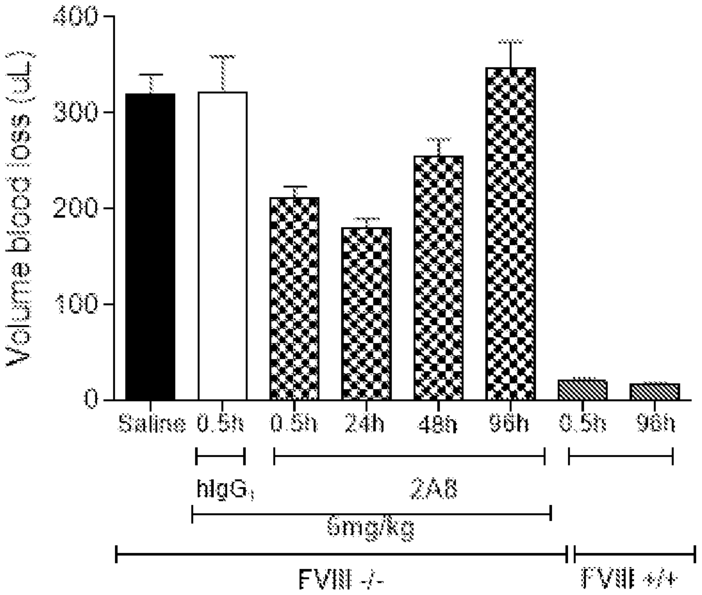
Figure 3C:
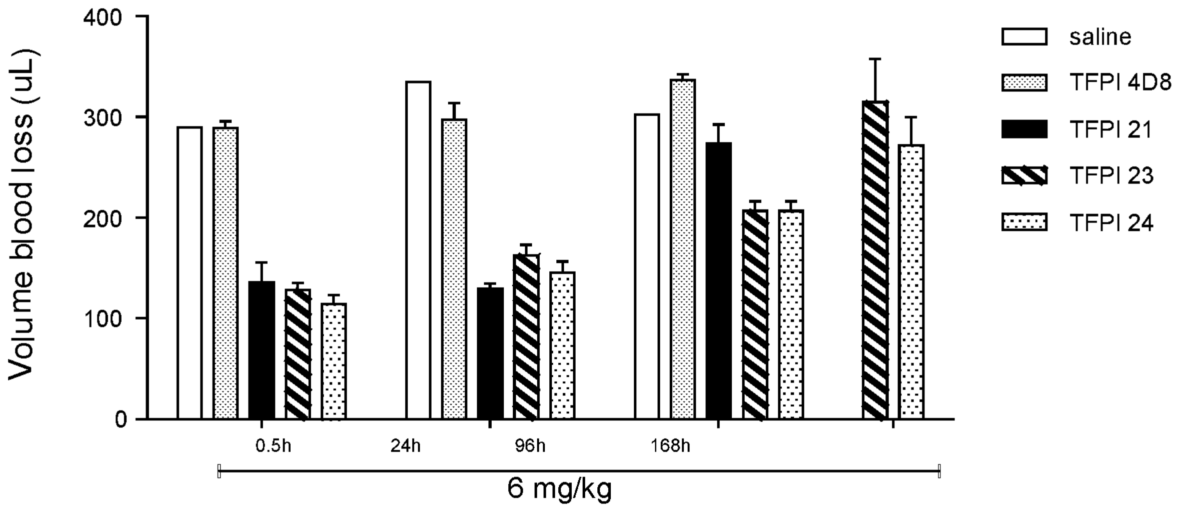
Figure 3D:
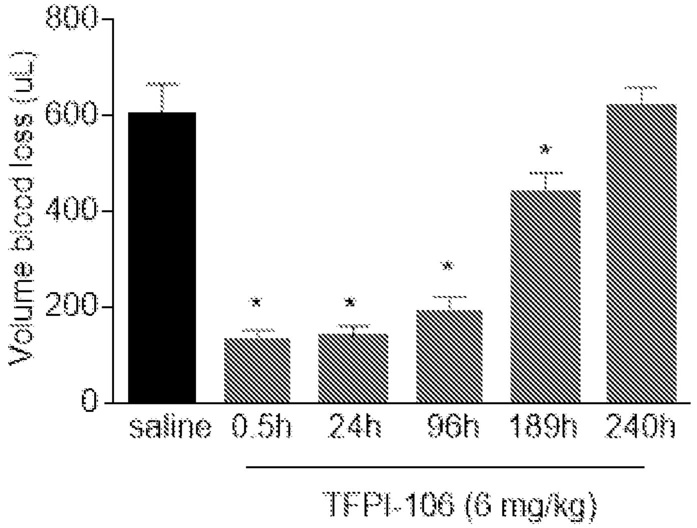
Figure 3E:
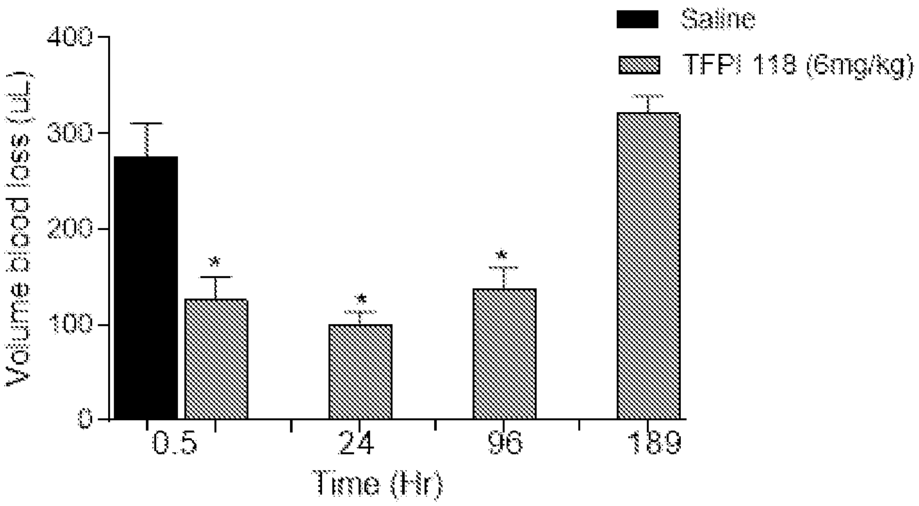
Figure 4:
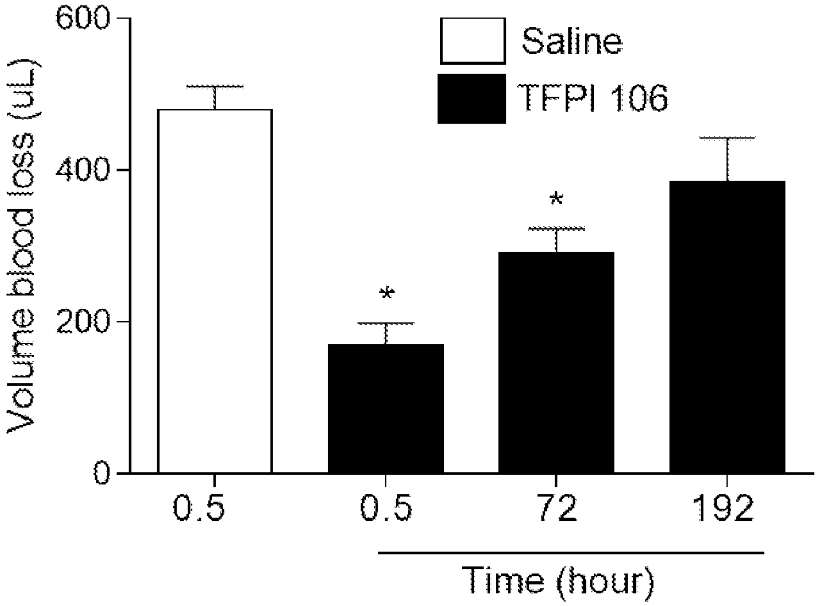
FIG. 4 shows the duration of bleeding in Hemophilia B mice after tail transection when TFPI-106 antibody was administered. Antibodies were administered to hemophilia B mice by intravenous injection at 6 mg/kg at the indicated time points (hours (h)) before injury. Total volume of blood loss (μL) was then measured after tail transection. Vehicle (saline) treated hemophilia A mice served as a control. All measurements are presented as mean±SEM. *=P<0.05. n=4-5/group.

FIG. 3A shows the effect on blood loss in hemophilia A mice (denoted FVIII −/−) after tail transection of dosing at different times before tail transection with the 2A8-200 antibody compared to vehicle control (saline). FIG. 3B shows the effect on blood loss in hemophilia A mice (denoted FVIII −/−) after tail transection of dosing at different times before tail transection with the 2A8 antibody compared to vehicle control (saline) and a non-specific human IgG1 (denoted $hIgG_1$). FIG. 3B also shows the effect on blood loss in normal mice (denoted FVIII+/+) after tail transection of dosing the 2A8 antibody at two different times before tail transection. FIG. 3C shows the effect on blood loss in hemophilia A mice after tail transection of dosing at different times before tail transection with the antibodies 4D8, 21, 23, and 24, compared to vehicle control (saline). FIG. 3D shows the effect on blood loss in hemophilia A mice after tail transection of dosing at different times before tail transection with antibody 106, compared to vehicle control (saline). FIG. 3E shows the effect on blood loss in hemophilia A mice after tail transection of dosing at different times before tail transection with antibody 118, compared to vehicle control (saline). FIG. 4 shows the effect on blood loss in hemophilia B mice after tail transection of dosing at different times before tail transection with antibody 106, compared to vehicle control (saline).

As shown in FIG. 3D and FIG. 4, administration of 6 mg/kg anti-TFPI antibody 106 to hemophilia A or hemophilia B mice decreased blood loss in an acute traumatic injury model when the antibodies were administered at different times before the tail transection injury. In hemophilia A mice, the hemostatic effect persisted at least as long as 189 hours after administration, although by 240 hours after administration the effect returned to control levels. In hemophilia B mice, the effect persisted at least as long as 72 hours after administration, and had returned to baseline by 192 hours after administration.

The data and results described above suggests that the antibodies tested, including antibody TFPI 106, can be administered prophylactically to subjects with hemophilia A or hemophilia B to reduce bleeding before a traumatic injury or other type of bleeding episode.

The effect of antibody TFPI 106 as a hemostatic in hemophilia A mice was also tested to determine if it could reduce bleeding when administered shortly after tail transection. These experiments were carried out using similar methodology as those testing the effect of antibodies when administered prior to tail transection, except that immediately after tail transection an IV dose of TFPI 106 (6 mg/kg) or recombinant Factor VIII (200 units/kg) was infused via a cannulus inserted into the jugular vein, after which blood was collected for 10 minutes before quantifying blood loss. In a second series of experiments different doses of TFPI 106 and Factor VIII (200 U/kg) were administered separately to hemophilia A mice 2 minutes after tail clip, and then blood collected for 10 minutes before quantifying blood loss.

FIG. 9A shows that 6 mg/ml of antibody TFPI 106 administered immediately after tail transection was effective to reduce blood loss in hemophilia A mice compared to vehicle control, although not to the same extent as 200 U/kg Factor VIII administered in the same way. FIG. 9B shows that antibody TFPI 106 dose-responsively reduces bleeding in hemophilia A mice when administered 2 minutes after injury by tail transection, and that at the highest dose tested (6 mg/kg), TFPI 106 was about as effective as recombinant Factor VIII at 200 U/kg when both were administered 2 min after tail transection. The data and results described in these figures suggests that antibody TFPI 106 can be effective as an on-demand treatment for bleeding that has already begun in subjects due to trauma, or some other cause.

Example 15. Pharmacokinetics and Product Metabolism

The pharmacokinetics (PK) and/or toxicokinetics (TK) of TFPI-106 were characterized after intravenous (IV) and/or subcutaneous (SC) dosing in Wistar Han rats, New Zealand White rabbits and cynomolgus monkeys.

Anti-TFPI in sodium citrated rabbit plasma was quantified using a sandwich immunoassay on the Gyrolab. Response Units were read by the Gyrolab instrument at 1% Photomultiplier tube (PMT) setting. Sample concentrations were determined by interpolation from a standard curve that was fit using a 5-parameter logistic curve fit with 1/y2 response weighting. The standard points in assay buffer contained 5% pooled sodium citrated rabbit plasma ranging from 0.78 ng/mL to 891 ng/mL, and the range of quantitation in 100% rabbit plasma matrix was 90 ng/mL to 5500 ng/mL. Five samples of Anti-TFPI at 0.45, 8.0, 47.15, 153, and 275 ng/ml in assay buffer containing 5% pooled sodium citrated rabbit plasma served as quality control.

Anti-TFPI in sodium citrated rat plasma was also quantified using a sandwich immunoassay on the Gyrolab as described above. The standard points in assay buffer containing 5% pooled sodium citrated rat plasma ranged from 0.78 ng/mL to 891 ng/mL, and the range of quantitation in 100% rat plasma matrix was 90 ng/mL to 5500 ng/mL. Five samples of anti-TFPI at 0.45, 8.1, 47.15, 153, and 275 ng/ml in assay buffer containing 5% pooled sodium citrated rat plasma served as quality control.

A total human Ig quantitative ligand-binding assay using the Meso-Scale Discovery (MSD) assay platform was used to quantify anti-TFPI antibody in cynomolgus monkey plasma. Bound anti-TFPI antibody was detected with a ruthenylated mouse anti-human IgG Fc antibody to produce an electrochemiluminescent signal within the MSD instrument. Sample concentrations were determined by interpolation from a standard curve that is fit using a 5-parameter logistic equation, weighting formula for standard curve is 1/y^2. The standard points in 5% monkey plasma ranged from 0.999 ng/mL to 1156 ng/mL anti-TFPI antibody, and the range of quantitation in 100% plasma was 64.8 ng/mL to 7136 ng/mL. Five samples of anti-TFPI antibody at 64.8, 117, 680, 3964 and 7136 ng/mL in 100% plasma diluted to the MRD of 1:20 (3.24, 5.83, 34.0, 198 and 357 ng/mL in 5% plasma, respectively) serve as quality control.

In New Zealand White rabbits, TFPI-106 exhibited a faster clearance (CL) compared to an isotype control monoclonal antibody (mAb). In cynomolgus monkeys, TFPI-106 exhibited nonlinear PK kinetics at low doses consistent with target-mediated drug disposition (TMDD) observed for anti-TFPI antibodies. See Table 32.

Table 32 summarizes certain pharmacokinetic properties and pharmacological activities of exemplary anti-TFPI antibodies of the invention (hum4D8, TFPI-106, and TFPI-108), as well as two reference antibodies (4F36 and 2A8-200).

TABLE 32

Pharmacokinetic properties and pharmacological activities of exemplary anti-TFPI antibodies

| Source | hz4D8 hybridoma | TFPI-106 lambda library | TFPI-118 lambda library | 4F36 Reference Ab | 2A8-200 Reference Ab |
|---|---|---|---|---|---|
| Germline frameworks | DP-54 & DPK9 | DP-47/VH3 & DPL8/VL1 | DP-31/VH3 & DPL3/VL1 | NA | NA |
| Human IgG subclass | | IgG1-3M | | IgG4 | |
| Kd (nM) Human TFPI K1K2 | 0.42 | 3.7 | 9.61 | 0.493 | 0.327 |
| Kd (nM) Cyno TFPI K1K2 | 0.067 | 1.22 | 1.8 | 0.425 | 0.637 |
| Kd (nM) Rabbit TFPI K1K2 | 0.502 | 4.25 | 5.79 | 1.81 | 0.145 |
| Kd (nM) Mouse TFPI K1K2 | No binding | 0.575 | 45.6 | No binding | 0.455 |
| Kd (nM) Rat TFPI K1K2 | No binding | 1.57 | 3.65 | No binding | NA |
| Epitope | K2 | K2 | K2 | K2 | K1K2 |
| Biacore competition with 4F36 | Yes | No | Yes | NA | Yes |
| Polyreactivity screen | negative | negative | negative | ND | Yes |
| Xa Inhibition Assay EC50 nM | 6.92 | 18.08 | 20.8 | 6.57 | 2.42 |
| FVIIa/TF/Xa $EC_{50}$ nM | 0.4 | 4.3 | 4.03 | 1.85 | 4.84 |
| TGA Velocity $EC_{50}$ nM | 3.9 | 3.07 | 7.72 | 1.7 | |
| Dilute PT $EC_{50}$ nM | 0.47 | 1.24 | 1.16 | 0.44 | 1 |

TABLE 32-continued

Pharmacokinetic properties and pharmacological activities of exemplary anti-TFPI antibodies

| Source | hz4D8 hybridoma | TFPI-106 lambda library | TFPI-118 lambda library | 4F36 Reference Ab | 2A8-200 Reference Ab |
|---|---|---|---|---|---|
| Mouse HA tail Clip $IC_{50}$ | NA | 2.4 | 1.1 | NA | NT |
| HA Mouse tail clip −0.5 h 96 h 196 h | NA | 55%<br>39%<br>~6% | 55%<br>39%<br>19% | NA | 32%<br>32% |
| Rabbit IHM Efficacy at 0.5 hr | 60% | 60% | 60% | 60% | 27% |
| Duration by aPTT/dil PT | ≥48 hours | ≥48 hours | ≥48 hours | ≥48 hours | ≥48 hours |
| Rabbit half life t½ at 2 mg/kg | 14 hours | 29 hours | 15 hours | 11 hours | 12 hours |

Example 16. Hemostatic Effect of Antibody Inhibition of TFPI Enhances Platelet Accumulation and Fibrin Generation In Vivo in a Laser Induced Injury Model in Hemophilic Mice As previously stated elsewhere herein, Tissue Factor Pathway Inhibitor (TFPI) is a plasma serine protease inhibitor that directly binds and inhibits the Tissue Factor (TF)/Factor Vila/Factor Xa complex and modulates the initiation of coagulation induced by TF. Blocking TFPI can potentially facilitate hemostasis initiated by TF/FVIIa compensating for loss of factor VIII (FVIII) or factor IX in hemophilia A or B. The antibodies of the invention inhibit TFPI with broad species cross reactivity. Herein, the hemostatic effect of TFPI-106 on platelet clot formation and fibrin deposition in vivo was assessed using intravital microscopy (IVM) in hemophilia A and B mice.

Materials and Methods:

TFPI-106 antibody, recombinant Factor VIII and vehicle (phosphate buffered saline) were prepared as previously described elsewhere herein. Dylight-649 anti-CD42c antibody was obtained from Emfret Analytics (Germany). Fibrin antibody clone 59D8 (Hui K Y et al. (1983) Science 222 (4628):1129-1132) was labeled with Alexa Fluor 488 using a protein labeling kit according to manufacturer's instructions (Life Technologies, Carlsbad, Calif.). Male hemophilia A mice (F8 KO) weighing 30 to 35 grams on average were obtained from a proprietary line maintained at Charles River laboratories (Wilmington, Mass.). Mice were acclimated for at least 3 days prior to experimental procedures.

Male hemophilia A, hemophilia B, or C57BL/6J wild type (WT) mice were dosed with a single intravenous dose of TFPI-106 (6 mg/kg), vehicle, recombinant human FVIII (rFVIII, 200 IU/kg) or Alexa-488 labeled TFPI-106 (0.7 mg/kg). Cremaster microcirculation in anesthetized mice was observed using IVM. Platelet accumulation and fibrin generation were quantified following a laser heat injury to the vessel wall of the cremaster artery. Platelets were visualized using Dylight-649 anti-CD42c (GP1bβ) and fibrin was detected by Alexa-488 anti-fibrin clone 59D8.

More specifically, to prepare hemophilia A mice for intravital microscopy imaging, animals were anesthetized with Ketamine/Xylazine cocktail delivered intraperitoneally. The jugular vein was cannulated and sodium pentobarbital (5 mg/kg, intravenous) was used as maintenance anesthesia. The trachea was cannulated to maintain a patent airway. The cremaster muscle was then exposed to visualize the microvasculature. The animals were maintained on a warm heating pad with a warm buffered solution bathing the exposed cremaster tissue throughout the imaging period. Labeled antibodies to platelet Dylight 649 CD42c (GP1bβ) and a fibrin antibody that does not cross react with fibrinogen (Alexa Fluor 488 anti-fibrin clone 59D8), were infused via the jugular cannulus. A focused beam of laser (532 nanometers) initiated the injury on the mouse cremaster microvasculature. Each mouse received 2 laser induced injuries. The first injury was made in untreated mouse to serve as control. The second injury was made in the same mouse and TFPI-106 (at 6 mg/kg) was immediately administered intravenously via the jugular cannulus. In both injuries, clot formation was monitored from fluorescent intensities of platelet accumulation and fibrin deposition.

Data points (fluorescence intensities) were collected and analyzed using SlideBook software (Version 6.0). Median fluorescence intensities were plotted as a function of time for each individual clot and the corresponding area under the curve was measured using GraphPad®Prism software (Version number 6.03). Statistical significance was determined using a Mann-Whitney test using GraphPad®Prism software (Version number 6.03).

Figure 5A:
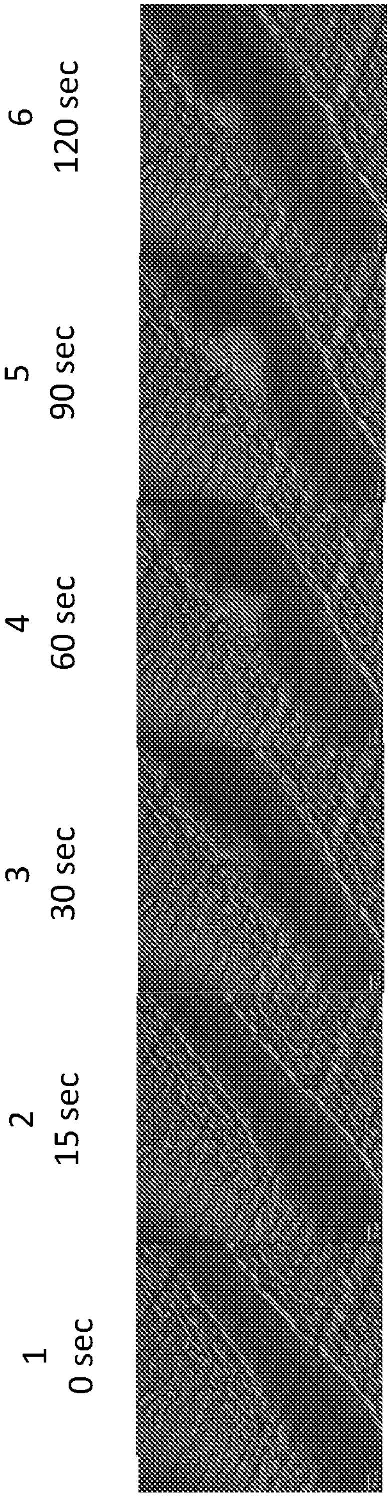
FIG. 5A shows the increase in platelet thrombus at the site of injury as detected using Dylight 649-labeled CD42c that binds GP1bβ on platelets. The presence or absence of platelets is demonstrated by the fluorescence signal detected in panel 1 (0 sec); panel 2 (15 sec); panel 3 (30 sec); panel 4 (60 sec); panel 5 (90 sec); and panel 6 (120 sec). Alexa 488-labeled negative control IgG was also administered, and no fluorescence was detected.
Figure 5B:
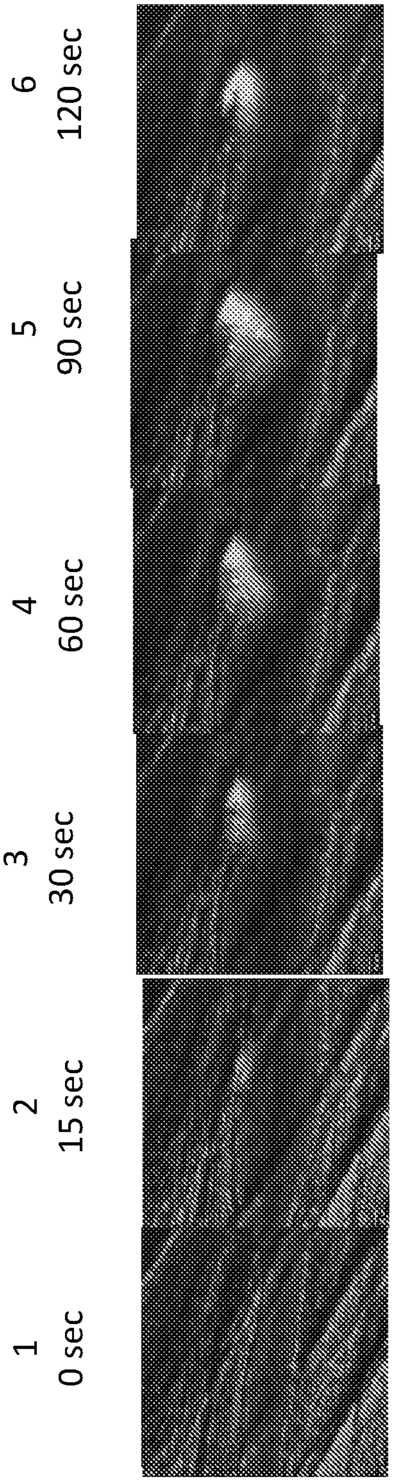
FIG. 5B, comprising panels 1-6, shows microphotographs of IVM demonstrating that TFPI is present in the platelet thrombus and along the endothelium after laser induced vessel injury in wild type mice. Alexa 488-labeled TFPI (green signal shown as gray) is not detected at 0 seconds (FIG. 5B, panel 1) and a faint signal can be seen at 15 seconds (FIG. 5B, panel 2). At 30 seconds (FIG. 5B, panel 3) the green fluorescence signal has increased and a faint red signal (Dylight 649-labeled CD42c) can be seen indicating detection of platelet accumulation at approximately the same site where TFPI is detected.
Figure 6A:
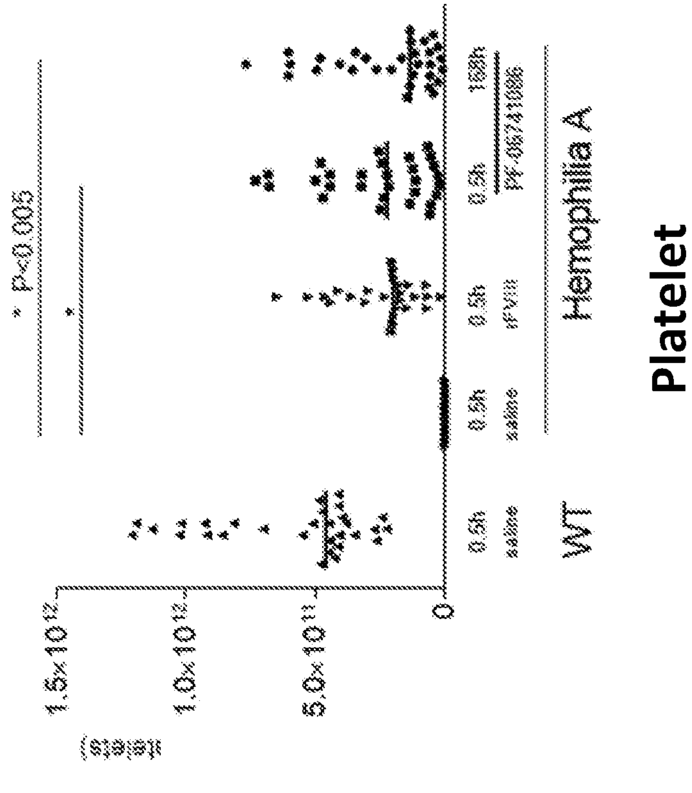
FIG. 6A is a graph showing the hemostatic effect of TFPI-106 in hemophilia A mice after laser induced vessel injury as assessed using IVM where the amount of platelet thrombus is expressed as the area under the curve (AUC) (*=P<0.005 is indicated).
Figure 6B:
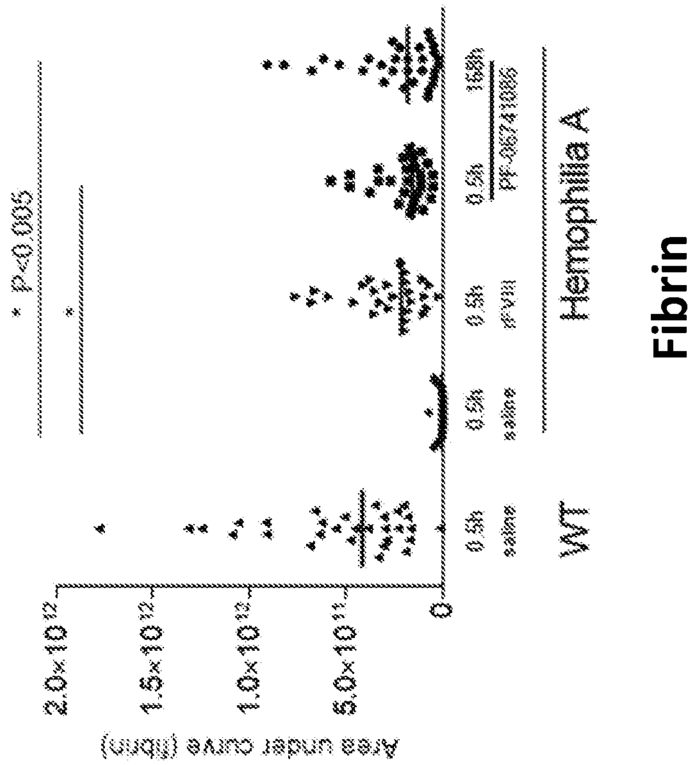
FIG. 6B is a graph showing the hemostatic effect of TFPI-106 in hemophilia A mice after laser induced vessel injury as assessed using IVM where the amount of fibrin generation is expressed as the area under the curve (AUC) (*=P<0.005 is indicated).

Results:

TFPI was detected at the site of platelet accumulation within the platelet clot and the lining the endothelium using Alexa-488 labeled TFPI-106 in WT mice (FIG. 5). FIG. 5A comprises six top panels (numbered 1 through 6) showing the detection of platelets using Dylight 649 CD42c in a WT mouse administered control IgG labeled using Alexa 488 at 0 (panel 5A-1), 15 (FIG. 5A-2), 30 (FIG. 5A-3), 60 (FIG. 5A-4), 90 (FIG. 5A-5) and 120 (FIG. 5A-6) seconds post-laser induced injury. No Alexa 488 label was detected in the platelet thrombus (detected using Dylight 649 CD42c) at the site of injury. FIG. 5B, comprising six panels (numbered 1-6) along the bottom of the Figure, shows that Alexa 488 labeled TFPI-106 was detected commencing at about 15 seconds (FIG. 5B-2) and increasing in fluorescent intensity at about 30 (FIG. 5B-3), 60 (FIG. 5B-4) and 90 (FIG. 5B-5) seconds and then sustained intensity at about 120 seconds (FIG. 5B-6) in the platelet thrombus along the endothelium after laser induced injury in the WT mouse, where the platelets were detected using Dylight 649 labeled CD42c.

TFPI-106 enhanced platelet accumulation and fibrin generation in hemophilia A (F8 KO) mice compared with hemophilia A mice treated with vehicle at about 0.5 hours and the effect persisted at about 168 hours. More specifically, in TFPI-106 treated F8 KO mice (hemophilia A), IVM showed increased green fluorescence (Alexa 488 anti-fibrin clone 59D8) and red fluorescence (Dylight 649 labeled CD42c anti-GP1bβ detecting platelets) at the injury site at about 0.5 hours which persisted at about 168 hours, and the fluorescence pattern was similar to that observed in WT mice treated with vehicle. However, such fluorescence was not detected in vehicle treated hemophilia A mice where neither platelet accumulation nor fibrin generation were observed.

Hemophilia A mice exhibited an increase in platelet accumulation (FIG. 6A) and fibrin deposition (FIG. 6B) at about 0.5 hours post dosing with TFPI-106, similar to levels achieved by rFVIII (*=P<0.005 is indicated on each graph). The hemostatic effect was persistent for up to 168 hours with TFPI-106 in Hemophilia A mice. Similarly, TFPI-106 treated Hemophilia B mice similarly demonstrated improved hemostasis at about 30 minutes post dosing with an increase in platelet accumulation and fibrin generation compared to vehicle controls. Neither TFPI-106 nor rFVIII dosed hemophilic mice reached the maximal level of fibrin deposition observed in non-hemophilic WT mice. Thus, the data show that following a laser injury to the endothelium, TFPI was detected at the site of injury. More importantly, the data demonstrate that administration of TFPI-106 to hemophilic mice results in a significant and persistent improvement in hemostasis in a laser injury model.

Example 17. Thrombin Generation Effect of Anti-TFPI Inhibition in Combination with FVIIA in Hemophilia A and B TGA Methods: Thrombin Generation Assays (TGA)

The effect of anti-TFPI antibody TFPI-106 on thrombin generation was evaluated alone and in combination with recombinant FVIIa (rFVIIa) in hemophilic plasmas using the thrombin generation assay (TGA). Citrated platelet poor severe hemophilia A (FVIII deficient), severe hemophilia A with an inhibitor, or hemophilia B (FIX deficient) plasma were from donors with a congenital deficiency obtained from George King Biomedical (Overland Park, Kans.) and HRF (Raleigh, N.C.). Normal pooled plasma (non-hemophilic) was obtained from George King Biomedical. Thrombin generation reagents; PPP-Reagent LOW (4 μl phospholipid and 1 pM tissue factor final in the reaction); FluCa buffer (containing calcium chloride and fluorogenic substrate) and thrombin calibrator were obtained from Diagnostica Stago (Parsippany, N.J.). Thrombin generation assays were performed using the Calibrated Automated Thrombogram (CAT) including the Fluoroskan Ascent fluorescent plate reader (Thrombinoscope BV, Maastricht, Netherlands).

Recombinant FVIIa (rFVIIa in 20 mM HEPES, 150 mM sodium chloride, 1% Bovine Serum Albumin (BSA), pH 7.4) was added to 70 μl hemophilia A plasma at concentrations up to 20 μg/mL. Twenty μl of PPP-Reagent LOW and 10 μl of anti-TFPI 106 were added to reaction wells at a final concentration of 16 μg/mL. Reference calibrated control reactions included 20 μl thrombin calibrator with 70 μl plasma. Vehicle (Phosphate buffered saline (PBS)) was used to test the 0 μg/mL concentration. Ten μl of vehicle was added to reference calibrator wells. In a second set of reactions rFVIIa (5 μl) in HEPES buffer or HEPES buffer (5 μl) were added to 70 μl of hemophilic plasma samples (hemophilia A, hemophilia A with an inhibitor or hemophilia B) for a final concentration of rFVIIa in the plasma of 2 μg/mL. Twenty μl of PPP Reagent LOW and 5 μL of anti-TFPI 106 (diluted in PBS) or PBS (5 μl) were added to the rFVIIa-dosed hemophilic plasma samples (75 μl) and to the HEPES buffer-treated hemophilic plasma (75 μl), to final concentrations of 16 μg/mL. In addition, anti-TFPI 106 (at 16 μg/mL) was assayed in HEPES buffer treated non-hemophilic plasma (75 μl). Control untreated non hemophilic plasma (80 μl) was included in the analysis. Reference calibrated reactions (20 μl thrombin calibrator with 80 μl of vehicle dosed hemophilic or non-hemophilic plasma or 80 μl of untreated non-hemophilic plasma) were run in parallel. All reactions were run in duplicate. Samples were incubated at 37° C. for 5 minutes and the reactions were then initiated by addition of 20 μl of FluCa a total reaction volume of 120 μl. Fluorescence of plasma reactions was read at 37° C. at 20 second intervals on a Fluoroskan Ascent fluorometer and compared to the reference thrombin calibrator reactions to determine thrombin concentrations. The intensity of the fluorescence signal was continuously monitored at 37° C. using the CAT.

Results:

The deficiencies in coagulation factors FVIII (hemophilia A) and FIX (hemophilia B) prevent sufficient thrombin generation for the conversion of fibrinogen to fibrin for the development of a stable clot. Anti-TFPI-106, a novel monoclonal antibody that specifically binds to and inhibits and/or neutralizes the inhibitory activity of TFPI, targets the extrinsic tissue factor/FVIIa pathway of coagulation. Patients with inhibitors receiving TFPI-106 may also receive rFVIIa to treat a breakthrough bleed. Thus, the effect of TFPI-106 on thrombin generation, in the presence and absence of rFVIIa, in hemophilia plasma, was examined in vitro using the art-recognized TGA (thrombin generation assay).

In vitro studies using the thrombin generation assay in citrated platelet poor factor VIII deficient human plasma were performed to study the activity of TFPI-106 in the presence of rFVIIa. In one study, anti-TFPI 106 was added to factor VIII deficient human plasma at a fixed concentration (16 μg/mL), a concentration of rFVIIa that is known to increase thrombin generation in hemophilia A plasma. rFVIIa was added to the assay at increasing concentrations up to 20 μg/mL. Surprisingly, the combination of TFPI-106 and rFVIIa restored thrombin generation to levels observed in normal plasma. The peak thrombin levels observed with the combination of TFPI-106 and a range of rFVIIa (eptacog alfa) from 0.2, 2, and 20 μg/mL were similar. The data, as shown in FIG. 7, demonstrate that TFPI-106 improved the thrombin generation response of severe hemophilia A plasma dosed with rFVIIa (FIG. 7, solid black, dark gray and light gray lines).

The effect of TFPI-106 (16 μg/mL; FIG. 7, dark gray dashed line) on thrombin generation was also measured in non-hemophilia plasma, which would have the full complement of coagulation factors. Consistent with the TFPI extrinsic pathway inhibitory activity of TFPI-106, the addition of anti-TFPI 106 resulted in an increase in thrombin generation with a decrease in the lag time and increase in peak thrombin. The peak thrombin ~200 nM with the addition of TFPI-106 and rFVIIa is within the range reported for normal non-hemophilic plasmas.

The TFPI inhibitory activity of TFPI-106 on thrombin generation in the presence and absence of rFVIIa was further studied in additional hemophilia A plasmas (FIG. 8A; 1 pM tissue factor and 4 μM phospholipids), hemophilia B plasma (FIG. 8C; 3 BU inhibitor) and in hemophilia A plasma (FIG. 8B; 3 BU inhibitor) with an inhibitor and the results are graphically shown in FIGS. 8A, 8C and 8B, respectively. TFPI-106 was added to the plasmas for a final concentration of 16 μg/mL. The final concentration of rFVIIa in these studies was 2 μg/mL. The addition of 2 μg/mL rFVIIa to a hemophilic plasma resulted in a modest increase in thrombin generation compared to vehicle control. The addition of 16 μg/mL TFPI-106 alone or in combination with rFVIIa resulted in an increase in thrombin generation including higher peak thrombin concentration and shortening of lag time compared to addition of rFVIIa alone. A minimal additive effect in thrombin generation was observed after co-treatment of rFVIIa and TFPI-106. The peak thrombin levels achieved at 16 μg/mL TFPI-106 alone or in combination with rFVIIa were comparable to those observed in non-hemophilic plasma and did not exceed the level observed in non-hemophilic plasma dosed with TFPI-106. These data demonstrate that TFPI-106 was effective in bypassing the deficiencies of thrombin generation in hemophilia A, hemophilia B and in hemophilia A plasma with inhibitors.

Example 18. Procoagulant Activity in Human Hemophilic Blood and Plasma

This example describes the hemostatic activity of antibody TFPI-106 when tested using whole blood and plasma obtained from human subjects having hemophilia A and B in comparison to recombinant coagulation factors Factor VIII and Factor IX.

Materials and methods. Whole blood and plasma (platelet rich and platelet poor) were obtained from volunteer hemophilia patients at least 18 years of age under an institutional review board approved protocol. The subjects had moderate or severe Factor VIII (FVIII) or Factor IX (FIX) deficiency, with or without inhibitory antibodies, but were otherwise healthy and in a non-bleeding state. Volunteers were excluded if they had used any factor replacement therapy within the previous 48 hours before study entry, had active bleeding or had a medical or family history of thrombosis. Of the 11 volunteers, 5 had severe FVIII deficiency, 2 had moderate FVIII deficiency, 1 had moderate FIX deficiency and 3 had severe FVIII deficiency with a FVIII inhibitor. To complete all aims of the study, 46 mL of blood (10 blood tubes) were collected from each volunteer via aseptic venipuncture into evacuated tubes containing 3.2% sodium citrate.

Test articles included TFPI 106, a negative control isotype matched anti-human $IgG_1$, recombinant human Factor VIII, and recombinant human Factor IX, which were added to whole blood or plasma, depending on the experiment. Depending on the assay, TFPI 106 was tested at 1, 5, 20, 50 or 100 nM, control $IgG_1$ antibody at 100 nM, and recombinant FVIII or FIX at levels that would achieve 5%, 10% or 40% of normal factor activity based on an activated partial thromboplastin time (aPTT) assay. To achieve desired concentrations, test articles were diluted with a dilution buffer at pH 7.4, comprising 20 mM HEPES, 150 mM NaCl, and 0.5% Bovine Serum Albumin.

Three types of assays were used to determine the procoagulant effect of the test articles, including rotational thromboelastography (ROTEM), thrombin generation assay (TGA), and dilute prothrombin time (dPT) assay.

ROTEM measures the viscoelastic properties of the whole blood sample as it clots under low shear conditions. As clotting proceeds, the viscosity of the sample increases, which can be analyzed graphically. ROTEM was performed using a ROTEM analyzer (Pentapharm GmbH, Munich, Germany) using Pentapharm software 1.0.04 to assess coagulation in whole blood. Clotting was initiated by adding 0.020 mL of a 1:2333 dilution of lipidated tissue factor (Innovin, Siemens Healthcare) for a final reaction dilution of 1:42000, and 0.020 mL of $CaCl_2$ to 0.300 ml of citrated whole blood. All reactions were run in duplicate. ROTEM parameters were monitored and ROTEM clotting time (CT) analyzed. Data collected by the device software was exported to Microsoft Excel 2010 and/or GraphPad Prism (version 6) for analysis. For each volunteer, the percent change in ROTEM clotting time of treated samples was calculated with respect to an untreated sample from the same volunteer.

Using the thrombin generation assay (TGA), the kinetics of thrombin generation were assessed in platelet rich plasma (PRP) and platelet poor plasma (PPP) prepared from volunteer blood according to the methods of Hemker, et al., Calibrated automated thrombin generation measurement in clotting plasma. Pathophysiolol Haemost Thromb, 33:4-15 (2003). Briefly, samples of whole blood dosed with test articles were centrifuged at 150×g for 10 minutes at room temperature to obtain PRP, or 2500×g for 15 minutes at room temperature to obtain PPP. Unused plasma was frozen and stored at −80° C. In the PRP plasma, the platelet count was adjusted to 150,000 platelets per microliter with autologous PPP. Thrombin generation was immediately measured in fresh PRP. For PRP samples, 20 uL of 1 μM tissue factor (PRP Reagent, Diagnostica Stago, Inc., Parsippany, N.J.) and 80 uL of PRP were added in triplicate to wells of a 96 well microtiter plate. Thrombin generation was initiated by adding 20 ul of FLUCa buffer (16.7 mmol/l final concentration of $CaCl_2$ and 417 mmol/L Z-Gly-Gly-Arg-AMC fluorogenic thrombin substrate). Fluorescence intensity was detected using a Fluoroskan Ascent Fluorometer. For PPP samples, PPP-reagent-LOW (final concentration of 1 μM tissue factor and 4 micromolar procoagulant phospholipids) was used in place of PRP-Reagent and run as described for PRP samples. Thrombin generation was calculated using Thrombinoscope software version 5.0.0.742 (Thrombinoscope BV, Maastricht, The Netherlands). Data obtained from Thrombinoscope software was exported to Microsoft Excel 2010 and/or GraphPad Prism (version 6) for analysis. For each volunteer, the percent change in TGA peak thrombin concentration of treated samples was calculated with respect to the untreated sample from the same volunteer.

Dilute prothrombin time (dPT) assays were performed on a STart 4 coagulation analyzer (Diagnostica Stago, Parsippany, N.J.). Frozen PPP was thawed and dosed with anti-TFPI 106 at concentrations of 1, 5, 20 and 100 nM or isotype control antibody at a concentration of 100 nM. Dosed plasmas were incubated at 37° C. for 30 minutes prior to dPT assay analysis. Fifty microliters of plasma was added to a STart 4 cuvette and incubated for 60 seconds at 37° C. The reaction was activated with addition of 1:6000 dilution of tissue factor reagent (Innovin) prepared in dilution buffer (50 mM Imidazole, 0.1 M sodium chloride, 1 mg/ml bovine serum albumin, and 8.34 mM $CaCl_2$, pH 7.4) and preincubated at 37° C. The time to clot was measured at 37° C. with reactions run in duplicate. Clotting times were exported to Microsoft Excel 2010 or GraphPad Prism (version 6) for analysis. The percentage change in dPT clotting for test article treated samples was calculated in reference to the dPT clotting time of the untreated sample for each volunteer.

As described in the figures, antibody TFPI-106 caused a dose-dependent increase in clotting of whole blood obtained from volunteers with hemophilia A or B, as measured using the ROTEM method. Specifically, the antibody reduced clotting time and increased maximum clot firmness compared to negative controls. In addition, TFPI-0106 resulted in dose-dependent increases in thrombin generation when added to both platelet rich and platelet poor plasma obtained from hemophilic patients, as evidenced by reductions in lag time and increased peak thrombin concentration generated, compared to negative controls.

FIGS. 10A and 10B illustrate the procoagulant effect of TFPI-106 in whole blood and plasma obtained from volunteers with severe hemophilia A. FIG. 10A shows the effect on blood clotting in the ROTEM assay of two concentrations of TFPI 106 compared to negative control IgG and concentrations of recombinant FVIII sufficient to achieve 5%, 10% and 40% of normal activity. FIG. 10B shows peak thrombin generation in platelet rich plasma of three concentrations of TFPI-106 compared to negative controls and FVIII. The assays show a dose dependent effect of reduced clotting time and increased peak thrombin generation due to TFPI 106.

FIGS. 11A, 11B, and 110 illustrate the procoagulant effect of TFPI-106 in whole blood and plasma from a volunteer with severe hemophilia A and inhibitory antibodies (inhibitors) to FVIII. FIG. 11A shows the effect on blood clotting in the ROTEM assay of two concentrations of TFPI 106 compared to negative control IgG. FIG. 11B shows peak thrombin generation in platelet rich plasma of three concentrations of TFPI-106 compared to negative control IgG. FIG. 11C shows the effect on clot formation from platelet poor plasma in the dilute PT assay of four concentrations of TFPI-106 compared to negative control IgG. The assays show a dose dependent effect of reduced clotting time and increased peak thrombin generation due to TFPI 106.

FIGS. 12A, 12B, and 12C illustrate the procoagulant effect of TFPI-106 in whole blood and plasma from a volunteer with moderate hemophilia A. FIG. 12A shows the effect on blood clotting in the ROTEM assay of two concentrations of TFPI 106 compared to negative control IgG and concentrations of recombinant FVIII sufficient to achieve 5%, 10% and 40% of normal activity. FIG. 12B shows peak thrombin generation in platelet rich plasma of three concentrations of TFPI 106 compared to negative controls and FVIII. FIG. 12C shows the effect on clot formation from platelet poor plasma in the dilute PT assay of four concentrations of TFPI 106 compared to negative control IgG. The assays show a dose dependent effect of reduced clotting time and increased peak thrombin generation due to TFPI 106.

FIGS. 13A, 13B, and 13C illustrate the procoagulant effect of TFPI-106 in whole blood and plasma from a volunteer with moderate hemophilia B. FIG. 13A shows the effect on blood clotting in the ROTEM assay of two concentrations of TFPI-106 compared to negative control IgG and concentrations of recombinant Factor IX (FIX) sufficient to achieve 5%, 10% and 40% of normal activity. FIG. 13B shows peak thrombin generation in platelet rich plasma of three concentrations of TFPI-106 compared to negative controls and FIX. FIG. 13C shows the effect on clot formation from platelet poor plasma in the dilute PT assay of four concentrations of TFPI 106 compared to negative control IgG. The assays show a dose dependent effect of reduced clotting time and increased peak thrombin generation due to TFPI-106.

FIGS. 14A, 14B, and 14C illustrate the procoagulant effect of TFPI-106 in whole blood and plasma from volunteers with moderate hemophilia A. FIG. 14A shows the effect on blood clotting in the ROTEM assay of three concentrations of TFPI-106 compared to concentrations of recombinant FVIII sufficient to achieve 5%, 10% and 40% of normal activity. Each data point represents the percent decrease in clotting time of a single volunteer's blood sample treated with TFPI-106 or FVIII, relative to clotting time of an untreated blood sample from the same volunteer. The widest horizontal bar among the data points for each treatment represents the mean percent reduction in clotting time of all volunteer samples tested. FIG. 14B shows the effect on peak thrombin generation in platelet rich plasma of three concentrations of TFPI 106 compared to FVIII. Each data point represents the percent increase in peak thrombin generation of a single volunteer's plasma sample treated with TFPI-106 or FVIII, relative to peak thrombin generation of an untreated plasma sample from the same volunteer. The widest horizontal bar among the data points for each treatment represents the mean percent increase in peak thrombin generation of all volunteer samples tested. FIG. 10 shows the effect on clot formation from platelet poor plasma in the dilute PT assay of four concentrations of TFPI 106. Each data point represents the percent decrease in clotting time of a single volunteer's plasma sample treated with TFPI-106 relative to clotting time of an untreated plasma sample from the same volunteer. The widest horizontal bar among the data points for each treatment represents the mean percent reduction in clotting time of all volunteer samples tested. The dilute PT assay showed a dose dependent decrease in clotting time caused by TFPI-106 and the thrombin generation assay showed a dose dependent increase in peak thrombin generation caused by TFPI-106.

TABLE 33

| SEQ ID NO: | Description | SEQUENCES<br>Sequence |
|---|---|---|
| 10 | mAb-TFPI-3 LC CDR1 | RASQGISSSL A |
| 11 | mAb-TFPI-3 LC CDR2 | AASTLQS |
| 12 | mAb-TFPI-3 LC CDR3 | QQLDSYPLS |
| 13 | mAb-TFPI-3 VL CDR1, CDR2, CDR3 are underline | AIQLTQSPSS LSASVGDRVT ITCRASQGIS SSLAWYQQKP GKAPKLLIYA ASTLQSGVPS RFSGSGSGTD FTLTISSLQP EDFATYYCQQ LDSYPLSFGQ GTKLEIK |
| 14 | Human Ig kappa constant | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |

TABLE 33-continued

SEQUENCES

| SEQ ID NO: | Description | Sequence |
|---|---|---|
| 15 | mAb-TFPI-3 LC CDR1, 2, 3 are underlined. Variable sequence in italics | AIQLTQSPSS LSASVGDRVT ITCRASQGIS SSLAWYQQKP<br>GKAPKLLIYA ASTLQSGVPS RFSGSGSGTD FTLTISSLQP<br>EDFATYYCQQ LDSYPLSFGQ GTKLEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 16 | mAb-TFPI-3 HC CDR1 | GYTFTGYYMH |
| 17 | mAb-TFPI-3 HC CDR2 | WINPNSGGTN YAQKFQG |
| 18 | mAb-TFPI-3 HC CDR3 | GIARLQWLPT EADFDY |
| 19 | mAb-TFPI-3 HL CDR1, CDR2, CDR3 are underlined | QVQLVQSGAE VKKPGASVKV SCKASGYTFT GYYMHWVRQA<br>PGQGLEWMGW INPNSGGTNY AQKFQGRVTM TRDTSISTAY<br>MELSRLRSDD TAVYYCARGI ARLQWLPTEA DFDYWGQGTL<br>VTVSS |
| 20 | Human IgG1 constant heavy chain Effector function mutations: L117A, L118A, G120A are underlined. C-terminal lysine deleted. | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVEP KSCDKTHTCP PCPAPEAAGA<br>PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPG |
| 21 | mAb-TFPI-3 HC CDR1, CDR2 and CDR3 underlined. Variable sequence in italics. Effector function mutations in bold. | QVQLVQSGAE VKKPGASVKV SCKASGYTFT GYYMHWVRQA<br>PGQGLEWMGW INPNSGGTNY AQKFQGRVTM TRDTSISTAY<br>MELSRLRSDD TAVYYCARGI ARLQWLPTEA DFDYWGQGTL<br>VTVSSASTKG PSVFPLAPSS KSTSGGTAAL GCLVKDYFPE<br>PVTVSWNSGA LTSGVHTFPA VLQSSGLYSL SSVVTVPSSS<br>LGTQTYICNV NHKPSNTKVD KKVEPKSCDK THTCPPCPAP<br>**EAAGA**PSVFL FPPKPKDTLM ISRTPEVTCV VVDVSHEDPE<br>VKFNWYVDGV EVHNAKTKPR EEQYNSTYRV VSVLTVLHQD<br>WLNGKEYKCK VSNKALPAPI EKTISKAKGQ PREPQVYTLP<br>PSREEMTKNQ VSLTCLVKGF YPSDIAVEWE SNGQPENNYK<br>TTPPVLDSDG SFFLYSKLTV DKSRWQQGNV FSCSVMHEAL<br>HNHYTQKSLS LSPG |
| 22 | mAb-TFPI-21 LC CDR1 | TGSSSNIGAG YDVH |
| 23 | mAb-TFPI-21 LC CDR2 | GNSNRPS |
| 24 | mAb-TFPI-21 LC CDR3 | QSYDSSLSGS VV |
| 25 | mAb-TFPI-21 VL CDR1, CDR2, CDR3 are underlined | QSVLTQPPSV SGAPGQRVTI SCTGSSSNIG AGYDVHWYQQ<br>LPGTAPKLLI YGNSNRPSGV PDRFSGSKSG TSASLAITGL<br>QAEDEADFYC QSYDSSLSGS VVFGGGTKVT VLG |
| 26 | Human Ig lamda CL | QPKAAPSVT LFPPSSEELQ ANKATLVCLI SDFYPGAVTVA<br>WKADSSPVKA GVETTTPSKQ SNNKYAASSY LSLTPEQWKS<br>HRSYSCQVTH EGSTVEKTVA PTECS |
| 27 | mAb-TFPI-21 LC CDR1, 2, 3 are underlined. Variable sequence in italics | QSVLTQPPSV SGAPGQRVTI SCTGSSSNIG AGYDVHWYQQ<br>LPGTAPKLLI YGNSNRPSGV PDRFSGSKSG TSASLAITGL<br>QAEDEADFYC QSYDSSLSGS VVFGGGTKVT VLGQPKAAP<br>SVTLFPPSSE ELQANKATLV CLISDFYPGA VTVAWKADSS<br>PVKAGVETTT PSKQSNNKYA ASSYLSLTPE QWKSHRSYSC<br>QVTHEGSTVE KTVAPTECS |
| 28 | mAb-TFPI-21 HC CDR1 | GFTFSSYAMS |
| 29 | mAb-TFPI-21 HC CDR2 | AISGSGGSTY YADSVKG |
| 30 | mAb-TFPI-21 HC CDR3 | LGATSLSAFD I |
| 31 | mAb-TFPI-21 VH | QVQLVESGGG LVQPGGSLRL SCAASGFTFS SYAMSWVRQA<br>PGKGLEWVSA ISGSGGSTYY ADSVKGRFTI SRDNSKNTLY<br>LQMNSLRAED TAVYYCAILG ATSLSAFDIW GQGTMVTVSS |

TABLE 33-continued

SEQUENCES

| SEQ ID NO: | Description | Sequence |
|---|---|---|
| 32 | mAb-TFPI-21 HC CDR1, CDR2 and CDR3 underlined. Variable sequence in italics. Effector function mutations in bold. | QVQLVESGGG LVQPGGSLRL SCAASGFTFS SYAMSWVRQA PGKGLEWVSA ISGSGGSTYY ADSVKGRFTI SRDNSKNTLY LQMNSLRAED TAVYYCAILG ATSLSAFDIW GQGTMVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPE**AAGA** PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 33 | mAb-TFPI-23 LC CDR1 | TGSSSNIGAG YDVH |
| 34 | mAb-TFPI-23 LC CDR2 | GNSNRPS |
| 35 | mAb-TFPI-23 LC CDR3 | QSYDSSLSGS GV |
| 36 | mAb-TFPI-23 VL CDR1, CDR2, CDR3 are underlined | QSVLTQPPSV SGAPGQRVTI SCTGSSSNIG AGYDVHWYQQ LPGTAPKLLI YGNSNRPSGV PDRFSGSKSG TSASLAITGL QAEDEADYYC QSYDSSLSGS GVFGGGTKLT VLG |
| 37 | mAb-TFPI-23 LC CDR1, 2, 3 are underlined. Variable sequence in italics | *QSVLTQPPSV SGAPGQRVTI SCTGSSSNIG AGYDVHWYQQ LPGTAPKLLI YGNSNRPSGV PDRFSGSKSG TSASLAITGL QAEDEADYYC QSYDSSLSGS GVFGGGTKLT VL*GQPKAAPS VTLFPPSSEE LQANKATLVC LISDFYPGAV TVAWKADSSP VKAGVETTTP SKQSNNKYAA SSYLSLTPEQ WKSHRSYSCQ VTHEGSTVEK TVAPTECS |
| 38 | mAb-TFPI-23 HC CDR1 | GFTFSSYAMS |
| 39 | mAb-TFPI-23 HC CDR2 | AISGSGGSTY YADSVKG |
| 40 | mAb-TFPI-23 HC CDR3 | LGATSLSAFD I |
| 41 | mAb-TFPI-23 VH | QVQLVESGGG LVQPGGSLRL SCAASGFTFS SYAMSWVRQA PGKGLEWVSA ISGSGGSTYY ADSVKGRFTI SRDNSKNTLY LQMNSLRAED TAVYYCAILG ATSLSAFDIW GQGTMVTVSS |
| 42 | mAb-TFPI-23 HC CDR1, CDR2 and CDR3 underlined. Variable sequence in italics. Effector function mutations in bold. | *QVQLVESGGG LVQPGGSLRL SCAASGFTFS SYAMSWVRQA PGKGLEWVSA ISGSGGSTYY ADSVKGRFTI SRDNSKNTLY LQMNSLRAED TAVYYCAILG ATSLSAFDIW* GQGTMVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPE**AAGA** PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 43 | mAb-TFPI-24 LC CDR1 | SGSTSNIGTM YVH |
| 44 | mAb-TFPI-24 LC CDR2 | RNNHRPS |
| 45 | mAb-TFPI-24 LC CDR3 | LAWDDTLRAY V |
| 46 | mAb-TFPI-24 VL CDR1, CDR2, CDR3 are underlined | QSVLTQPPSV SGTPGQRVTI SCSGSTSNIG TMYVHWYQHV PGTAPKLLIY RNNHRPSGVP DRFSGSKSGT SGSLAISGLR SEDEADYYCL AWDDTLRAYV FGTGTKVTVL G |
| 47 | mAb-TFPI-24 LC CDR1, 2, 3 are underlined. Variable sequence in italics | *QSVLTQPPSV SGTPGQRVTI SCSGSTSNIG TMYVHWYQHV PGTAPKLLIY RNNHRPSGVP DRFSGSKSGT SGSLAISGLR SEDEADYYCL AWDDTLRAYV FGTGTKVTVL* GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |
| 48 | mAb-TFPI-24 HC CDR1 | GLTIDNYAMQ |
| 49 | mAb-TFPI-24 HC CDR2 | GISGNSRSIG YADSVKG |
| 50 | mAb-TFPI-24 HC CDR3 | FLHESDY |

TABLE 33-continued

SEQUENCES

| SEQ ID NO: | Description | Sequence |
|---|---|---|
| 51 | mAb-TFPI-24 VH CDR1, CDR2, CDR3 are underlined | EVQLVESGGG SVQPGRSLRL SCAVSGLTID NYAMQWVRQR<br>PGKGLEWVSG ISGNSRSIGY ADSVKGRLTI SRDNAKNSLY<br>LQIDSLRADD TALYYCAIFL HESDYWGQGT LVTVSS |
| 52 | mAb-TFPI-24 HC CDR1, CDR2 and CDR3 underlined. Variable sequence in italics. Effector function mutations in bold. | EVQLVESGGG SVQPGRSLRL SCAVSGLTID NYAMQWVRQR<br>PGKGLEWVSG ISGNSRSIGY ADSVKGRLTI SRDNAKNSLY<br>LQIDSLRADD TALYYCAIFL HESDYWGQGT LVTVSSASTK<br>GPSVFPLAPS SKSTSGGTAA LGCLVKDYFP EPVTVSWNSG<br>ALTSGVHTFP AVLQSSGLYS LSSVVTVPSS SLGTQTYICN<br>VNHKPSNTKV DKKVEPKSCD KTHTCPPCPA PE**AAGA**PSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN<br>QVSLTCLVKG FYPSDIAVEW ESNGQPENNY KTTPPVLDSD<br>GSFFLYSKLT VDKSRWQQGN VFSCSVMHEA LHNHYTQKSL<br>SLSPG |
| 53 | mAb-TFPI-26 LC CDR1 | TGSSSNLGAD YDVQ |
| 54 | mAb-TFPI-26 LC CDR2 | GNNNRPS |
| 55 | mAb-TFPI-26 LC CDR3 | QSYDRSLSGS MV |
| 56 | mAb-TFPI-26 VL CDR1, CDR2, CDR3 are underlined | QSVLTQPPSL SGAPGQRVTI SCTGSSSNLG ADYDVQWYQQ<br>LPGTAPKLLI FGNNNRPSGV PDRFSGSRSG TSASLAITGL<br>QAEDEANYYC QSYDRSLSGS MVFGGGTKLT VLG |
| 57 | mAb-TFPI-26 LC CDR1, 2, 3 are underlined. Variable sequence in italics | QSVLTQPPSL SGAPGQRVTI SCTGSSSNLG ADYDVQWYQQ<br>LPGTAPKLLI FGNNNRPSGV PDRFSGSRSG TSASLAITGL<br>QAEDEANYYC QSYDRSLSGS MVFGGGTKLT VLGQPKAAP<br>SVTLFPPSSE ELQANKATLV CLISDFYPGA VTVAWKADSS<br>PVKAGVETTT PSKQSNNKYA ASSYLSLTPE QWKSHRSYSC<br>QVTHEGSTVE KTVAPTECS |
| 58 | mAb-TFPI-26 HC CDR1 | GFTFSSYAMS |
| 59 | mAb-TFPI-26 HC CDR2 | AISGSGGSTY YADSVKG |
| 60 | mAb-TFPI-26 HC CDR3 | NGAAAAWDY |
| 61 | mAb-TFPI-26 VH CDR1, CDR2, CDR3 are underlined | EVQLVESGGG LVQPGGSLRL SCAASGFTFS SYAMSWVRQA<br>PGKGLEWVSA ISGSGGSTYY ADSVKGRFTI SRDNSKNTLY<br>LQMNSLRAED TAVYYCANNG AAAAWDYWGQ GTLVTVSS |
| 62 | mAb-TFPI-26 HC CDR1, CDR2 and CDR3 underlined. Variable sequence in italics. Effector function mutations in bold. | EVQLVESGGG LVQPGGSLRL SCAASGFTFS SYAMSWVRQA<br>PGKGLEWVSA ISGSGGSTYY ADSVKGRFTI SRDNSKNTLY<br>LQMNSLRAED TAVYYCANNG AAAAWDYWGQ GTLVTVSSAS<br>TKGPSVFPLA PSSKSTSGGT AALGCLVKDY FPEPVTVSWN<br>SGALTSGVHT FPAVLQSSGL YSLSSVVTVP SSSLGTQTYI<br>CNVNHKPSNT KVDKKVEPKS CDKTHTCPPC PAPE**AAGA**PS<br>VFLFPPKPKD TLMISRTPEV TCVVVDVSHE DPEVKFNWYV<br>DGVEVHNAKT KPREEQYNST YRVVSVLTVL HQDWLNGKEY<br>KCKVSNKALP APIEKTISKA KGQPREPQVY TLPPSREEMT<br>KNQVSLTCLV KGFYPSDIAV EWESNGQPEN NYKTTPPVLD<br>SDGSFFLYSK LTVDKSRWQQ GNVFSCSVMH EALHNHYTQK<br>SLSLSPG |
| 63 | mAb-TFPI-106 VH SEQ 26 with Q1E, V5L mutations in bold | **E**VQL**L**ESGGG LVQPGGSLRL SCAASGFTFS SYAMSWVRQA<br>PGKGLEWVSA ISGSGGSTYY ADSVKGRFTI SRDNSKNTLY<br>LQMNSLRAED TAVYYCAILG ATSLSAFDIW GQGTMVTVSS |
| 64 | mAb-TFPI-106 HC CDR1, CDR2 and CDR3 underlined. Variable sequence in italics. Q1E,V5L mutations in bold | **E**VQL**L**ESGGG LVQPGGSLRL SCAASGFTFS SYAMSWVRQA<br>PGKGLEWVSA ISGSGGSTYY ADSVKGRFTI SRDNSKNTLY<br>LQMNSLRAED TAVYYCAILG ATSLSAFDIW GQGTMVTVSS<br>ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVEP KSCDKTHTCP PCPAPE**AAGA**<br>PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPG |

TABLE 33-continued

SEQUENCES

| SEQ ID NO: | Description | Sequence |
|---|---|---|
| 65 | mAb-TFPI-107 VH SEQ 26 with Q1E, V5L, I94K mutations in bold | **E**VQL**L**ESGGG LVQPGGSLRL SCAASGFTFS SYAMSWVRQA PGKGLEWVSA ISGSGGSTYY ADSVKGRFTI SRDNSKNTLY LQMNSLRAED TAVYYCA**K**LG ATSLSAFDIW GQGTMVTVSS |
| 66 | mAb-TFPI-107 HC CDR1, CDR2 and CDR3 underlined. Variable sequence in italics. Q1E, V5L, I94K mutations in bold | ***E****VQL****L****ESGGG LVQPGGSLRL SCAASGFTFS SYAMSWVRQA PGKGLEWVSA ISGSGGSTYY ADSVKGRFTI SRDNSKNTLY LQMNSLRAED TAVYYCA****K****LG ATSLSAFDIW GQGTMVTVSS* ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPE**AAGA** PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 67 | mAb-TFPI-108 VH CDR1, CDR2, CDR3 are underlined. SEQ 38 with S11L, R40A, L67F, I82M, D82aN, D85E mutations in bold | EVQLVESGGG **L**VQPGRSLRL SCAVSGLTID NYAMQWVRQ**A** PGKGLEWVSG ISGNSRSIGY ADSVKGR**F**TI SRDNAKNSLY LQ**MN**SLRA**E**D TALYYCAIFL HESDYWGQGT LVTVSS |
| 68 | mAb-TFPI-108 HC CDR1, CDR2 and CDR3 underlined. Variable sequence in italics. S11L, R40A, L67F, I82M, D82aN, D85E mutations in bold | *EVQLVESGGG* **L***VQPGRSLRL SCAVSGLTID NYAMQWVRQ****A****A PGKGLEWVSG ISGNSRSIGY ADSVKGR****F****TI SRDNAKNSLY LQ****MN****SLRA****E****D TALYYCAIFL HESDYWGQGT LVTVSS*ASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PEAAGAPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPG |
| 69 | mAb-TFPI-109 VH CDR1, CDR2, CDR3 are underlined. SEQ 38 with S11L, V24A, R40A, I82M, D82aN, D85E mutations in bold | EVQLVESGGG **L**VQPGRSLRL SCA**A**SGLTID NYAMQWVRQ**A** PGKGLEWVSG ISGNSRSIGY ADSVKGRLTI SRDNAKNSLY LQ**MN**SLRA**E**D TALYYCAIFL HESDYWGQGT LVTVSS |
| 70 | mAb-TFPI-109 HC CDR1, CDR2 and CDR3 underlined. Variable sequence in italics. S11L, V24A, R40A, I82M, D82aN, D85E mutations in bold | *EVQLVESGGG* **L***VQPGRSLRL SCA****A****SGLTID NYAMQWVRQ****A*** *PGKGLEWVSG ISGNSRSIGY ADSVKGRLTI SRDNAKNSLY LQ****MN****SLRA****E****D TALYYCAIFL HESDYWGQGT LVTVSS*ASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PEAAGAPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPG |
| 71 | mAb-TFPI-110 VL CDR1, CDR2, CDR3 are underlined. SEQ 32 with V10A, V39L, G71A mutations in bold. | QSVLTQPPS**A** SGTPGQRVTI SCSGSTSNIG TMYVHWYQH**L** PGTAPKLLIY RNNHRPSGVP DRFSGSKSGT S**A**SLAISGLR SEDEADYYCL AWDDTLRAYV FGTGTKVTVL G |
| 72 | mAb-TFPI-110 LC CDR1, 2, 3 are underlined. Variable sequence in italics. V10A, V39L, G71A mutations in bold. | *QSVLTQPPS****A*** *SGTPGQRVTI SCSGSTSNIG TMYVHWYQH***L** *PGTAPKLLIY RNNHRPSGVP DRFSGSKSGT S****A****SLAISGLR SEDEADYYCL AWDDTLRAYV FGTGTKVTVL* GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |

TABLE 33-continued

SEQUENCES

| SEQ ID NO: | Description | Sequence |
|---|---|---|
| 73 | mAb-TFPI-111 VL CDR1, CDR2, CDR3 are underlined. SEQ 32 with V10A, H38Q, V39L mutations in bold. | QSVLTQPPSA SGTPGQRVTI SC<u>SGSTSNIG TMYVHWYQ**QL**</u> PGTAPKLLIY <u>RNNHRPS</u>GVP DRFSGSKSGT SGSLAISGLR SEDEADYYC<u>L AWDDTLRAYV</u> FGTGTKVTVL G |
| 74 | mAb-TFPI-111 LC CDR1, 2, 3 are underlined. Variable sequence in italics. V10A, H38Q, V39L mutations in bold. | *QSVLTQPPS**A** SGTPGQRVTI SC<u>SGSTSNIG TMYVHWYQ**QL**</u> PGTAPKLLIY <u>RNNHRPS</u>GVP DRFSGSKSGT SGSLAISGLR SEDEADYYC<u>L AWDDTLRAYV</u> FGTGTKVTVL* GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |
| 75 | mAb-TFPI-112 VL CDR1, CDR2, CDR3 are underlined. SEQ 32 with V10A, V39L mutations in bold. | QSVLTQPPSA SGTPGQRVTI SC<u>SGSTSNIG TMYVHWYQH**L**</u> PGTAPKLLIY <u>RNNHRPS</u>GVP DRFSGSKSGT SGSLAISGLR SEDEADYYC<u>L AWDDTLRAYV</u> FGTGTKVTVL G |
| 76 | mAb-TFPI-112 LC CDR1, 2, 3 are underlined. Variable sequence in italics. V10A, V39L mutations in bold. | *QSVLTQPPS**A** SGTPGQRVTI SC<u>SGSTSNIG TMYVHWYQH**L**</u> PGTAPKLLIY <u>RNNHRPS</u>GVP DRFSGSKSGT SGSLAISGLR SEDEADYYC<u>L AWDDTLRAYV</u> FGTGTKVTVL* GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |
| 77 | mAb-TFPI-113 VL CDR1, CDR2, CDR3 are underlined. SEQ 32 with V10A, H38Q, V39L, G71A mutations in bold. | QSVLTQPPSA SGTPGQRVTI SC<u>SGSTSNIG TMYVHWYQ**QL**</u> PGTAPKLLIY <u>RNNHRPS</u>GVP DRFSGSKSGT S**A**SLAISGLR SEDEADYYC<u>L AWDDTLRAYV</u> FGTGTKVTVL G |
| 78 | mAb-TFPI-113 LC CDR1, 2, 3 are underlined. Variable sequence in italics. V11A, H38Q, V39L, G71A mutations in bold. | *QSVLTQPPS**A** SGTPGQRVTI SC<u>SGSTSNIG TMYVHWYQ**QL**</u> PGTAPKLLIY <u>RNNHRPS</u>GVP DRFSGSKSGT S**A**SLAISGLR SEDEADYYC<u>L AWDDTLRAYV</u> FGTGTKVTVL* GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |
| 79 | mAb-TFPI-114 HC VH CDR1, CDR2, CDR3 are underlined. SEQ 38 with S11L, R40A, I82M, D82AN, D85E mutations in bold | EVQLVESGGG **L**VQPGRSLRL SCAVS<u>GLTID NYAMQ</u>WVRQ**A** PGKGLEWVSG <u>ISGNSRSIGY ADSVKG</u>RLTI SRDNAKNSLY LQ**MN**SLRA**E**D TALYYCAI<u>FL HESDYW</u>GQGT LVTVSS |
| 80 | mAb-TFPI-114 HC CDR1, CDR2 and CDR3 underlined. Variable sequence in italics. S11L, R40A, I82M, D82AN, D85E mutations in bold | *EVQLVESGGG **L**VQPGRSLRL SCAVS<u>GLTID NYAMQ</u>WVRQ**A** PGKGLEWVSG <u>ISGNSRSIGY ADSVKG</u>RLTI SRDNAKNSLY LQ**MN**SLRA**E**D TALYYCAI<u>FL HESDYW</u>GQGT LVTVSS*ASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PEAAGAPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPG |
| 81 | mouse 4d8.b1 VL CDR1 | KASQDVHTAV A |
| 82 | mouse 4d8.b1 VL CDR2 | WASTRHT |
| 83 | mouse 4d8.b1 VL CDR3 | QQHYTTPYT |
| 84 | mouse 4d8.b1 VL CDR1, CDR2, CDR3 underlined | DIVMTQSHKF MSTSVGDRVS ITC<u>KASQDVH TAVA</u>WYQQKP GQSPRLLIY<u>W ASTRHT</u>GVPD RFTGCGSGTD YTLTISSVQA EDLALYYC<u>QQ HYTTPYT</u>FGG GTKLEMK |

TABLE 33-continued

SEQUENCES

| SEQ ID NO: | Description | Sequence |
|---|---|---|
| 85 | Mouse Ig kappa constant | ADAAPTVSIF PPSSEQLTSG GASVVCFLNN FYPKDINVKW<br>KIDGSERQNG VLNSWTDQDS KDSTYSMSST LTLTKDEYER<br>HNSYTCEATH KTSTSPIVKS FNRNEC |
| 86 | mouse 4d8.b1 LC CDR1, CDR2, CDR3 underlined Variable sequence in italics | DIVMTQSHKF MSTSVGDRVS ITCKASQDVH TAVAWYQQKP<br>GQSPRLLIYW ASTRHTGVPD RFTGCGSGTD YTLTISSVQA<br>EDLALYYCQQ HYTTPYTFGG GTKLEMKADA APTVSIFPPS<br>SEQLTSGGAS VVCFLNNFYP KDINVKWKID GSERQNGVLN<br>SWTDQDSKDS TYSMSSTLTL TKDEYERHNS YTCEATHKTS<br>TSPIVKSFNR NEC |
| 87 | mouse 4d8.b1 VH CDR1 | GYTFTDYNLD |
| 88 | mouse 4d8.b1 VH CDR2 | DINPINGATL YNQKFKG |
| 89 | mouse 4d8.b1 VH CDR3 | YYGDYDAMDY |
| 90 | mouse 4d8.b1 VH CDR1, CDR2, CDR3 underlined | EVLLQQSGPE LVKPGASVKI PCKASGYTFT DYNLDWVKQS<br>HGKSLEWIGD INPINGATLY NQKFKGKATL TVDQSSSTAY<br>MELRSLTSED TAVYYCSIYY GDYDAMDYWG QGASVTVSS |
| 91 | Mouse Igh constant heavy | AKTTPPSVYP LAPGSAAQTN SMVTLGCLVK GYFPEPVTVT<br>WNSGSLSSGV HTFPAVLQSD LYTLSSSVTV PSSTWPSETV<br>TCNVAHPASS TKVDKKIVPR DCGCKPCICT VPEVSSVFIF<br>PPKPKDVLTI TLTPKVTCVV VDISKDDPEV QFSWFVDDVE<br>VHTAQTQPRE EQFNSTFRSV SELPIMHQDW LNGKEFKCRV<br>NSAAFPAPIE KTISKTKGRP KAPQVYTIPP PKEQMAKDKV<br>SLTCMITDFF PEDITVEWQW NGQPAENYKN TQPIMDTDGS<br>YFVYSKLNVQ KSNWEAGNTF TCSVLHEGLH NHHTEKSLSH<br>SPGK |
| 92 | mouse 4d8.b1 HC CDR1, CDR2, CDR3 underlined Variable sequence in italics | EVLLQQSGPE LVKPGASVKI PCKASGYTFT DYNLDWVKQS<br>HGKSLEWIGD INPINGATLY NQKFKGKATL TVDQSSSTAY<br>MELRSLTSED TAVYYCSIYY GDYDAMDYWG QGASVTVSSA<br>KTTPPSVYPL APGSAAQTNS MVTLGCLVKG YFPEPVTVTW<br>NSGSLSSGVH TFPAVLQSDL YTLSSSVTVP SSTWPSETVT<br>CNVAHPASST KVDKKIVPRD CGCKPCICTV PEVSSVFIFP<br>PKPKDVLTIT LTPKVTCVVV DISKDDPEVQ FSWFVDDVEV<br>HTAQTQPREE QFNSTFRSVS ELPIMHQDWL NGKEFKCRVN<br>SAAFPAPIEK TISKTKGRPK APQVYTIPPP KEQMAKDKVS<br>LTCMITDFFP EDITVEWQWN GQPAENYKNT QPIMDTDGSY<br>FVYSKLNVQK SNWEAGNTFT CSVLHEGLHN HHTEKSLSHS<br>PGK |
| 93 | Mu-hu 4d8 chimera LC CDR1, 2, 3 are underlined. Variable sequence in italics | DIVMTQSHKF MSTSVGDRVS ITCKASQDVH TAVAWYQQKP<br>GQSPRLLIYW ASTRHTGVPD RFTGCGSGTD YTLTISSVQA<br>EDLALYYCQQ HYTTPYTFGG GTKLEMKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |
| 94 | Mu-hu 4d8 chimera HC CDR1, 2, 3 are underlined. Variable sequence in italics | EVLLQQSGPE LVKPGASVKI PCKASGYTFT DYNLDWVKQS<br>HGKSLEWIGD INPINGATLY NQKFKGKATL TVDQSSSTAY<br>MELRSLTSED TAVYYCSIYY GDYDAMDYWG QGASVTVSSA<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPEAAGAP<br>SVFLFPPKPK DTLMISRTPE VTCVVVDVSH EDPEVKFNWY<br>VDGVEVHNAK TKPREEQYNS TYRVVSVLTV LHQDWLNGKE<br>YKCKVSNKAL PAPIEKTISK AKGQPREPQV YTLPPSREEM<br>TKNQVSLTCL VKGFYPSDIA VEWESNGQPE NNYKTTPPVL<br>DSDGSFFLYS KLTVDKSRWQ QGNVFSCSVM HEALHNHYTQ<br>KSLSLSPG |
| 95 | 4d8-VH1.0 VH CDR1, CDR2, CDR3 underlined | EVQLVESGGG LVQPGGSLRL SCAASGYTFT DYNLDWVRQA<br>PGKGLEWVAD INPINGATLY NQKFKGRFTI SRDNAKNSLY<br>LQMNSLRAED TAVYYCARYY GDYDAMDYWG QGTLVTVSS |
| 96 | 4d8-VH1.0 HC CDR1, CDR2, CDR3 underlined Variable sequence in italics | EVQLVESGGG LVQPGGSLRL SCAASGYTFT DYNLDWVRQA<br>PGKGLEWVAD INPINGATLY NQKFKGRFTI SRDNAKNSLY<br>LQMNSLRAED TAVYYCARYY GDYDAMDYWG QGTLVTVSSA<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPEAAGAP<br>SVFLFPPKPK DTLMISRTPE VTCVVVDVSH EDPEVKFNWY<br>VDGVEVHNAK TKPREEQYNS TYRVVSVLTV LHQDWLNGKE |

TABLE 33-continued

SEQUENCES

| SEQ ID NO: | Description | Sequence |
|---|---|---|
| | | YKCKVSNKAL PAPIEKTISK AKGQPREPQV YTLPPSREEM<br>TKNQVSLTCL VKGFYPSDIA VEWESNGQPE NNYKTTPPVL<br>DSDGSFFLYS KLTVDKSRWQ QGNVFSCSVM HEALHNHYTQ<br>KSLSLSPG |
| 97 | 4d8-VH1.1 VH<br>CDR1, CDR2, CDR3<br>underlined<br>Back mutations A49G,<br>F67A, R71V, N73Q,<br>L78A are in bold | EVQLVESGGG LVQPGGSLRL SCAASGYTFT DYNLDWVRQA<br>PGKGLEWV**G**D INPINGATLY NQKFKGR**A**TI S**V**D**Q**AKNS**A**Y<br>LQMNSLRAED TAVYYCARYY GDYDAMDYWG QGTLVTVSS |
| 98 | 4d8-VH1.1 HC<br>CDR1, CDR2, CDR3<br>underlined<br>Variable sequence in<br>italics<br>Back mutations A49G,<br>F67A, R71V, N73Q,<br>L78A are in bold | *EVQLVESGGG LVQPGGSLRL SCAASGYTFT DYNLDWVRQA*<br>*PGKGLEWV**G**D INPINGATLY NQKFKGR**A**TI S**V**D**Q**AKNS**A**Y*<br>*LQMNSLRAED TAVYYCARYY GDYDAMDYWG QGTLVTVSS*A<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPEAAGAP<br>SVFLFPPKPK DTLMISRTPE VTCVVVDVSH EDPEVKFNWY<br>VDGVEVHNAK TKPREEQYNS TYRVVSVLTV LHQDWLNGKE<br>YKCKVSNKAL PAPIEKTISK AKGQPREPQV YTLPPSREEM<br>TKNQVSLTCL VKGFYPSDIA VEWESNGQPE NNYKTTPPVL<br>DSDGSFFLYS KLTVDKSRWQ QGNVFSCSVM HEALHNHYTQ<br>KSLSLSPG |
| 99 | 4d8-VH1.2 VH<br>CDR1, CDR2, CDR3<br>underlined<br>Back mutation A49G<br>is in bold | EVQLVESGGG LVQPGGSLRL SCAASGYTFT DYNLDWVRQA<br>PGKGLEWV**G**D INPINGATLY NQKFKGRFTI SRDNAKNSLY<br>LQMNSLRAED TAVYYCARYY GDYDAMDYWG QGTLVTVSS |
| 100 | 4d8-VH1.2 HC<br>CDR1, CDR2, CDR3<br>underlined<br>Variable sequence in<br>italics<br>Back mutation A49G<br>is in bold | *EVQLVESGGG LVQPGGSLRL SCAASGYTFT DYNLDWVRQA*<br>*PGKGLEWV**G**D INPINGATLY NQKFKGRFTI SRDNAKNSLY*<br>*LQMNSLRAED TAVYYCARYY GDYDAMDYWG QGTLVTVSS*A<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPEAAGAP<br>SVFLFPPKPK DTLMISRTPE VTCVVVDVSH EDPEVKFNWY<br>VDGVEVHNAK TKPREEQYNS TYRVVSVLTV LHQDWLNGKE<br>YKCKVSNKAL PAPIEKTISK AKGQPREPQV YTLPPSREEM<br>TKNQVSLTCL VKGFYPSDIA VEWESNGQPE NNYKTTPPVL<br>DSDGSFFLYS KLTVDKSRWQ QGNVFSCSVM HEALHNHYTQ<br>KSLSLSPG |
| 101 | 4d8-VH1.3 VH<br>CDR1, CDR2, CDR3<br>underlined<br>Back mutation F67A<br>is in bold | EVQLVESGGG LVQPGGSLRL SCAASGYTFT DYNLDWVRQA<br>PGKGLEWVAD INPINGATLY NQKFKGR**A**TI SRDNAKNSLY<br>LQMNSLRAED TAVYYCARYY GDYDAMDYWG QGTLVTVSS |
| 102 | 4d8-VH1.3 HC<br>CDR1, CDR2, CDR3<br>underlined<br>Variable sequence in<br>italics<br>Back mutation F67A<br>is in bold | *EVQLVESGGG LVQPGGSLRL SCAASGYTFT DYNLDWVRQA*<br>*PGKGLEWVAD INPINGATLY NQKFKGR**A**TI SRDNAKNSLY*<br>*LQMNSLRAED TAVYYCARYY GDYDAMDYWG QGTLVTVSS*A<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPEAAGAP<br>SVFLFPPKPK DTLMISRTPE VTCVVVDVSH EDPEVKFNWY<br>VDGVEVHNAK TKPREEQYNS TYRVVSVLTV LHQDWLNGKE<br>YKCKVSNKAL PAPIEKTISK AKGQPREPQV YTLPPSREEM<br>TKNQVSLTCL VKGFYPSDIA VEWESNGQPE NNYKTTPPVL<br>DSDGSFFLYS KLTVDKSRWQ QGNVFSCSVM HEALHNHYTQ<br>KSLSLSPG |
| 103 | 4d8-VH1.4 VH<br>CDR1, CDR2, CDR3<br>underlined<br>Back mutation N73Q<br>is in bold | EVQLVESGGG LVQPGGSLRL SCAASGYTFT DYNLDWVRQA<br>PGKGLEWVAD INPINGATLY NQKFKGRFTI SRD**Q**AKNSLY<br>LQMNSLRAED TAVYYCARYY GDYDAMDYWG QGTLVTVSS |
| 104 | 4d8-VH1.4 HC<br>CDR1, CDR2, CDR3<br>underlined<br>Variable sequence in<br>italics<br>Back mutation N73Q<br>is in bold | *EVQLVESGGG LVQPGGSLRL SCAASGYTFT DYNLDWVRQA*<br>*PGKGLEWVAD INPINGATLY NQKFKGRFTI SRD**Q**AKNSLY*<br>*LQMNSLRAED TAVYYCARYY GDYDAMDYWG QGTLVTVSS*A<br>STKGPSVFPL APSSKSTSGG TAALGCLVKD YFPEPVTVSW<br>NSGALTSGVH TFPAVLQSSG LYSLSSVVTV PSSSLGTQTY<br>ICNVNHKPSN TKVDKKVEPK SCDKTHTCPP CPAPEAAGAP<br>SVFLFPPKPK DTLMISRTPE VTCVVVDVSH EDPEVKFNWY |

TABLE 33-continued

| SEQ ID NO: | Description | Sequence |
|---|---|---|
| | | VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPG |
| 105 | 4d8-VH1.5 VH CDR1, CDR2, CDR3 underlined Back mutation L78A is in bold | EVQLVESGGG LVQPGGSLRL SCAASGYTFT DYNLDWVRQA PGKGLEWVAD INPINGATLY NQKFKGRFTI SRDNAKNS**A**Y LQMNSLRAED TAVYYCARYY GDYDAMDYWG QGTLVTVSS |
| 106 | 4d8-VH1.5 HC CDR1, CDR2, CDR3 underlined Variable sequence in italics Back mutation L78A is in bold | *EVQLVESGGG LVQPGGSLRL SCAASGYTFT DYNLDWVRQA PGKGLEWVAD INPINGATLY NQKFKGRFTI SRDNAKNS**A**Y LQMNSLRAED TAVYYCARYY GDYDAMDYWG QGTLVTVSS*A STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL aAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPG |
| 107 | 4d8-VH1.6 VH CDR1, CDR2, CDR3 underlined Back mutations A49G, F67A, R71V, N73Q, L78A, A93S, R94I are in bold | EVQLVESGGG LVQPGGSLRL SCAASGYTFT DYNLDWVRQA PGKGLEWV**G**D INPINGATLY NQKFKGR**A**TI S**V**D**Q**AKNS**A**Y LQMNSLRAED TAVYYC**SI**YY GDYDAMDYWG QGTLVTVSSA |
| 108 | 4d8-VH1.6 HC CDR1, CDR2, CDR3 underlined Variable sequence in italics Back mutations A49G, F67A, R71V, N73Q, L78A, A93S, R94I are in bold | *EVQLVESGGG LVQPGGSLRL SCAASGYTFT DYNLDWVRQA PGKGLEWV**G**D INPINGATLY NQKFKGR**A**TI S**V**D**Q**AKNS**A**Y LQMNSLRAED TAVYYC**SI**YY GDYDAMDYWG QGTLVTVSS*A STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPG |
| 109 | 4D8-VK1.0 VL CDR1, CDR2, CDR3 underlined | DIQMTQSPSS LSASVGDRVT ITCKASQDVH TAVAWYQQKP GKAPKLLIYW ASTRHTGVPS RFSGSGSGTD FTLTISSLQP EDFATYYCQQ HYTTPYTFGQ GTKLEIK |
| 110 | 4D8-VK1.0 LC CDR1, CDR2, CDR3 underlined VL in italics | *DIQMTQSPSS LSASVGDRVT ITCKASQDVH TAVAWYQQKP GKAPKLLIYW ASTRHTGVPS RFSGSGSGTD FTLTISSLQP EDFATYYCQQ HYTTPYTFGQ GTKLEIK*RTV AAPSVFIFPP SDEQLKSGTA SVVCLLNNFY PREAKVQWKV DNALQSGNSQ ESVTEQDSKD STYSLSSTLT LSKADYEKHKV YACEVTHQGL SSPVTKSFNR GEC |
| 111 | 4D8-VK1.1 VL CDR1, CDR2, CDR3 underlined Back mutation F71Y is in bold | DIQMTQSPSS LSASVGDRVT ITCKASQDVH TAVAWYQQKP GKAPKLLIYW ASTRHTGVPS RFSGSGSGTD **Y**TLTISSLQP EDFATYYCQQ HYTTPYTFGQ GTKLEIK |
| 112 | 4D8-VK1.1 LC CDR1, CDR2, CDR3 underlined VL in italics | *DIQMTQSPSS LSASVGDRVT ITCKASQDVH TAVAWYQQKP GKAPKLLIYW ASTRHTGVPS RFSGSGSGTD YTLTISSLQP EDFATYYCQQ HYTTPYTFGQ GTKLEIK*RTV AAPSVFIFPP SDEQLKSGTA SVVCLLNNFY PREAKVQWKV DNALQSGNSQ ESVTEQDSKD STYSLSSTLT LSKADYEKHKV YACEVTHQGL SSPVTKSFNR GEC |
| 113 | mouse 6b7.c5 VL CDR1 | KASQDVITAV A |
| 114 | mouse 6b7.c5 VL CDR2 | WASTRHT |
| 115 | mouse 6b7.c5 VL CDR3 | QQHYSTPYT |

TABLE 33-continued

SEQUENCES

| SEQ ID NO: | Description | Sequence |
|---|---|---|
| 116 | mouse 6b7.c5 VL CDR1, CDR2, CDR3 underlined | DIVMTQSHKF MSTSVGDRVS ITCKASQDVI TAVAWYQQKP GQSPKLLIYW ASTRHTGVPV RFTGSGSGTD YTLTIISVQA EDLALYYCQQ HYSTPYTFGG GTKLEIK |
| 117 | mouse 6b7.c5 LC CDR1, CDR2, CDR3 underlined Variable sequence in italics | DIVMTQSHKF MSTSVGDRVS ITCKASQDVI TAVAWYQQKP GQSPKLLIYW ASTRHTGVPV RFTGSGSGTD YTLTIISVQA EDLALYYCQQ HYSTPYTFGG GTKLEIKADA APTVSIFPPS SEQLTSGGAS VVCFLNNFYP KDINVKWKID GSERQNGVLN SWTDQDSKDS TYSMSSTLTL TKDEYERHNS YTCEATHKTS TSPIVKSFNR NEC |
| 118 | mouse 6b7.c5 VH CDR1 | GYTFTDYTMD |
| 119 | mouse 6b7.c5 VH CDR2 | DINPSNGGSI YNRKFKG |
| 120 | mouse 6b7.c5 VH CDR3 | MHYNYDGFPY |
| 121 | mouse 6b7.c5 VH CDR1, CDR2, CDR3 underlined | EVLLQQSGPE LVKPGSSVKI PCKASGYTFT DYTMDWVKQS HGKSLEWIGD INPSNGGSIY NRKFKGKATL TVDKSSSTAY MELRSLTSED TAVYYCARMH YNYDGFPYWG QGTLVTVSA |
| 122 | mouse 6b7.c5 HC CDR1, CDR2, CDR3 underlined Variable sequence in italics | EVLLQQSGPE LVKPGSSVKI PCKASGYTFT DYTMDWVKQS HGKSLEWIGD INPSNGGSIY NRKFKGRATL TVDKSSSTAY MELRSLTSED TAVYYCARMH YNYDGFPYWG QGTLVTVSAA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCDKTHTCPP CPAPEAAGAP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPG |
| 123 | mouse 7A4.D9 VL CDR1 | RASKSVSTSG YTYMH |
| 124 | mouse 7A4.D9 VL CDR2 | LASNLES |
| 125 | mouse 7A4.D9 VL CDR3 | QHIRELPFT |
| 126 | mouse 7A4.D9 VL CDR1, CDR2, CDR3 underlined | DIVLTQSPAS LAVSLGQRAT ISCRASKSVS TSGYTYMHWY QQKPGQPPKL LIYLASNLES GVPARFSGSG SGTDFTLNIH PVEEEDAAAY YCQHIRELPF TFGSGTKLEI K |
| 127 | mouse 7A4.D9 LC CDR1, CDR2, CDR3 underlined Variable sequence in italics | DIVLTQSPAS LAVSLGQRAT ISCRASKSVS TSGYTYMHWY QQKPGQPPKL LIYLASNLES GVPARFSGSG SGTDFTLNIH PVEEEDAAAY YCQHIRELPF TFGSGTKLEI KADAAPTVSI FPPSSEQLTS GGASVVCFLN NFYPKDINVK WKIDGSERQN GVLNSWTDQD SKDSTYSMSS TLTLTKDEYE RHNSYTCEAT HKTSTSPIVK SFNRNEC |
| 128 | mouse 7A4.D9 VH CDR1 | GYTFTSYVMH |
| 129 | mouse 7A4.D9 VH CDR2 | YLNPYNDGTK YNEKFKG |
| 130 | mouse 7A4.D9 VH CDR3 | TLLYAMDY |
| 131 | mouse 7A4.D9 VH CDR1, CDR2, CDR3 underlined | EVQLQQSGPE LVKPGASVKM SCKASGYTFT SYVMHWVKQK PGQGLEWIGY LNPYNDGTKY NEKFKGKASL ISDKSSSTVY MELSSLTSED SAVYYCATTL LYAMDYWGQG SSVTVSS |
| 132 | mouse 7A4.D9 HC CDR1, CDR2, CDR3 underlined Variable sequence in italics | EVQLQQSGPE LVKPGASVKM SCKASGYTFT SYVMHWVKQK PGQGLEWIGY LNPYNDGTKY NEKFKGKASL ISDKSSSTVY MELSSLTSED SAVYYCATTL LYAMDYWGQG SSVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEM |
| 133 | 2A8 VL CDR1 | SGDNLRNYYA H |
| 134 | 2A8 VL CDR2 | YDNNRPS |
| 135 | 2A8 VL CDR3 | QSWDDGVPV |

TABLE 33-continued

SEQUENCES

| SEQ ID NO: | Description | Sequence |
|---|---|---|
| 136 | 2A8 VL CDR1, CDR2, CDR3 underlined | DIELTQPPSV SVAPGQTARI SCSGDNLRNY YAHWYQQKPG QAPVVVIYYD NNRPSGIPER FSGSNSGNTA TLTISGTQAE DEADYYCQSW DDGVPVFGGG TKLTVLG |
| 137 | 2A8 LC CDR1, CDR2, CDR3 underlined Variable sequence in italics | DIELTQPPSV SVAPGQTARI SCSGDNLRNY YAHWYQQKPG QAPVVVIYYD NNRPSGIPER FSGSNSGNTA TLTISGTQAE DEADYYCQSW DDGVPVFGGG TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE CS |
| 138 | 2A8 VH CDR1 | GFTFRSYGMS |
| 139 | 2A8 VH CDR2 | SIRGSSSSTY YADSVKG |
| 140 | 2A8 VH CDR3 | KYRYWFDY |
| 141 | 2A8 VH CDR1, CDR2, CDR3 underlined | QVQLVESGGG LVQPGGSLRL SCAASGFTFR SYGMSWVRQA PGKGLEWVSS IRGSSSSTYY ADSVKGRFTI SRDNSKNTLY LQMNSLRAED TAVYYCARKY RYWFDYWGQG TLVTVSS |
| 142 | 2A8 HC CDR1, CDR2, CDR3 underlined Variable sequence in italics | QVQLVESGGG LVQPGGSLRL SCAASGFTFR SYGMSWVRQA PGKGLEWVSS IRGSSSSTYY ADSVKGRFTI SRDNSKNTLY LQMNSLRAED TAVYYCARKY RYWFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 143 | 2A8-200 VL CDR1 | SGDNLRNYYA H |
| 144 | 2A8-200 VL CDR2 | YDVNRPS |
| 145 | 2A8-200 VL CDR3 | QSWWDGVPV |
| 146 | 2A8-200 VL CDR1, CDR2, CDR3 underlined | DIELTQPPSV SVAPGQTARI SCSGDNLRNY YAHWYQQKPG QAPVVVIFYD VNRPSGIPER FSGSNSGNTA TLTISGTQAE DEADYYCQSW WDGVPVFGGG TKLTVLG |
| 147 | 2A8-200 LC CDR1, CDR2, CDR3 underlined Variable sequence in italics | DIELTQPPSV SVAPGQTARI SCSGDNLRNY YAHWYQQKPG QAPVVVIFYD VNRPSGIPER FSGSNSGNTA TLTISGTQAE DEADYYCQSW WDGVPVFGGG TKLTVLGQPK AAPSVTLFPP SSEELQANKA TLVCLISDFY PGAVTVAWKA DSSPVKAGVE TTTPSKQSNN KYAASSYLSL TPEQWKSHRS YSCQVTHEGS TVEKTVAPTE CS |
| 148 | 2A8-200 VH CDR1 | GFTERSYGMD |
| 149 | 2A8-200 VH CDR2 | SIRGSRSSTY YADSVKG |
| 150 | 2A8-200 VH CDR3 | LYRYWFDY |
| 151 | 2A8-200 VH CDR1, CDR2, CDR3 underlined | QVQLVESGGG LVQPGGSLRL SCAASGFTFR SYGMDWVRQA PGKGLEWVSS IRGSRSSTYY ADSVKGRFTI SRDNSKNTLY LQMNSLRAED TAVYYCARLY RYWFDYWGQG TLVTVSS |
| 152 | 2A8-200 HC CDR1, CDR2, CDR3 underlined Variable sequence in italics | QVQLVESGGG LVQPGGSLRL SCAASGFTFR SYGMDWVRQA PGKGLEWVSS IRGSRSSTYY ADSVKGRFTI SRDNSKNTLY LQMNSLRAED TAVYYCARLY RYWFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 153 | 3F18 VL CDR1 | SGDNLRNYYA H |

TABLE 33-continued

| SEQUENCES | | |
|---|---|---|
| SEQ ID NO: | Description | Sequence |
| 154 | 3F18 VL CDR2 | YDNNRPS |
| 155 | 3F18 VL CDR3 | QSWDDGVPV |
| 156 | 3F18 VL<br>CDR1, CDR2, CDR3<br>underlined | DIELTQPPSV SVAPGQTARI SCSGDNLRNY YAHWYQQKPG<br>QAPVVVIYYD NNRPSGIPER FSGSNSGNTA TLTISGTQAE<br>DEADYYCQSW DDGVPVFGGG TKLTVLG |
| 157 | Mouse Ig lamda CL | QPKAAPSVT LFPPSSEELQ ANKATLVCLI SDFYPGAVTV<br>AWKADSSPVK AGVETTTPSK QSNNKYAASS YLSLTPEQWK<br>SHRSYSCQVT HEGSTVEKTV APTECS |
| 158 | 3F18 LC<br>CDR1, CDR2, CDR3<br>underlined<br>Variable sequence in<br>italics | *DIELTQPPSV SVAPGQTARI SCSGDNLRNY YAHWYQQKPG*<br>*QAPVVVIYYD NNRPSGIPER FSGSNSGNTA TLTISGTQAE*<br>*DEADYYCQSW DDGVPVFGGG* TKLTVLGQPK AAPSVTLFPP<br>SSEELQANKA TLVCLISDFY PGAVTVAWKA DSSPVKAGVE<br>TTTPSKQSNN KYAASSYLSL TPEQWKSHRS YSCQVTHEGS<br>TVEKTVAPTE CS |
| 159 | 3F18 VH CDR1 | GFTFSNYALS |
| 160 | 3F18 VH CDR2 | SISSGGATYY PDSVEG |
| 161 | 3F18 VH CDR3 | GAYGSDYFDY |
| 162 | 3F18 VH<br>CDR1, CDR2, CDR3<br>underlined | EVKLVESGGG LVKPGGSLRL SCAASGFTFS NYALSWVRQT<br>PDKRLEWVAS ISSGGATYYP DSVEGRFTIS RDNVRNILYL<br>QMSSLQSEDT AMYYCTRGAY GSDYFDYWGQ GTTLTVSS |
| 163 | 3F18 HC<br>CDR1, CDR2, CDR3<br>underlined<br>Variable sequence in<br>italics | *EVKLVESGGG LVKPGGSLRL SCAASGFTFS NYALSWVRQT*<br>*PDKRLEWVAS ISSGGATYYP DSVEGRFTIS RDNVRNILYL*<br>*QMSSLQSEDT AMYYCTRGAY GSDYFDYWGQ GTTLTVSS*AK<br>TTPPSVYPLA PGSAAQTNSM VTLGCLVKGY FPEPVTVTWN<br>SGSLSSGVHT FPAVLQSDLY TLSSSVTVPS STWPSETVTC<br>NVAHPASSTK VDKKIVPRDC GCKPCICTVP EVSSVFIFPP<br>KPKDVLTITL TPKVTCVVVD ISKDDPEVQF SWFVDDVEVH<br>TAQTQPREEQ FNSTFRSVSE LPIMHQDWLN GKEFKCRVNS<br>AAFPAPIEKT ISKTKGRPKA PQVYTIPPPK EQMAKDKVSL<br>TCMITDFFPE DITVEWQWNG QPAENYKNTQ PIMDTDGSYF<br>VYSKLNVQKS NWEAGNTFTC SVLHEGLHNH HTEKSLSHSP G |
| 164 | hz4F36 VL CDR1 | KSSQSLLESD GKTYLN |
| 165 | hz4F36 VL CDR2 | LVSILDS |
| 166 | hz4F36 VL CDR3 | LQATHFPQT |
| 167 | hz4F36 VL<br>CDR1, CDR2, CDR3<br>underlined | DIVMTQTPLS LSVTPGQPAS ISCKSSQSLL ESDGKTYLNW<br>YLQKPGQSPQ LLIYLVSILD SGVPDRFSGS GSGTDFTLKI<br>SRVEAEDVGV YYCLQATHFP QTFGGGTKVE IK |
| 168 | hz4F36 LC<br>CDR1, CDR2, CDR3<br>underlined<br>Variable sequence in<br>italics | *DIVMTQTPLS LSVTPGQPAS ISCKSSQSLL ESDGKTYLNW*<br>*YLQKPGQSPQ LLIYLVSILD SGVPDRFSGS GSGTDFTLKI*<br>*SRVEAEDVGV YYCLQATHFP QTFGGGTKVE IK*RTVAAPSV<br>FIFPPSDEQL KSGTASVVCL LNNFYPREAK VQWKVDNALQ<br>SGNSQESVTE QDSKDSTYSL SSTLTLSKAD YEKHKVYACE<br>VTHQGLSSPV TKSFNRGEC |
| 169 | hz4F36 VH CDR1 | GFTFSNYAMS |
| 170 | hz4F36 VH CDR2 | TISRSGSYSY FPDSVQG |
| 171 | hz4F36 VH CDR3 | LGGYDEGDAM DS |
| 172 | hz4F36 VH<br>CDR1, CDR2, CDR3<br>underlined | EVQLVESGGG LVKPGGSLRL SCAASGFTFS NYAMSWVRQT<br>PEKRLEWVAT ISRSGSYSYF PDSVQGRFTI SRDNAKNSLY<br>LQMNSLRAED TAVYYCARLG GYDEGDAMDS WGQGTTVTVS S |
| 173 | hz4F36 CH<br>Human IgG4 constant<br>heavy | ASTKGPSVFP LAPCSRSTSE STAALGCLVK DYFPEPVTVS<br>WNSGALTSGV HTFPAVLQSS GLYSLSSVVT VPSSSLGTKT<br>YTCNVDHKPS NTKVDKRVES KYGPPCPPCP APEFLGGPSV<br>FLFPPKPKDT LMISRTPEVT CVVVDVSQED PEVQFNWYVD<br>GVEVHNAKTK PREEQFNSTY RVVSVLTVLH QDWLNGKEYK<br>CKVSNKGLPS SIEKTISKAK GQPREPQVYT LPPSQEEMTK<br>NQVSLTCLVK GFYPSDIAVE WESNGQPENN YKTTPPVLDS |

TABLE 33-continued

SEQUENCES

| SEQ ID NO: | Description | Sequence |
| --- | --- | --- |
| | | DGSFFLYSRL TVDKSRWQEG NVFSCSVMHE ALHNHYTQKS<br>LSLSLGK |
| 174 | hz4F36 HC<br>CDR1, CDR2, CDR3 underlined<br>Variable sequence in italics | *EVQLVESGGG LVKPGGSLRL SCAASGFTFS NYAMSWVRQT*<br>*PEKRLEWVAT ISRSGSYSYF PDSVQGRFTI SRDNAKNSLY*<br>*LQMNSLRAED TAVYYCARLG GYDEGDAMDS WGQGTTVTVS*<br>*S*ASTKGPSVF PLAPCSRSTS ESTAALGCLV KDYFPEPVTV<br>SWNSGALTSG VHTFPAVLQS SGLYSLSSVV TVPSSSLGTK<br>TYTCNVDHKP SNTKVDKRVE SKYGPPCPPC PAPEFLGGPS<br>VFLFPPKPKD TLMISRTPEV TCVVVDVSQE DPEVQFNWYV<br>DGVEVHNAKT KPREEQFNST YRVVSVLTVL HQDWLNGKEY<br>KCKVSNKGLP SSIEKTISKA KGQPREPQVY TLPPSQEEMT<br>KNQVSLTCLV KGFYPSDIAV EWESNGQPEN NYKTTPPVLD<br>SDGSFFLYSR LTVDKSRWQE GNVFSCSVMH EALHNHYTQK<br>SLSLSLGK |
| 175 | mAb-TFPI-106 VH nucleic acids encoding CDR1, CDR2, CDR3 underlined | GAGGTGCAGCTGCTGGAGTCTGGCGGAGGCTTGGTACAGCCTGGGGG<br>GTCCCTGAGACTCTCCTGTGCAGCCTCTGGATTCACCTTTAGCAGCT<br>ATGCCATGAGCTGGGTCCGCCAGGCTCCAGGGAAGGGGCTGGAGTGG<br>GTCTCAGCTATTAGTGGTAGTGGTGGTAGCACATACTACGCAGACTC<br>CGTGAAGGGCCGGTTCACCATCTCCAGAGACAATTCCAAGAACACGC<br>TGTATCTGCAAATGAACAGCCTGAGAGCCGAGGACACGGCCGTATAT<br>TACTGTGCGATTCTGGGAGCTACTTCGTTATCGGCTTTTGATATCTG<br>GGGCCAAGGGACAATGGTCACCGTCTCGAGC |
| 176 | mAb-TFPI-106 VL nucleic acids encoding CDR1, CDR2, CDR3 underlined | CAGTCTGTGCTGACGCAGCCGCCCTCAGTGTCTGGGGCCCCAGGGCA<br>GAGGGTCACCATCTCCTGCACTGGGAGCAGCTCCAACATCGGGGCAG<br>GTTATGATGTACACTGGTACCAGCAGCTTCCAGGAACAGCCCCCAAA<br>CTCCTCATCTATGGTAACAGCAATCGGCCCTCAGGGGTCCCTGACCG<br>ATTCTCTGGCTCCAAGTCTGGCACCTCAGCCTCCCTGGCCATCACTG<br>GGCTCCAGGCTGAGGATGAGGCTGATTATTACTGCCAGTCCTATGAC<br>AGCAGCCTGAGTGGTTCAGGGGTATTCGGCGGAGGGACCAAGCTGAC<br>CGTCCTA |
| 177 | mAb-TFPI-106 HC nucleic acids encoding CDR1, CDR2, CDR3 underlined;<br>Variable sequence in italics | *GAGGTGCAGCTGCTGGAGTCTGGCGGAGGCTTGGTACAGCCTGGGGG*<br>*GTCCCTGAGACTCTCCTGTGCAGCCTCTGGATTCACCTTTAGCAGCT*<br>*ATGCCATGAGCTGGGTCCGCCAGGCTCCAGGGAAGGGGCTGGAGTGG*<br>*GTCTCAGCTATTAGTGGTAGTGGTGGTAGCACATACTACGCAGACTC*<br>*CGTGAAGGGCCGGTTCACCATCTCCAGAGACAATTCCAAGAACACGC*<br>*TGTATCTGCAAATGAACAGCCTGAGAGCCGAGGACACGGCCGTATAT*<br>*TACTGTGCGATTCTGGGAGCTACTTCGTTATCGGCTTTTGATATCTG*<br>*GGGCCAAGGGACAATGGTCACCGTCTCGAGC*GCGTCGACCAAGGGCC<br>CATCGGTCTTCCCCCTGGCACCCTCCTCCAAGAGCACCTCTGGGGGC<br>ACAGCGGCCCTGGGCTGCCTGGTCAAGGACTACTTCCCCGAACCGGT<br>GACGGTGTCGTGGAACTCAGGCGCCCTGACCAGCGGCGTGCACACCT<br>TCCCGGCTGTCCTACAGTCCTCAGGACTCTACTCCCTCAGCAGCGTG<br>GTGACCGTGCCCTCCAGCAGCTTGGGCACCCAGACCTACATCTGCAA<br>CGTGAATCACAAGCCCAGCAACACCAAGGTGGACAAGAAAGTTGAGC<br>CCAAATCTTGTGACAAAACTCACACATGCCCACCGTGCCCAGCACCT<br>GAAGCCGCTGGGGCACCGTCAGTCTTCCTCTTCCCCCCAAAACCCAA<br>GGACACCCTCATGATCTCCCGGACCCCTGAGGTCACATGCGTGGTGG<br>TGGACGTGAGCCACGAAGACCCTGAGGTCAAGTTCAACTGGTACGTG<br>GACGGCGTGGAGGTGCATAATGCCAAGACAAAGCCGCGGGAGGAGCA<br>GTACAACAGCACGTACCGTGTGGTCAGCGTCCTCACCGTCCTGCACC<br>AGGACTGGCTGAATGGCAAGGAGTACAAGTGCAAGGTCTCCAACAAA<br>GCCCTCCCAGCCCCCATCGAGAAAACCATCTCCAAAGCCAAAGGGCA<br>GCCCCGAGAACCACAGGTGTACACCCTGCCCCCATCCCGGGAGGAGA<br>TGACCAAGAACCAGGTCAGCCTGACCTGCCTGGTCAAAGGCTTCTAT<br>CCCAGCGACATCGCCGTGGAGTGGGAGAGCAATGGGCAGCCGGAGAA<br>CAACTACAAGACCACGCCTCCCGTGCTGGACTCCGACGGCTCCTTCT<br>TCCTCTATAGCAAGCTCACCGTGGACAAGAGCAGGTGGCAGCAGGGG<br>AACGTCTTCTCATGCTCCGTGATGCATGAGGCTCTGCACAACCACTA<br>CACGCAGAAGAGCCTCTCCCTGTCCCCGGGT |
| 178 | mAb-TFPI-106 LC nucleic acids encoding CDR1, CDR2, CDR3 underlined;<br>Variable sequence in italics | *CAGTCTGTGCTGACGCAGCCGCCCTCAGTGTCTGGGGCCCCAGGGCA*<br>*GAGGGTCACCATCTCCTGCACTGGGAGCAGCTCCAACATCGGGGCAG*<br>*GTTATGATGTACACTGGTACCAGCAGCTTCCAGGAACAGCCCCCAAA*<br>*CTCCTCATCTATGGTAACAGCAATCGGCCCTCAGGGGTCCCTGACCG*<br>*ATTCTCTGGCTCCAAGTCTGGCACCTCAGCCTCCCTGGCCATCACTG*<br>*GGCTCCAGGCTGAGGATGAGGCTGATTATTACTGCCAGTCCTATGAC*<br>*AGCAGCCTGAGTGGTTCAGGGGTATTCGGCGGAGGGACCAAGCTGAC*<br>*CGTCCTA*GGTCAGCCCAAGGCTGCCCCCTCGGTCACTCTGTTCCCGC<br>CCTCCTCTGAGGAGCTTCAAGCCAACAAGGCCACACTGGTGTGTCTC<br>ATAAGTGACTTCTACCCGGGAGCCGTGACAGTGGCCTGGAAGGCAGA<br>TAGCAGCCCCGTCAAGGCGGGAGTGGAGACCACCACACCCTCCAAAC<br>AAAGCAACAACAAGTACGCGGCCAGCAGCTATCTGAGCCTGACGCCT |

TABLE 33-continued

SEQUENCES

| SEQ ID NO: | Description | Sequence |
|---|---|---|
| | | GAGCAGTGGAAGTCCCACAGAAGCTACAGCTGCCAGGTCACGCATGA<br>AGGGAGCACCGTGGAGAAGACAGTGGCCCCTACAGAATGTTCA |

Description and sequence composition for antibody SeqID (sequence identification) numbers (Kabat numbering is used when referring to specific residues. VH and VL CDR beginning and end points are defined by using Kabat definitions)

The various features and embodiments of the present invention, referred to in individual sections above apply, as appropriate, to other sections, mutatis mutandis. Consequently features specified in one section may be combined with features specified in other sections, as appropriate. All references cited herein, including patents, patent applications, papers, text books, and cited sequence Accession numbers, and the references cited therein are hereby incorporated by reference in their entirety. In the event that one or more of the incorporated literature and similar materials differs from or contradicts this application, including but not limited to defined terms, term usage, described techniques, or the like, this application controls.

What is claimed is:

1. A method of reducing the activity of Tissue Factor Pathway Inhibitor (TFPI) in a subject in need thereof, comprising administering to said subject a therapeutically effective amount of an antibody or antigen-binding fragment thereof that specifically binds to an epitope in Kunitz Domain 2 (K2) of Tissue Pathway Factor Inhibitor (TFPI), wherein the antibody is selected from the group consisting of an antibody comprising:

(a) a heavy chain variable region (VH) comprising a VH complementarity determining region one (CDR-H1) comprising the amino acid sequence of SEQ ID NO:38, a CDR-H2 comprising the amino acid sequence of SEQ ID NO:39, and a CDR-H3 comprising the amino acid sequence of SEQ ID NO:40, and a light chain variable region (VL) comprising a VL complementarity determining region one (CDR-L1) comprising the amino acid sequence of SEQ ID NO:33, a CDR-L2 comprising the amino acid sequence of SEQ ID NO:34, and a CDR-L3 comprising the amino acid sequence of SEQ ID NO:35;

(b) a VH comprising the amino acid sequence of SEQ ID NO:63 and a VL comprising the amino acid sequence of SEQ ID NO:36;

(c) a heavy chain consisting of the amino acid sequence of SEQ ID NO:64 and a light chain consisting of the amino acid sequence of SEQ ID NO:37;

(d) a VH comprising the amino acid sequence of SEQ ID NO:41 and a VL comprising the amino acid sequence of SEQ ID NO: 36; and (e) a heavy chain consisting of the amino acid sequence of SEQ ID NO: 42 and a light chain consisting of the amino acid sequence of SEQ ID NO: 37.

2. The method of claim 1, comprising administering to said subject a therapeutically effective amount of the antibody, or antigen-binding fragment thereof, wherein the antibody comprises a VH comprising the amino acid sequence of SEQ ID NO:63 and a VL comprising the amino acid sequence of SEQ ID NO:36.

3. A method of shortening bleeding time in a subject in need thereof, comprising administering to said subject a therapeutically effective amount of an antibody, or antigen-binding fragment thereof, that specifically binds to an epitope in Kunitz Domain 2 (K2) of Tissue Pathway Factor Inhibitor (TFPI), wherein the antibody is selected from the group consisting of an antibody comprising:

(a) a heavy chain variable region (VH) comprising a VH complementarity determining region one (CDR-H1) comprising the amino acid sequence of SEQ ID NO:38, a CDR-H2 comprising the amino acid sequence of SEQ ID NO:39, and a CDR-H3 comprising the amino acid sequence of SEQ ID NO:40, and a light chain variable region (VL) comprising a VL complementarity determining region one (CDR-L1) comprising the amino acid sequence of SEQ ID NO:33, a CDR-L2 comprising the amino acid sequence of SEQ ID NO:34, and a CDR-L3 comprising the amino acid sequence of SEQ ID NO:35;

(b) a VH comprising the amino acid sequence of SEQ ID NO:63 and a VL comprising the amino acid sequence of SEQ ID NO:36;

(c) a heavy chain consisting of the amino acid sequence of SEQ ID NO:64 and a light chain consisting of the amino acid sequence of SEQ ID NO:37;

(d) a VH comprising the amino acid sequence of SEQ ID NO:41 and a VL comprising the amino acid sequence of SEQ ID NO: 36; and (e) a heavy chain consisting of the amino acid sequence of SEQ ID NO: 42 and a light chain consisting of the amino acid sequence of SEQ ID NO: 37.

4. The method of claim 3, said method comprising administering the antibody, or antigen-binding fragment thereof, wherein the antibody comprises a VH comprising the amino acid sequence of SEQ ID NO:63 and a VL comprising the amino acid sequence of SEQ ID NO:36.

5. The method of claim 1, wherein said subject suffers from or is susceptible to hemophilia A, hemophilia B, von Willebrand Disease (vWD), or a platelet disorder.

6. The method of claim 3, wherein said subject suffers from or is susceptible to hemophilia A, hemophilia B, von Willebrand Disease (vWD), or a platelet disorder.

7. The method of claim 1, further comprising administering a therapeutically effective amount of FVIIa.

8. The method of claim 3, further comprising administering a therapeutically effective amount of FVIIa.

9. The method of claim 3 further comprising administering a therapeutically effective amount of a clotting agent.

10. The method of claim 9, wherein said subject suffers from or is susceptible to hemophilia A or hemophilia B and said clotting agent is selected from the group consisting of factor VIIa, factor VIII, factor IX and tranexamic acid.

11. The method of claim 1, further comprising administering a therapeutically effective amount of a clotting agent.

12. The method of claim 11, wherein said subject suffers from or is susceptible to hemophilia A or hemophilia B and said clotting agent is selected from the group consisting of factor VIIa, factor VIII, factor IX and tranexamic acid.

13. The method of claim 1, comprising administering to said subject a therapeutically effective amount of the antibody, or antigen-binding fragment thereof, wherein the antibody comprises a heavy chain consisting of the amino acid sequence of SEQ ID NO:64 and a light chain consisting of the amino acid sequence of SEQ ID NO:37.

14. The method of claim 3, comprising administering to said subject a therapeutically effective amount of the antibody, or antigen-binding fragment thereof, wherein the antibody comprises a heavy chain consisting of the amino acid sequence of SEQ ID NO:64 and a light chain consisting of the amino acid sequence of SEQ ID NO:37.

15. The method of claim 5, wherein said subject has hemophilia A and inhibitory antibodies against human Factor VIII.

16. The method of claim 5, wherein said subject has hemophilia B and inhibitory antibodies against human Factor FIX.

17. The method of claim 6, wherein said subject has hemophilia A and inhibitory antibodies against human Factor VIII.

18. The method of claim 6, wherein said subject has hemophilia B and inhibitory antibodies against human Factor IX.

* * * * *